US009492482B2

(12) United States Patent
Beech et al.

(10) Patent No.: US 9,492,482 B2
(45) Date of Patent: Nov. 15, 2016

(54) ENGINEERED CELLS EXPRESSING MULTIPLE IMMUNOMODULATORS AND USES THEREOF

(75) Inventors: Robert P. Beech, Cincinnati, OH (US); Thomas D. Reed, Arlington, VA (US)

(73) Assignee: Intrexon Corporation, Blacksburg, VA (US)

( * ) Notice: Subject to any disclaimer, the term of this patent is extended or adjusted under 35 U.S.C. 154(b) by 840 days.

(21) Appl. No.: 13/123,129

(22) PCT Filed: Oct. 8, 2009

(86) PCT No.: PCT/US2009/005510
§ 371 (c)(1),
(2), (4) Date: Jul. 13, 2011

(87) PCT Pub. No.: WO2010/042189
PCT Pub. Date: Apr. 15, 2010

(65) Prior Publication Data
US 2011/0268766 A1  Nov. 3, 2011

Related U.S. Application Data

(60) Provisional application No. 61/103,810, filed on Oct. 8, 2008.

(51) Int. Cl.
| A61K 35/15 | (2015.01) |
| A61K 31/7088 | (2006.01) |
| A61K 39/00 | (2006.01) |
| A61K 45/06 | (2006.01) |
| C12N 15/86 | (2006.01) |
| A61K 38/20 | (2006.01) |
| A61K 9/00 | (2006.01) |
| A61K 38/00 | (2006.01) |
| A61K 35/12 | (2015.01) |

(52) U.S. Cl.
CPC ........... *A61K 35/15* (2013.01); *A61K 31/7088* (2013.01); *A61K 38/208* (2013.01); *A61K 39/0011* (2013.01); *A61K 45/06* (2013.01); *C12N 15/86* (2013.01); *A61K 9/0095* (2013.01); *A61K 38/00* (2013.01); *A61K 2035/124* (2013.01); *A61K 2039/5154* (2013.01); *C12N 2710/10343* (2013.01); *C12N 2830/002* (2013.01); *C12N 2840/206* (2013.01)

(58) Field of Classification Search
None
See application file for complete search history.

(56) References Cited

U.S. PATENT DOCUMENTS

| 5,698,413 A | 12/1997 | Hollingshead |
| 5,811,231 A | 9/1998 | Farr et al. |
| 5,851,822 A | 12/1998 | Munford |
| 5,922,685 A | 7/1999 | Rakhmilevich et al. |
| 6,060,273 A | 5/2000 | Dirks et al. |
| 6,306,649 B1 | 10/2001 | Gilman et al. |
| 6,482,405 B1 | 11/2002 | Tahara et al. |
| 2002/0098559 A1 | 7/2002 | Opara |
| 2002/0106689 A1 | 8/2002 | Faustman et al. |
| 2002/0119521 A1 | 8/2002 | Palli et al. |
| 2002/0182698 A1 | 12/2002 | O'Malley et al. |
| 2003/0109683 A1 | 6/2003 | O'Malley et al. |
| 2003/0180719 A1 | 9/2003 | Herget et al. |
| 2003/0221203 A1 | 11/2003 | Siamak et al. |
| 2004/0082535 A1 | 4/2004 | Mahuran et al. |
| 2004/0086494 A1 | 5/2004 | John |
| 2004/0103448 A1 | 5/2004 | Bjorklund |
| 2004/0171651 A1 | 9/2004 | Hormann et al. |
| 2004/0209836 A1 | 10/2004 | Spencer et al. |
| 2004/0235169 A1 | 11/2004 | Evans et al. |
| 2004/0265288 A1 | 12/2004 | Gilman |
| 2005/0191659 A1 | 9/2005 | Voellmy |
| 2005/0196751 A1 | 9/2005 | Burcin et al. |
| 2005/0265978 A1 | 12/2005 | Chancellor et al. |
| 2005/0267027 A1 | 12/2005 | Lounsbury et al. |
| 2006/0019362 A1 | 1/2006 | Yu et al. |
| 2006/0020146 A1* | 1/2006 | Hormann et al. ............ 564/123 |
| 2006/0067942 A1 | 3/2006 | Salama |
| 2006/0154852 A1 | 7/2006 | Boden et al. |
| 2006/0177418 A1 | 8/2006 | Braiman-Wiksman et al. |
| 2006/0222636 A1 | 10/2006 | Rambukkana |
| 2006/0281703 A1 | 12/2006 | Bauzon et al. |
| 2006/0292119 A1 | 12/2006 | Chen et al. |
| 2007/0036771 A1 | 2/2007 | Wagner et al. |
| 2007/0053845 A1 | 3/2007 | Sengupta et al. |

(Continued)

FOREIGN PATENT DOCUMENTS

| AU | 2003266903 A2 | 10/2003 |
| WO | WO 2004/035787 A2 | 4/2004 |

(Continued)

OTHER PUBLICATIONS

Gillet et al., The Development of Gene Therapy: From Monogenic Recessive Disorders to Complex Diseases Such as Cancer; Methods in Molecular Biology, Gene Therapy of Cancer, vol. 542, pp. 5-54, 2009.*
Imhof et al., Interaction of tumor cells with the immune system: implications for dendritic cell therapy and cancer progression; Drug Discovery Today; vol. 18, No. 1-2, pp. 35-42, 2013.*
Naldini, L., Ex vivo gene transfer and correction for cell-based therapies, Nature Reviews: Genetics, vol. 12, pp. 301-315, 2011.*
Agha-Mohammadi, S. and Lotze, M.T., "Regulatable systems: applications in gene therapy and replicating viruses," *The Journal of Clinical Investigation* 105(9):1177-1183, American Society for Clinical Investigation , USA (May 2000).

(Continued)

*Primary Examiner* — Addison D Ault
(74) *Attorney, Agent, or Firm* — Sterne, Kessler, Goldstein and Fox, P.L.L.C.

(57) ABSTRACT

This invention relates to the field of therapeutics. Most specifically invention provides methods of generating in vitro engineered immune cells conditionally expressing interleukin-12 (IL-12) and one or more immunomodulators under the control of a gene expression modulation system in the presence of activating ligand and uses for therapeutic purposes in animals.

11 Claims, 9 Drawing Sheets

(56) References Cited

U.S. PATENT DOCUMENTS

| | | |
|---|---|---|
| 2007/0116671 A1 | 5/2007 | Prakash et al. |
| 2007/0154524 A1 | 7/2007 | Kauper et al. |
| 2007/0225243 A1 | 9/2007 | Horton et al. |
| 2007/0287731 A1 | 12/2007 | Hormann et al. |
| 2008/0181874 A1 | 7/2008 | Kharazi |
| 2008/0241100 A1 | 10/2008 | Strobl et al. |
| 2008/0260690 A1 | 10/2008 | De Luca |
| 2009/0017108 A1 | 1/2009 | Yuzhakov |
| 2009/0098055 A1 | 4/2009 | Beech et al. |
| 2009/0123441 A1 | 5/2009 | Braughler et al. |
| 2009/0136465 A1 | 5/2009 | Merenick et al. |
| 2009/0163592 A1 | 6/2009 | Hormann et al. |
| 2012/0114620 A1 | 5/2012 | Braughler et al. |

FOREIGN PATENT DOCUMENTS

| | | |
|---|---|---|
| WO | WO 2009/045370 A2 | 4/2009 |
| WO | WO 2009/048560 A1 | 4/2009 |
| WO | WO 2011/119773 A1 | 9/2011 |

OTHER PUBLICATIONS

Karzenowski, D. et al., "Inducible control of transgene expression with ecdysone receptor: gene switches with high sensitivity, robust expression, and reduced size," *BioTechniques* 39(2):191-200, Informa Healthcare USA, Inc., USA (Aug. 2005).

Melero, I., et al., "IL-12 gene therapy for cancer: in synergy with other immunotherapies," *TRENDS in Immunology* 22(3):113-115, Elsevier Science Ltd., England (Mar. 2001).

Tatsumi, T., et al., "Intratumoral Delivery of Dendric Cells Engineered to Secrete Both Interleukin (IL)-12 and IL-8 Effectively Treats Local Distant Disease in Association with Broadly Reactive Tel-type Immunity," *Cancer Research* 63:6378-6386, American Association for Cancer Research, Inc., USA (Oct. 2003).

Yamanaka, R., et al., "Marked enhancement of antitumor immune responses in mouse brain tumor models by genetically modified dendric cells producing Semliki Forest virus-mediated interleukin-12," *Journal of Neurosurgery* 97(3):611-618, American Association of Neurological Surgeons, USA (Sep. 2002).

International Search Report and Written Opinion for International Application No. PCT/US2005/05510, International Searching Authority, United States, mailed Nov. 4, 2010.

Akiyama, Y., et al. "Enhancement of antitumor immunity against B16 melanoma tumor using genetically modified dendritic cells to produce cytokines," *Gene Therapy* 7:2113-2121, Macmillan Publishers Ltd., England (2000).

Karzenowski, D., et al., "RheoSwitch® Therapeutic System-Inducible Recombinant AAV Vectors for Tightly Regulated Transgene Expression," *Molecular Therapy* 13(1):S194, The American Society of Gene Therapy, United States (May 2006).

Leeser, D.B., et al., "Pulsatile Pump Perfusion of Pancreata Before Human Islet Cell Isolation," *Transplant Proc.* 36(4):1050-1051, Elsevier Inc., United States (2004).

Mazzolini, G., et al.,"Intratumoral Injection of Dendritic Cells Engineered to Secrete Interleukin-12 by Recombinant Adenovirus in Patients With Metastatic Gastrointestinal Carcinomas," *J. Clin. Oncol.* 23(5):999-1010, American Society of Clinical Oncology, United States (Feb. 2006).

"Material Safely Data Sheet: RheoSwitch Ligand RSL1 #E3000," New England Biolabs Inc., 19 pages, revised Jan. 2006, retrieved from neb.com/nebecomm/MSDSFiles/msdsE3000.pdf.

Tsugawa, T., et al., "Sequential delivery of interferon-α gene and DCs to intracranial gliomas promotes an effective antitumor response," *Gene Therapy* 11:1551-1558, Nature Publishing Group, England (2004).

Vujanovic, L., et al., "IL-12p70 and IL-18 gene-modified dendritic cells loaded with tumor antigen-derived peptides or recombinant protein effectively stimulate specific Type-1 $CD4^+$ T-cell responses from normal donors and melanoma patients in vitro," *Cancer Gene Therapy* 13:798-805, Nature Publishing Group, England (2006).

Weber, M., et al., "Formation of cartilage matrix proteins by BMP-transfected murine mesenchymal stem cells encapsulated in a novel class of alginates," *Biomaterials* 23:2003-2013, Elsevier Science, Ltd., England (2002).

International Search Report for International Application No. PCT/US08/11270, International Searching Authority US, United States, mailed on Jan. 26, 2010.

The Written Opinion of the International Searching Authority for International Application No. PCT/US08/11270, International Searching Authority US, United States, mailed on Jan. 26, 2010.

International Search Report for International Application No. PCT/US08/11563, International Searching Authority US, United States, mailed on Dec. 17, 2008.

The Written Opinion of the International Searching Authority for International Application No. PCT/US08/11563, International Searching Authority US, United States, mailed on Jan. 17, 2008.

International Search Report for International Application No. PCT/US11/29682 International Searching Authority US, United States, mailed on Aug. 25, 2011.

Office Action mailed Mar. 25, 2010, in U.S. Appl. No. 12/241,018, Merenick, et al., filed Sep. 29, 2008.

Office Action mailed May 26, 2011, in U.S. Appl. No. 12/241,018, Merenick, et al., filed Sep. 29, 2008.

Office Action mailed Nov. 8, 2011, in U.S. Appl. No. 12/241,018, Merenick, et al., filed Sep. 29, 2008.

Office Action mailed Mar. 9, 2010, in U.S. Appl. No. 12/247,738, Braughler, et al., filed Oct. 8, 2008.

Office Action mailed May 23, 2011, in U.S. Appl. No. 12/247,738, Braughler, et al., filed Oct. 8, 2008.

Alexander, H.K., et al., "Selected technologies to control genes and their products for experimental and clinical purposes," *Arch. Immunol. Ther. Exp.* 55:139-149, Warszawa, Panstwowy Zaklad Wydawn, Switzerland (2007).

Goverdhana, S., et al., "Regulatable Gene Expression Systems for Gene Therapy Applications: Progress and Future Challenges," *Curr Gene Ther.* 6(4):421-438, Academic Press, United States (2006).

Lessard, J., et al., "Characterization of the RSLI-Dependent Conditional Expression System in LNCaP Prostate Cancer Cells and Development of a Single Vector Format," *The Prostate* 67:808-819, Wiley-Liss, Inc., United States (2007).

Mazzolini, G.D., et al., "Intratumoral Injection of Dendritic Cells Engineered to Secrete Interleukin-12 by Recombinant Adenovirus in Patients with Metastatic Gastrointestinal Carcinomas," *Molecular Therapy 11 (Supplemental 1)*:S437-S438, The American Society of Gene Therapy, United States (2005).

Pandolfi, F., et al., "Strategies to Overcome Obstacles to Successful Immunotherapy of Melanoma," *Int J Immunoputhol Pharmacol.* 21(3):493-500, Biomedical Research Press, Italy (2008).

New England Biolabs online catalog datasheet for RheoSwitch Mammalian Inducible Expression System, New England Biolabs Inc., Ipswich, MA (2006).

\* cited by examiner

UV-VQ-Ad-Research Switch-bicistronic hIL-12

UV-VQ-Ad-Research Switch-bicistronic hIL-21+hIL-15

UV-VQ-Ad-Research Switch-bicistronic mIL-12

UV-VQ-Ad-Research Switch-bicistronic mIL-21+mIL-15

UV-VQ- Ad-Research Switch-monocistronic hIL-21

UV-VQ- Ad-Research Switch-monocistronic mIL-21

UV-VQ-Ad-Research Switch-tricistronic-hIL-12+hIL-21

UV-VQ-Ad-Research Switch-tricistronic-mIL-12+mIL-21

SEQUENCE LISTING

<160> NUMBER OF SEQ ID NOS: 29

<210> SEQ ID NO 1
<211> LENGTH: 13294
<212> TYPE: DNA
<213> ORGANISM: Artificial Sequence
<220> FEATURE:
<223> OTHER INFORMATION: Synthetic mIL-12 and mIL-21

<400> SEQUENCE: 1

```
taaacaaata ggggttccgc gcacatttcc ccgaaaagtg ccacctgacg tctaagaaac      60
cattattatc atgacattaa cctataaaaa taggcgtatc acgaggccct ttcgtcttca     120
```

```
attaatcgca ccggtatcta tgtcgggtgc ggagaaagag gtaatgaaat ggcagctagc      180
atcatcaata atatacctta ttttggattg aagccaatat gataatgagg gggtggagtt      240
tgtgacgtgg cgcggggcgt gggaacgggg cgggtgacgt agtagtgtgg cggaagtgtg      300
atgttgcaag tgtggcggaa cacatgtaag cgacggatgt ggcaaaagtg acgttttgg       360 tgtgcgccgg tgtacacagg aagtgacaat tttcgcgcgg ttttaggcgg atgttgtagt      420
aaatttgggc gtaaccgagt aagatttggc cattttcgcg ggaaaactga ataagaggaa      480
gtgaaatctg aataattttg tgttactcat agcgcgtaat atttgtctag ggagatccgg      540
taccgatatc ctagacaacg atgctgagct aactataacg gtcctaaggt agcgaccgcg      600
gagactaggt gtatttatct aagcgatcgc ttaattaagg ccggccgccg caataaaata      660
tctttatttt cattacatct gtgtgttggt tttttgtgtg aatccatagt actaacatac      720
gctctccatc aaaacaaaac gaaacaaaac aaactagcaa aataggctgt ccccagtgca      780
agtccaggtg ccagaacatt tctctatcca taatgcaggg gtaccgggtg atgacggtga      840
aaacctccaa ttgcggagta ctgtcctccg agcggagtac tgtcctccga gcggagtact      900
gtcctccgag cggagtactg tcctccgagc ggagtactgt cctccgagcg gagtactgtc      960
ctccgagcgg agagtccccg gggacctaga gggtatataa tgggtgcctt agctggtgtg     1020
tgacctcatc ttcctgtacg cccctgcagg ggcgcgccac cgtcgaagaa aggtgagtaa     1080
tcttaacatg ctctttttt ttttttttgc taatcccttt tgtgtgctga tgttaggatg      1140
acatttacaa caaatgtttg ttcctgacag gaaaaacctt gctgggtacc ttcgttgccg     1200
gacacttctt gtcctctact ttggaaaaaa ggaattgaga gccgctagcc caccatgtgc     1260
ccccagaagc tgaccatcag ctggttcgcc atcgtgctgc tggtgagccc cctgatggcc     1320
atgtgggagc tggagaagga cgtgtacgtg gtggaggtgg actggacccc cgacgccccc     1380
ggcgagaccg tgaacctgac ttgcgacacc cccgaggagg acgacatcac ctggaccagc     1440
gaccagagac acggcgtcat cggcagcggc aagaccctga ccatcaccgt gaaggagttc     1500
ctggacgccg acagtacac ctgtcacaag gcggcgaga ccctgagcca cagccacctg      1560
ttgctgcaca agaaggagaa cggcatctgg agcaccgaga tcctgaagaa cttcaagaac     1620
aagaccttcc tgaagtgcga ggcccccaac tacagcggca gattcacctg tagctggctg     1680
gtgcagagaa acatggacct gaagttcaac atcaagagca gcagcagcag ccccgacagc     1740
agagccgtga catgcggcat ggccagcctg agcgccgaga aggtgaccct ggaccagaga     1800
gactacgaga agtacagcgt gagctgccag gaggacgtga cctgtcccac cgccgaggag     1860 acccctgccca tcgagcttgc cctggaagcc agacagcaga acaagtacga gaactacagc     1920
accagcttct tcatcagaga catcatcaag cccgaccccc ccaagaacct ccagatgaag     1980
cccctgaaga cagccaggt ggaggtgtcc tgggagtacc ccgacagctg gagcaccccc      2040
cacagctact tcagcctgaa gttcttcgtg agaatccaga gaaagaagga gaagatgaag     2100
gagaccgagg agggctgcaa ccagaagggc gctttcctgg tggagaaaac cagcaccgag     2160
gtgcagtgca agggcggcaa cgtgtgtgtg caggcccagg acagatacta caacagcagc     2220
tgctccaagt gggcctgcgt gccctgccgc gtgagaagct gaatcgattg cgcaaagctc     2280
ccctctcccc tccccccccc ctaacgttac tggccgaagc cgcttggaat aaggccggtg     2340
tgcgtttgtc tatatgttat tttccaccat attgccgtct tttggcaatg tgagggcccg     2400
gaaacctggc cctgtcttct tgacgagcat tcctagggt cttccccctc tcgccaaagg      2460
aatgcaaggt ctgttgaatg tcgtgaagga agcagttcct ctggaagctt cttgaagaca     2520
```

```
aacaacgtct gtagcgaccc tttgcaggca gcggaacccc ccacctggcg acaggtgcct   2580
ctgcggccaa aagccacgtg tataagatac acctgcaaag gcggcacaac cccagtgcca   2640
cgttgtgagt tggatagttg tggaaagagt caaatggctc tcctcaagcg tattcaacaa   2700
ggggctgaag gatgcccaga aggtacccca ttgtatggga tctgatctgg ggcctcggtg   2760
cacatgcttt acatgtgttt agtcgaggtt aaaaacgtc taggccccccc gaaccacggg   2820 gacgtggttt tcctttgaaa aacacgatct cttaagtcta gcgccaccat gtgccagagc   2880
agatacctgt tgttcctggc taccctggcc ctgctgaacc acctgagcct ggcccgcgtg   2940
atccccgtga gcggccccgc cagatgcctg agccagagca gaaacctgtt gaaaacaacc   3000
gacgacatgg tgaaaaccgc cagagagaag ctgaagcact acagctgcac cgccgaggac   3060
atcgaccacg aggacatcac cagagaccag accagcaccc tgaaaacctg tctgcccctg   3120
gagctgcaca gaacgagag ctgcctggct accagagaga ccagcagcac caccagaggc   3180
agctgcctgc cccccagaa aaccagcctg atgatgaccc tgtgcctggg cagcatctac   3240
gaggacctga agatgtacca gaccgagttc caggccatca cgccgccct gcaaaaccac   3300 aaccaccagc agatcatcct ggacaagggc atgttggtgg ccatcgacga gctgatgcag   3360
agcctgaacc acaacggcga gaccctgaga cagaagcccc ccgtgggcga ggccgacccc   3420
tacagagtga agatgaagct gtgcatcctg ctgcacgcct tcagcaccag agtggtgacc   3480
atcaacagag tgatgggcta cctgagcagc gcctgaatcg aatgcgcact cgagtggtat   3540
tacgctcaac ttcagaatct cactaaaaga atagatagtc ttcctttaac tgaaaatttt   3600
tccttacaaa cagatatgga cgtcactagc accaccatgg agaggaccct ggtgtgcctg   3660
gtggtgatct tcctgggcac cgtggcccac aagagcagcc cccagggacc cgacaggctg   3720
ctgatccggc tgagacacct gatcgacatc gtggagcagc tgaagattta cgagaacgac   3780
ctggaccccg agctgctgtc cgcccccag gacgtgaagg gccactgcga gcacgccgcc   3840
ttcgcctgct tccagaaggc caagctgaag cccagcaacc ccggcaacaa caagaccttc   3900
atcatcgacc tggtgcccca gctgagaagg aggctgcccg ccaggagggg cggcaagaag   3960
cagaagcaca tcgccaagtg ccccagctgc gacagctacg agaagcggac ccccaaggag   4020
ttcctggaga ggctgaagtg gctgctgcaa aagatgatcc accagcacct gagctgaatc   4080
gcctgcgcag catgctcgcg acctaagtcg gccgctaaag tttacgtagc ggccgcgtcg   4140
acgatagctt gatgggtggc atccctgtga cccctcccca gtgcctctcc tggccctgga   4200
agttgccact ccagtgccca ccagccttgt cctaataaaa ttaagttgca tcattttgtc   4260
tgactaggtg tccttctata atattatggg gtggaggggg gtggtatgga gcaagggca   4320 agttgggaag acaacctgta gggcctgcgg ggtctattgg gaaccaagct ggagtgcagt   4380
ggcacaatct ggctcactg caatctccgc ctcctgggtt caagcgattc tcctgcctca   4440
gcctcccgag ttgttgggat tccaggcatg catgaccagg ctcagctaat ttttgttttt   4500
ttggtagaga cggggtttca ccatattggc caggctggtc tccaactcct aatctcaggt   4560
gatctaccca ccttggcctc ccaaattgct gggattacag gcgtgaacca ctgctccctt   4620
ccctgtcctt ctgattttaa aataactata ccagcaggag gacgtccaga cacagcatag   4680
gctacctggc catgcccaac cggtgggaca tttgagttgc ttgcttggca ctgtcctctc   4740
atgcgttggg tccactcagt agatgccgt tgaattctga tttaaatcgg tccgcgtacg   4800
gcgtggtagg tccgaacgaa tccatggatt accctgttat ccctatccgg agttaacctc   4860
```

```
gaggacttcg gaacttctag aaccagaccg ttcagtttaa acgctcttct cccctcgag    4920
ggcctccgcg ccgggttttg gcgcctcccg cgggcgcccc cctcctcacg gcgagcgctg    4980
ccacgtcaga cgaagggcgc agcgagcgtc ctgatccttc cgcccggacg ctcaggacag    5040
cggcccgctg ctcataagac tcggccttag aaccccagta tcagcagaag gacattttag    5100
gacgggactt gggtgactct agggcactgg ttttctttcc agagagcgga acaggcgagg    5160
aaaagtagtc ccttctcggc gattctgcgc agggatctcc gtggggcggt gaacgccgat    5220
gattatataa ggacgcgccg ggtgtggcac agctagttcc gtcgcagccg ggatttgggt    5280
cgcggttctt gtttgtggat cgctgtgatc gtcacttggt gagtagcggg ctgctgggct    5340
gggtacgtgc gctcggggtt ggcgagtgtg ttttgtgaag ttttttaggc accttttgaa    5400
atgtaatcat ttgggtcaat atgtaatttt cagtgttaga ctagtaaatt gtccgctaaa    5460
ttctggccgt ttttggcttt tttgttagac ggcatgcggg gggggggggg ggcaattggc    5520
caccatgggc cccaagaaga aaggaaggt ggcccccccc accgacgtga gcctgggcga    5580
cgagctgcac ctgacggcg aggacgtggc catggcccac gccgacgccc tggacgactt    5640
cgacctggac atgctgggcg acggcgacag cccggcccc ggcttcaccc cccacgacag    5700
cgcccctac ggcgccctgg acatggccga cttcgagttc gagcagatgt tcaccgacgc    5760
cctgggcatc gacgagtacg gcggccatat ggagatgccc gtggacagga ttctggaggc    5820
cgaactcgcc gtggagcaga aagcgacca gggcgtggag ggccccggcg aaccggcgg    5880
cagcggcagc agccccaacg accccgtgac caacatctgc caggccgccg acaagcagct    5940
gttcacccctg gtggagtggg ccaagaggat tccccacttc agcagcctgc ccctggacga    6000
ccaggtgatc ctgctgaggg ccggatggaa cgagctgctg atcgccagct tcagccacag    6060
gagcatcgac gtgagggacg gcatcctgct ggccaccggc ctgcacgtcc ataggaacag    6120
cgcccacagc gccggagtgg gcgccatctt cgacagggtg ctgaccgagc tggtgagcaa    6180
gatgagggac atgaggatgg acaagaccga gctgggctgc ctgagggcca tcatcctgtt    6240
caaccccgag gtgagggcc tgaaaagcgc ccaggaggtg gagctgctga gggagaaggt    6300
gtacgccgcc ctgaggagt acaccaggac caccccacccc gacgagcccg gcagattcgc    6360
caagctgctg ctgaggctgc ccagcctgag gagcatcggc ctgaagtgcc tggagcacct    6420
gttcttcttc aggctgatcg gcgacgtgcc catcgacacc ttcctgatgg agatgctgga    6480
gagccccagc gacagctgag ccggcaactc gctgtagtaa ttccagcgag aggcagaggg    6540
agcgagcggg cggcgggcta gggtggagga gccggcgag cagagctgcg ctgcgggcgt    6600
cctgggaagg gagatccgga gcgaataggg ggcttcgcct ctggcccagc cctcccgctg    6660
atccccagc cagcggtgcg caaccctagc cgcatccacg aaactttgcc catagcagcg    6720
ggcgggcact ttgcactgga acttacaaca cccgagcaag gacgcgactc tcccgacgcg    6780
gggaggctat tctgcccatt tggggacact tccccgccgc tgccaggacc cgcttctctg    6840
aaaggctctc cttgcagctg cttagacgct ggatttttt cgggtagtgg aaaaccagca    6900
gcctccgcg accagatctg ccaccatgaa gctgctgagc agcatcgagc aggcttgcga    6960
catctgcagg ctgaagaagc tgaagtgcag caaggagaag cccaagtgcg ccaagtgcct    7020
gaagaacaac tgggagtgca gatacagccc caagaccaag aggagccccc tgaccagggc    7080
ccacctgacc gaggtggaga gcaggctgga gaggctggag cagctgttcc tgctgatctt    7140
cccaggggag gacctggaca tgatcctgaa gatggacagc ctgcaagaca tcaaggccct    7200
gctgaccggc ctgttcgtgc aggacaacgt gaacaaggac gccgtgaccg acaggctggc    7260
```

```
cagcgtggag accgacatgc ccctgaccct gaggcagcac aggatcagcg ccaccagcag    7320
cagcgaggag agcagcaaca agggccagag gcagctgacc gtgagcccg  agtttcccgg    7380 gatcaggccc gagtgcgtgg tgcccgagac ccagtgcgcc atgaaaagga aggagaagaa    7440
ggcccagaag gagaaggaca agctgcccgt gagcaccacc accgtcgatg accacatgcc    7500
ccccatcatg cagtgcgagc ccccccccc  cgaggccgcc aggattcacg aggtcgtgcc    7560
caggttcctg agcgacaagc tgctggtgac caacaggcag aagaacatcc cccagctgac    7620
cgccaaccag cagttcctga tcgccaggct gatctggtat caggacggct acgagcagcc    7680
cagcgacgag gacctgaaaa ggatcaccca gacctggcag caggccgacg acgagaacga    7740
ggagagcgac accccttca  ggcagatcac cgagatgacc atcctgaccg tgcagctgat    7800
cgtggagttc gccaagggcc tgcccggatt cgccaagatc agccagcccg accagatcac    7860
cctgctgaag gcttgcagca gcgaggtgat gatgctgagg gtggccagga ggtacgacgc    7920
cgccagcgac agcatcctgt tcgccaacaa ccaggcttac accagggaca actacaggaa    7980
ggctggcatg gccgaggtga tcgaggacct cctgcacttc tgcagatgta tgtacagcat    8040
ggccctggac aacatccact acgccctgct gaccgccgtg gtgatcttca gcgacaggcc    8100
cggcctggag cagccccagc tggtggagga gatccagagg tactacctga acaccctgag    8160
gatctacatc ctgaaccagc tgagcggcag cgccaggagc agcgtgatct acggcaagat    8220
cctgagcatc ctgagcgagc tgaggaccct gggaatgcag aacagcaata tgtgtatcag    8280
cctgaagctg aagaacagga agctgccccc cttcctggag gagatttggg acgtggccga    8340
catgagccac acccagcccc cccccatcct ggagagcccc accaacctgt gaatcgatta    8400
gacatgataa gatacattga tgagtttgga caaaccacaa ctagaatgca gtgaaaaaaa    8460
tgcttaattt gtgaaatttg tgatgctatt gctttaatttg taaccattat aagctgcaat    8520
aaacaagtta ataaaacatt tgcattcatt ttatgtttca ggttcagggg gagatgtggg    8580
aggtttttta aagcaagtaa aacctctaca aatgtggtat ctagagctct tccaaataga    8640
tctggaaggt gctgaggtac gatgagaccc gcaccaggtg cagaccctgc gagtgtggcg    8700
gtaaacatat taggaaccag cctgtgatgc tggatgtgac cgaggagctg aggcccgatc    8760
acttggtgct ggcctgcacc cgcgctgagt ttggctctag cgatgaagat acagattgag    8820
gtactgaaat gtgtgggcgt ggcttaaggg tgggaaagaa tatataaggt gggggtctta    8880
tgtagttttg tatctgtttt gcagcagccg ccgccgccat gagcaccaac tcgtttgatg    8940
gaagcattgt gagctcatat ttgacaacgc gcatgccccc atgggccggg gtgcgtcaga    9000
atgtgatggg ctccagcatt gatggtcgcc ccgtcctgcc cgcaaactct actaccttga    9060
cctacgagac cgtgtctgga acgccgttgg agactgcagc ctccgccgcc gcttcagccg    9120
ctgcagccac cgcccgcggg attgtgactg actttgcttt cctgagcccg cttgcaagca    9180
gtgcagcttc ccgttcatcc gcccgcgatg acaagttgac ggctcttttg gcacaattgg    9240
attctttgac ccgggaactt aatgtcgttt ctcagcagct gttggatctg cgccagcagg    9300
tttctgccct gaaggcttcc tcccctccca atgcggttta aacataaat aaaaaaccag    9360 actctgtttg gatttggatc aagcaagtgt cttgctgtct ttatttaggg gttttgcgcg    9420
cgcggtaggc ccgggaccag cggtctcggt cgttgagggt cctgtgtatt ttttccagga    9480
cgtggtaaag gtgactctgg atgttcgat  acatgggcat aagcccgtct ctggggtgga    9540
ggtagcacca ctgcagagct tcatgctgcg gggtggtgtt gtagatgatc cagtcgtagc    9600
```

```
aggagcgctg ggcgtggtgc ctaaaaatgt ctttcagtag caagctgatt gccaggggca   9660
ggcccttggt gtaagtgttt acaaagcggt taagctggga tgggtgcata cgtggggata   9720
tgagatgcat cttggactgt attttaggt tggctatgtt cccagccata tccctccggg    9780
gattcatgtt gtgcagaacc accagcacag tgtatccggt gcacttggga aatttgtcat   9840
gtagcttaga aggaaatgcg tggaagaact tggagacgcc cttgtgacct ccaagatttt   9900
ccatgcattc gtccataatg atggcaatgg gcccacgggc ggcggcctgg gcgaagatat   9960
ttctgggatc actaacgtca tagttgtgtt ccaggatgag atcgtcatag gccatttta   10020 caaagcgcgg gcggagggtg ccagactgcg gtataatggt tccatccggc caggggcgt    10080 agttaccctc acagatttgc atttcccacg ctttgagttc agatgggggg atcatgtcta   10140 cctgcgggc gatgaagaaa acggtttccg gggtagggga gatcagctgg gaagaaagca   10200
ggttcctgag cagctgcgac ttaccgcagc cggtgggccc gtaaatcaca cctattaccg   10260
ggtgcaactg gtagttaaga gagctgcagc tgccgtcatc cctgagcagg ggggccactt   10320
cgttaagcat gtccctgact cgcatgtttt ccctgaccaa atccgccaga aggcgctcgc   10380
cgcccagcga tagcagttct tgcaaggaag caaagttttt caacggtttg agaccgtccg   10440
ccgtaggcat gcttttgagc gtttgaccaa gcagttccag gcggtcccac agctcggtca   10500
cctgctctac ggcatctcga tccagcatat ctcctcgttt cgcgggttgg ggcggctttc   10560
gctgtacggc agtagtcggt gctcgtccag acgggccagg gtcatgtctt tccacgggcg   10620
cagggtcctc gtcagcgtag tctgggtcac ggtgaagggg tgcgctccgg gctgcgcgct   10680 ggccaggtg cgcttgaggc tggtcctgct ggtgctgaag cgctgccggt cttcgccctg    10740
cgcgtcggcc aggtagcatt tgaccatggt gtcatagtcc agcccctccg cggcgtggcc   10800
cttggcgcgc agcttgccct tggaggaggc gccgcacgag gggcagtgca gactttgag    10860 ggcgtagagc ttgggcgcga gaaataccga ttccggggag taggcatccg cgccgcaggc   10920
cccgcagacg gtctcgcatt ccacgagcca ggtgagctct ggccgttcgg ggtcaaaaac   10980
caggttcccc ccatgctttt tgatgcgttt cttacctctg gtttccatga gccggtgtcc   11040
acgctcggtg acgaaaaggc tgtccgtgtc cccgtataca gacttgagag gcctgtcctc   11100
gaccgatgcc cttgagagcc ttcaacccag tcagctcctt ccggtgggcg ggggcatga    11160 ctatcgtcgc cgcacttatg actgtcttct ttatcatgca actcgtagga caggtgccgg   11220
cagcgctctg ggtcattttc ggcgaggacc gctttcgctg gagcgcgacg atgatcggcc   11280
tgtcgcttgc ggtattcgga atcttgcacg ccctcgctca agccttcgtc actggtcccg   11340
ccaccaaacg tttcggcgag aagcaggcca ttatcgccgg catggcggcc gacgcgctgg   11400
gctacgtctt gctggcgttc gcgacgcgag gctggatggc cttccccatt atgattcttc   11460
tcgcttccgg cggcatcggg atgcccgcgt tgcaggccat gctgtccagg caggtagatg   11520
acgaccatca gggacagctt caaggccagc aaaaggccag gaaccgtaaa aaggccgcgt   11580
tgctggcgtt tttccatagg ctccgccccc ctgacgagca tcacaaaaat cgacgctcaa   11640
gtcagaggtg gcgaaacccg acaggactat aaagatacca ggcgtttccc cctggaagct   11700
ccctcgtgcg ctctcctgtt ccgacccctg cgcttaccgg atacctgtcc gcctttctcc   11760
cttcgggaag cgtggcgctt tctcatagct cacgctgtag gtatctcagt tcggtgtagg   11820
tcgttcgctc caagctgggc tgtgtgcacg aaccccccgt tcagcccgac cgctgcgcct   11880
tatccggtaa ctatcgtctt gagtccaacc cggtaagaca cgacttatcg ccactggcag   11940
cagccactgg taacaggatt agcagagcga ggtatgtagg cggtgctaca gagttcttga   12000
```

```
agtggtggcc taactacggc tacactagaa ggacagtatt tggtatctgc gctctgctga   12060
agccagttac cttcggaaaa agagttggta gctcttgatc cggcaaacaa accaccgctg   12120
gtagcggtgg ttttttttgtt tgcaagcagc agattacgcg cagaaaaaaa ggatctcaag   12180
aagatccttt gatcttttct acggggtctg acgctcagtg gaacgaaaac tcacgttaag   12240
ggattttggt catgagatta tcaaaaagga tcttcaccta gatccttta aattaaaaat   12300 gaagttttaa atcaatctaa agtatatatg agtaaacttg gtctgacagt taccaatgct   12360
taatcagtga ggcacctatc tcagcgatct gtctatttcg ttcatccata gttgcctgac   12420
tccccgtcgt gtagataact acgatacggg agggcttacc atctggcccc agtgctgcaa   12480
tgataccgcg agacccacgc tcaccggctc cagatttatc agcaataaac cagccagccg   12540
gaagggccga gcgcagaagt ggtcctgcaa ctttatccgc ctccatccag tctattaatt   12600
gttgccggga agctagagta agtagttcgc cagttaatag tttgcgcaac gttgttgcca   12660
ttgctgcagg catcgtggtg tcacgctcgt cgtttggtat ggcttcattc agctccggtt   12720
cccaacgatc aaggcgagtt acatgatccc ccatgttgtg caaaaaagcg gttagctcct   12780
tcggtcctcc gatcgttgtc agaagtaagt tggccgcagt gttatcactc atggttatgg   12840
cagcactgca taattctctt actgtcatgc catccgtaag atgcttttct gtgactggtg   12900
agtactcaac caagtcattc tgagaatagt gtatgcggcg accgagttgc tcttgcccgg   12960
cgtcaacacg ggataatacc gcgccacata gcagaacttt aaaagtgctc atcattggaa   13020
aacgttcttc ggggcgaaaa ctctcaagga tcttaccgct gttgagatcc agttcgatgt   13080
aacccactcg tgcacccaac tgatcttcag catcttttac tttcaccagc gtttctgggt   13140
gagcaaaaac aggaaggcaa aatgccgcaa aaaagggaat aagggcgaca cggaaatgtt   13200
gaatactcat actcttcctt tttcaatatt attgaagcat ttatcagggt tattgtctca   13260
tgagcggata catatttgaa tgtatttaga aaaa                               13294
```

<210> SEQ ID NO 2
<211> LENGTH: 13333
<212> TYPE: DNA
<213> ORGANISM: Artificial Sequence
<220> FEATURE:
<223> OTHER INFORMATION: Synthetic hIL-12 and hIL-21

<400> SEQUENCE: 2

```
taaacaaata ggggttccgc gcacatttcc ccgaaaagtg ccacctgacg tctaagaaac     60
cattattatc atgacattaa cctataaaaa taggcgtatc acgaggccct ttcgtcttca    120
attaatcgca ccggtatcta tgtcgggtgc ggagaaagag gtaatgaaat ggcagctagc    180
atcatcaata atatacctta ttttggattg aagccaatat gataatgagg gggtggagtt    240
tgtgacgtgg cgcggggcgt gggaacgggg cgggtgacgt agtagtgtgg cggaagtgtg    300
atgttgcaag tgtggcggaa cacatgtaag cgacggatgg ggcaaaagtg acgttttttgg    360 tgtgcgccgg tgtacacagg aagtgacaat tttcgcgcgg ttttaggcgg atgttgtagt    420
aaatttgggc gtaaccgagt aagatttggc cattttcgcg ggaaaactga ataagaggaa    480
gtgaaatctg ataattttg tgttactcat agcgcgtaat atttgtctag ggagatccgg    540
taccgatatc ctagacaacg atgctgagct aactataacg gtcctaaggt agcgaccgcg    600
gagactaggt gtatttatct aagcgatcgc ttaattaagg ccggccgccg caataaaata    660
tctttatttt cattacatct gtgtgttggt tttttgtgtg aatccatagt actaacatac    720
```

```
gctctccatc aaaacaaaac gaaacaaaac aaactagcaa ataggctgt  ccccagtgca      780
agtccaggtg ccagaacatt tctctatcca taatgcaggg gtaccgggtg atgacggtga      840
aaacctccaa ttgcggagta ctgtcctccg agcggagtac tgtcctccga gcggagtact      900
gtcctccgag cggagtactg tcctccgagc ggagtactgt cctccgagcg gagtactgtc      960
ctccgagcgg agagtccccg ggacctaga  gggtatataa tgggtgcctt agctggtgtg     1020
tgacctcatc ttcctgtacg cccctgcagg ggcgcgccac cgtcgaaga  aggtgagtaa     1080
tcttaacatg ctcttttttt tttttttgc  taatcccttt tgtgtgctga tgttaggatg     1140
acatttacaa caaatgtttg ttcctgacag gaaaaacctt gctgggtacc ttcgttgccg     1200
gacacttctt gtcctctact ttggaaaaaa ggaattgaga gccgctagcc caccatgggt     1260
caccagcagt tggtcatctc ttggtttcc  ctggttttc  tggcatctcc cctcgtggcc     1320
atatgggaac tgaagaaaga tgtttatgtc gtagaattgg attggtatcc ggatgcccct     1380
ggagaaatgg tggtcctcac ctgtgacacc cctgaagaag atggtatcac ctggaccttg     1440
gaccagagca gtgaggtctt aggctctggc aaaaccctga ccatccaagt caaagagttt     1500
ggagatgctg ccagtacac  ctgtcacaaa ggaggcgagg ttctaagcca ttcgctcctg     1560
ctgcttcaca aaaaggaaga tggaatttgg tccactgata ttttaaagga ccagaaagaa     1620
cccaaaaata gacctttct  aagatgcgag gccaagaatt attctggacg tttcacctgc     1680
tggtggctga cgacaatcag tactgatttg acattcagtg tcaaaagcag cagaggctct     1740
tctgaccccc aagggtgac  gtgcggagct gctacactct ctgcagagag agtcagaggg     1800
gacaacaagg agtatgagta ctcagtggag tgccaggagg acagtgcctg cccagctgct     1860
gaggagagtc tgcccattga ggtcatggtg gatgccgttc acaagctcaa gtatgaaaac     1920
tacaccagca gcttcttcat cagggacatc atcaaacctg acccacccaa gaacttgcag     1980
ctgaagccat taagaattc  tcggcaggtg gaggtcagct gggagtaccc tgacacctgg     2040
agtactccac attcctactt ctcccctgaca ttctgcgttc aggtccaggg caagagcaag     2100
agagaaaaga aagatagagt cttcacggac aagacctcag ccacggtcat ctgccgcaaa     2160
aatgccagca ttagcgtgcg ggcccaggac cgctactata gctcatcttg gagcgaatgg     2220
gcatctgtgc cctgcagtta gatcgattgc gcaaagctcc ccctctccct cccccccccc     2280
taacgttact ggccgaagcc gcttggaata aggccggtgt gcgtttgtct atatgttatt     2340
ttccaccata ttgccgtctt ttggcaatgt gagggcccgg aaacctggcc ctgtcttctt     2400
gacgagcatt cctaggggtc tttcccctct cgccaaagga atgcaaggtc tgttgaatgt     2460
cgtgaaggaa gcagttcctc tggaagcttc ttgaagacaa acaacgtctg tagcgaccct     2520
ttgcaggcag cggaaccccc cacctggcga caggtgcctc tgcggccaaa agccacgtgt     2580
ataagataca cctgcaaagg cggcacaacc ccagtgccac gttgtgagtt ggatagttgt     2640
ggaaagagtc aaatggctct cctcaagcgt attcaacaag gggctgaagg atgcccagaa     2700
ggtaccccat tgtatgggat ctgatctggg gcctcggtgc acatgcttta catgtgttta     2760
gtcgaggtta aaaaacgtct aggccccccg aaccacgggg acgtggtttt cctttgaaaa     2820
acacgatctc ttaagtctag cgccaccatg gtccagcgc  gcagcctcct ccttgtggct     2880
accctggtcc tcctggacca cctcagtttg gccagaaacc tccccgtggc cactccagac     2940
ccaggaatgt tcccatgcct tcaccactcc caaaacctgc tgagggccgt cagcaacatg     3000
ctccagaagg ccagacaaac tctagaattt taccccttgca cttctgaaga gattgatcat     3060
gaagatatca caaaagataa aaccagcaca gtggaggcct gtttaccatt ggaattaacc     3120
```

```
aagaatgaga gttgcctaaa ttccagagag acctctttca taactaatgg gagttgcctg    3180
gcctccagaa agacctcttt tatgatggcc ctgtgcctta gtagtattta tgaagacttg    3240
aagatgtacc aggtggagtt caagaccatg aatgcaaagc ttctgatgga tcctaagagg    3300
cagatctttc tagatcaaaa catgctggca gttattgatg agctgatgca ggccctgaat    3360
ttcaacagtg agactgtgcc acaaaaatcc tcccttgaag aaccggattt ttataaaact    3420
aaaatcaagc tctgcatact tcttcatgct ttcagaattc gggcagtgac tattgataga    3480
gtgatgagct atctgaatgc ttcctaaatc gaatgcgcac tcgagtggta ttacgctcaa    3540
cttcagaatc tcactaaaag aatagatagt cttcctttaa ctgaaaattt ttccttacaa    3600
acagatatgg acgtcactag caccaccatg agaagcagcc ccggcaacat ggagagaatc    3660
gtgatctgcc tgatggtgat cttcctgggc accctggtgc ataagagcag cagccagggc    3720
caggacagac acatgatccg catgagacag ctgatcgaca tcgtggacca gctgaagaac    3780
tacgtgaacg acctggtgcc cgagttcctg cccgcccccg aggacgtgga gaccaactgc    3840
gagtggagcg ccttcagctg cttccagaag gcccagctga gtccgccaa caccggcaac    3900 aacgagagaa tcatcaacgt gagcatcaag aagctgaagc ggaagccccc cagcaccaac    3960
gccggaagaa gacagaagca cagactgacc tgtcccagct gcgacagcta cgagaagaag    4020
ccccccaagg agttcctgga gagattcaag agcctgctgc aaaagatgat ccaccagcac    4080
ctgagcagca gaacccacgg cagcgaggac agctgaatcg cctgcgcagc atgctcgcga    4140
cctaagtcgg ccgctaaagt ttacgtagcg gccgcgtcga cgatagcttg atgggtggca    4200
tccctgtgac ccctccccag tgcctctcct ggccctggaa gttgccactc cagtgcccac    4260
cagccttgtc ctaataaaat taagttgcat cattttgtct gactaggtgt ccttctataa    4320
tattatgggg tggaggggggg tggtatggag caaggggcaa gttgggaaga caacctgtag    4380
ggcctgcggg gtctattggg aaccaagctg gagtgcagtg gcacaatctt ggctcactgc    4440
aatctccgcc tcctgggttc aagcgattct cctgcctcag cctcccgagt tgtgggatt    4500 ccaggcatgc atgaccaggc tcagctaatt tttgtttttt tggtagagac ggggtttcac    4560
catattggcc aggctggtct ccaactccta atctcaggtg atctacccac cttggcctcc    4620
caaattgctg ggattacagg cgtgaaccac tgctcccttc cctgtccttc tgattttaaa    4680
ataactatac cagcaggagg acgtccagac acagcatagg ctacctggcc atgcccaacc    4740
ggtgggacat ttgagttgct tgcttggcac tgtcctctca tgcgttgggt ccactcagta    4800
gatgcctgtt gaattctgat ttaaatcggt ccgcgtacgg cgtggtaggt ccgaacgaat    4860
ccatggatta ccctgttatc cctatccgga gttaacctcg aggacttcgg aacttctaga    4920
accagaccgt tcagtttaaa cgctcttctc ccctcgagg gcctccgcgc cgggttttgg    4980
cgcctcccgc gggcgccccc ctcctcacgg cgagcgctgc cacgtcagac gaagggcgca    5040
gcgagcgtcc tgatccttcc gcccggacgc tcaggacagc ggcccgctgc tcataagact    5100
cggccttaga accccagtat cagcagaagg acattttagg acgggacttg ggtgactcta    5160
gggcactggt tttctttcca gagagcggaa caggcgagga aaagtagtcc cttctcggcg    5220
attctgcgga gggatctccg tggggcggtg aacgccgatg attatataag gacgcgccgg    5280
gtgtggcaca gctagttccg tcgcagccgg gatttgggtc gcggttcttg tttgtggatc    5340
gctgtgatcg tcacttggtg agtagcgggc tgctgggctg ggtacgtgcg ctcggggttg    5400
gcgagtgtgt tttgtgaagt ttttaggca ccttttgaaa tgtaatcatt tgggtcaata    5460
```

```
tgtaattttc agtgttagac tagtaaattg tccgctaaat tctggccgtt tttggctttt    5520
ttgttagacg gcatgcgggg gggggggggg gcaattggcc accatgggcc ccaagaagaa    5580
aaggaaggtg gccccccca ccgacgtgag cctgggcgac gagctgcacc tggacggcga     5640
ggacgtggcc atggcccacg ccgacgccct ggacgacttc gacctggaca tgctgggcga    5700
cggcgacagc cccggccccg gcttcacccc ccacgacagc gcccctacg gcgccctgga     5760
catggccgac ttcgagttcg agcagatgtt caccgacgcc ctgggcatcg acagtacgg     5820
cggccatatg gagatgcccg tggacaggat tctggaggcc gaactcgccg tggagcagaa    5880
aagcgaccag ggcgtggagg gccccggcgg aaccggcggc agcggcagca gcccaacga    5940
ccccgtgacc aacatctgcc aggccgccga caagcagctg ttcaccctgg tggagtgggc    6000
caagaggatt ccccacttca gcagcctgcc cctggacgac caggtgatcc tgctgagggc    6060
cggatggaac gagctgctga tcgccagctt cagccacagg agcatcgacg tgagggacgg    6120
catcctgctg gccaccggcc tgcacgtcca taggaacagc gcccacagcg ccggagtggg    6180
cgccatcttc gacagggtgc tgaccgagct ggtgagcaag atgagggaca tgaggatgga    6240
caagaccgag ctgggctgcc tgagggccat catcctgttc aaccccgagg tgagggcct     6300
gaaaagcgcc caggaggtgg agctgctgag ggagaaggtg tacgccgccc tggaggagta    6360
caccaggacc acccaccccg acgagcccgg cagattcgcc aagctgctgc tgaggctgcc    6420
cagcctgagg agcatcggcc tgaagtgcct ggagcacctg ttcttcttca ggctgatcgg    6480
cgacgtgccc atcgacacct tcctgatgga gatgctggag agcccagcg acagctgagc     6540
cggcaactcg ctgtagtaat tccagcgaga ggcagaggga gcgagcgggc ggcgggctag    6600
ggtggaggag cccggcgagc agagctgcgc tgcgggcgtc ctgggaaggg agatccggag    6660
cgaatagggg gcttcgcctc tggcccagcc ctcccgctga tccccagcc agcggtgcgc     6720
aaccctagcc gcatccacga aactttgccc atagcagcgg gcgggcactt tgcactggaa    6780
cttacaacac ccgagcaagg acgcgactct cccgacgcgg ggaggctatt ctgcccattt    6840
ggggacactt ccccgccgct gccaggaccc gcttctctga aaggctctcc ttgcagctgc    6900
ttagacgctg gatttttttc gggtagtgga aaaccagcag cctcccgcga ccagatctgc    6960
caccatgaag ctgctgagca gcatcgagca ggcttgcgac atctgcaggc tgaagaagct    7020
gaagtgcagc aaggagaagc caagtgcgc caagtgcctg aagaacaact gggagtgcag    7080
atacagcccc aagaccaaga ggagccccct gaccagggcc cacctgaccg aggtggagag    7140
caggctggag aggctggagc agctgttcct gctgatcttc ccagggagg acctggacat     7200
gatcctgaag atggacagcc tgcaagacat caaggccctg ctgaccggcc tgttcgtgca    7260
ggacaacgtg aacaaggacg ccgtgaccga caggctggcc agcgtggaga ccgacatgcc    7320
cctgaccctg aggcagcaca ggatcagcgc caccagcagc agcgaggaga gcagcaacaa    7380
gggccagagg cagctgaccg tgagccccga gtttcccggg atcaggcccg agtgcgtggt    7440
gccccgagacc cagtgcgcca tgaaaaggaa ggagaagaag gccagaaagg agaaggacaa    7500
gctgcccgtg agcaccacca ccgtcgatga ccacatgccc cccatcatgc agtgcgagcc    7560
ccccccccc gaggccgcca ggattcacga ggtcgtgccc aggttcctga gcacaagct     7620
gctggtgacc aacaggcaga gaacatcccc cagctgacc gccaaccagc agttcctgat    7680
cgccaggctg atctggtatc aggacggcta cgagcagccc agcgacgagg acctgaaaag    7740
gatcacccag acctggcagc aggccgacga cgagaacgag gagagcgaca cccccttcag    7800
gcagatcacc gagatgacca tcctgaccgt gcagctgatc gtggagttcg ccaagggcct    7860
```

```
gcccggattc gccaagatca gccagcccga ccagatcacc ctgctgaagg cttgcagcag   7920
cgaggtgatg atgctgaggg tggccaggag gtacgacgcc gccagcgaca gcatcctgtt   7980
cgccaacaac caggcttaca ccagggacaa ctacaggaag gctggcatgg ccgaggtgat   8040
cgaggacctc ctgcacttct gcagatgtat gtacagcatg ccctggaca acatccacta    8100
cgccctgctg accgccgtgg tgatcttcag cgacaggccc ggcctggagc agccccagct   8160
ggtggaggag atccagaggt actacctgaa caccctgagg atctacatcc tgaaccagct   8220
gagcggcagc gccaggagca gcgtgatcta cggcaagatc ctgagcatcc tgagcgagct   8280
gaggaccctg ggaatgcaga acagcaatat gtgtatcagc ctgaagctga agaacaggaa   8340
gctgccccc ttcctggagg agatttggga cgtggccgac atgagccaca cccagccccc    8400
ccccatcctg gagagcccca ccaacctgtg aatcgattag acatgataag atacattgat   8460
gagtttggac aaaccacaac tagaatgcag tgaaaaaaat gcttaatttg tgaaatttgt   8520
gatgctattg cttaatttgt aaccattata agctgcaata aacaagttaa taaaacattt   8580
gcattcattt tatgtttcag gttcaggggg agatgtggga ggttttttaa agcaagtaaa   8640
acctctacaa atgtggtatc tagagctctt ccaaatagat ctggaaggtg ctgaggtacg   8700
atgagacccg caccaggtgc agaccctgcg agtgtggcgg taaacatatt aggaaccagc   8760
ctgtgatgct ggatgtgacc gaggagctga ggcccgatca cttggtgctg gcctgcaccc   8820
gcgctgagtt tggctctagc gatgaagata cagattgagg tactgaaatg tgtgggcgtg   8880
gcttaagggt gggaaagaat atataaggtg ggggtcttat gtagttttgt atctgttttg   8940
cagcagccgc cgccgccatg agcaccaact cgtttgatgg aagcattgtg agctcatatt   9000
tgacaacgcg catgccccca tgggccgggg tgcgtcagaa tgtgatgggc tccagcattg   9060
atggtcgccc cgtcctgccc gcaaactcta ctaccttgac ctacgagacc gtgtctggaa   9120
cgccgttgga gactgcagcc tccgccgccg cttcagccgc tgcagccacc gcccgcggga   9180
ttgtgactga ctttgctttc ctgagcccgc ttgcaagcag tgcagcttcc cgttcatccg   9240
cccgcgatga caagttgacg gctctttttgg cacaattgga ttctttgacc cgggaactta   9300
atgtcgtttc tcagcagctg ttggatctgc gccagcaggt ttctgccctg aaggcttcct   9360
cccctcccaa tgcggtttaa acataaata aaaaaccaga ctctgtttgg atttggatca    9420
agcaagtgtc ttgctgtctt tatttagggg ttttgcgcgc gcggtaggcc cgggaccagc   9480
ggtctcggtc gttgagggtc ctgtgtattt tttccaggac gtggtaaagg tgactctgga   9540
tgttcagata catgggcata agcccgtctc tggggtggag gtagcaccac tgcagagctt   9600
catgctgcgg ggtggtgttg tagatgatcc agtcgtagca ggagcgctgg gcgtggtgcc   9660
taaaaatgtc tttcagtagc aagctgattg ccaggggcag gccttggtg taagtgttta    9720
caaagcggtt aagctgggat gggtgcatac gtggggatat gagatgcatc ttggactgta   9780
ttttttaggtt ggctatgttc ccagccatat ccctccgggg attcatgttg tgcagaacca   9840
ccagcacagt gtatccggtg cacttgggaa atttgtcatg tagcttagaa ggaaatgcgt   9900
ggaagaactt ggagacgccc ttgtgacctc caagatttc catgcattcg tccataatga    9960
tggcaatggg cccacgggcg gcggcctggg cgaagatatt tctgggatca ctaacgtcat  10020
agttgtgttc caggatgaga tcgtcatagg ccattttttac aaagcgcggg cggagggtgc  10080
cagactgcgg tataatggtt ccatccggcc caggggcgta gttaccctca cagatttgca  10140
tttcccacgc tttgagttca gatgggggga tcatgtctac ctgcggggcg atgaagaaaa  10200
```

```
cggtttccgg ggtaggggag atcagctggg aagaaagcag gttcctgagc agctgcgact    10260
taccgcagcc ggtgggcccg taaatcacac ctattaccgg gtgcaactgg tagttaagag    10320
agctgcagct gccgtcatcc ctgagcaggg gggccacttc gttaagcatg tccctgactc    10380
gcatgttttc cctgaccaaa tccgccagaa ggcgctcgcc gcccagcgat agcagttctt    10440
gcaaggaagc aaagtttttc aacggtttga gaccgtccgc cgtaggcatg cttttgagcg    10500
tttgaccaag cagttccagg cggtcccaca gctcggtcac ctgctctacg gcatctcgat    10560
ccagcatatc tcctcgtttc gcgggttggg gcggctttcg ctgtacggca gtagtcggtg    10620
ctcgtccaga cgggccaggg tcatgtcttt ccacgggcgc agggtcctcg tcagcgtagt    10680
ctgggtcacg gtgaaggggt gcgctccggg ctgcgcgctg gccagggtgc gcttgaggct    10740
ggtcctgctg gtgctgaagc gctgccggtc ttcgccctgc gcgtcggcca ggtagcattt    10800
gaccatggtg tcatagtcca gccctccgc ggcgtggccc ttggcgcgca gcttgccctt    10860
ggaggaggcg ccgcacgagg ggcagtgcag acttttgagg gcgtagagct tgggcgcgag    10920
aaataccgat tccggggagt aggcatccgc gccgcaggcc ccgcagacgg tctcgcattc    10980
cacgagccag gtgagctctg gccgttcggg gtcaaaaacc aggtttcccc catgcttttt    11040
gatgcgtttc ttacctctgg tttcatgag ccggtgtcca cgctcggtga cgaaaaggct    11100
gtccgtgtcc ccgtatacag acttgagagg cctgtcctcg accgatgccc ttgagagcct    11160
tcaacccagt cagctccttc cggtgggcgc ggggcatgac tatcgtcgcc gcacttatga    11220
ctgtcttctt tatcatgcaa ctcgtaggac aggtgccggc agcgctctgg gtcattttcg    11280
gcgaggaccg ctttcgctgg agcgcgacga tgatcggcct gtcgcttgcg gtattcggaa    11340
tcttgcacgc cctcgctcaa gccttcgtca ctggtcccgc caccaaacgt ttcggcgaga    11400
agcaggccat tatcgccggc atggcggccg acgcgctggg ctacgtcttg ctggcgttcg    11460
cgacgcgagg ctggatggcc ttccccatta tgattcttct cgcttccggc ggcatcggga    11520
tgcccgcgtt gcaggccatg ctgtccaggc aggtagatga cgaccatcag ggacagcttc    11580
aaggccagca aaaggccagg aaccgtaaaa aggccgcgtt gctggcgttt ttccataggc    11640
tccgcccccc tgacgagcat cacaaaaatc gacgctcaag tcagaggtgg cgaaacccga    11700
caggactata aagataccag gcgtttcccc ctggaagctc cctcgtgcgc tctcctgttc    11760
cgaccctgcc gcttaccgga tacctgtccg cctttctccc ttcgggaagc gtggcgcttt    11820
ctcatagctc acgctgtagg tatctcagtt cggtgtaggt cgttcgctcc aagctgggct    11880
gtgtgcacga accccccgtt cagcccgacc gctgcgcctt atccggtaac tatcgtcttg    11940
agtccaaccc ggtaagacac gacttatcgc cactggcagc agccactggt aacaggatta    12000
gcagagcgag gtatgtaggc ggtgctacag agttcttgaa gtggtggcct aactacggct    12060
acactagaag gacagtattt ggtatctgcg ctctgctgaa gccagttacc ttcggaaaaa    12120
gagttggtag ctcttgatcc ggcaaacaaa ccaccgctgg tagcggtggt ttttttgttt    12180
gcaagcagca gattacgcgc agaaaaaaag gatctcaaga agatcctttg atcttttcta    12240
cggggtctga cgctcagtgg aacgaaaact cacgttaagg gattttggtc atgagattat    12300
caaaaaggat cttcacctag atccttttaa attaaaaatg aagttttaaa tcaatctaaa    12360
gtatatatga gtaaacttgg tctgacagtt accaatgctt aatcagtgag gcacctatct    12420
cagcgatctg tctatttcgt tcatccatag ttgcctgact ccccgtcgtg tagataacta    12480
cgatacggga gggcttacca tctggcccca gtgctgcaat gataccgcga gacccacgct    12540
caccggctcc agatttatca gcaataaacc agccagccgg aagggccgag cgcagaagtg    12600
```

-continued

```
gtcctgcaac tttatccgcc tccatccagt ctattaattg ttgccgggaa gctagagtaa    12660
gtagttcgcc agttaatagt ttgcgcaacg ttgttgccat tgctgcaggc atcgtggtgt    12720
cacgctcgtc gtttggtatg gcttcattca gctccggttc ccaacgatca aggcgagtta    12780
catgatcccc catgttgtgc aaaaaagcgg ttagctcctt cggtcctccg atcgttgtca    12840
gaagtaagtt ggccgcagtg ttatcactca tggttatggc agcactgcat aattctctta    12900
ctgtcatgcc atccgtaaga tgcttttctg tgactggtga gtactcaacc aagtcattct    12960
gagaatagtg tatgcggcga ccgagttgct cttgcccggc gtcaacacgg ataataccg     13020 cgccacatag cagaacttta aaagtgctca tcattggaaa acgttcttcg gggcgaaaac    13080
tctcaaggat cttaccgctg ttgagatcca gttcgatgta acccactcgt gcacccaact    13140
gatcttcagc atcttttact ttcaccagcg tttctgggtg agcaaaaaca ggaaggcaaa    13200
atgccgcaaa aaagggaata agggcgacac ggaaatgttg aatactcata ctcttccttt    13260
ttcaatatta ttgaagcatt tatcagggtt attgtctcat gagcggatac atatttgaat    13320
gtatttagaa aaa                                                        13333
```

<210> SEQ ID NO 3
<211> LENGTH: 11553
<212> TYPE: DNA
<213> ORGANISM: Artificial Sequence
<220> FEATURE:
<223> OTHER INFORMATION: Synthetic mIL-21 and mIL-15

<400> SEQUENCE: 3

```
taaacaaata ggggttccgc gcacatttcc ccgaaaagtg ccacctgacg tctaagaaac      60
cattattatc atgacattaa cctataaaaa taggcgtatc acgaggccct ttcgtcttca     120
attaatcgca ccggtatcta tgtcgggtgc ggagaaagag gtaatgaaat ggcagctagc     180
atcatcaata atataccttat ttttggattg aagccaatat gataatgagg gggtggagtt     240
tgtgacgtgg cgcggggcgt gggaacgggg cgggtgacgt agtagtgtgg cggaagtgtg     300
atgttgcaag tgtggcggaa cacatgtaag cgacggatgt ggcaaaagtg acgttttttgg     360 tgtgcgccgg tgtacacagg aagtgacaat tttcgcgcgg ttttaggcgg atgttgtagt     420
aaatttgggc gtaaccgagt aagatttggc cattttcgcg ggaaaactga ataagaggaa     480
gtgaaatctg ataaattttg tgttactcat agcgcgtaat atttgtctag ggagatccgg     540
taccgatatc ctagacaacg atgctgagct aactataacg gtcctaaggt agcgaccgcg     600
gagactaggt gtatttatct aagcgatcgc ttaattaagg ccggccgccg caataaaata     660
tctttatttt cattacatct gtgtgttggt tttttgtgtg aatcgatagt actaacatac     720
gctctccatc aaaacaaaac gaaacaaaac aaactagcaa ataggctgt ccccagtgca      780 agtgcaggtg ccagaacatt tctctatcga taatgcaggt cggagtactg tcctccgagc     840
ggagtactgt cctccgagcg gagtactgtc ctccgagcgg agtactgtcc tccgagcgga     900
gtactgtcct ccgagcggag tactgtcctc cgagcggaga ctcttcgaag gaagagggggc    960 ggggtcgatc gaccccgccc ctcttccttc gaaggaagag gggcgggggt gaagacctag     1020
agggtatata atgggtgcct tagctggtgt gtgagctcat cttcctgtag atcacgcgtc     1080
gaagaaggtg agtaatctta acatgctctt tttttttttt tttgctaatc ccttttgtgt     1140
gctgatgtta ggatgacatt tacaacaaat gtttgttcct gacaggaaaa accttgctgg    1200
gtaccttcgt tgccggacac ttcttgtcct ctactttgga aaaaggaat tgagagccgc     1260
```

```
tagcgccacc atggagagga ccctggtgtg cctggtggtg atcttcctgg gcaccgtggc      1320
ccacaagagc agcccccagg gacccgacag gctgctgatc cggctgagac acctgatcga      1380
catcgtggag cagctgaaga tttacgagaa cgacctggac cccgagctgc tgtccgcccc      1440
ccaggacgtg aagggccact gcgagcacgc cgccttcgcc tgcttccaga aggccaagct      1500
gaagcccagc aaccccggca caacaagac cttcatcatc gacctggtgg cccagctgag       1560
aaggaggctg cccgccagga ggggcggcaa gaagcagaag cacatcgcca agtgccccag      1620
ctgcgacagc tacgagaagc ggaccccaa ggagttcctg gagaggctga gtggctgct        1680 gcaaaagatg atccaccagc acctgagctg agttgggcga gctcgaattc attgatcccc      1740
cgggctgcag gaattcgata tcaagctcgg gatccgaatt ccgcccccc cccccccccc       1800 cccctaacgt tactggccga agccgcttgg aataaggccg gtgtgcgttt gtctatatgt      1860 tatttccac catattgccg tcttttggca atgtgagggc ccggaaacct ggccctgtct       1920
tcttgacgag cattcctagg ggtctttccc ctctcgccaa aggaatgcaa ggtctgttga      1980
atgtcgtgaa ggaagcagtt cctctggaag cttcttgaag acaaacaacg tctgtagcga      2040 cccctttgcag gcagcggaac ccccacctg gcgacaggtg cctctgcggc caaaagccac      2100
gtgtataaga tacacctgca aaggcggcac aaccccagtg ccacgttgtg agttggatag      2160
ttgtggaaag agtcaaatgg ctctcctcaa gcgtattcaa caaggggctg aaggatgccc      2220
agaaggtacc ccattgtatg ggatctgatc tggggcctcg gtgcacatgc tttacatgtg      2280
tttagtcgag gttaaaaaaa cgtctaggcc ccccgaacca cggggacgtg gttttccttt      2340
gaaaaacacg atgataatat ggccacaacc atgaagatcc tgaagcccta catgaggaac      2400
accagcatca gctgttacct gtgcttcctg ctgaacagcc acttcctgac cgaggccgga      2460
atccacgtct tcatcctggg ctgcgtgagc gtgggcctgc caagaccga ggccaactgg       2520 atcgacgtga ggtacgacct ggagaagatc gagagcctga tccagagcat ccacatcgac      2580
accaccctgt acaccgacag cgacttccac cccagctgca aggtgaccgc catgaactgc      2640
ttcctgctgg agctgcaagt gatcctgcac gagtacagca acatgaccct gaacgagacc      2700
gtgaggaacg tgctgtacct ggctaacagc accctgagca gcaacaagaa cgtggccgag      2760
agcggctgca aggagtgtga ggagctggag gagaagacct tcaccgagtt cctccagagc      2820
ttcatcagga tcgtgcagat gttcatcaac accagctgaa tcgattgcgc aaagctttcg      2880
cgataggcga gaccaatggg tgtgtacgta gcggccgctc gagaacttgt ttattgcagc      2940
ttataatggt tacaaataaa gcaatagcat cacaaatttc acaaataaag cattttttc       3000 actgcattct agttgtggtt tgtccaaact catcaatgta tcttatcatg tctcgtacgg      3060
cgtggtaggt ccgaacgaat ccatggatta ccctgttatc cctatccgga gttaacctcg      3120
aggacttcgg aacttctaga accagaccgt tcagtttaaa cgctcttctc cccctcgagg      3180
gcctccgcgc cgggttttgg cgcctcccgc gggcgccccc ctcctcacgg cgagcgctgc      3240
cacgtcagac gaagggcgca gcgagcgtcc tgatccttcc gcccggacgc tcaggacagc      3300
ggcccgctgc tcataagact cggccttaga accccagtat cagcagaagg acattttagg      3360
acgggacttg ggtgactcta gggcactggt tttctttcca gagagcggaa caggcgagga      3420
aaagtagtcc cttctcggcg attctgcgga gggatctccg tggggcggtg aacgccgatg      3480
attatataag gacgcgccgg gtgtggcaca gctagttccg tcgcagccgg gatttgggtc      3540
gcggttcttg tttgtggatc gctgtgatcg tcacttggtg agtagcgggc tgctgggct       3600 ggtacgtgcg ctcggggttg gcgagtgtgt tttgtgaagt ttttttaggca ccttttgaaa     3660
```

```
tgtaatcatt tgggtcaata tgtaattttc agtgttagac tagtaaattg tccgctaaat    3720
tctggccgtt tttggcttttt ttgttagacg gcatgcgggg ggggggggggg gcaattggcc   3780 accatgggcc ccaagaagaa aaggaaggtg gcccccccca ccgacgtgag cctgggcgac    3840
gagctgcacc tggacggcga ggacgtggcc atggcccacg ccgacgccct ggacgacttc    3900
gacctggaca tgctgggcga cggcgacagc cccggccccg gcttcacccc ccacgacagc    3960
gccccctacg gcgccctgga catggccgac ttcgagttcg agcagatgtt caccgacgcc    4020
ctgggcatcg acgagtacgg cggccatatg gagatgcccg tggacaggat tctggaggcc    4080
gaactcgccg tggagcagaa aagcgaccag ggcgtggagg gccccggcgg aaccggcggc    4140
agcggcagca gccccaacga ccccgtgacc aacatctgcc aggccgccga caagcagctg    4200
ttcaccctgg tggagtgggc caagaggatt ccccacttca gcagcctgcc cctggacgac    4260
caggtgatcc tgctgagggc cggatggaac gagctgctga tcgccagctt cagccacagg    4320
agcatcgacg tgagggacgg catcctgctg gccaccggcc tgcacgtcca taggaacagc    4380
gcccacagcg ccggagtggg cgccatcttc gacagggtgc tgaccgagct ggtgagcaag    4440
atgagggaca tgaggatgga caagaccgag ctgggctgcc tgagggccat catcctgttc    4500
aaccccgagg tgagggggcct gaaaagcgcc caggaggtgg agctgctgag ggagaaggtg    4560
tacgccgccc tggaggagta caccaggacc acccaccccg acgagcccgg cagattcgcc    4620
aagctgctgc tgaggctgcc cagcctgagg agcatcggcc tgaagtgcct ggagcacctg    4680
ttcttcttca ggctgatcgg cgacgtgccc atcgacacct tcctgatgga gatgctggag    4740
agccccagcg acagctgagc cggcaactcg ctgtagtaat tccagcgaga ggcagaggga    4800
gcgagcgggc ggcgggctag ggtggaggag cccggcgagc agagctgcgc tgcgggcgtc    4860
ctgggaaggg agatccggag cgaataggggg gcttcgcctc tggcccagcc ctcccgctga    4920 tccccccagcc agcggtgcgc aaccctagcc gcatccacga aactttgccc atagcagcgg    4980
gcgggcactt tgcactggaa cttacaacac ccgagcaagg acgcgactct cccgacgcgg    5040
ggaggctatt ctgcccattt ggggacactt ccccgccgct gccaggaccc gcttctctga    5100
aaggctctcc ttgcagctgc ttagacgctg gattttttttc gggtagtgga aaaccagcag    5160
cctcccgcga ccagatctgc caccatgaag ctgctgagca gcatcgagca ggcttgcgac    5220
atctgcaggc tgaagaagct gaagtgcagc aaggagaagc caagtgcgc caagtgcctg    5280 aagaacaact gggagtgcag atacagcccc aagaccaaga ggagcccccct gaccagggcc    5340 cacctgaccg aggtggagag caggctggag aggctggagc agctgttcct gctgatcttc    5400
cccagggagg acctggacat gatcctgaag atggacagcc tgcaagacat caaggccctg    5460
ctgaccggcc tgttcgtgca ggacaacgtg aacaaggacg ccgtgaccga caggctggcc    5520
agcgtggaga ccgacatgcc cctgaccctg aggcagcaca ggatcagcgc caccagcagc    5580
agcgaggaga gcagcaacaa gggccagagg cagctgaccg tgagccccga gtttcccggg    5640
atcaggcccg agtgcgtggt gcccgagacc cagtgcgcca tgaaaaggaa ggagaagaag    5700
gcccagaagg agaaggacaa gctgcccgtg agcaccacca ccgtcgatga ccacatgccc    5760
cccatcatgc agtgcgagcc cccccccccc gaggccgcca ggattcacga ggtcgtgccc    5820
aggttcctga gcgacaagct gctggtgacc aacaggcaga gaacatccc ccagctgacc    5880 gccaaccagc agttcctgat cgccaggctg atctggtatc aggacggcta cgagcagccc    5940
agcgacgagg acctgaaaag gatcacccag acctggcagc aggccgacga cgagaacgag    6000
```

```
gagagcgaca cccccttcag gcagatcacc gagatgacca tcctgaccgt gcagctgatc    6060
gtggagttcg ccaagggcct gcccggattc gccaagatca gccagcccga ccagatcacc    6120
ctgctgaagg cttgcagcag cgaggtgatg atgctgaggg tggccaggag gtacgacgcc    6180
gccagcgaca gcatcctgtt cgccaacaac caggcttaca ccagggacaa ctacaggaag    6240
gctggcatgg ccgaggtgat cgaggacctc ctgcacttct gcagatgtat gtacagcatg    6300
gccctggaca catccacta cgccctgctg accgccgtgg tgatcttcag cgacaggccc    6360
ggcctggagc agccccagct ggtggaggag atccagaggt actacctgaa caccctgagg    6420
atctacatcc tgaaccagct gagcggcagc gccaggagca gcgtgatcta cggcaagatc    6480
ctgagcatcc tgagcgagct gaggaccctg ggaatgcaga acagcaatat gtgtatcagc    6540
ctgaagctga agaacaggaa gctgccccc ttcctggagg agatttggga cgtggccgac    6600
atgagccaca cccagccccc ccccatcctg gagagcccca ccaacctgtg aatcgattag    6660
acatgataag atacattgat gagtttggac aaaccacaac tagaatgcag tgaaaaaaat    6720
gcttaatttg tgaatttgt gatgctattg cttaatttgt aaccattata agctgcaata    6780
aacaagttaa taaacatttt gcattcattt tatgtttcag gttcaggggg agatgtggga    6840
ggtttttttaa agcaagtaaa acctctacaa atgtggtatc tagagctctt ccaaatagat    6900
ctggaaggtg ctgaggtacg atgagacccg caccaggtgc agaccctgcg agtgtggcgg    6960
taaacatatt aggaaccagc ctgtgatgct ggatgtgacc gaggagctga ggcccgatca    7020
cttggtgctg gcctgcaccc gcgctgagtt tggctctagc gatgaagata cagattgagg    7080
tactgaaatg tgtgggcgtg gcttaagggt gggaaagaat atataaggtg ggggtcttat    7140
gtagttttgt atctgttttg cagcagccgc cgccgccatg agcaccaact cgtttgatgg    7200
aagcattgtg agctcatatt tgacaacgcg catgccccca tgggccgggg tgcgtcagaa    7260
tgtgatgggc tccagcattg atggtcgccc cgtcctgccc gcaaactcta ctaccttgac    7320
ctacgagacc gtgtctggaa cgccgttgga gactgcagcc tccgccgccg cttcagccgc    7380
tgcagccacc gcccgcggga ttgtgactga ctttgctttc ctgagcccgc ttgcaagcag    7440
tgcagcttcc cgttcatccg cccgcgatga caagttgacg gctcttttgg cacaattgga    7500
ttctttgacc cgggaactta atgtcgtttc tcagcagctg ttggatctgc gccagcaggt    7560
ttctgccctg aaggcttcct cccctcccaa tgcggtttaa aacataaata aaaaaccaga    7620
ctctgtttgg atttggatca agcaagtgtc ttgctgtctt tatttagggg ttttgcgcgc    7680
gcggtaggcc cgggaccagc ggtctcggtc gttgagggtc ctgtgtattt tttccaggac    7740
gtggtaaagg tgactctgga tgttcagata catgggcata agcccgtctc tggggtggag    7800
gtagcaccac tgcagagctt catgctgcgg ggtggtgttg tagatgatcc agtcgtagca    7860
ggagcgctgg gcgtggtgcc taaaaatgtc tttcagtagc aagctgattg ccaggggcag    7920
gcccttggtg taagtgttta caaagcggtt aagctgggat gggtgcatac gtgggatat    7980
gagatgcatc ttggactgta ttttaggtt ggctatgttc ccagccatat ccctccgggg    8040
attcatgttg tgcagaacca ccagcacagt gtatccggtg cacttgggaa atttgtcatg    8100
tagcttagaa ggaaatgcgt ggaagaactt ggagacgccc ttgtgacctc caagattttc    8160
catgcattcg tccataatga tggcaatggg cccacgggcg gcggcctggg cgaagatatt    8220
tctgggatca ctaacgtcat agttgtgttc caggatgaga tcgtcatagg ccatttttac    8280
aaagcgcggg cggagggtgc cagactgcgg tataatggtt ccatccggcc caggggcgta    8340
gttaccctca cagatttgca tttcccacgc tttgagttca gatggggga tcatgtctac    8400
```

```
ctgcggggcg atgaagaaaa cggtttccgg ggtaggggag atcagctggg aagaaagcag   8460
gttcctgagc agctgcgact taccgcagcc ggtgggcccg taaatcacac ctattaccgg   8520
gtgcaactgg tagttaagag agctgcagct gccgtcatcc ctgagcaggg gggccacttc   8580
gttaagcatg tccctgactc gcatgttttc cctgaccaaa tccgccagaa ggcgctcgcc   8640
gcccagcgat agcagttctt gcaaggaagc aaagtttttc aacggtttga ccgtccgc    8700 cgtaggcatg cttttgagcg tttgaccaag cagttccagg cggtcccaca gctcggtcac   8760
ctgctctacg gcatctcgat ccagcatatc tcctcgtttc gcgggttggg gcggctttcg   8820
ctgtacggca gtagtcggtg ctcgtccaga cgggccaggg tcatgtcttt ccacgggcgc   8880
agggtcctcg tcagcgtagt ctgggtcacg gtgaaggggt gcgctccggg ctgcgcgctg   8940
gccagggtgc gcttgaggct ggtcctgctg gtgctgaagc gctgccggtc ttcgccctgc   9000
gcgtcggcca ggtagcattt gaccatggtg tcatagtcca gcccctccgc ggcgtggccc   9060
ttggcgcgca gcttgccctt ggaggaggcg ccgcacgagg ggcagtgcag acttttgagg   9120
gcgtagagct tgggcgcgag aaataccgat tccggggagt aggcatccgc gccgcaggcc   9180
ccgcagacgt tctcgcattc cacgagccag gtgagctctg gccgttcggg gtcaaaaacc   9240
aggtttcccc catgcttttt gatgcgtttc ttacctctgg tttccatgag ccggtgtcca   9300
cgctcggtga cgaaaaggct gtccgtgtcc ccgtatacag acttgagagg cctgtcctcg   9360
accgatgccc ttgagagcct tcaacccagt cagctccttc cggtgggcgc ggggcatgac   9420
tatcgtcgcc gcacttatga ctgtcttctt tatcatgcaa ctcgtaggac aggtgccggc   9480
agcgctctgg gtcattttcg gcgaggaccg cttctgctgg agcgcgacga tgatcggcct   9540
gtcgcttgcg gtattcggaa tcttgcacgc cctcgctcaa gccttcgtca ctggtcccgc   9600
caccaaacgt ttcggcgaga agcaggccat tatcgccggc atggcggccg acgcgctggg   9660
ctacgtcttg ctggcgttcg cgacgcgagg ctggatggcc ttccccatta tgattcttct   9720
cgcttccggc ggcatcggga tgcccgcgtt gcaggccatg ctgtccaggc aggtagatga   9780
cgaccatcag ggacagcttc aaggccagca aaaggccagg aaccgtaaaa aggccgcgtt   9840
gctggcgttt ttccataggc tccgcccccc tgacgagcat cacaaaaatc gacgctcaag   9900
tcagaggtgg cgaaacccga caggactata aagataccag gcgtttcccc ctggaagctc   9960
cctcgtgcgc tctcctgttc cgaccctgcc gcttaccgga tacctgtccg cctttctccc   10020
ttcgggaagc gtggcgcttt ctcatagctc acgctgtagg tatctcagtt cggtgtaggt   10080
cgttcgctcc aagctgggct gtgtgcacga accccccgtt cagcccgacc gctgcgcctt   10140
atccggtaac tatcgtcttg agtccaaccc ggtaagacac gacttatcgc cactggcagc   10200
agccactggt aacaggatta gcagagcgag gtatgtaggc ggtgctacag agttcttgaa   10260
gtggtggcct aactacggct acactagaag gacagtattt ggtatctgcg ctctgctgaa   10320
gccagttacc ttcggaaaaa gagttggtag ctcttgatcc ggcaaacaaa ccaccgctgg   10380
tagcggtggt ttttttgttt gcaagcagca gattacgcgc agaaaaaaag gatctcaaga   10440
agatcctttg atcttttcta cggggtctga cgctcagtgg aacgaaaact cacgttaagg   10500
gattttggtc atgagattat caaaaaggat cttcacctag atccttttaa attaaaaatg   10560
aagttttaaa tcaatctaaa gtatatatga gtaaacttgg tctgacagtt accaatgctt   10620
aatcagtgag gcacctatct cagcgatctg tctatttcgt tcatccatag ttgcctgact   10680
ccccgtcgtg tagataacta cgatacggga gggcttacca tctggcccca gtgctgcaat   10740
```

| | |
|---|---|
| gataccgcga gacccacgct caccggctcc agatttatca gcaataaacc agccagccgg | 10800 |
| aagggccgag cgcagaagtg gtcctgcaac tttatccgcc tccatccagt ctattaattg | 10860 |
| ttgccgggaa gctagagtaa gtagttcgcc agttaatagt ttgcgcaacg ttgttgccat | 10920 |
| tgctgcaggc atcgtggtgt cacgctcgtc gtttggtatg gcttcattca gctccggttc | 10980 |
| ccaacgatca aggcgagtta catgatcccc catgttgtgc aaaaaagcgg ttagctcctt | 11040 |
| cggtcctccg atcgttgtca gaagtaagtt ggccgcagtg ttatcactca tggttatggc | 11100 |
| agcactgcat aattctctta ctgtcatgcc atccgtaaga tgcttttctg tgactggtga | 11160 |
| gtactcaacc aagtcattct gagaatagtg tatgcggcga ccgagttgct cttgcccggc | 11220 |
| gtcaacacgg ataataccg cgccacatag cagaacttta aaagtgctca tcattggaaa | 11280 |
| acgttcttcg gggcgaaaac tctcaaggat cttaccgctg ttgagatcca gttcgatgta | 11340 |
| acccactcgt gcacccaact gatcttcagc atcttttact ttcaccagcg tttctgggtg | 11400 |
| agcaaaaaca ggaaggcaaa atgccgcaaa aagggaata agggcgacac ggaaatgttg | 11460 |
| aatactcata ctcttccttt tcaatatta ttgaagcatt tatcagggtt attgtctcat | 11520 |
| gagcggatac atatttgaat gtatttagaa aaa | 11553 |

<210> SEQ ID NO 4
<211> LENGTH: 12279
<212> TYPE: DNA
<213> ORGANISM: Artificial Sequence
<220> FEATURE:
<223> OTHER INFORMATION: Synthetic mIL-12

<400> SEQUENCE: 4

| | |
|---|---|
| taaacaaata ggggttccgc gcacatttcc ccgaaaagtg ccacctgacg tctaagaaac | 60 |
| cattattatc atgacattaa cctataaaaa taggcgtatc acgaggccct tcgtcttca | 120 |
| attaatcgca ccggtatcta tgtcgggtgc ggagaaagag gtaatgaaat ggcagctagc | 180 |
| atcatcaata atataccta ttttggattg aagccaatat gataatgagg gggtggagtt | 240 |
| tgtgacgtgg cgcggggcgt gggaacgggg cgggtgacgt agtagtgtgg cggaagtgtg | 300 |
| atgttgcaag tgtggcggaa cacatgtaag cgacggatgt ggcaaaagtg acgttttgg | 360 |
| tgtgcgccgg tgtacacagg aagtgacaat tttcgcgcgg ttttaggcgg atgttgtagt | 420 |
| aaatttgggc gtaaccgagt aagatttggc cattttcgcg ggaaaactga ataagaggaa | 480 |
| gtgaaatctg ataaattttg tgttactcat agcgcgtaat atttgtctag ggagatccgg | 540 |
| taccgatatc ctagacaacg atgctgagct aactataacg gtcctaaggt agcgaccgcg | 600 |
| gagactaggt gtatttatct aagcgatcgc ttaattaagg ccggccgccg caataaaata | 660 |
| tcttatttt cattacatct gtgtgttggt ttttgtgtg aatcgatagt actaacatac | 720 |
| gctctccatc aaaacaaaac gaaacaaaac aaactagcaa ataggctgt ccccagtgca | 780 |
| agtgcaggtg ccagaacatt tctctatcga taatgcaggt cggagtactg tcctccgagc | 840 |
| ggagtactgt cctccgagcg gagtactgtc ctccgagcgg agtactgtcc tccgagcgga | 900 |
| gtactgtcct ccgagcggag tactgtcctc cgagcggaga ctcttcgaag gaagagggc | 960 |
| ggggtcgatc gacccgccc ctcttccttc aaggaagag gggcggggtc gaagacctag | 1020 |
| agggtatata atgggtgcct tagctggtgt gtgagctcat cttcctgtag atcacgcgtc | 1080 |
| gaagaaggtg agtaatctta acatgctctt tttttttttt tttgctaatc ccttttgtgt | 1140 |
| gctgatgtta ggatgacatt tacaacaaat gtttgttcct gacaggaaaa accttgctgg | 1200 |
| gtaccttcgt tgccggacac ttcttgtcct ctactttgga aaaaaggaat tgagagccgc | 1260 |

```
tagcgccacc atgtgccccc agaagctgac catcagctgg ttcgccatcg tgctgctggt   1320 gagcccctg atggccatgt gggagctgga aaggacgtg tacgtggtgg aggtggactg    1380 gaccccgac gccccggcg agaccgtgaa cctgacttgc gacaccccg aggaggacga    1440 catcacctgg accagcgacc agagacacg cgtcatcggc agcggcaaga ccctgaccat    1500
caccgtgaag gagttcctgg acgccggaca gtacacctgt cacaagggcg gcgagaccct   1560
gagccacagc cacctgttgc tgcacaagaa ggagaacgc atctggagca ccgagatcct    1620
gaagaacttc aagaacaaga ccttcctgaa gtgcgaggcc ccaactaca gcggcagatt    1680 cacctgtagc tggctggtgc agagaaacat ggacctgaag ttcaacatca agagcagcag   1740
cagcagcccc gacagcagag ccgtgacatg cggcatggcc agcctgagcg ccgagaaggt    1800
gaccctggac cagagagact acgagaagta cagcgtgagc tgccaggagg acgtgacctg    1860
tcccaccgcc gaggagaccc tgcccatcga gcttgccctg aagccagac agcagaacaa    1920 gtacgagaac tacagcacca gcttcttcat cagagacatc atcaagcccg ccccccccaa   1980
gaacctccag atgaagcccc tgaagaacag ccaggtggag gtgtcctggg agtaccccga   2040
cagctggagc accccccaca gctacttcag cctgaagttc ttcgtgagaa tccagagaaa   2100
gaaggagaag atgaaggaga ccgaggaggg ctgcaaccag aagggcgctt tcctggtgga    2160
gaaaaccagc accgaggtgc agtgcaaggg cggcaacgtg tgtgtgcagg cccaggacag    2220
atactacaac agcagctgct ccaagtgggc ctgcgtgccc tgccgcgtga agctgagtg    2280 tgggcgagct cgaattcatt gatccccgg gctgcaggaa ttcgatatca agctcgggat    2340
ccgaattccg ccccccccc cccccccccc ctaacgttac tggccgaagc cgcttggaat    2400
aaggccggtg tgcgtttgtc tatatgttat tttccaccat attgccgtct tttggcaatg    2460
tgagggcccg gaaacctggc cctgtcttct tgacgagcat tcctaggggt ctttcccctc    2520
tcgccaaagg aatgcaaggt ctgttgaatg tcgtgaagga agcagttcct ctggaagctt    2580
cttgaagaca acaacgtct gtagcgaccc tttgcaggca gcggaacccc ccacctggcg    2640
acaggtgcct ctgcggccaa aagccacgtg tataagatac acctgcaaag gcggcacaac    2700
cccagtgcca cgttgtgagt tggatagttg tggaaagagt caaatggctc tcctcaagcg    2760
tattcaacaa ggggctgaag gatgcccaga aggtaccca ttgtatggga tctgatctgg    2820
ggcctcggtg cacatgcttt acatgtgttt agtcgaggtt aaaaaaacgt ctaggccccc    2880
cgaaccacgg gacgtggtt ttcctttgaa aaacacgatg ataatatggc cacaaccatg    2940
tgccagagca gatacctgtt gttcctggct accctggccc tgctgaacca cctgagcctg    3000
gcccgcgtga tccccgtgag cggccccgcc agatgcctga gccagagcag aaacctgttg    3060
aaaacaaccg acgacatggt gaaaccgcc agagagaagc tgaagcacta cagctgcacc    3120
gccgaggaca tcgaccacga ggacatcacc agagaccaga ccagcaccct gaaaacctgt    3180
ctgcccctgg agctgcacaa gaacgagagc tgcctggcta ccagagagac cagcagcacc    3240
accagaggca gctgcctgcc ccccagaaa accagcctga tgatgaccct gtgcctgggc    3300
agcatctacg aggacctgaa gatgtaccag accgagttcc aggccatcaa cgccgccctg    3360
caaaaccaca ccaccagca gatcatcctg gacaagggca tgttggtggc catcgacgag    3420
ctgatgcaga gcctgaacca caacggcgag accctgagac agaagccccc cgtgggcgag    3480 gccgaccccct acagagtgaa gatgaagctg tgcatcctgc tgcacgcctt cagcaccaga    3540
gtggtgacca tcaacagagt gatgggctac ctgagcagcg cctgaatcga ttgcgcaaag    3600
```

```
ctttcgcgat aggcgagacc aatgggtgtg tacgtagcgg ccgctcgaga acttgtttat      3660
tgcagcttat aatggttaca aataaagcaa tagcatcaca aatttcacaa ataaagcatt      3720
tttttcactg cattctagtt gtggtttgtc caaactcatc aatgtatctt atcatgtctc      3780
gtacggcgtg gtaggtccga acgaatccat ggattaccct gttatcccta tccggagtta      3840
acctcgagga cttcggaact tctagaacca gaccgttcag tttaaacgct cttctccccc      3900
tcgagggcct ccgcgccggg ttttggcgcc tcccgcgggc gccccctcc tcacggcgag       3960 cgctgccacg tcagacgaag ggcgcagcga gcgtcctgat ccttccgccc ggacgctcag      4020
gacagcggcc cgctgctcat aagactcggc cttagaaccc cagtatcagc agaaggacat      4080
tttaggacgg gacttgggtg actctagggc actggttttc tttccagaga gcggaacagg      4140
cgaggaaaag tagtcccttc tcggcgattc tgcggaggga tctccgtggg gcggtgaacg      4200
ccgatgatta tataaggacg cgccgggtgt ggcacagcta gttccgtcgc agccgggatt      4260
tgggtcgcgg ttcttgtttg tggatcgctg tgatcgtcac ttggtgagta gcgggctgct      4320
gggctgggta cgtgcgctcg ggggttggcga gtgtgttttg tgaagttttt taggcacctt    4380
ttgaaatgta atcatttggg tcaatatgta attttcagtg ttagactagt aaattgtccg     4440
ctaaattctg gccgttttttg gcttttttgt tagacggcat gcggggggggg ggggggggcaa  4500 ttggccacca tgggcccaa gaagaaaagg aaggtggccc cccccaccga cgtgagcctg       4560
ggcgacgagc tgcacctgga cggcgaggac gtggccatgg cccacgccga cgccctggac     4620
gacttcgacc tggacatgct gggcgacggc gacagccccg gccccggctt caccccccac     4680
gacagcgccc cctacggcgc cctgacatg gccgacttcg agttcgagca gatgttcacc       4740
gacgccctgg gcatcgacga gtacggcggc catatggaga tgcccgtgga caggattctg     4800
gaggccgaac tcgccgtgga gcagaaaagc gaccagggc tggagggccc cggcggaacc      4860
ggcggcagcg gcagcagccc caacgacccc gtgaccaaca tctgccaggc cgccgacaag     4920
cagctgttca ccctggtgga gtgggccaag aggattcccc acttcagcag cctgcccctg     4980
gacgaccagg tgatcctgct gagggccgga tggaacgagc tgctgatcgc cagcttcagc     5040
cacaggagca tcgacgtgag ggacggcatc ctgctggcca ccggcctgca cgtccatagg     5100
aacagcgccc acagcgccgg agtgggcgcc atcttcgaca gggtgctgac cgagctggtg    5160
agcaagatga gggacatgag gatggacaag accgagctgg gctgcctgag ggccatcatc    5220
ctgttcaacc ccgaggtgag gggcctgaaa agcgcccagg aggtggagct gctgagggag    5280
aaggtgtacg ccgccctgga ggagtacacc aggaccaccc accccgacga gcccggcaga    5340
ttcgccaagc tgctgctgag gctgcccagc ctgaggagca tcggcctgaa gtgcctggag    5400
cacctgttct tcttcaggct gatcggcgac gtgcccatcg acaccttcct gatggagatg   5460
ctggagagcc ccagcgacag ctgagccggc aactcgctgt agtaattcca gcgagaggca    5520
gagggagcga gcggcggcg ggctagggtg gaggagcccg gcgagcagag ctgcgctgcg     5580
ggcgtcctgg gaagggagat ccggagcgaa taggggcctt cgcctctggc ccagccctcc     5640
cgctgatccc ccagccagcg gtgcgcaacc ctagccgcat ccacgaaact ttgcccatag     5700 cagcggcg gcactttgca ctggaactta caacacccga gcaaggacgc gactctcccg       5760
acgcggggag gctattctgc ccatttgggg acacttcccc gccgctgcca ggacccgctt     5820
ctctgaaagg ctctccttgc agctgcttag acgctggatt ttttcgggt agtggaaaac     5880 cagcagcctc ccgcgaccag atctgccacc atgaagctgc tgagcagcat cgagcaggct   5940
tgcgacatct gcaggctgaa gaagctgaag tgcagcaagg agaagcccaa gtgcgccaag   6000
```

```
tgcctgaaga acaactggga gtgcagatac agccccaaga ccaagaggag cccctgacc      6060
agggcccacc tgaccgaggt ggagagcagg ctggagaggc tggagcagct gttcctgctg      6120
atcttcccca gggaggacct ggacatgatc ctgaagatgg acagcctgca agacatcaag      6180
gccctgctga ccggcctgtt cgtgcaggac aacgtgaaca aggacgccgt gaccgacagg      6240
ctggccagcg tggagaccga catgcccctg accctgaggc agcacaggat cagcgccacc      6300
agcagcagcg aggagagcag caacaagggc cagaggcagc tgaccgtgag ccccgagttt      6360
cccgggatca ggcccgagtg cgtggtgccc gagacccagt gcgccatgaa aggaaggag      6420
aagaaggccc agaaggagaa ggacaagctg ccgtgagca ccaccaccgt cgatgaccac      6480
atgcccccca tcatgcagtg cgagccccc ccccgagg ccgccaggat tcacgaggtc      6540
gtgcccaggt tcctgagcga caagctgctg gtgaccaaca ggcagaagaa catcccccag      6600
ctgaccgcca accagcagtt cctgatcgcc aggctgatct ggtatcagga cggctacgag      6660
cagcccagcg acgaggacct gaaaaggatc acccagacct ggcagcaggc cgacgacgag      6720
aacgaggaga gcgacacccc cttcaggcag atcaccgaga tgaccatcct gaccgtgcag      6780
ctgatcgtgg agttcgccaa gggcctgccc ggattcgcca agatcagcca gcccgaccag      6840
atcaccctgc tgaaggcttg cagcagcgag gtgatgatgc tgagggtggc caggaggtac      6900
gacgccgcca gcgacagcat cctgttcgcc aacaaccagg cttacaccag ggacaactac      6960
aggaaggctg gcatggccga ggtgatcgag gacctcctgc acttctgcag atgtatgtac      7020
agcatggccc tggacaacat ccactacgcc ctgctgaccg ccgtggtgat cttcagcgac      7080
aggcccggcc tggagcagcc ccagctggtg gaggagatcc agaggtacta cctgaacacc      7140
ctgaggatct acatcctgaa ccagctgagc ggcagcgcca ggagcagcgt gatctacggc      7200
aagatcctga gcatcctgag cgagctgagg accctgggaa tgcagaacag caatatgtgt      7260
atcagcctga agctgaagaa caggaagctg cccccttcc tggaggagat ttgggacgtg      7320
gccgacatga gccacaccca gccccccccc atcctggaga gccccaccaa cctgtgaatc      7380
gattagacat gataagatac attgatgagt ttggacaaac cacaactaga atgcagtgaa      7440
aaaaatgctt aatttgtgaa atttgtgatg ctattgctta atttgtaacc attataagct      7500
gcaataaaca agttaataaa acatttgcat tcattttatg tttcaggttc agggggagat      7560
gtgggaggtt ttttaaagca agtaaaacct ctacaaatgt ggtatctaga gctcttccaa      7620
atagatctgg aaggtgctga ggtacgatga acccgcacc aggtgcagac cctgcgagtg      7680
tggcggtaaa catattagga accagcctgt gatgctggat gtgaccgagg agctgaggcc      7740
cgatcacttg gtgctggcct gcacccgcgc tgagtttggc tctagcgatg aagatacaga      7800
ttgaggtact gaaatgtgtg ggcgtggctt aagggtggga aagaatatat aaggtgggg      7860
tcttatgtag ttttgtatct gttttgcagc agccgccgcc gccatgagca ccaactcgtt      7920
tgatggaagc attgtgagct catatttgac aacgcgcatg ccccatggg ccggggtgcg      7980
tcagaatgtg atgggctcca gcattgatgg tcgccccgtc ctgcccgcaa actctactac      8040
cttgacctac gagaccgtgt ctggaacgcc gttggagact gcagcctccg ccgccgcttc      8100
agccgctgca gccaccgccc gcgggattgt gactgacttt gctttcctga gcccgcttgc      8160
aagcagtgca gcttcccgtt catccgcccg cgatgacaag ttgacggctc ttttggcaca      8220
attggattct ttgaccccgg gaacttaatgt cgtttctcag cagctgttgg atctgcgcca      8280
gcaggtttct gccctgaagg cttcctcccc tcccaatgcg gtttaaaaca taataaaaa      8340
```

```
accagactct gtttggattt ggatcaagca agtgtcttgc tgtctttatt tagggtttt    8400
gcgcgcgcgg taggcccggg accagcggtc tcggtcgttg agggtcctgt gtattttttc    8460
caggacgtgg taaaggtgac tctggatgtt cagatacatg gcataagcc cgtctctggg    8520
gtggaggtag caccactgca gagcttcatg ctgcggggtg gtgttgtaga tgatccagtc    8580
gtagcaggag cgctgggcgt ggtgcctaaa aatgtctttc agtagcaagc tgattgccag    8640
gggcaggccc ttggtgtaag tgtttacaaa gcggttaagc tgggatgggt gcatacgtgg    8700
ggatatgaga tgcatcttgg actgtatttt taggttggct atgttcccag ccatatccct    8760
ccggggattc atgttgtgca gaaccaccag cacagtgtat ccggtgcact tgggaaattt    8820
gtcatgtagc ttagaaggaa atgcgtggaa gaacttggag acgcccttgt gacctccaag    8880
attttccatg cattcgtcca taatgatggc aatgggccca cgggcggcgg cctgggcgaa    8940
gatatttctg ggatcactaa cgtcatagtt gtgttccagg atgagatcgt cataggccat    9000
ttttacaaag cgcgggcgga gggtgccaga ctgcggtata atggttccat ccggcccagg    9060
ggcgtagtta ccctcacaga tttgcatttc ccacgctttg agttcagatg gggggatcat    9120
gtctacctgc ggggcgatga agaaaacggt ttccggggta ggggagatca gctgggaaga    9180
aagcaggttc ctgagcagct gcgacttacc gcagccggtg ggcccgtaaa tcacacctat    9240
taccgggtgc aactggtagt taagagagct gcagctgccg tcatccctga gcaggggggc    9300
cacttcgtta agcatgtccc tgactcgcat gttttccctg accaaatccg ccagaaggcg    9360
ctcgccgccc agcgatagca gttcttgcaa ggaagcaaag ttttcaacg gtttgagacc    9420
gtccgccgta ggcatgcttt tgagcgtttg accaagcagt tccaggcggt cccacagctc    9480
ggtcacctgc tctacggcat ctcgatccag catatctcct cgtttcgcgg gttggggcgg    9540
cttttcgctgt acggcagtag tcggtgctcg tccagacggg ccagggtcat gtcttttccac   9600
gggcgcaggg tcctcgtcag cgtagtctgg gtcacggtga aggggtgcgc tccgggctgc    9660
gcgctggcca gggtgcgctt gaggctggtc ctgctggtgc tgaagcgctg ccggtcttcg    9720
ccctgcgcgt cggccaggta gcatttgacc atggtgtcat agtccagccc ctccgcggcg    9780
tggcccttgg cgcgcagctt gcccttggag gaggcgccgc acgaggggca gtgcagactt    9840
ttgagggcgt agagcttggg cgcgagaaat accgattccg gggagtaggc atccgcgccg    9900
caggccccgc agacggtctc gcattccacg agccaggtga gctctggccg ttcgggtca    9960
aaaaccaggt ttcccccatg ctttttgatg cgtttcttac ctctggtttc catgagccgg   10020
tgtccacgct cggtgacgaa aaggctgtcc gtgtccccgt atacagactt gagaggcctg   10080
tcctcgaccg atgcccttga gagccttcaa cccagtcagc tccttccggt gggcgcgggg   10140
catgactatc gtcgccgcac ttatgactgt cttctttatc atgcaactcg taggacaggt   10200
gccggcagcg ctctgggtca tttcggcga ggaccgcttt cgctggagcg cgacgatgat   10260
cggcctgtcg cttgcggtat tcggaatctt gcacgccctc gctcaagcct tcgtcactgg   10320
tcccgccacc aaacgtttcg gcgagaagca ggccattatc gccggcatgg cggccgacgc   10380
gctgggctac gtcttgctgg cgttcgcgac gcgaggctgg atggccttcc ccattatgat   10440
tcttctcgct tccggcggca tcgggatgcc cgcgttgcag gccatgctgt ccaggcaggt   10500
agatgacgac catcagggac agcttcaagg ccagcaaaag gccaggaacc gtaaaaaggc   10560
cgcgttgctg gcgttttttcc ataggctccg ccccctgac gagcatcaca aaaatcgacg   10620
ctcaagtcag aggtggcgaa acccgacagg actataaaga taccaggcgt ttccccctgg   10680
aagctccctc gtgcgctctc ctgttccgac cctgccgctt accggatacc tgtccgcctt   10740
```

```
tctcccttcg ggaagcgtgg cgctttctca tagctcacgc tgtaggtatc tcagttcggt    10800
gtaggtcgtt cgctccaagc tgggctgtgt gcacgaaccc cccgttcagc ccgaccgctg    10860
cgccttatcc ggtaactatc gtcttgagtc caacccggta agacacgact tatcgccact    10920
ggcagcagcc actggtaaca ggattagcag agcgaggtat gtaggcggtg ctacagagtt    10980
cttgaagtgg tggcctaact acggctacac tagaaggaca gtatttggta tctgcgctct    11040
gctgaagcca gttaccttcg gaaaagagt tggtagctct tgatccggca aacaaaccac    11100
cgctggtagc ggtggttttt tgtttgcaa gcagcagatt acgcgcagaa aaaaggatc    11160
tcaagaagat cctttgatct tttctacggg gtctgacgct cagtggaacg aaaactcacg    11220
ttaagggatt ttggtcatga gattatcaaa aaggatcttc acctagatcc ttttaaatta    11280
aaaatgaagt tttaaatcaa tctaaagtat atatgagtaa acttggtctg acagttacca    11340
atgcttaatc agtgaggcac ctatctcagc gatctgtcta tttcgttcat ccatagttgc    11400
ctgactcccc gtcgtgtaga taactacgat acgggagggc ttaccatctg gccccagtgc    11460
tgcaatgata ccgcgagacc cacgctcacc ggctccagat ttatcagcaa taaaccagcc    11520
agccggaagg gccgagcgca gaagtggtcc tgcaacttta tccgcctcca tccagtctat    11580
taattgttgc cgggaagcta gagtaagtag ttcgccagtt aatagtttgc gcaacgttgt    11640
tgccattgct gcaggcatcg tggtgtcacg ctcgtcgttt ggtatggctt cattcagctc    11700
cggttcccaa cgatcaaggc gagttacatg atccccatg ttgtgcaaaa aagcggttag    11760
ctccttcggt cctccgatcg ttgtcagaag taagttggcc gcagtgttat cactcatggt    11820
tatggcagca ctgcataatt ctcttactgt catgccatcc gtaagatgct tttctgtgac    11880
tggtgagtac tcaaccaagt cattctgaga atagtgtatg cggcgaccga gttgctcttg    11940
cccggcgtca acacgggata ataccgcgcc acatagcaga actttaaaag tgctcatcat    12000
tggaaaacgt tcttcggggc gaaaactctc aaggatctta ccgctgttga tccagttc    12060
gatgtaaccc actcgtgcac ccaactgatc ttcagcatct tttactttca ccagcgtttc    12120
tgggtgagca aaaacaggaa ggcaaaatgc cgcaaaaaag gaataagggc gacacggaa    12180
atgttgaata ctcatactct tcctttttca atattattga agcatttatc agggttattg    12240
tctcatgagc ggatacatat ttgaatgtat ttagaaaaa                           12279
```

<210> SEQ ID NO 5
<211> LENGTH: 11601
<212> TYPE: DNA
<213> ORGANISM: Artificial Sequence
<220> FEATURE:
<223> OTHER INFORMATION: Synthetic hIL-21 and hIL-15

<400> SEQUENCE: 5

```
taaacaaata ggggttccgc gcacatttcc ccgaaaagtg ccacctgacg tctaagaaac      60
cattattatc atgacattaa cctataaaaa taggcgtatc acgaggccct ttcgtcttca     120
attaatcgca ccggtatcta tgtcgggtgc ggagaaagag gtaatgaaat ggcagctagc     180
atcatcaata atataccta ttttggattg aagccaatat gataatgagg gggtggagtt     240
tgtgacgtgg cgcggggcgt gggaacgggc gggtgacgt agtagtgtgg cggaagtgtg     300
atgttgcaag tgtggcggaa cacatgtaag cgacggatgt ggcaaaagtg acgtttttgg     360
tgtgcgccgg tgtacacagg aagtgacaat tttcgcgcgg tttaggcgg atgttgtagt     420
aaatttgggc gtaaccgagt aagatttggc cattttcgcg ggaaaactga ataagaggaa     480
```

```
gtgaaatctg aataattttg tgttactcat agcgcgtaat atttgtctag ggagatccgg    540
taccgatatc ctagacaacg atgctgagct aactataacg gtcctaaggt agcgaccgcg    600
gagactaggt gtatttatct aagcgatcgc ttaattaagg ccggccgccg caataaaata    660
tctttatttt cattacatct gtgtgttggt tttttgtgtg aatcgatagt actaacatac    720
gctctccatc aaaacaaaac gaaacaaaac aaactagcaa aataggctgt ccccagtgca    780
agtgcaggtg ccagaacatt tctctatcga taatgcaggt cggagtactg tcctccgagc    840
ggagtactgt cctccgagcg gagtactgtc ctccgagcgg agtactgtcc tccgagcgga    900
gtactgtcct ccgagcggag tactgtcctc cgagcggaga ctcttcgaag gaagaggggc    960
ggggtcgatc gaccccgccc ctcttccttc gaaggaagag gggcggggtc gaagacctag   1020
agggtatata atgggtgcct agctggtgt gtgagctcat cttcctgtag atcacgcgtc   1080
gaagaaggtg agtaatctta acatgctctt tttttttttt tttgctaatc ccttttgtgt   1140
gctgatgtta ggatgacatt tacaacaaat gtttgttcct gacaggaaaa accttgctgg   1200
gtaccttcgt tgccggacac ttcttgtcct ctactttgga aaaaggaat tgagagccgc    1260
tagcgccacc atgagaagca gccccggcaa catggagaga atcgtgatct gcctgatggt   1320
gatcttcctg ggcaccctgg tgcataagag cagcagccag ggccaggaca gacacatgat   1380
ccgcatgaga cagctgatcg acatcgtgga ccagctgaag aactacgtga acgacctggt   1440
gcccgagttc ctgcccgccc ccgaggacgt ggagaccaac tgcgagtgga cgccttcag    1500
ctgcttccag aaggcccagc tgaagtccgc caacaccggc aacaacgaga gaatcatcaa   1560
cgtgagcatc aagaagctga gcggaagcc ccccagcacc aacgccggaa gaagacagaa    1620
gcacagactg acctgtccca gctgcgacag ctacgagaag aagcccccca aggagttcct   1680
ggagagattc aagagcctgc tgcaaaagat gatccaccag cacctgagca gcagaaccca   1740
cggcagcgag gacagctgag ttgggcgagc tcgaattcat tgatccccg ggctgcagga    1800
attcgatatc aagctcggga tccgaattcc gccccccccc ccccccccc cctaacgtta    1860
ctggccgaag ccgcttggaa taaggccggt gtgcgtttgt ctatatgtta ttttccacca   1920
tattgccgtc ttttggcaat gtgagggccc ggaaacctgg ccctgtcttc ttgacgagca   1980
ttcctagggg tctttcccct ctcgccaaag gaatgcaagg tctgttgaat gtcgtgaagg   2040
aagcagttcc tctggaagct tcttgaagac aaacaacgtc tgtagcgacc ctttgcaggc   2100
agcggaaccc cccacctggc gacaggtgcc tctgcggcca aaagccacgt gtataagata   2160
cacctgcaaa ggcggcacaa ccccagtgcc acgttgtgag ttggatagtt gtggaaagag   2220
tcaaatggct ctcctcaagc gtattcaaca aggggctgaa ggatgcccag aaggtacccc   2280
attgtatggg atctgatctg gggcctcggt gcacatgctt tacatgtgtt tagtcgaggt   2340
taaaaaaacg tctaggcccc ccgaaccacg gggacgtggt tttcctttga aaaacacgat   2400
gataatatgg ccacaaccat gagaatcagc aagcccacc tgagaagcat cagcatccag    2460
tgttacctgt gcctgctgct gaacagccac ttcctgaccg aggccggtat ccacgtcttc   2520
atcctgggct gcttcagcgc cggactgccc aagaccgagg ccaactgggt gaacgtgatc   2580
tctgacctga gaagatcga ggacctgatc cagtccatgc acatcgacgc caccctgtac   2640
accgagagcg acgttcatcc cagctgcaag gtgaccgcca tgaagtgctt cctgctggag   2700
ctgcaagtga tctccctgga gagcggcgac gccagcatcc acgacaccgt ggagaacctg   2760
attatcctgc taacaacag cctgagcagc aacggcaacg tgaccgagag cggctgcaag   2820
gagtgtgagg agctggagga gaagaacatc aaggagttcc tccagagctt cgtgcatatc   2880
```

```
gtccagatgt tcatcaacac cagctgaatc gattgcgcaa agctttcgcg ataggcgaga   2940
ccaatgggtg tgtacgtagc ggccgctcga aacttgttt attgcagctt ataatggtta    3000
caaataaagc aatagcatca caaatttcac aaataaagca ttttttttcac tgcattctag  3060 ttgtggtttg tccaaactca tcaatgtatc ttatcatgtc tcgtacgcg tggtaggtcc    3120 gaacgaatcc atggattacc ctgttatccc tatccggagt taacctcgag gacttcggaa   3180
cttctagaac cagaccgttc agtttaaacg ctcttctccc cctcgagggc ctccgcgccg   3240
ggttttggcg cctcccgcgg gcgcccccct cctcacggcg agcgctgcca cgtcagacga   3300
agggcgcagc gagcgtcctg atccttccgc ccggacgctc aggacagcgg cccgctgctc   3360
ataagactcg gccttagaac cccagtatca gcagaaggac attttaggac gggacttggg   3420
tgactctagg gcactggttt tctttccaga gagcggaaca ggcgaggaaa agtagtccct   3480
tctcggcgat tctgcggagg gatctccgtg gggcggtgaa cgccgatgat tatataagga   3540
cgcgccgggt gtggcacagc tagttccgtc gcagccggga tttgggtcgc ggttcttgtt   3600
tgtggatcgc tgtgatcgtc acttggtgag tagcgggctg ctgggctggg tacgtgcgct   3660
cggggttggc gagtgtgttt tgtgaagttt tttaggcacc ttttgaaatg taatcatttg   3720
ggtcaatatg taattttcag tgttagacta gtaaattgtc cgctaaattc tggccgtttt   3780 tggcttttt gttagacggc atgcgggggg ggggggggc aattggccac catgggcccc     3840
aagaagaaaa ggaaggtggc ccccccacc gacgtgagcc tgggcgacga gctgcacctg    3900
gacggcgagg acgtggccat ggcccacgcc gacgccctgg acgacttcga cctggacatg   3960
ctgggcgacg gcgacagccc cggccccggc ttcacccccc acgacagcgc cccctacggc   4020
gccctggaca tggccgactt cgagttcgag cagatgttca ccgacgccct gggcatcgac   4080
gagtacggcg gccatatgga gatgcccgtg gacaggattc tggaggccga actcgccgtg   4140
gagcagaaaa gcgaccaggg cgtggagggc cccggcggaa ccggcggcag cggcagcagc   4200
cccaacgacc ccgtgaccaa catctgccag gccgccgaca agcagctgtt caccctggtg   4260
gagtgggcca agaggattcc ccacttcagc agcctgcccc tggacgacca ggtgatcctg   4320
ctgagggccg gatggaacga gctgctgatc gccagcttca gccacaggag catcgacgtg   4380
agggacggca tcctgctggc caccggcctg cacgtccata ggaacagcgc ccacagcgcc   4440
ggagtgggcg ccatcttcga cagggtgctg accgagctgg tgagcaagat gagggacatg   4500
aggatggaca agaccgagct gggctgcctg agggccatca tcctgttcaa ccccgaggtg   4560
aggggcctga aaagcgccca ggaggtggag ctgctgaggg agaaggtgta cgccgccctg   4620
gaggagtaca ccaggaccac ccaccccgac gagcccggca gattcgccaa gctgctgctg   4680
aggctgccca gcctgaggag catcggcctg aagtgcctgg agcacctgtt cttcttcagg   4740
ctgatcggcg acgtgcccat cgacaccttc ctgatggaga tgctggagag ccccagcgac   4800
agctgagccg gcaactcgct gtagtaattc agcgagagg cagagggagc gagcgggcgg    4860
cgggctaggg tggaggagcc cggcgagcag agctgcgctg cgggcgtcct gggaagggag   4920
atccggagcg aataggggc ttcgcctctg gcccagccct cccgctgatc ccccagccag    4980
cggtgcgcaa ccctagccgc atccacgaaa ctttgcccat agcagcgggc gggcactttg   5040
cactggaact tacaacaccc gagcaaggac gcgactctcc cgacgcgggg aggctattct   5100
gcccatttgg ggacacttcc ccgccgctgc caggacccgc ttctctgaaa ggctctcctt   5160
gcagctgctt agacgctgga ttttttttcgg gtagtggaaa accagcagcc tcccgcgacc   5220
```

```
agatctgcca ccatgaagct gctgagcagc atcgagcagg cttgcgacat ctgcaggctg      5280
aagaagctga agtgcagcaa ggagaagccc aagtgcgcca agtgcctgaa gaacaactgg      5340
gagtgcagat acagccccaa gaccaagagg agcccctga ccagggccca cctgaccgag       5400
gtggagagca ggctggagag gctggagcag ctgttcctgc tgatcttccc cagggaggac      5460
ctggacatga tcctgaagat ggacagcctg caagacatca aggccctgct gaccggcctg      5520
ttcgtgcagg acaacgtgaa caaggacgcc gtgaccgaca ggctggccag cgtggagacc      5580
gacatgcccc tgaccctgag gcagcacagg atcagcgcca ccagcagcag cgaggagagc      5640
agcaacaagg ccagaggca gctgaccgtg agccccgagt ttcccgggat caggcccgag       5700
tgcgtggtgc ccgagaccca gtgcgccatg aaaaggaagg agaagaaggc ccagaaggag      5760
aaggacaagc tgcccgtgag caccaccacc gtcgatgacc acatgccccc catcatgcag      5820
tgcgagcccc ccccccccga ggccgccagg attcacgagg tcgtgcccag gttcctgagc      5880
gacaagctgc tggtgaccaa caggcagaag aacatccccc agctgaccgc caaccagcag      5940
ttcctgatcg ccaggctgat ctggtatcag gacggctacg agcagcccag cgacgaggac      6000
ctgaaaagga tcacccagac ctggcagcag gccgacgacg agaacgagga gagcgacacc      6060
cccttcaggc agatcaccga gatgaccatc ctgaccgtgc agctgatcgt ggagttcgcc      6120
aagggcctgc ccggattcgc caagatcagc cagcccgacc agatcaccct gctgaaggct      6180
tgcagcagcg aggtgatgat gctgagggtg gccaggaggt acgacgccgc cagcgacagc      6240
atcctgttcg ccaacaacca ggcttacacc agggacaact acaggaaggc tggcatggcc      6300
gaggtgatcg aggacctcct gcacttctgc agatgtatgt acagcatggc cctggacaac      6360
atccactacg ccctgctgac cgccgtggtg atcttcagcg acaggcccgg cctggagcag      6420
ccccagctgg tggaggagat ccagaggtac tacctgaaca ccctgaggat ctacatcctg      6480
aaccagctga gcggcagcgc caggagcagc gtgatctacg gcaagatcct gagcatcctg      6540
agcgagctga ggaccctggg aatgcagaac agcaatatgt gtatcagcct gaagctgaag      6600
aacaggaagc tgcccccctt cctggaggag atttgggacg tggccgacat gagccacacc      6660
cagccccccc ccatcctgga gagccccacc aacctgtgaa tcgattagac atgataagat      6720
acattgatga gtttggacaa accacaacta gaatgcagtg aaaaaaatgc ttaatttgtg      6780
aaatttgtga tgctattgct taatttgtaa ccattataag ctgcaataaa caagttaata      6840
aaacatttgc attcatttta tgtttcaggt tcaggggag atgtgggagg ttttttaaag       6900
caagtaaaac ctctacaaat gtggtatcta gagctcttcc aaatagatct ggaaggtgct      6960
gaggtacgat gagacccgca ccaggtgcag accctgcgag tgtgcggta aacatattag       7020 gaaccagcct gtgatgctgg atgtgaccga ggagctgagg cccgatcact tggtgctggc      7080
ctgcacccgc gctgagtttg gctctagcga tgaagataca gattgaggta ctgaaatgtg      7140
tgggcgtggc ttaagggtgg gaaagaatat ataaggtggg ggtcttatgt agttttgtat      7200
ctgttttgca gcagccgccg ccgccatgag caccaactcg tttgatggaa gcattgtgag      7260
ctcatatttg acaacgcgca tgccccatg ggccggggtg cgtcagaatg tgatgggctc       7320
cagcattgat ggtcgccccg tcctgcccgc aaactctact accttgacct acgagaccgt      7380
gtctggaacg ccgttggaga ctgcagcctc cgccgccgct tcagccgctg cagccaccgc      7440
ccgcgggatt gtgactgact tgcttttcct gagcccgctt gcaagcagtg cagcttcccg      7500
ttcatccgcc cgcgatgaca agttgacggc tcttttggca caattggatt ctttgacccg      7560
ggaacttaat gtcgtttctc agcagctgtt ggatctgcgc cagcaggttt ctgccctgaa      7620
```

```
ggcttcctcc cctcccaatg cggtttaaaa cataaataaa aaaccagact ctgtttggat   7680
ttggatcaag caagtgtctt gctgtcttta tttaggggtt ttgcgcgcgc ggtaggcccg   7740
ggaccagcgg tctcggtcgt tgagggtcct gtgtattttt tccaggacgt ggtaaaggtg   7800
actctggatg ttcagataca tgggcataag cccgtctctg gggtggaggt agcaccactg   7860
cagagcttca tgctgcgggg tggtgttgta gatgatccag tcgtagcagg agcgctgggc   7920
gtggtgccta aaaatgtctt tcagtagcaa gctgattgcc aggggcaggc ccttggtgta   7980
agtgtttaca aagcggttaa gctgggatgg gtgcatacgt ggggatatga gatgcatctt   8040
ggactgtatt tttaggttgg ctatgttccc agccatatcc ctccggggat tcatgttgtg   8100
cagaaccacc agcacagtgt atccggtgca cttgggaaat ttgtcatgta gcttagaagg   8160
aaatgcgtgg aagaacttgg agacgcccct gtgacctcca agattttcca tgcattcgtc   8220
cataatgatg gcaatgggcc cacgggcggc ggcctgggcg aagatatttc tgggatcact   8280
aacgtcatag ttgtgttcca ggatgagatc gtcataggcc attttacaa agcgcgggcg   8340 gagggtgcca gactgcggta taatggttcc atccggccca ggggcgtagt taccctcaca   8400
gatttgcatt tcccacgctt tgagttcaga tgggggatc atgtctacct gcggggcgat   8460
gaagaaaacg gtttccgggg taggggagat cagctgggaa gaaagcaggt tcctgagcag   8520
ctgcgactta ccgcagccgg tgggcccgta aatcacacct attaccgggt gcaactggta   8580
gttaagagag ctgcagctgc cgtcatccct gagcaggggg gccacttcgt taagcatgtc   8640
cctgactcgc atgttttccc tgaccaaatc cgccagaagg cgctcgccgc ccagcgatag   8700
cagttcttgc aaggaagcaa agttttttcaa cggtttgaga ccgtccgccg taggcatgct   8760
tttgagcgtt tgaccaagca gttccaggcg gtcccacagc tcggtcacct gctctacggc   8820
atctcgatcc agcatatctc ctcgtttcgc ggggttgggc ggctttcgct gtacggcagt   8880
agtcggtgct cgtccagacg ggccagggtc atgtctttcc acgggcgcag ggtcctcgtc   8940
agcgtagtct gggtcacggt gaaggggtgc gctccgggct gcgcgctggc cagggtgcgc   9000
ttgaggctgg tcctgctggt gctgaagcgc tgccggtctt cgccctgcgc gtcggccagg   9060
tagcatttga ccatggtgtc atagtccagc ccctccgcgg cgtggccctt ggcgcgcagc   9120
ttgcccttgg aggaggcgcc gcacgagggg cagtgcagac ttttgagggc gtagagcttg   9180
ggcgcgagaa ataccgattc cggggagtag gcatccgcgc cgcaggcccc gcagacggtc   9240
tcgcattcca cgagccaggt gagctctggc cgttcggggt caaaaaccag gtttccccca   9300 tgcttttga tgcgtttctt acctctggtt tccatgagcc ggtgtccacg ctcggtgacg   9360
aaaaggctgt ccgtgtcccc gtatacagac ttgagaggcc tgtcctcgac cgatgccctt   9420
gagagccttc aacccagtca gctccttccg gtgggcgcgg ggcatgacta tcgtcgccgc   9480
acttatgact gtcttcttta tcatgcaact cgtaggacag gtgccggcag cgctctgggt   9540
cattttcggc gaggaccgct ttcgctggag cgcgacgatg atcggcctgt cgcttgcggt   9600
attcggaatc ttgcacgccc tcgctcaagc cttcgtcact ggtcccgcca ccaaacgttt   9660
cggcgagaag caggccatta tcgccggcat ggcggccgac gcgctgggct acgtcttgct   9720
ggcgttcgcg acgcgaggct ggatggcctt ccccattatg attcttctcg cttccggcgg   9780
catcgggatg cccgcgttgc aggccatgct gtccaggcag gtagatgacg accatcaggg   9840
acagcttcaa ggccagcaaa aggccaggaa ccgtaaaaag gccgcgttgc tggcgttttt   9900
ccataggctc cgcccccctg acgagcatca caaaaatcga cgctcaagtc agaggtggcg   9960
```

| | | | |
|---|---|---|---|
| aaacccgaca | ggactataaa | gataccaggc | gtttccccct ggaagctccc tcgtgcgctc | 10020 |
| tcctgttccg | accctgccgc | ttaccggata | cctgtccgcc tttctccctt cgggaagcgt | 10080 |
| ggcgctttct | catagctcac | gctgtaggta | tctcagttcg gtgtaggtcg ttcgctccaa | 10140 |
| gctgggctgt | gtgcacgaac | cccccgttca | gcccgaccgc tgcgccttat ccggtaacta | 10200 |
| tcgtcttgag | tccaacccgg | taagacacga | cttatcgcca ctggcagcag ccactggtaa | 10260 |
| caggattagc | agagcgaggt | atgtaggcgg | tgctacagag ttcttgaagt ggtgcctaa | 10320 |
| ctacggctac | actagaagga | cagtatttgg | tatctgcgct ctgctgaagc cagttacctt | 10380 |
| cggaaaaaga | gttggtagct | cttgatccgg | caaacaaacc accgctggta gcggtggttt | 10440 |
| ttttgtttgc | aagcagcaga | ttacgcgcag | aaaaaaagga tctcaagaag atcctttgat | 10500 |
| cttttctacg | gggtctgacg | ctcagtggaa | cgaaaactca cgttaaggga ttttggtcat | 10560 |
| gagattatca | aaaaggatct | tcacctagat | ccttttaaat taaaaatgaa gttttaaatc | 10620 |
| aatctaaagt | atatatgagt | aaacttggtc | tgacagttac caatgcttaa tcagtgaggc | 10680 |
| acctatctca | gcgatctgtc | tatttcgttc | atccatagtt gcctgactcc ccgtcgtgta | 10740 |
| gataactacg | atacgggagg | gcttaccatc | tggccccagt gctgcaatga taccgcgaga | 10800 |
| cccacgctca | ccggctccag | atttatcagc | aataaaccag ccagccggaa gggccgagcg | 10860 |
| cagaagtggt | cctgcaactt | tatccgcctc | catccagtct attaattgtt gccgggaagc | 10920 |
| tagagtaagt | agttcgccag | ttaatagttt | gcgcaacgtt gttgccattg ctgcaggcat | 10980 |
| cgtggtgtca | cgctcgtcgt | ttggtatggc | ttcattcagc tccggttccc aacgatcaag | 11040 |
| gcgagttaca | tgatccccca | tgttgtgcaa | aaaagcggtt agctccttcg gtcctccgat | 11100 |
| cgttgtcaga | agtaagttgg | ccgcagtgtt | atcactcatg gttatggcag cactgcataa | 11160 |
| ttctcttact | gtcatgccat | ccgtaagatg | cttttctgtg actggtgagt actcaaccaa | 11220 |
| gtcattctga | gaatagtgta | tgcggcgacc | gagttgctct tgcccggcgt caacacggga | 11280 |
| taataccgcg | ccacatagca | gaactttaaa | agtgctcatc attggaaaac gttcttcggg | 11340 |
| gcgaaaactc | tcaaggatct | taccgctgtt | gagatccagt tcgatgtaac ccactcgtgc | 11400 |
| acccaactga | tcttcagcat | cttttacttt | caccagcgtt tctgggtgag caaaaacagg | 11460 |
| aaggcaaaat | gccgcaaaaa | agggaataag | ggcgacacgg aaatgttgaa tactcatact | 11520 |
| cttcctttt | caatattatt | gaagcattta | tcagggttat tgtctcatga gcggatacat | 11580 |
| atttgaatgt | atttagaaaa | a | | 11601 |

<210> SEQ ID NO 6
<211> LENGTH: 12270
<212> TYPE: DNA
<213> ORGANISM: Artificial Sequence
<220> FEATURE:
<223> OTHER INFORMATION: Synthetic hIL-12

<400> SEQUENCE: 6

| | | | |
|---|---|---|---|
| taaacaaata | ggggttccgc | gcacatttcc | ccgaaaagtg ccacctgacg tctaagaaac | 60 |
| cattattatc | atgacattaa | cctataaaaa | taggcgtatc acgaggccct ttcgtcttca | 120 |
| attaatcgca | ccggtatcta | tgtcgggtgc | ggagaaagag gtaatgaaat ggcagctagc | 180 |
| atcatcaata | atataccttta | ttttggattg | aagccaatat gataatgagg gggtggagtt | 240 |
| tgtgacgtgg | cgcggggcgt | gggaacgggg | cgggtgacgt agtagtgtgg cggaagtgtg | 300 |
| atgttgcaag | tgtggcggaa | cacatgtaag | cgacggatgg ggcaaaagtg acgttttttgg | 360 |
| tgtgcgccgg | tgtacacagg | aagtgacaat | tttcgcgcgg ttttaggcgg atgttgtagt | 420 |

```
aaatttgggc gtaaccgagt aagatttggc cattttcgcg ggaaaactga ataagaggaa    480
gtgaaatctg aataattttg tgttactcat agcgcgtaat atttgtctag ggagatccgg    540
taccgatatc ctagacaacg atgctgagct aactataacg gtcctaaggt agcgaccgcg    600
gagactaggt gtatttatct aagcgatcgc ttaattaagg ccggccgccg caataaaata    660
tctttatttt cattacatct gtgtgttggt ttttttgtgtg aatcgatagt actaacatac    720
gctctccatc aaaacaaaac gaaacaaaac aaactagcaa aataggctgt ccccagtgca    780
agtgcaggtg ccagaacatt tctctatcga taatgcaggt cggagtactg tcctccgagc    840
ggagtactgt cctccgagcg gagtactgtc ctccgagcgg agtactgtcc tccgagcgga    900
gtactgtcct ccgagcggag tactgtcctc cgagcggaga ctcttcgaag gaagagggggc    960
ggggtcgatc gaccccgccc ctcttccttc gaaggaagag gggcggggtc gaagacctag   1020
agggtatata atgggtgcct tagctggtgt gtgagctcat cttcctgtag atcacgcgtc   1080
gaagaaggtg agtaatctta acatgctctt tttttttttt tttgctaatc ccttttgtgt   1140
gctgatgtta ggatgacatt tacaacaaat gtttgttcct gacaggaaaa accttgctgg   1200
gtaccttcgt tgccggacac ttcttgtcct ctactttgga aaaaaggaat tgagagccgc   1260
tagcgccacc atgggtcacc agcagttggt catctcttgg ttttccctgg tttttctggc   1320
atctcccctc gtggccatat gggaactgaa gaaagatgtt tatgtcgtag aattggattg   1380
gtatccggat gcccctggag aaatggtggt cctcacctgt gacacccctg aagaagatgg   1440
tatcacctgg accttggacc agagcagtga ggtcttaggc tctggcaaaa ccctgaccat   1500
ccaagtcaaa gagtttggag atgctggcca gtacacctgt cacaaaggag gcgaggttct   1560
aagccattcg ctcctgctgc ttcacaaaaa ggaagatgga atttggtcca ctgatatttt   1620
aaaggaccag aaagaaccca aaaataagac ctttctaaga tgcgaggcca agaattattc   1680
tggacgtttc acctgctggt ggctgacgac aatcagtact gatttgacat tcagtgtcaa   1740
aagcagcaga ggctcttctg accccaagg ggtgacgtgc ggagctgcta cactctctgc   1800
agagagagtc agaggggaca acaaggagta tgagtactca gtggagtgcc aggaggacag   1860
tgcctgccca gctgctgagg agagtctgcc cattgaggtc atggtggatg ccgttcacaa   1920
gctcaagtat gaaaactaca ccagcagctt cttcatcagg gacatcatca aacctgaccc   1980
acccaagaac ttgcagctga agccattaaa gaattctcgg caggtggagg tcagctggga   2040
gtaccctgac acctggagta ctccacattc ctacttctcc ctgacattct gcgttcaggt   2100
ccagggcaag agcaagagag aaaagaaaga tagagtcttc acggacaaga cctcagccac   2160
ggtcatctgc cgcaaaaatg ccagcattag cgtgcgggcc caggaccgct actatagctc   2220
atcttggagc gaatgggcat ctgtgccctg cagttaggtt gggcgagctc gaattcattg   2280
atccccgggg ctgcaggaat tcgatatcaa gctcgggatc cgaattccgc cccccccccc   2340
cccccccccc taacgttact ggccgaagcc gcttggaata aggccggtgt gcgtttgtct   2400
atatgttatt ttccaccata ttgccgtctt ttggcaatgt gagggcccgg aaacctggcc   2460
ctgtcttctt gacgagcatt cctagggtc tttccctct cgccaaagga atgcaaggtc   2520
tgttgaatgt cgtgaaggaa gcagttcctc tggaagcttc ttgaagacaa caacgtctg   2580
tagcgaccct ttgcaggcag cggaacccc cacctggcga caggtgcctc tgcggccaaa   2640
agccacgtgt ataagataca cctgcaaagg cggcacaacc ccagtgccac gttgtgagtt   2700
ggatagttgt ggaaagagtc aaatggctct cctcaagcgt attcaacaag gggctgaagg   2760
```

```
atgcccagaa ggtaccccat tgtatgggat ctgatctggg gcctcggtgc acatgcttta   2820
catgtgttta gtcgaggtta aaaaaacgtc taggccccccc gaaccacggg gacgtggttt   2880
tcctttgaaa aacacgatga taatatggcc acaaccatgg gtccagcgcg cagcctcctc   2940
cttgtggcta ccctggtcct cctgaccac ctcagtttgg ccagaaacct ccccgtggcc    3000
actccagacc caggaatgtt cccatgcctt caccactccc aaaacctgct gagggccgtc   3060
agcaacatgc tccagaaggc cagacaaact ctagaatttt acccttgcac ttctgaagag   3120
attgatcatg aagatatcac aaaagataaa accagcacag tggaggcctg tttaccattg   3180
gaattaacca agaatgagag ttgcctaaat tccagagaga cctctttcat aactaatggg   3240
agttgcctgg cctccagaaa gacctctttt atgatggccc tgtgccttag tagtatttat   3300
gaagacttga agatgtacca ggtggagttc aagaccatga atgcaaagct tctgatggat   3360
cctaagaggc agatctttct agatcaaaac atgctggcag ttattgatga gctgatgcag   3420
gccctgaatt tcaacagtga gactgtgcca caaaaatcct cccttgaaga accggatttt   3480
tataaaacta aaatcaagct ctgcatactt cttcatgctt tcagaattcg ggcagtgact   3540
attgatagag tgatgagcta tctgaatgct tcctaaatcg attgcgcaaa gctttcgcga   3600
taggcgagac caatgggtgt gtacgtagcg ccgctcgag aacttgttta ttgcagctta    3660
taatggttac aaataaagca atagcatcac aaatttcaca aataaagcat ttttttcact   3720
gcattctagt tgtggtttgt ccaaactcat caatgtatct tatcatgtct cgtacgcgt    3780
ggtaggtccg aacgaatcca tggattaccc tgttatccct atccggagtt aacctcgagg   3840
acttcggaac ttctagaacc agaccgttca gtttaaacgc tcttctcccc ctcgagggcc   3900
tccgcgccgg gttttggcgc ctcccgcggg cgcccccctc ctcacggcga gcgctgccac   3960
gtcagacgaa gggcgcagcg agcgtcctga tccttccgcc cggacgctca ggacagcggc   4020
ccgctgctca taagactcgg ccttagaacc ccagtatcag cagaaggaca ttttaggacg   4080
ggacttgggt gactctaggg cactggtttt ctttccagag agcggaacag gcgaggaaaa   4140
gtagtcccctt ctcggcgatt ctgcggaggg atctccgtgg ggcggtgaac gccgatgatt   4200
atataaggac gcgccgggtg tggcacagct agttccgtcg cagccgggat ttgggtcgcg   4260
gttcttgttt gtggatcgct gtgatcgtca cttggtgagt agcgggctgc tgggctgggt   4320
acgtgcgctc ggggttggcg agtgtgtttt gtgaagtttt ttaggcacct tttgaaatgt   4380
aatcatttgg gtcaatatgt aattttcagt gttagactag taaattgtcc gctaaattct   4440
ggccgttttt ggcttttttg ttagacggca tgcggggggg ggggggggca attggccacc   4500
atgggcccca agaagaaaag gaaggtggcc cccccaccg acgtgagcct gggcgacgag    4560
ctgcacctgg acggcgagga cgtggccatg gcccacgccg acgccctgga cgacttcgac   4620
ctggacatgc tgggcgacgg cgacagcccc ggccccggct tcacccccca cgacagcgcc   4680
ccctacggcg ccctggacat ggccgacttc gagttcgagc agatgttcac cgacgccctg   4740
ggcatcgacg agtacggcgg ccatatggag atgcccgtgg acaggattct ggaggccgaa   4800
ctcgccgtgg agcagaaaag cgaccagggc gtggagggcc ccgcggaac cggcggcagc   4860
ggcagcagcc ccaacgaccc cgtgaccaac atctgccagg ccgccgacaa gcagctgttc   4920
accctggtgg agtgggccaa gaggattccc cacttcagca gcctgccct ggacgaccag    4980
gtgatcctgc tgagggccgg atggaacgag ctgctgatcg ccagcttcag ccacaggagc   5040
atcgacgtga gggacggcat cctgctggcc accggcctgc acgtccatag gaacagcgcc   5100
cacagcgccg gagtgggcgc catcttcgac agggtgctga ccgagctggt gagcaagatg   5160
```

```
agggacatga ggatggacaa gaccgagctg ggctgcctga gggccatcat cctgttcaac    5220
cccgaggtga ggggcctgaa aagcgcccag gaggtggagc tgctgaggga aaggtgtac     5280
gccgccctgg aggagtacac caggaccacc caccccgacg agcccggcag attcgccaag    5340
ctgctgctga ggctgcccag cctgaggagc atcggcctga agtgcctgga gcacctgttc    5400
ttcttcaggc tgatcggcga cgtgcccatc gacaccttcc tgatggagat gctggagagc    5460
cccagcgaca gctgagccgg caactcgctg tagtaattcc agcgagaggc agagggagcg    5520
agcgggcggc gggctagggt ggaggagccc ggcgagcaga gctgcgctgc gggcgtcctg    5580
ggaagggaga tccggagcga ataggggget tcgcctctgg cccagccctc ccgctgatcc    5640
cccagccagc ggtgcgcaac cctagccgca tccacgaaac tttgcccata gcagcgggcg    5700
ggcactttgc actggaactt acaacacccg agcaaggacg cgactctccc gacgcgggga    5760
ggctattctg cccatttggg gacacttccc cgccgctgcc aggacccgct tctctgaaag    5820
gctctccttg cagctgctta gacgctggat ttttttcggg tagtggaaaa ccagcagcct    5880
cccgcgacca gatctgccac catgaagctg ctgagcagca tcgagcaggc ttgcgacatc    5940
tgcaggctga agaagctgaa gtgcagcaag gagaagccca gtgcgccaa gtgcctgaag    6000
aacaactggg agtgcagata cagccccaag accaaggaga gcccctgac cagggcccac    6060
ctgaccgagg tggagagcag gctggagagg ctggagcagc tgttcctgct gatcttcccc    6120
agggaggacc tggacatgat cctgaagatg gacagcctgc aagacatcaa ggccctgctg    6180
accggcctgt tcgtgcagga caacgtgaac aaggacgccg tgaccgacag gctggccagc    6240
gtggagaccg acatgcccct gaccctgagg cagcacagga tcagcgccac cagcagcagc    6300
gaggagagca gcaacaaggg ccagaggcag ctgaccgtga gccccgagtt tcccgggatc    6360
aggcccgagt gcgtggtgcc cgagacccag tgcgccatga aaaggaagga gaagaaggcc    6420
cagaaggaga aggacaagct gcccgtgagc accaccaccg tcgatgacca catgcccccc    6480
atcatgcagt gcgagccccc ccccccgag gccgccagga ttcacgaggt cgtgcccagg    6540
ttcctgagcg acaagctgct ggtgaccaac aggcagaaga acatccccca gctgaccgcc    6600
aaccagcagt tcctgatcgc caggctgatc tggtatcagg acggctacga gcagcccagc    6660
gacgaggacc tgaaaaggat cacccagacc tggcagcagg ccgacgacga aacgaggag    6720
agcgacaccc ccttcaggca gatcaccgag atgaccatcc tgaccgtgca gctgatcgtg    6780
gagttcgcca agggcctgcc cggattcgcc aagatcagcc agcccgacca gatcaccctg    6840
ctgaaggctt gcagcagcga ggtgatgatg ctgagggtgg ccaggaggta cgacgccgcc    6900
agcgacagca tcctgttcgc caacaaccag gcttacacca gggacaacta caggaaggct    6960
ggcatggccg aggtgatcga ggacctcctg cacttctgca gatgtatgta cagcatggcc    7020
ctggacaaca tccactacgc cctgctgacc gccgtggtga tcttcagcga caggcccggc    7080
ctggagcagc cccagctggt ggaggagatc cagaggtact acctgaacac cctgaggatc    7140
tacatcctga accagctgag cggcagcgcc aggagcagcg tgatctacgg caagatcctg    7200
agcatcctga cgcagctgag gaccctggga atgcagaaca gcaatatgtg tatcagcctg    7260
aagctgaaga acaggaagct gccccccttc ctggaggaga tttgggacgt ggccgacatg    7320
agccacaccc agccccccc catcctggag agccccacca acctgtgaat cgattagaca    7380
tgataagata cattgatgag tttggacaaa ccacaactag aatgcagtga aaaaaatgct    7440
taatttgtga aatttgtgat gctattgctt aatttgtaac cattataagc tgcaataaac    7500
```

```
aagttaataa aacatttgca ttcattttat gtttcaggtt caggggagga tgtgggaggt      7560 ttttttaaagc aagtaaaacc tctacaaatg tggtatctag agctcttcca aatagatctg     7620
gaaggtgctg aggtacgatg agacccgcac caggtgcaga ccctgcgagt gtggcggtaa      7680
acatattagg aaccagcctg tgatgctgga tgtgaccgag gagctgaggc ccgatcactt      7740
ggtgctggcc tgcacccgcg ctgagtttgg ctctagcgat gaagatacag attgaggtac      7800
tgaaatgtgt gggcgtggct taagggtggg aaagaatata aaggtgggg gtcttatgta      7860 gttttgtatc tgttttgcag cagccgccgc cgccatgagc accaactcgt ttgatggaag      7920
cattgtgagc tcatatttga caacgcgcat gcccccatgg gccggggtgc gtcagaatgt      7980
gatgggctcc agcattgatg gtcgccccgt cctgcccgca aactctacta ccttgaccta      8040
cgagaccgtg tctggaacgc cgttggagac tgcagcctcc gccgccgctt cagccgctgc      8100
agccaccgcc cgcgggattg tgactgactt tgctttcctg agcccgcttg caagcagtgc      8160
agcttcccgt tcatccgccc gcgatgacaa gttgacggct cttttggcac aattggattc      8220
tttgacccgg gaacttaatg tcgtttctca gcagctgttg gatctgcgcc agcaggtttc      8280
tgccctgaag gcttcctccc ctcccaatgc ggtttaaaac ataaataaaa aaccagactc      8340
tgtttggatt tggatcaagc aagtgtcttg ctgtctttat ttaggggttt tgcgcgcgcg      8400
gtaggcccgg gaccagcggt ctcggtcgtt gagggtcctg tgtattttt ccaggacgtg      8460 gtaaaggtga ctctggatgt tcagatacat gggcataagc ccgtctctgg ggtggaggta      8520
gcaccactgc agagcttcat gctgcgggt ggtgttgtag atgatccagt cgtagcagga      8580
gcgctgggcg tggtgcctaa aaatgtcttt cagtagcaag ctgattgcca ggggcaggcc      8640
cttggtgtaa gtgtttacaa agcggttaag ctgggatggg tgcatacgtg gggatatgag      8700
atgcatcttg gactgtattt ttaggttggc tatgttccca gccatatccc tccgggggatt     8760 catgttgtgc agaaccacca gcacagtgta tccggtgcac ttgggaaatt tgtcatgtag      8820
cttagaagga aatgcgtgga agaacttgga gacgcccttg tgacctccaa gatttttccat    8880 gcattcgtcc ataatgatgg caatgggccc acgggcggcg gcctgggcga agatatttct     8940
gggatcacta acgtcatagt tgtgttccag gatgagatcg tcataggcca ttttttacaaa    9000 gcgcgggcgg agggtgccag actgcggtat aatggttcca tccggcccag gggcgtagtt     9060
accctcacag atttgcattt cccacgcttt gagttcagat gggggggatca tgtctacctg    9120 cggggcgatg aagaaaacgg tttccggggt aggggagatc agctgggaag aaagcaggtt     9180
cctgagcagc tgcgacttac cgcagccggt gggcccgtaa atcacaccta ttaccgggtg     9240
caactggtag ttaagagagc tgcagctgcc gtcatccctg agcaggggg ccacttcgtt      9300 aagcatgtcc ctgactcgca tgttttccct gaccaaatcc gccagaaggc gctcgccgcc     9360
cagcgatagc agttcttgca aggaagcaaa gttttttcaac ggtttgagac cgtccgccgt    9420
aggcatgctt ttgagcgttt gaccaagcag ttccaggcgg tcccacagct cggtcacctg     9480
ctctacggca tctcgatcca gcatatctcc tcgtttcgcg ggttggggcg gctttcgctg     9540
tacggcagta gtcggtgctc gtccagacgg gccagggtca tgtctttcca cgggcgcagg    9600
gtcctcgtca gcgtagtctg ggtcacggtg aagggggtgcg ctccgggctg cgcgctggcc   9660
agggtgcgct tgaggctggt cctgctggtg ctgaagcgct gccggtcttc gccctgcgcg    9720
tcggccaggt agcatttgac catggtgtca tagtccagcc cctccgcggc gtggcccttg    9780
gcgcgcagct tgcccttgga ggaggcgccg cacgagggga agtgcagact tttgagggcg    9840
tagagcttgg gcgcgagaaa taccgattcc ggggagtagg catccgcgcc gcaggccccg    9900
```

```
cagacggtct cgcattccac gagccaggtg agctctggcc gttcggggtc aaaaaccagg      9960
tttcccccat gcttttgat gcgtttctta cctctggttt ccatgagccg gtgtccacgc     10020
tcggtgacga aaaggctgtc cgtgtccccg tatacagact tgagaggcct gtcctcgacc    10080
gatgcccttg agagccttca acccagtcag ctccttccgg tgggcgcggg gcatgactat    10140
cgtcgccgca cttatgactg tcttctttat catgcaactc gtaggacagg tgccggcagc    10200
gctctgggtc attttcggcg aggaccgctt tcgctggagc gcgacgatga tcggcctgtc    10260
gcttgcggta ttcggaatct tgcacgccct cgctcaagcc ttcgtcactg gtcccgccac    10320
caaacgtttc ggcgagaagc aggccattat cgccggcatg gcggccgacg cgctgggcta    10380
cgtcttgctg gcgttcgcga cgcgaggctg gatggccttc cccattatga ttcttctcgc    10440
ttccggcggc atcgggatgc ccgcgttgca ggccatgctg tccaggcagg tagatgacga    10500
ccatcaggga cagcttcaag gccagcaaaa ggccaggaac cgtaaaaagg ccgcgttgct    10560
ggcgtttttc cataggctcc gcccccctga cgagcatcac aaaaatcgac gctcaagtca    10620
gaggtggcga aacccgacag gactataaag ataccaggcg tttccccctg gaagctccct    10680
cgtgcgctct cctgttccga ccctgccgct taccggatac ctgtccgcct ttctcccttc    10740
gggaagcgtg gcgctttctc atagctcacg ctgtaggtat ctcagttcgg tgtaggtcgt    10800
tcgctccaag ctgggctgtg tgcacgaacc ccccgttcag cccgaccgct gcgccttatc    10860
cggtaactat cgtcttgagt ccaacccggt aagacacgac ttatcgccac tggcagcagc    10920
cactggtaac aggattagca gagcgaggta tgtaggcggt gctacagagt tcttgaagtg    10980
gtggcctaac tacggctaca ctagaaggac agtatttggt atctgcgctc tgctgaagcc    11040
agttaccttc ggaaaaagag ttggtagctc ttgatccggc aaacaaacca ccgctggtag    11100
cggtggtttt tttgtttgca agcagcagat tacgcgcaga aaaaaggat ctcaagaaga    11160 tcctttgatc ttttctacgg ggtctgacgc tcagtggaac gaaaactcac gttaagggat    11220
tttggtcatg agattatcaa aaaggatctt cacctagatc cttttaaatt aaaaatgaag    11280
ttttaaatca atctaaagta tatatgagta aacttggtct gacagttacc aatgcttaat    11340
cagtgaggca cctatctcag cgatctgtct atttcgttca tccatagttg cctgactccc    11400
cgtcgtgtag ataactacga tacgggaggg cttaccatct ggccccagtg ctgcaatgat    11460
accgcgagac ccacgctcac cggctccaga tttatcagca ataaaccagc cagccggaag    11520
ggccgagcgc agaagtggtc ctgcaacttt atccgcctcc atccagtcta ttaattgttg    11580
ccgggaagct agagtaagta gttcgccagt taatagtttg cgcaacgttg ttgccattgc    11640
tgcaggcatc gtggtgtcac gctcgtcgtt tggtatggct tcattcagct ccggttccca    11700
acgatcaagg cgagttacat gatccccat gttgtgcaaa aaagcggtta gctccttcgg    11760
tcctccgatc gttgtcagaa gtaagttggc cgcagtgtta tcactcatgg ttatggcagc    11820
actgcataat tctcttactg tcatgccatc cgtaagatgc ttttctgtga ctggtgagta    11880
ctcaaccaag tcattctgag aatagtgtat gcggcgaccg agttgctctt gcccggcgtc    11940
aacacgggat aataccgcgc cacatagcag aactttaaaa gtgctcatca ttggaaaacg    12000
ttcttcgggg cgaaaactct caaggatctt accgctgttg agatccagtt cgatgtaacc    12060
cactcgtgca cccaactgat cttcagcatc ttttactttc accagcgttt ctgggtgagc    12120
aaaaacagga aggcaaaatg ccgcaaaaaa gggaataagg gcgacacgga aatgttgaat    12180
actcatactc ttccttttc aatattattg aagcatttat cagggttatt gtctcatgag    12240
```
cggatacata tttgaatgta tttagaaaaa             12270

<210> SEQ ID NO 7
<211> LENGTH: 10404
<212> TYPE: DNA
<213> ORGANISM: Artificial Sequence
<220> FEATURE:
<223> OTHER INFORMATION: Synthetic mIL-21

<400> SEQUENCE: 7

| | | |
|---|---|---|
| taaacaaata ggggttccgc gcacatttcc ccgaaaagtg ccacctgacg tctaagaaac | 60 |
| cattattatc atgacattaa cctataaaaa taggcgtatc acgaggccct ttcgtcttca | 120 |
| attaatcgca ccggtatcta tgtcgggtgc ggagaaagag gtaatgaaat ggcagctagc | 180 |
| atcatcaata atatacctta ttttggattg aagccaatat gataatgagg gggtggagtt | 240 |
| tgtgacgtgg cgcggggcgt gggaacgggg cgggtgacgt agtagtgtgg cggaagtgtg | 300 |
| atgttgcaag tgtggcggaa cacatgtaag cgacggatgt ggcaaaagtg acgttttttgg | 360 |
| tgtgcgccgg tgtacacagg aagtgacaat tttcgcgcgg ttttaggcgg atgttgtagt | 420 |
| aaatttgggc gtaaccgagt aagatttggc cattttcgcg ggaaaactga ataagaggaa | 480 |
| gtgaaatctg aataattttg tgttactcat agcgcgtaat atttgtctag ggagatccgg | 540 |
| taccgatatc ctagacaacg atgctgagct aactataacg gtcctaaggt agcgaccgcg | 600 |
| gagactaggt gtatttatct aagcgatcgc ttaattaagg ccggccgccg caataaaata | 660 |
| tctttatttt cattacatct gtgtgttggt tttttgtgtg aatcgatagt actaacatac | 720 |
| gctctccatc aaaacaaaac gaaacaaaac aaactagcaa aataggctgt ccccagtgca | 780 |
| agtgcaggtg ccagaacatt tctctatcga taatgcaggt cggagtactg tcctccgagc | 840 |
| ggagtactgt cctccgagcg gagtactgtc ctccgagcgg agtactgtcc tccgagcgga | 900 |
| gtactgtcct ccgagcggag tactgtcctc cgagcggaga ctcttcgaag gaagaggggc | 960 |
| gggggtcgatc gaccccgccc ctcttccttc aaggaagag gggcggggtc gaagacctag | 1020 |
| agggtatata atgggtgcct tagctggtgt gtgagctcat cttcctgtag atcacgcgtc | 1080 |
| gaagaaggtg agtaatctta acatgctctt ttttttttttt tttgctaatc ccttttgtgt | 1140 |
| gctgatgtta ggatgacatt tacaacaaat gtttgttcct gacaggaaaa accttgctgg | 1200 |
| gtaccttcgt tgccggacac ttcttgtcct ctactttgga aaaaaggaat tgagagccgc | 1260 |
| tagcccacca tggagaggac cctggtgtgc ctggtggtga tcttcctggg caccgtggcc | 1320 |
| cacaagagca gcccccaggg acccgacagg ctgctgatcc ggctgagaca cctgatcgac | 1380 |
| atcgtggagc agctgaagat ttacgagaac gacctggacc ccgagctgct gtccgccccc | 1440 |
| caggacgtga agggccactg cgagcacgcc gccttcgcct gcttccagaa ggccaagctg | 1500 |
| aagcccagca ccccggcaa caacaagacc ttcatcatcg acctggtggc ccagctgaga | 1560 |
| aggaggctgc cgccaggag gggcggcaag aagcagaagc acatcgccaa gtgccccagc | 1620 |
| tgcgacagct acgagaagcg gaccccccaag gagttcctgg agaggctgaa gtggctgctg | 1680 |
| caaaagatga tccaccagca cctgagctga atcgattgcg caaagctttc gcgataggcg | 1740 |
| agaccaatgg gtgtgtacgt agcggccgct cgagaacttg tttattgcag cttataatgg | 1800 |
| ttacaaataa agcaatagca tcacaaattt cacaaataaa gcatttttt cactgcattc | 1860 |
| tagttgtggt ttgtccaaac tcatcaatgt atcttatcat gtctcgtacg gcgtggtagg | 1920 |
| tccgaacgaa tccatggatt accctgttat ccctatccgg agttaacctc gaggacttcg | 1980 |
| gaacttctag aaccagaccg ttcagtttaa acgctcttct cccctcgag ggcctccgcg | 2040 |

```
ccgggttttg gcgcctcccg cgggcgcccc cctcctcacg gcgagcgctg ccacgtcaga    2100
cgaagggcgc agcgagcgtc ctgatccttc cgcccgacag ctcaggacag cggcccgctg    2160
ctcataagac tcggccttag aaccccagta tcagcagaag gacattttag gacgggactt    2220
gggtgactct agggcactgg ttttctttcc agagagcgga acaggcgagg aaaagtagtc    2280
ccttctcggc gattctgcgg agggatctcc gtggggcggt gaacgccgat gattatataa    2340
ggacgcgccg ggtgtggcac agctagttcc gtcgcagccg ggatttgggt cgcggttctt    2400
gtttgtggat cgctgtgatc gtcacttggt gagtagcggg ctgctgggct gggtacgtgc    2460
gctcgggggtt ggcgagtgtg ttttgtgaag ttttttaggc accttttgaa atgtaatcat    2520
ttgggtcaat atgtaatttt cagtgttaga ctagtaaatt gtccgctaaa ttctggccgt    2580
ttttggctttt tttgttagac ggcatgcggg ggggggggg ggcaattggc caccatgggc    2640
cccaagaaga aaaggaaggt ggcccccccc accgacgtga gcctgggcga cgagctgcac    2700
ctggacggcg aggacgtggc catggcccac gccgacgccc tggacgactt cgacctggac    2760
atgctgggcg acggcgacag ccccggcccc ggcttcaccc ccacgacag cgcccctac    2820
ggcgccctgg acatggccga cttcgagttc gagcagatgt tcaccgacgc cctgggcatc    2880
gacgagtacg gcggccatat ggagatgccc gtggacagga ttctggaggc cgaactcgcc    2940
gtggagcaga aaagcgacca gggcgtggag ggccccggcg aaccggcgg cagcggcagc    3000
agccccaacg accccgtgac caacatctgc caggccgccg acaagcagct gttcaccctg    3060
gtggagtggg ccaagaggat tccccacttc agcagcctgc ccctggacga ccaggtgatc    3120
ctgctgaggg ccggatggaa cgagctgctg atcgccagct cagccacag gagcatcgac    3180
gtgagggacg gcatcctgct ggccaccggc ctgcacgtcc ataggaacag cgcccacagc    3240
gccggagtgg gcgccatctt cgacagggtg ctgaccgagc tggtgagcaa gatgagggac    3300
atgaggatgg acaagaccga gctgggctgc ctgagggcca tcatcctgtt caaccccgag    3360
gtgaggggcc tgaaaagcgc ccaggaggtg gagctgctga gggagaaggt gtacgccgcc    3420
ctggaggagt acaccaggac cacccacccc gacgagcccg gcagattcgc caagctgctg    3480
ctgaggctgc ccagcctgag gagcatcggc ctgaagtgcc tggagcacct gttcttcttc    3540
aggctgatcg gcgacgtgcc catcgacacc ttcctgatgg agatgctgga gagcccagc    3600
gacagctgag ccggcaactc gctgtagtaa ttccagcgag aggcagaggg agcgagcggg    3660
cggcgggcta gggtggagga gcccggcgag cagagctgcg ctgcgggcgt cctgggaagg    3720
gagatccgga gcgaataggg ggcttcgcct ctggcccagc cctcccgctg atccccagc    3780
cagcggtgcg caaccctagc cgcatccacg aaactttgcc catagcagcg ggcgggcact    3840
ttgcactgga acttacaaca cccgagcaag gacgcgactc tcccgacgcg gggaggctat    3900
tctgcccatt tggggacact tccccgccgc tgccaggacc cgcttctctg aaaggctctc    3960
cttgcagctg cttagacgct ggatttttt cgggtagtgg aaaaccagca gcctcccgcg    4020
accagatctg ccaccatgaa gctgctgagc agcatcgagc aggcttgcga catctgcagg    4080
ctgaagaagc tgaagtgcag caaggagaag cccaagtgcg ccaagtgcct gaagaacaac    4140
tgggagtgca gatacagccc caagaccaag aggagccccc tgaccaggc ccacctgacc    4200
gaggtggaga gcaggctgga gaggctggag cagctgttcc tgctgatctt ccccagggag    4260
gacctggaca tgatcctgaa gatggacagc ctgcaagaca tcaaggccct gctgaccggc    4320
ctgttcgtgc aggacaacgt gaacaaggac gccgtgaccg acaggctggc cagcgtggag    4380
```

```
accgacatgc ccctgaccct gaggcagcac aggatcagcg ccaccagcag cagcgaggag    4440
agcagcaaca agggccagag gcagctgacc gtgagcccg  agtttccgg  gatcaggccc    4500 gagtgcgtgg tgcccgagac ccagtgcgcc atgaaaagga aggagaagaa ggcccagaag    4560
gagaaggaca agctgcccgt gagcaccacc accgtcgatg accacatgcc ccccatcatg    4620
cagtgcgagc cccccccccc cgaggccgcc aggattcacg aggtcgtgcc caggttcctg    4680
agcgacaagc tgctggtgac caacaggcag aagaacatcc cccagctgac cgccaaccag    4740
cagttcctga tcgccaggct gatctggtat caggacggct acgagcagcc cagcgacgag    4800
gacctgaaaa ggatcaccca gacctggcag caggccgacg acgagaacga ggagagcgac    4860 accccttca  ggcagatcac cgagatgacc atcctgaccg tgcagctgat cgtggagttc    4920
gccaagggcc tgcccggatt cgccaagatc agccagcccg accagatcac cctgctgaag    4980
gcttgcagca gcgaggtgat gatgctgagg gtggccagga ggtacgacgc cgccagcgac    5040
agcatcctgt tcgccaacaa ccaggcttac accagggaca actacaggaa ggctggcatg    5100
gccgaggtga tcgaggacct cctgcacttc tgcagatgta tgtacagcat ggccctggac    5160
aacatccact acgccctgct gaccgccgtg gtgatcttca gcgacaggcc cggcctggag    5220
cagccccagc tggtggagga gatccagagg tactacctga acaccctgag gatctacatc    5280
ctgaaccagc tgagcggcag cgccaggagc agcgtgatct acggcaagat cctgagcatc    5340
ctgagcgagc tgaggaccct gggaatgcag aacagcaata tgtgtatcag cctgaagctg    5400
aagaacagga agctgccccc cttcctggag gagatttggg acgtggccga catgagccac    5460
acccagcccc cccccatcct ggagagcccc accaacctgt gaatcgatta gacatgataa    5520
gatacattga tgagtttgga caaaccacaa ctagaatgca gtgaaaaaaa tgcttaattt    5580
gtgaaatttg tgatgctatt gctttaattt gtaaccattat aagctgcaat aaacaagtta    5640
ataaaacatt tgcattcatt ttatgtttca ggttcagggg gagatgtggg aggtttttta    5700
aagcaagtaa aacctctaca aatgtggtat ctagagctct tccaaataga tctgaaggt    5760 gctgaggtac gatgagaccc gcaccaggtg cagaccctgc gagtgtggcg gtaaacatat    5820
taggaaccag cctgtgatgc tggatgtgac cgaggagctg aggcccgatc acttggtgct    5880
ggcctgcacc cgcgctgagt ttggctctag cgatgaagat acagattgag gtactgaaat    5940
gtgtgggcgt ggcttaaggg tgggaaagaa tatataaggt gggggtctta tgtagttttg    6000
tatctgtttt gcagcagccg ccgccgccat gagcaccaac tcgtttgatg gaagcattgt    6060
gagctcatat ttgacaacgc gcatgccccc atgggccggg gtgcgtcaga atgtgatggg    6120
ctccagcatt gatggtcgcc ccgtcctgcc cgcaaactct actaccttga cctacgagac    6180
cgtgtctgga acgccgttgg agactgcagc ctccgccgcc gcttcagccg ctgcagccac    6240
cgcccgcggg attgtgactg actttgcttt cctgagcccg cttgcaagca gtgcagcttc    6300
ccgttcatcc gcccgcgatg acaagttgac ggctcttttg gcacaattgg attctttgac    6360
ccgggaactt aatgtcgttt ctcagcagct gttggatctg cgccagcagg tttctgccct    6420
gaaggcttcc tcccctccca atgcggttta aacataaat  aaaaaaccag actctgtttg    6480
gatttggatc aagcaagtgt cttgctgtct ttatttaggg gttttgcgcg cgcggtaggc    6540
ccgggaccag cggtctcggt cgttgagggt cctgtgtatt ttttccagga cgtggtaaag    6600
gtgactctgg atgttcagat acatgggcat aagcccgtct ctgggtgga  ggtagcacca    6660 ctgcagagct tcatgctgcg gggtggtgtt gtagatgatc cagtcgtagc aggagcgctg    6720
ggcgtggtgc ctaaaaatgt ctttcagtag caagctgatt gccaggggca ggcccttggt    6780
```

-continued

```
gtaagtgttt acaaagcggt taagctggga tgggtgcata cgtggggata tgagatgcat    6840
cttggactgt atttttaggt tggctatgtt cccagccata tccctccggg gattcatgtt    6900
gtgcagaacc accagcacag tgtatccggt gcacttggga aatttgtcat gtagcttaga    6960
aggaaatgcg tggaagaact tggagacgcc cttgtgacct ccaagatttt ccatgcattc    7020
gtccataatg atggcaatgg gcccacgggc ggcggcctgg gcgaagatat ttctgggatc    7080
actaacgtca tagttgtgtt ccaggatgag atcgtcatag gccattttta caaagcgcgg    7140
gcggagggtg ccagactgcg gtataatggt tccatccggc ccaggggcgt agttaccctc    7200
acagatttgc atttcccacg ctttgagttc agatgggggg atcatgtcta cctgcggggc    7260
gatgaagaaa acggtttccg gggtagggga gatcagctgg aagaaagca ggttcctgag     7320
cagctgcgac ttaccgcagc cggtgggccc gtaaatcaca cctattaccg ggtgcaactg    7380
gtagttaaga gagctgcagc tgccgtcatc cctgagcagg ggggccactt cgttaagcat    7440
gtccctgact cgcatgtttt ccctgaccaa atccgccaga aggcgctcgc cgcccagcga    7500
tagcagttct tgcaaggaag caaagttttt caacggtttg agaccgtccg ccgtaggcat    7560
gcttttgagc gtttgaccaa gcagttccag gcggtccac agctcggtca cctgctctac     7620
ggcatctcga tccagcatat ctcctcgttt cgcggttgg ggcggctttc gctgtacggc     7680
agtagtcggt gctcgtccag acgggccagg gtcatgtctt tccacggggcg cagggtcctc   7740
gtcagcgtag tctgggtcac ggtgaagggg tgcgctccgg gctgcgcgct ggccagggtg    7800
cgcttgaggc tggtcctgct ggtgctgaag cgctgccggt cttcgccctg cgcgtcggcc    7860
aggtagcatt tgaccatggt gtcatagtcc agcccctccg cggcgtggcc cttggcgcgc    7920
agcttgccct tggaggaggc gccgcacgag gggcagtgca gacttttgag ggcgtagagc    7980
ttgggcgcga gaaataccga ttccggggag taggcatccg cgccgcaggc cccgcagacg    8040
gtctcgcatt ccacgagcca ggtgagctct ggccgttcgg ggtcaaaaac caggtttccc    8100
ccatgctttt tgatgcgttt cttacctctg gtttccatga gccggtgtcc acgctcggtg    8160
acgaaaaggc tgtccgtgtc cccgtataca gacttgagag gcctgtcctc gaccgatgcc    8220
cttgagagcc ttcaacccag tcagctcctt ccggtgggcg cggggcatga ctatcgtcgc    8280
cgcacttatg actgtcttct ttatcatgca actcgtagga caggtgccgg cagcgctctg    8340
ggtcattttc ggcgaggacc gctttcgctg gagcgcgacg atgatcggcc tgtcgcttgc    8400
ggtattcgga atcttgcacg ccctcgctca agccttcgtc actggtcccg ccaccaaacg    8460
tttcggcgag aagcaggcca ttatcgccgg catggcggcc gacgcgctgg gctacgtctt    8520
gctggcgttc gcgacgcgag gctggatggc cttccccatt atgattcttc tcgcttccgg    8580
cggcatcggg atgcccgcgt tgcaggccat gctgtccagg caggtagatg acgaccatca    8640
gggacagctt caaggccagc aaaaggccag gaaccgtaaa aaggccgcgt tgctggcgtt    8700
tttccatagg ctccgccccc ctgacgagca tcacaaaaat cgacgctcaa gtcagaggtg    8760
gcgaaacccg acaggactat aaagatacca ggcgtttccc cctggaagct ccctcgtgcg    8820
ctctcctgtt ccgaccctgc cgcttaccgg atacctgtcc gcctttctcc cttcgggaag    8880
cgtggcgctt tctcatagct cacgctgtag gtatctcagt tcggtgtagg tcgttcgctc    8940
caagctgggc tgtgtgcacg aaccccccgt tcagcccgac cgctgcgcct tatccggtaa    9000
ctatcgtctt gagtccaacc cggtaagaca cgacttatcg ccactggcag cagccactgg    9060
taacaggatt agcagagcga ggtatgtagg cggtgctaca gagttcttga agtggtggcc    9120
```

| | | |
|---|---|---|
| taactacggc tacactagaa ggacagtatt tggtatctgc gctctgctga agccagttac | 9180 | |
| cttcggaaaa agagttggta gctcttgatc cggcaaacaa accaccgctg gtagcggtgg | 9240 | |
| ttttttttgtt tgcaagcagc agattacgcg cagaaaaaaa ggatctcaag aagatccttt | 9300 | |
| gatcttttct acggggtctg acgctcagtg gaacgaaaac tcacgttaag gattttggt | 9360 | |
| catgagatta tcaaaaagga tcttcaccta gatcctttta aattaaaaat gaagttttaa | 9420 | |
| atcaatctaa agtatatatg agtaaacttg gtctgacagt taccaatgct taatcagtga | 9480 | |
| ggcacctatc tcagcgatct gtctatttcg ttcatccata gttgcctgac tccccgtcgt | 9540 | |
| gtagataact acgatacggg agggcttacc atctggcccc agtgctgcaa tgataccgcg | 9600 | |
| agacccacgc tcaccggctc cagatttatc agcaataaac cagccagccg aagggccga | 9660 | |
| gcgcagaagt ggtcctgcaa ctttatccgc ctccatccag tctattaatt gttgccggga | 9720 | |
| agctagagta agtagttcgc cagttaatag tttgcgcaac gttgttgcca ttgctgcagg | 9780 | |
| catcgtggtg tcacgctcgt cgtttggtat ggcttcattc agctccggtt cccaacgatc | 9840 | |
| aaggcgagtt acatgatccc ccatgttgtg caaaaaagcg gttagctcct tcggtcctcc | 9900 | |
| gatcgttgtc agaagtaagt tggccgcagt gttatcactc atggttatgg cagcactgca | 9960 | |
| taattctctt actgtcatgc catccgtaag atgcttttct gtgactggtg agtactcaac | 10020 | |
| caagtcattc tgagaatagt gtatgcggcg accgagttgc tcttgcccgg cgtcaacacg | 10080 | |
| ggataatacc gcgccacata gcagaacttt aaaagtgctc atcattggaa aacgttcttc | 10140 | |
| ggggcgaaaa ctctcaagga tcttaccgct gttgagatcc agttcgatgt aacccactcg | 10200 | |
| tgcacccaac tgatcttcag catctttac tttcaccagc gtttctgggt gagcaaaaac | 10260 | |
| aggaaggcaa aatgccgcaa aaaagggaat aagggcgaca cggaaatgtt gaatactcat | 10320 | |
| actcttcctt tttcaatatt attgaagcat ttatcagggt tattgtctca tgagcggata | 10380 | |
| catatttgaa tgtatttaga aaaa | 10404 | |

<210> SEQ ID NO 8
<211> LENGTH: 10452
<212> TYPE: DNA
<213> ORGANISM: Artificial Sequence
<220> FEATURE:
<223> OTHER INFORMATION: Synthetic hIL-21

<400> SEQUENCE: 8

| | | |
|---|---|---|
| taaacaaata ggggttccgc gcacatttcc ccgaaaagtg ccacctgacg tctaagaaac | 60 | |
| cattattatc atgacattaa cctataaaaa taggcgtatc acgaggccct ttcgtcttca | 120 | |
| attaatcgca ccggtatcta tgtcgggtgc ggagaaagag gtaatgaaat ggcagctagc | 180 | |
| atcatcaata atataccta ttttggattg aagccaatat gataatgagg gggtggagtt | 240 | |
| tgtgacgtgg cgcggggcgt gggaacgggg cgggtgacgt agtagtgtgg cggaagtgtg | 300 | |
| atgttgcaag tgtggcggaa cacatgtaag cgacggatgt ggcaaaagtg acgttttgg | 360 | |
| tgtgcgccgg tgtacacagg aagtgacaat tttcgcgcgg ttttaggcgg atgttgtagt | 420 | |
| aaatttgggc gtaaccgagt aagatttggc cattttcgcg ggaaaactga ataagaggaa | 480 | |
| gtgaaatctg aataatttg tgttactcat agcgcgtaat atttgtctag ggagatccgg | 540 | |
| taccgatatc ctagacaacg atgctgagct aactataacg gtcctaaggt agcgaccgcg | 600 | |
| gagactaggt gtatttatct aagcgatcgc ttaattaagg ccggccgccg caataaaata | 660 | |
| tcttattttt cattacatct gtgtgttggt ttttgtgtg aatcgatagt actaacatac | 720 | |
| gctctccatc aaaacaaaac gaaacaaaac aaactagcaa aataggctgt ccccagtgca | 780 | |

```
agtgcaggtg ccagaacatt tctctatcga taatgcaggt cggagtactg tcctccgagc    840
ggagtactgt cctccgagcg gagtactgtc ctccgagcgg agtactgtcc tccgagcgga    900
gtactgtcct ccgagcggag tactgtcctc cgagcggaga ctcttcgaag aagaggggc    960 ggggtcgatc gaccccgccc ctcttccttc gaaggaagag gggcggggtc gaagacctag   1020
agggtatata atgggtgcct tagctggtgt gtgagctcat cttcctgtag atcacgcgtc   1080
gaagaaggtg agtaatctta acatgctctt ttttttttt tttgctaatc ccttttgtgt    1140
gctgatgtta ggatgacatt tacaacaaat gtttgttcct gacaggaaaa accttgctgg   1200
gtaccttcgt tgccggacac ttcttgtcct ctactttgga aaaaggaat tgagagccgc    1260 tagcccacca tgagaagcag ccccggcaac atggagagaa tcgtgatctg cctgatggtg   1320
atcttcctgg gcaccctggt gcataagagc agcagccagg gccaggacag acacatgatc   1380
cgcatgagac agctgatcga catcgtggac cagctgaaga actacgtgaa cgacctggtg   1440
cccgagttcc tgcccgcccc cgaggacgtg gagaccaact gcgagtggag cgccttcagc   1500
tgcttccaga aggcccagct gaagtccgcc aacaccggca caacgagag aatcatcaac    1560 gtgagcatca agaagctgaa gcggaagccc ccagcacca cgccggaag aagacagaag     1620 cacagactga cctgtcccag ctgcgacagc tacgagaaga gccccccaa ggagttcctg    1680 gagagattca gagcctgct gcaaaagatg atccaccagc acctgagcag cagaacccac    1740
ggcagcgagg acagctgaat cgattgcgca agctttcgc gataggcgag accaatgggt    1800
gtgtacgtag cggccgctcg agaacttgtt tattgcagct tataatggtt acaaataaag   1860
caatagcatc acaaatttca caaataaagc attttttca ctgcattcta gttgtggttt    1920
gtccaaactc atcaatgtat cttatcatgt ctcgtacggc gtggtaggtc cgaacgaatc   1980
catggattac cctgttatcc ctatccggag ttaacctcga ggacttcgga acttctagaa   2040
ccagaccgtt cagtttaaac gctcttctcc ccctcgaggg cctccgcgcc gggttttggc   2100
gcctcccgcg ggcgccccc tcctcacggc gagcgctgcc acgtcagacg aagggcgcag    2160
cgagcgtcct gatccttccg cccggacgct caggacagcg gcccgctgct cataagactc   2220
ggccttagaa ccccagtatc agcagaagga cattttagga cgggacttgg gtgactctag   2280
ggcactggtt ttcttccag agagcggaac aggcgaggaa aagtagtccc ttctcggcga    2340
ttctgcggag ggatccgct ggggcggtga acgccgatga ttatataagg acgcgccggg    2400
tgtggcacag ctagttccgt cgcagccggg atttgggtcg cggttcttgt ttgtggatcg   2460
ctgtgatcgt cacttggtga gtagcgggct gctgggctgg gtacgtgcgc tcggggttgg   2520
cgagtgtgtt ttgtgaagtt ttttaggcac cttttgaaat gtaatcattt gggtcaatat   2580
gtaattttca gtgttagact agtaaattgt ccgctaaatt ctggccgttt ttggcttttt   2640
tgttagacgg catgcggggg gggggggggg caattggcca ccatgggccc caagaagaaa   2700
aggaaggtgg ccccccccac cgacgtgagc ctgggcgacg agctgcacct ggacggcgag   2760
gacgtggcca tggcccacgc cgacgccctg gacgacttcg acctggacat gctgggcgac   2820
ggcgacagcc ccggcccggg cttcacccc cacgacagcg cccctacgg cgccctggac    2880 atggccgact tcgagttcga gcagatgttc accgacgccc tgggcatcga cgagtacggc   2940
ggccatatgg agatgcccgt ggacaggatt ctggaggccg aactcgccgt ggagcagaaa   3000
agcgaccagg gcgtggaggg ccccggcgga accggcggca gcggcagcag ccccaacgac   3060
cccgtgacca acatctgcca ggccgccgac aagcagctgt tcaccctggt ggagtgggcc   3120
```

```
aagaggattc cccacttcag cagcctgccc ctggacgacc aggtgatcct gctgagggcc    3180
ggatggaacg agctgctgat cgccagcttc agccacagga gcatcgacgt gagggacggc    3240
atcctgctgg ccaccggcct gcacgtccat aggaacagcg cccacagcgc cggagtgggc    3300
gccatcttcg acagggtgct gaccgagctg gtgagcaaga tgagggacat gaggatggac    3360
aagaccgagc tgggctgcct gagggccatc atcctgttca accccgaggt gaggggcctg    3420
aaaagcgccc aggaggtgga gctgctgagg gagaaggtgt acgccgccct ggaggagtac    3480
accaggacca cccaccccga cgagcccggc agattcgcca agctgctgct gaggctgccc    3540
agcctgagga gcatcggcct gaagtgcctg gagcacctgt tcttcttcag gctgatcggc    3600
gacgtgccca tcgacacctt cctgatggag atgctggaga gccccagcga cagctgagcc    3660
ggcaactcgc tgtagtaatt ccagcgagag gcagagggag cgagcgggcg gcgggctagg    3720
gtggaggagc ccggcgagca gagctgcgct gcgggcgtcc tgggaaggga gatccggagc    3780
gaataggggg cttcgcctct ggcccagccc tcccgctgat cccccagcca gcggtgcgca    3840
accctagccg catccacgaa actttgccca tagcagcggg cgggcacttt gcactggaac    3900
ttacaacacc cgagcaagga cgcgactctc ccgacgcggg gaggctattc tgcccatttg    3960
gggacacttc cccgccgctg ccaggacccg cttctctgaa aggctctcct tgcagctgct    4020
tagacgctgg attttttcg ggtagtggaa aaccagcagc ctcccgcgac cagatctgcc    4080
accatgaagc tgctgagcag catcgagcag gcttgcgaca tctgcaggct gaagaagctg    4140
aagtgcagca aggagaagcc caagtgcgcc aagtgcctga gaacaactg ggagtgcaga    4200 tacagcccca agaccaagag gagcccctg accaggccc acctgaccga ggtggagagc    4260
aggctggaga ggctggagca gctgttcctg ctgatcttcc ccagggagga cctggacatg    4320
atcctgaaga tggacagcct gcaagacatc aaggccctgc tgaccggcct gttcgtgcag    4380
gacaacgtga acaaggacgc cgtgaccgac aggctggcca gcgtggagac cgacatgccc    4440
ctgaccctga ggcagcacag gatcagcgcc accagcagca gcgaggagag cagcaacaag    4500
ggccagaggc agctgaccgt gagccccgag tttcccggga tcaggcccga gtgcgtggtg    4560
cccgagaccc agtgcgccat gaaaaggaag gagaagaagg cccagaagga gaaggacaag    4620
ctgcccgtga gcaccaccac cgtcgatgac cacatgcccc ccatcatgca gtgcgagccc    4680
cccccccccg aggccgccag gattcacgag gtcgtgccca ggttcctgag cgacaagctg    4740
ctggtgacca acaggcagaa gaacatcccc cagctgaccg ccaaccagca gttcctgatc    4800
gccaggctga tctggtatca ggacggctac agcagccca gcgacgagga cctgaaaagg    4860
atcacccaga cctggcagca ggccgacgac gagaacgagg agagcgacac ccccttcagg    4920
cagatcaccg agatgaccat cctgaccgtg cagctgatcg tggagttcgc caagggcctg    4980
cccggattcg ccaagatcag ccagcccgac cagatcaccc tgctgaaggc ttgcagcagc    5040
gaggtgatga tgctgagggt ggccaggagg tacgacgccg ccagcgacag catcctgttc    5100
gccaacaacc aggcttacac cagggacaac tacaggaagg ctggcatggc cgaggtgatc    5160
gaggacctcc tgcacttctg cagatgtatg tacagcatgg ccctggacaa catccactac    5220
gccctgctga ccgccgtggt gatcttcagc gacaggcccg gcctggagca gccccagctg    5280
gtggaggaga tccagaggta ctacctgaac accctgagga tctacatcct gaaccagctg    5340
agcggcagcg ccaggagcag cgtgatctac ggcaagatcc tgagcatcct gagcgagctg    5400
aggaccctgg gaatgcagaa cagcaatatg tgtatcagcc tgaagctgaa gaacaggaag    5460
ctgcccccct tcctggagga gatttgggac gtggccgaca tgagccacac ccagccccc    5520
```

```
cccatcctgg agagccccac caacctgtga atcgattaga catgataaga tacattgatg    5580
agtttggaca aaccacaact agaatgcagt gaaaaaaatg cttaatttgt gaaatttgtg    5640
atgctattgc ttaatttgta accattataa gctgcaataa acaagttaat aaaacatttg    5700
cattcatttt atgtttcagg ttcaggggga gatgtgggag ttttttaaa gcaagtaaaa    5760 cctctacaaa tgtggtatct agagctcttc caaatagatc tggaaggtgc tgaggtacga    5820
tgagacccgc accaggtgca gaccctgcga gtgtggcggt aaacatatta ggaaccagcc    5880
tgtgatgctg gatgtgaccg aggagctgag gcccgatcac ttggtgctgg cctgcacccg    5940
cgctgagttt ggctctagcg atgaagatac agattgaggt actgaaatgt gtgggcgtgg    6000
cttaagggtg ggaaagaata tataaggtgg gggtcttatg tagttttgta tctgttttgc    6060
agcagccgcc gccgccatga gcaccaactc gtttgatgga agcattgtga gctcatattt    6120
gacaacgcgc atgcccccat gggccggggt gcgtcagaat gtgatgggct ccagcattga    6180
tggtcgcccc gtcctgcccg caaactctac taccttgacc tacgagaccg tgtctggaac    6240
gccgttggag actgcagcct ccgccgccgc ttcagccgct gcagccaccg cccgcgggat    6300
tgtgactgac tttgctttcc tgagcccgct tgcaagcagt gcagcttccc gttcatccgc    6360
ccgcgatgac aagttgacgg ctcttttggc acaattggat tctttgaccc gggaacttaa    6420
tgtcgtttct cagcagctgt tggatctgcg ccagcaggtt tctgccctga aggcttcctc    6480
ccctcccaat gcggtttaaa acataaataa aaaaccagac tctgtttgga tttggatcaa    6540
gcaagtgtct tgctgtcttt atttaggggt tttgcgcgcg cggtaggccc gggaccagcg    6600
gtctcggtcg ttgagggtcc tgtgtatttt ttccaggacg tggtaaaggt gactctggat    6660
gttcagatac atgggcataa gcccgtctct ggggtggagg tagcaccact gcagagcttc    6720
atgctgcggg gtggtgttgt agatgatcca gtcgtagcag gagcgctggg cgtggtgcct    6780
aaaaatgtct ttcagtagca agctgattgc caggggcagg cccttggtgt aagtgtttac    6840
aaagcggtta agctgggatg ggtgcatacg tggggatatg agatgcatct tggactgtat    6900
ttttaggttg gctatgttcc cagccatatc cctccgggga ttcatgttgt gcagaaccac    6960
cagcacagtg tatccggtgc acttgggaaa tttgtcatgt agcttagaag gaaatgcgtg    7020
gaagaacttg gagacgccct tgtgacctcc aagattttcc atgcattcgt ccataatgat    7080
ggcaatgggc ccacgggcgg cggcctgggc gaagatattt ctgggatcac taacgtcata    7140
gttgtgttcc aggatgagat cgtcataggc cattttttaca aagcgcgggc ggagggtgcc    7200
agactgcggt ataatggttc catccggccc aggggcgtag ttaccctcac agatttgcat    7260
ttcccacgct ttgagttcag atgggggat catgtctacc tgcgggcga tgaagaaaac    7320 ggtttccggg gtaggggaga tcagctggga agaaagcagg ttcctgagca gctgcgactt    7380
accgcagccg gtgggcccgt aaatcacacc tattaccggg tgcaactggt agttaagaga    7440
gctgcagctg ccgtcatccc tgagcagggg ggccacttcg ttaagcatgt ccctgactcg    7500 catgtttcc ctgaccaaat ccgccagaag gcgctcgccg cccagcgata gcagttcttg    7560
caaggaagca aagttttca acggtttgag accgtccgcc gtaggcatgc ttttgagcgt    7620
ttgaccaagc agttccaggc ggtcccacag ctcggtcacc tgctctacgg catctcgatc    7680
cagcatatct cctcgtttcg cgggttgggg cggctttcgc tgtacggcag tagtcggtgc    7740
tcgtccagac gggccaggt catgtctttc cacgggcgca gggtcctcgt cagcgtagtc    7800
tgggtcacgg tgaagggtgt gcgctccggg ctgcgcgctgg ccagggtgcg cttgaggctg    7860
```

```
gtcctgctgg tgctgaagcg ctgccggtct tcgccctgcg cgtcggccag gtagcatttg    7920
accatggtgt catagtccag cccctccgcg gcgtggccct tggcgcgcag cttgcccttg    7980
gaggaggcgc cgcacgaggg gcagtgcaga cttttgaggg cgtagagctt gggcgcgaga    8040
aataccgatt ccgggagta ggcatccgcg ccgcaggccc cgcagacggt ctcgcattcc    8100
acgagccagg tgagctctgg ccgttcgggg tcaaaaacca ggtttccccc atgcttttg    8160 atgcgtttct tacctctggt ttccatgagc cggtgtccac gctcggtgac gaaaaggctg    8220
tccgtgtccc cgtatacaga cttgagaggc ctgtcctcga ccgatgccct tgagagcctt    8280
caacccagtc agctccttcc ggtgggcgcg gggcatgact atcgtcgccg cacttatgac    8340
tgtcttcttt atcatgcaac tcgtaggaca ggtgccggca gcgctctggg tcattttcgg    8400
cgaggaccgc tttcgctgga gcgcgacgat gatcggcctg tcgcttgcgg tattcggaat    8460
cttgcacgcc ctcgctcaag ccttcgtcac tggtcccgcc accaaacgtt tcggcgagaa    8520
gcaggccatt atcgccggca tggcggccga cgcgctgggc tacgtcttgc tggcgttcgc    8580
gacgcgaggc tggatggcct tccccattat gattcttctc gcttccggcg gcatcgggat    8640
gcccgcgttg caggccatgc tgtccaggca ggtagatgac gaccatcagg gacagcttca    8700
aggccagcaa aaggccagga accgtaaaaa ggccgcgttg ctggcgtttt tccataggct    8760 ccgccccct gacgagcatc acaaaaatcg acgctcaagt cagaggtggc gaaacccgac    8820
aggactataa agataccagg cgtttccccc tggaagctcc ctcgtgcgct ctcctgttcc    8880
gaccctgccg cttaccggat acctgtccgc ctttctccct tcgggaagcg tggcgctttc    8940
tcatagctca cgctgtaggt atctcagttc ggtgtaggtc gttcgctcca agctgggctg    9000
tgtgcacgaa ccccccgttc agcccgaccg ctgcgcctta tccggtaact atcgtcttga    9060
gtccaacccg gtaagacacg acttatcgcc actggcagca gccactggta acaggattag    9120
cagagcgagg tatgtaggcg gtgctacaga gttcttgaag tggtggccta actacggcta    9180
cactagaagg acagtatttg gtatctgcgc tctgctgaag ccagttacct tcggaaaaag    9240
agttggtagc tcttgatccg gcaaacaaac caccgctggt agcggtggtt ttttgtttg    9300 caagcagcag attacgcgca gaaaaaaagg atcctttga tcttttctac    9360 ggggtctgac gctcagtgga acgaaaactc acgttaaggg attttggtca tgagattatc    9420
aaaaaggatc ttcacctaga tccttttaaa ttaaaatga agttttaaat caatctaaag    9480
tatatatgag taaacttggt ctgacagtta ccaatgctta atcagtgagg cacctatctc    9540
agcgatctgt ctatttcgtt catccatagt tgcctgactc cccgtcgtgt agataactac    9600
gatacgggag ggcttaccat ctggccccag tgctgcaatg ataccgcgag acccacgctc    9660
accggctcca gatttatcag caataaacca gccagccgga agggccgagc gcagaagtgg    9720
tcctgcaact ttatccgcct ccatccagtc tattaattgt tgccgggaag ctagagtaag    9780
tagttcgcca gttaatagtt tgcgcaacgt tgttgccatt gctgcaggca tcgtggtgtc    9840
acgctcgtcg tttggtatgg cttcattcag ctccggttcc caacgatcaa ggcgagttac    9900
atgatccccc atgttgtgca aaaaagcggt tagctccttc ggtcctccga tcgttgtcag    9960
aagtaagttg gccgcagtgt tatcactcat ggttatggca gcactgcata attctcttac    10020
tgtcatgcca tccgtaagat gcttttctgt gactggtgag tactcaacca agtcattctg    10080
agaatagtgt atgcggcgac cgagttgctc ttgcccggcg tcaacacggg ataataccgc    10140
gccacatagc agaactttaa aagtgctcat cattggaaaa cgttcttcgg ggcgaaaact    10200
ctcaaggatc ttaccgctgt tgagatccag ttcgatgtaa cccactcgtg cacccaactg    10260
```

```
atcttcagca tctttactt tcaccagcgt ttctgggtga gcaaaaacag gaaggcaaaa      10320
tgccgcaaaa aagggaataa gggcgacacg gaaatgttga atactcatac tcttcctttt      10380
tcaatattat tgaagcattt atcagggtta ttgtctcatg agcggataca tatttgaatg      10440
tatttagaaa aa                                                          10452
```

<210> SEQ ID NO 9
<211> LENGTH: 489
<212> TYPE: DNA
<213> ORGANISM: Artificial Sequence
<220> FEATURE:
<223> OTHER INFORMATION: Synthetic mIL-21
<220> FEATURE:
<221> NAME/KEY: CDS
<222> LOCATION: (1)..(489)

<400> SEQUENCE: 9

```
atg aag atc ctg aag ccc tac atg agg aac acc agc atc agc tgt tac         48
Met Lys Ile Leu Lys Pro Tyr Met Arg Asn Thr Ser Ile Ser Cys Tyr
1               5                   10                  15 ctg tgc ttc ctg ctg aac agc cac ttc ctg acc gag gcc gga atc cac         96
Leu Cys Phe Leu Leu Asn Ser His Phe Leu Thr Glu Ala Gly Ile His
            20                  25                  30 gtc ttc atc ctg ggc tgc gtg agc gtg ggc ctg ccc aag acc gag gcc        144
Val Phe Ile Leu Gly Cys Val Ser Val Gly Leu Pro Lys Thr Glu Ala
35                  40                  45 aac tgg atc gac gtg agg tac gac ctg gag aag atc gag agc ctg atc        192
Asn Trp Ile Asp Val Arg Tyr Asp Leu Glu Lys Ile Glu Ser Leu Ile
    50                  55                  60 cag agc atc cac atc gac acc acc ctg tac acc gac agc gac ttc cac        240
Gln Ser Ile His Ile Asp Thr Thr Leu Tyr Thr Asp Ser Asp Phe His
65                  70                  75                  80 ccc agc tgc aag gtg acc gcc atg aac tgc ttc ctg ctg gag ctg caa        288
Pro Ser Cys Lys Val Thr Ala Met Asn Cys Phe Leu Leu Glu Leu Gln
                85                  90                  95 gtg atc ctg cac gag tac agc aac atg acc ctg aac gag acc gtg agg        336
Val Ile Leu His Glu Tyr Ser Asn Met Thr Leu Asn Glu Thr Val Arg
            100                 105                 110 aac gtg ctg tac ctg gct aac agc acc ctg agc agc aac aag aac gtg        384
Asn Val Leu Tyr Leu Ala Asn Ser Thr Leu Ser Ser Asn Lys Asn Val
        115                 120                 125 gcc gag agc ggc tgc aag gag tgt gag gag ctg gag gag aag acc ttc        432
Ala Glu Ser Gly Cys Lys Glu Cys Glu Glu Leu Glu Glu Lys Thr Phe
    130                 135                 140 acc gag ttc ctc cag agc ttc atc agg atc gtg cag atg ttc atc aac        480
Thr Glu Phe Leu Gln Ser Phe Ile Arg Ile Val Gln Met Phe Ile Asn
145                 150                 155                 160 acc agc tga                                                            489
Thr Ser
```

<210> SEQ ID NO 10
<211> LENGTH: 162
<212> TYPE: PRT
<213> ORGANISM: Artificial Sequence
<220> FEATURE:
<223> OTHER INFORMATION: Synthetic Construct

<400> SEQUENCE: 10

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
```

```
                    20                  25                  30
Val Phe Ile Leu Gly Cys Val Ser Val Gly Leu Pro Lys Thr Glu Ala
            35                  40                  45

Asn Trp Ile Asp Val Arg Tyr Asp Leu Glu Lys Ile Glu Ser Leu Ile
 50                  55                  60

Gln Ser Ile His Ile Asp Thr Thr Leu Tyr Thr Asp Ser Asp Phe His
 65                  70                  75                  80

Pro Ser Cys Lys Val Thr Ala Met Asn Cys Phe Leu Leu Glu Leu Gln
                 85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser

<210> SEQ ID NO 11
<211> LENGTH: 489
<212> TYPE: DNA
<213> ORGANISM: Artificial Sequence
<220> FEATURE:
<223> OTHER INFORMATION: Synthetic mIL-15
<220> FEATURE:
<221> NAME/KEY: CDS
<222> LOCATION: (1)..(489)

<400> SEQUENCE: 11 atg aag atc ctg aag ccc tac atg agg aac acc agc atc agc tgt tac      48
Met Lys Ile Leu Lys Pro Tyr Met Arg Asn Thr Ser Ile Ser Cys Tyr
 1               5                  10                  15 ctg tgc ttc ctg ctg aac agc cac ttc ctg acc gag gcc gga atc cac      96
Leu Cys Phe Leu Leu Asn Ser His Phe Leu Thr Glu Ala Gly Ile His
             20                  25                  30 gtc ttc atc ctg ggc tgc gtg agc gtg ggc ctg ccc aag acc gag gcc     144
Val Phe Ile Leu Gly Cys Val Ser Val Gly Leu Pro Lys Thr Glu Ala
         35                  40                  45 aac tgg atc gac gtg agg tac gac ctg gag aag atc gag agc ctg atc     192
Asn Trp Ile Asp Val Arg Tyr Asp Leu Glu Lys Ile Glu Ser Leu Ile
 50                  55                  60 cag agc atc cac atc gac acc acc ctg tac acc gac agc gac ttc cac     240
Gln Ser Ile His Ile Asp Thr Thr Leu Tyr Thr Asp Ser Asp Phe His
 65                  70                  75                  80 ccc agc tgc aag gtg acc gcc atg aac tgc ttc ctg ctg gag ctg caa     288
Pro Ser Cys Lys Val Thr Ala Met Asn Cys Phe Leu Leu Glu Leu Gln
                 85                  90                  95 gtg atc ctg cac gag tac agc aac atg acc ctg aac gag acc gtg agg     336
Val Ile Leu His Glu Tyr Ser Asn Met Thr Leu Asn Glu Thr Val Arg
            100                 105                 110 aac gtg ctg tac ctg gct aac agc acc ctg agc agc aac aag aac gtg     384
Asn Val Leu Tyr Leu Ala Asn Ser Thr Leu Ser Ser Asn Lys Asn Val
        115                 120                 125 gcc gag agc ggc tgc aag gag tgt gag gag ctg gag gag aag acc ttc     432
Ala Glu Ser Gly Cys Lys Glu Cys Glu Glu Leu Glu Glu Lys Thr Phe
    130                 135                 140 acc gag ttc ctc cag agc ttc atc agg atc gtg cag atg ttc atc aac     480
Thr Glu Phe Leu Gln Ser Phe Ile Arg Ile Val Gln Met Phe Ile Asn
```

```
                     145                 150                 155                 160 acc agc tga                                                                               489
Thr Ser <210> SEQ ID NO 12
<211> LENGTH: 162
<212> TYPE: PRT
<213> ORGANISM: Artificial Sequence
<220> FEATURE:
<223> OTHER INFORMATION: Synthetic Construct

<400> SEQUENCE: 12

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser

<210> SEQ ID NO 13
<211> LENGTH: 1008
<212> TYPE: DNA
<213> ORGANISM: Artificial Sequence
<220> FEATURE:
<223> OTHER INFORMATION: Synthetic mIL-12, mp40
<220> FEATURE:
<221> NAME/KEY: CDS
<222> LOCATION: (1)..(1008)

<400> SEQUENCE: 13 atg tgc ccc cag aag ctg acc atc agc tgg ttc gcc atc gtg ctg ctg      48
Met Cys Pro Gln Lys Leu Thr Ile Ser Trp Phe Ala Ile Val Leu Leu
1               5                   10                  15 gtg agc ccc ctg atg gcc atg tgg gag ctg gag aag gac gtg tac gtg      96
Val Ser Pro Leu Met Ala Met Trp Glu Leu Glu Lys Asp Val Tyr Val
            20                  25                  30 gtg gag gtg gac tgg acc ccc gac gcc ccc ggc gag acc gtg aac ctg     144
Val Glu Val Asp Trp Thr Pro Asp Ala Pro Gly Glu Thr Val Asn Leu
        35                  40                  45 act tgc gac acc ccc gag gag gac gac atc acc tgg acc agc gac cag     192
Thr Cys Asp Thr Pro Glu Glu Asp Asp Ile Thr Trp Thr Ser Asp Gln
    50                  55                  60 aga cac ggc gtc atc ggc agc ggc aag acc ctg acc atc acc gtg aag     240
Arg His Gly Val Ile Gly Ser Gly Lys Thr Leu Thr Ile Thr Val Lys
65                  70                  75                  80
```

-continued

```
gag ttc ctg gac gcc gga cag tac acc tgt cac aag ggc ggc gag acc      288
Glu Phe Leu Asp Ala Gly Gln Tyr Thr Cys His Lys Gly Gly Glu Thr
                85                  90                  95 ctg agc cac agc cac ctg ttg ctg cac aag aag gag aac ggc atc tgg      336
Leu Ser His Ser His Leu Leu Leu His Lys Lys Glu Asn Gly Ile Trp
            100                 105                 110 agc acc gag atc ctg aag aac ttc aag aac aag acc ttc ctg aag tgc      384
Ser Thr Glu Ile Leu Lys Asn Phe Lys Asn Lys Thr Phe Leu Lys Cys
        115                 120                 125 gag gcc ccc aac tac agc ggc aga ttc acc tgt agc tgg ctg gtg cag      432
Glu Ala Pro Asn Tyr Ser Gly Arg Phe Thr Cys Ser Trp Leu Val Gln
    130                 135                 140 aga aac atg gac ctg aag ttc aac atc aag agc agc agc agc agc ccc      480
Arg Asn Met Asp Leu Lys Phe Asn Ile Lys Ser Ser Ser Ser Ser Pro
145                 150                 155                 160 gac agc aga gcc gtg aca tgc ggc atg gcc agc ctg agc gcc gag aag      528
Asp Ser Arg Ala Val Thr Cys Gly Met Ala Ser Leu Ser Ala Glu Lys
                165                 170                 175 gtg acc ctg gac cag aga gac tac gag aag tac agc gtg agc tgc cag      576
Val Thr Leu Asp Gln Arg Asp Tyr Glu Lys Tyr Ser Val Ser Cys Gln
            180                 185                 190 gag gac gtg acc tgt ccc acc gcc gag gag acc ctg ccc atc gag ctt      624
Glu Asp Val Thr Cys Pro Thr Ala Glu Glu Thr Leu Pro Ile Glu Leu
        195                 200                 205 gcc ctg gaa gcc aga cag cag aac aag tac gag aac tac agc acc agc      672
Ala Leu Glu Ala Arg Gln Gln Asn Lys Tyr Glu Asn Tyr Ser Thr Ser
    210                 215                 220 ttc ttc atc aga gac atc atc aag ccc gac ccc ccc aag aac ctc cag      720
Phe Phe Ile Arg Asp Ile Ile Lys Pro Asp Pro Pro Lys Asn Leu Gln
225                 230                 235                 240 atg aag ccc ctg aag aac agc cag gtg gag gtg tcc tgg gag tac ccc      768
Met Lys Pro Leu Lys Asn Ser Gln Val Glu Val Ser Trp Glu Tyr Pro
                245                 250                 255 gac agc tgg agc acc ccc cac agc tac ttc agc ctg aag ttc ttc gtg      816
Asp Ser Trp Ser Thr Pro His Ser Tyr Phe Ser Leu Lys Phe Phe Val
            260                 265                 270 aga atc cag aga aag aag gag aag atg aag gag acc gag gag ggc tgc      864
Arg Ile Gln Arg Lys Lys Glu Lys Met Lys Glu Thr Glu Glu Gly Cys
        275                 280                 285 aac cag aag ggc gct ttc ctg gtg gag aaa acc agc acc gag gtg cag      912
Asn Gln Lys Gly Ala Phe Leu Val Glu Lys Thr Ser Thr Glu Val Gln
    290                 295                 300 tgc aag ggc ggc aac gtg tgt gtg cag gcc cag gac aga tac tac aac      960
Cys Lys Gly Gly Asn Val Cys Val Gln Ala Gln Asp Arg Tyr Tyr Asn
305                 310                 315                 320 agc agc tgc tcc aag tgg gcc tgc gtg ccc tgc cgc gtg aga agc tga     1008
Ser Ser Cys Ser Lys Trp Ala Cys Val Pro Cys Arg Val Arg Ser
                325                 330                 335

<210> SEQ ID NO 14
<211> LENGTH: 335
<212> TYPE: PRT
<213> ORGANISM: Artificial Sequence
<220> FEATURE:
<223> OTHER INFORMATION: Synthetic Construct

<400> SEQUENCE: 14

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
```

```
            20                  25                  30
Val Glu Val Asp Trp Thr Pro Asp Ala Pro Gly Glu Thr Val Asn Leu
         35                  40                  45

Thr Cys Asp Thr Pro Glu Glu Asp Asp Ile Thr Trp Thr Ser Asp Gln
 50                  55                  60

Arg His Gly Val Ile Gly Ser Gly Lys Thr Leu Thr Ile Thr Val Lys
 65                  70                  75                  80

Glu Phe Leu Asp Ala Gly Gln Tyr Thr Cys His Lys Gly Gly Glu Thr
                 85                  90                  95

Leu Ser His Ser His Leu Leu Leu His Lys Lys Glu Asn Gly Ile Trp
             100                 105                 110

Ser Thr Glu Ile Leu Lys Asn Phe Lys Asn Lys Thr Phe Leu Lys Cys
         115                 120                 125

Glu Ala Pro Asn Tyr Ser Gly Arg Phe Thr Cys Ser Trp Leu Val Gln
     130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                 165                 170                 175

Val Thr Leu Asp Gln Arg Asp Tyr Glu Lys Tyr Ser Val Ser Cys Gln
             180                 185                 190

Glu Asp Val Thr Cys Pro Thr Ala Glu Glu Thr Leu Pro Ile Glu Leu
         195                 200                 205

Ala Leu Glu Ala Arg Gln Gln Asn Lys Tyr Glu Asn Tyr Ser Thr Ser
     210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                 245                 250                 255

Asp Ser Trp Ser Thr Pro His Ser Tyr Phe Ser Leu Lys Phe Phe Val
             260                 265                 270

Arg Ile Gln Arg Lys Lys Glu Lys Met Lys Glu Thr Glu Glu Gly Cys
         275                 280                 285

Asn Gln Lys Gly Ala Phe Leu Val Glu Lys Thr Ser Thr Glu Val Gln
     290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                 325                 330                 335
```

<210> SEQ ID NO 15
<211> LENGTH: 648
<212> TYPE: DNA
<213> ORGANISM: Artificial Sequence
<220> FEATURE:
<223> OTHER INFORMATION: Synthetic mIL-12, mp35
<220> FEATURE:
<221> NAME/KEY: CDS
<222> LOCATION: (1)..(648)

<400> SEQUENCE: 15

```
atg tgc cag agc aga tac ctg ttg ttc ctg gct acc ctg gcc ctg ctg    48
Met Cys Gln Ser Arg Tyr Leu Leu Phe Leu Ala Thr Leu Ala Leu Leu
 1               5                  10                  15 aac cac ctg agc ctg gcc cgc gtg atc ccc gtg agc ggc ccc gcc aga    96
Asn His Leu Ser Leu Ala Arg Val Ile Pro Val Ser Gly Pro Ala Arg
             20                  25                  30
```

```
tgc agc cag agc aga aac ctg ttg aaa aca acc gac gac atg gtg      144
Cys Leu Ser Gln Ser Arg Asn Leu Leu Lys Thr Thr Asp Asp Met Val
        35                  40                  45 aaa acc gcc aga gag aag ctg aag cac tac agc tgc acc gcc gag gac  192
Lys Thr Ala Arg Glu Lys Leu Lys His Tyr Ser Cys Thr Ala Glu Asp
 50                  55                  60 atc gac cac gag gac atc acc aga gac cag acc agc acc ctg aaa acc  240
Ile Asp His Glu Asp Ile Thr Arg Asp Gln Thr Ser Thr Leu Lys Thr
 65                  70                  75                  80 tgt ctg ccc ctg gag ctg cac aag aac gag agc tgc ctg gct acc aga  288
Cys Leu Pro Leu Glu Leu His Lys Asn Glu Ser Cys Leu Ala Thr Arg
                85                  90                  95 gag acc agc agc acc acc aga ggc agc tgc ctg ccc ccc cag aaa acc  336
Glu Thr Ser Ser Thr Thr Arg Gly Ser Cys Leu Pro Pro Gln Lys Thr
            100                 105                 110 agc ctg atg atg acc ctg tgc ctg ggc agc atc tac gag gac ctg aag  384
Ser Leu Met Met Thr Leu Cys Leu Gly Ser Ile Tyr Glu Asp Leu Lys
        115                 120                 125 atg tac cag acc gag ttc cag gcc atc aac gcc gcc ctg caa aac cac  432
Met Tyr Gln Thr Glu Phe Gln Ala Ile Asn Ala Ala Leu Gln Asn His
    130                 135                 140 aac cac cag cag atc atc ctg gac aag ggc atg ttg gtg gcc atc gac  480
Asn His Gln Gln Ile Ile Leu Asp Lys Gly Met Leu Val Ala Ile Asp
145                 150                 155                 160 gag ctg atg cag agc ctg aac cac aac ggc gag acc ctg aga cag aag  528
Glu Leu Met Gln Ser Leu Asn His Asn Gly Glu Thr Leu Arg Gln Lys
                165                 170                 175 ccc ccc gtg ggc gag gcc gac ccc tac aga gtg aag atg aag ctg tgc  576
Pro Pro Val Gly Glu Ala Asp Pro Tyr Arg Val Lys Met Lys Leu Cys
            180                 185                 190 atc ctg ctg cac gcc ttc agc acc aga gtg gtg acc atc aac aga gtg  624
Ile Leu Leu His Ala Phe Ser Thr Arg Val Val Thr Ile Asn Arg Val
        195                 200                 205 atg ggc tac ctg agc agc gcc tga                                  648
Met Gly Tyr Leu Ser Ser Ala
    210                 215

<210> SEQ ID NO 16
<211> LENGTH: 215
<212> TYPE: PRT
<213> ORGANISM: Artificial Sequence
<220> FEATURE:
<223> OTHER INFORMATION: Synthetic Construct

<400> SEQUENCE: 16

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110
```

```
    Ser Leu Met Met Thr Leu Cys Leu Gly Ser Ile Tyr Glu Asp Leu Lys
                115                 120                 125

Met Tyr Gln Thr Glu Phe Gln Ala Ile Asn Ala Ala Leu Gln Asn His
        130                 135                 140

Asn His Gln Gln Ile Ile Leu Asp Lys Gly Met Leu Val Ala Ile Asp
    145                 150                 155                 160

Glu Leu Met Gln Ser Leu Asn His Asn Gly Glu Thr Leu Arg Gln Lys
                    165                 170                 175

Pro Pro Val Gly Glu Ala Asp Pro Tyr Arg Val Lys Met Lys Leu Cys
                180                 185                 190

Ile Leu Leu His Ala Phe Ser Thr Arg Val Val Thr Ile Asn Arg Val
                195                 200                 205

Met Gly Tyr Leu Ser Ser Ala
                210                 215

<210> SEQ ID NO 17
<211> LENGTH: 489
<212> TYPE: DNA
<213> ORGANISM: Artificial Sequence
<220> FEATURE:
<223> OTHER INFORMATION: Synthetic hIL-21
<220> FEATURE:
<221> NAME/KEY: CDS
<222> LOCATION: (1)..(489)

<400> SEQUENCE: 17 atg aga agc agc ccc ggc aac atg gag aga atc gtg atc tgc ctg atg      48
Met Arg Ser Ser Pro Gly Asn Met Glu Arg Ile Val Ile Cys Leu Met
1               5                   10                  15 gtg atc ttc ctg ggc acc ctg gtg cat aag agc agc agc cag ggc cag      96
Val Ile Phe Leu Gly Thr Leu Val His Lys Ser Ser Ser Gln Gly Gln
            20                  25                  30 gac aga cac atg atc cgc atg aga cag ctg atc gac atc gtg gac cag     144
Asp Arg His Met Ile Arg Met Arg Gln Leu Ile Asp Ile Val Asp Gln
        35                  40                  45 ctg aag aac tac gtg aac gac ctg gtg ccc gag ttc ctg ccc gcc ccc     192
Leu Lys Asn Tyr Val Asn Asp Leu Val Pro Glu Phe Leu Pro Ala Pro
50                  55                  60 gag gac gtg gag acc aac tgc gag tgg agc gcc ttc agc tgc ttc cag     240
Glu Asp Val Glu Thr Asn Cys Glu Trp Ser Ala Phe Ser Cys Phe Gln
65                  70                  75                  80 aag gcc cag ctg aag tcc gcc aac acc ggc aac aac gag aga atc atc     288
Lys Ala Gln Leu Lys Ser Ala Asn Thr Gly Asn Asn Glu Arg Ile Ile
                85                  90                  95 aac gtg agc atc aag aag ctg aag cgg aag ccc ccc agc acc aac gcc     336
Asn Val Ser Ile Lys Lys Leu Lys Arg Lys Pro Pro Ser Thr Asn Ala
            100                 105                 110 gga aga aga cag aag cac aga ctg acc tgt ccc agc tgc gac agc tac     384
Gly Arg Arg Gln Lys His Arg Leu Thr Cys Pro Ser Cys Asp Ser Tyr
        115                 120                 125 gag aag aag ccc ccc aag gag ttc ctg gag aga ttc aag agc ctg ctg     432
Glu Lys Lys Pro Pro Lys Glu Phe Leu Glu Arg Phe Lys Ser Leu Leu
130                 135                 140 caa aag atg atc cac cag cac ctg agc agc aga acc cac ggc agc gag     480
Gln Lys Met Ile His Gln His Leu Ser Ser Arg Thr His Gly Ser Glu
145                 150                 155                 160 gac agc tga                                                         489
Asp Ser
```

```
<210> SEQ ID NO 18
<211> LENGTH: 162
<212> TYPE: PRT
<213> ORGANISM: Artificial Sequence
<220> FEATURE:
<223> OTHER INFORMATION: Synthetic Construct

<400> SEQUENCE: 18

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 19
<211> LENGTH: 489
<212> TYPE: DNA
<213> ORGANISM: Artificial Sequence
<220> FEATURE:
<223> OTHER INFORMATION: Synthetic hIL-15
<220> FEATURE:
<221> NAME/KEY: CDS
<222> LOCATION: (1)..(489)

<400> SEQUENCE: 19 atg aga atc agc aag ccc cac ctg aga agc atc agc atc cag tgt tac      48
Met Arg Ile Ser Lys Pro His Leu Arg Ser Ile Ser Ile Gln Cys Tyr
1               5                   10                  15 ctg tgc ctg ctg ctg aac agc cac ttc ctg acc gag gcc ggt atc cac      96
Leu Cys Leu Leu Leu Asn Ser His Phe Leu Thr Glu Ala Gly Ile His
            20                  25                  30 gtc ttc atc ctg ggc tgc ttc agc gcc gga ctg ccc aag acc gag gcc     144
Val Phe Ile Leu Gly Cys Phe Ser Ala Gly Leu Pro Lys Thr Glu Ala
        35                  40                  45 aac tgg gtg aac gtg atc tct gac ctg aag aag atc gag gac ctg atc     192
Asn Trp Val Asn Val Ile Ser Asp Leu Lys Lys Ile Glu Asp Leu Ile
    50                  55                  60 cag tcc atg cac atc gac gcc acc ctg tac acc gag agc gac gtt cat     240
Gln Ser Met His Ile Asp Ala Thr Leu Tyr Thr Glu Ser Asp Val His
65                  70                  75                  80 ccc agc tgc aag gtg acc gcc atg aag tgc ttc ctg ctg gag ctg caa     288
Pro Ser Cys Lys Val Thr Ala Met Lys Cys Phe Leu Leu Glu Leu Gln
                85                  90                  95 gtg atc tcc ctg gag agc ggc gac gcc agc atc cac gac acc gtg gag     336
```

```
                Val Ile Ser Leu Glu Ser Gly Asp Ala Ser Ile His Asp Thr Val Glu
                                100                 105                 110 aac ctg att atc ctg gct aac aac agc ctg agc agc aac ggc aac gtg             384
Asn Leu Ile Ile Leu Ala Asn Asn Ser Leu Ser Ser Asn Gly Asn Val
            115                 120                 125 acc gag agc ggc tgc aag gag tgt gag gag ctg gag gag aag aac atc             432
Thr Glu Ser Gly Cys Lys Glu Cys Glu Glu Leu Glu Glu Lys Asn Ile
130                 135                 140 aag gag ttc ctc cag agc ttc gtg cat atc gtc cag atg ttc atc aac             480
Lys Glu Phe Leu Gln Ser Phe Val His Ile Val Gln Met Phe Ile Asn
145                 150                 155                 160 acc agc tga                                                                  489
Thr Ser
```

<210> SEQ ID NO 20
<211> LENGTH: 162
<212> TYPE: PRT
<213> ORGANISM: Artificial Sequence
<220> FEATURE:
<223> OTHER INFORMATION: Synthetic Construct

<400> SEQUENCE: 20

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 21
<211> LENGTH: 987
<212> TYPE: DNA
<213> ORGANISM: Artificial Sequence
<220> FEATURE:
<223> OTHER INFORMATION: Synthetic hIL-12, p40
<220> FEATURE:
<221> NAME/KEY: CDS
<222> LOCATION: (1)..(987)

<400> SEQUENCE: 21

```
atg ggt cac cag cag ttg gtc atc tct tgg ttt tcc ctg gtt ttt ctg              48
Met Gly His Gln Gln Leu Val Ile Ser Trp Phe Ser Leu Val Phe Leu
1               5                   10                  15 gca tct ccc ctc gtg gcc ata tgg gaa ctg aag aaa gat gtt tat gtc              96
Ala Ser Pro Leu Val Ala Ile Trp Glu Leu Lys Lys Asp Val Tyr Val
```

```
                 20                  25                  30
gta gaa ttg gat tgg tat ccg gat gcc cct gga gaa atg gtg gtc ctc       144
Val Glu Leu Asp Trp Tyr Pro Asp Ala Pro Gly Glu Met Val Val Leu
         35                  40                  45 acc tgt gac acc cct gaa gaa gat ggt atc acc tgg acc ttg gac cag       192
Thr Cys Asp Thr Pro Glu Glu Asp Gly Ile Thr Trp Thr Leu Asp Gln
 50                  55                  60 agc agt gag gtc tta ggc tct ggc aaa acc ctg acc atc caa gtc aaa       240
Ser Ser Glu Val Leu Gly Ser Gly Lys Thr Leu Thr Ile Gln Val Lys
 65                  70                  75                  80 gag ttt gga gat gct ggc cag tac acc tgt cac aaa gga ggc gag gtt       288
Glu Phe Gly Asp Ala Gly Gln Tyr Thr Cys His Lys Gly Gly Glu Val
                 85                  90                  95 cta agc cat tcg ctc ctg ctg ctt cac aaa aag gaa gat gga att tgg       336
Leu Ser His Ser Leu Leu Leu Leu His Lys Lys Glu Asp Gly Ile Trp
             100                 105                 110 tcc act gat att tta aag gac cag aaa gaa ccc aaa aat aag acc ttt       384
Ser Thr Asp Ile Leu Lys Asp Gln Lys Glu Pro Lys Asn Lys Thr Phe
         115                 120                 125 cta aga tgc gag gcc aag aat tat tct gga cgt ttc acc tgc tgg tgg       432
Leu Arg Cys Glu Ala Lys Asn Tyr Ser Gly Arg Phe Thr Cys Trp Trp
130                 135                 140 ctg acg aca atc agt act gat ttg aca ttc agt gtc aaa agc agc aga       480
Leu Thr Thr Ile Ser Thr Asp Leu Thr Phe Ser Val Lys Ser Ser Arg
145                 150                 155                 160 ggc tct tct gac ccc caa ggg gtg acg tgc gga gct gct aca ctc tct       528
Gly Ser Ser Asp Pro Gln Gly Val Thr Cys Gly Ala Ala Thr Leu Ser
                 165                 170                 175 gca gag aga gtc aga ggg gac aac aag gag tat gag tac tca gtg gag       576
Ala Glu Arg Val Arg Gly Asp Asn Lys Glu Tyr Glu Tyr Ser Val Glu
             180                 185                 190 tgc cag gag gac agt gcc tgc cca gct gct gag gag agt ctg ccc att       624
Cys Gln Glu Asp Ser Ala Cys Pro Ala Ala Glu Glu Ser Leu Pro Ile
         195                 200                 205 gag gtc atg gtg gat gcc gtt cac aag ctc aag tat gaa aac tac acc       672
Glu Val Met Val Asp Ala Val His Lys Leu Lys Tyr Glu Asn Tyr Thr
210                 215                 220 agc agc ttc ttc atc agg gac atc atc aaa cct gac cca ccc aag aac       720
Ser Ser Phe Phe Ile Arg Asp Ile Ile Lys Pro Asp Pro Pro Lys Asn
225                 230                 235                 240 ttg cag ctg aag cca tta aag aat tct cgg cag gtg gag gtc agc tgg       768
Leu Gln Leu Lys Pro Leu Lys Asn Ser Arg Gln Val Glu Val Ser Trp
                 245                 250                 255 gag tac cct gac acc tgg agt act cca cat tcc tac ttc tcc ctg aca       816
Glu Tyr Pro Asp Thr Trp Ser Thr Pro His Ser Tyr Phe Ser Leu Thr
             260                 265                 270 ttc tgc gtt cag gtc cag ggc aag agc aag aga gaa aag aaa gat aga       864
Phe Cys Val Gln Val Gln Gly Lys Ser Lys Arg Glu Lys Lys Asp Arg
         275                 280                 285 gtc ttc acg gac aag acc tca gcc acg gtc atc tgc cgc aaa aat gcc       912
Val Phe Thr Asp Lys Thr Ser Ala Thr Val Ile Cys Arg Lys Asn Ala
290                 295                 300 agc att agc gtg cgg gcc cag gac cgc tac tat agc tca tct tgg agc       960
Ser Ile Ser Val Arg Ala Gln Asp Arg Tyr Tyr Ser Ser Ser Trp Ser
305                 310                 315                 320 gaa tgg gca tct gtg ccc tgc agt tag                                   987
Glu Trp Ala Ser Val Pro Cys Ser
                 325
```

<210> SEQ ID NO 22
<211> LENGTH: 328
<212> TYPE: PRT
<213> ORGANISM: Artificial Sequence
<220> FEATURE:
<223> OTHER INFORMATION: Synthetic Construct

<400> SEQUENCE: 22

```
Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 23
<211> LENGTH: 660
<212> TYPE: DNA
<213> ORGANISM: Artificial Sequence
<220> FEATURE:
<223> OTHER INFORMATION: Synthetic hIL-12, p35

```
<220> FEATURE:
<221> NAME/KEY: CDS
<222> LOCATION: (1)..(660)

<400> SEQUENCE: 23 atg ggt cca gcg cgc agc ctc ctc ctt gtg gct acc ctg gtc ctc ctg      48
Met Gly Pro Ala Arg Ser Leu Leu Leu Val Ala Thr Leu Val Leu Leu
1               5                   10                  15 gac cac ctc agt ttg gcc aga aac ctc ccc gtg gcc act cca gac cca      96
Asp His Leu Ser Leu Ala Arg Asn Leu Pro Val Ala Thr Pro Asp Pro
            20                  25                  30 gga atg ttc cca tgc ctt cac cac tcc caa aac ctg ctg agg gcc gtc     144
Gly Met Phe Pro Cys Leu His His Ser Gln Asn Leu Leu Arg Ala Val
        35                  40                  45 agc aac atg ctc cag aag gcc aga caa act cta gaa ttt tac cct tgc     192
Ser Asn Met Leu Gln Lys Ala Arg Gln Thr Leu Glu Phe Tyr Pro Cys
    50                  55                  60 act tct gaa gag att gat cat gaa gat atc aca aaa gat aaa acc agc     240
Thr Ser Glu Glu Ile Asp His Glu Asp Ile Thr Lys Asp Lys Thr Ser
65                  70                  75                  80 aca gtg gag gcc tgt tta cca ttg gaa tta acc aag aat gag agt tgc     288
Thr Val Glu Ala Cys Leu Pro Leu Glu Leu Thr Lys Asn Glu Ser Cys
                85                  90                  95 cta aat tcc aga gag acc tct ttc ata act aat ggg agt tgc ctg gcc     336
Leu Asn Ser Arg Glu Thr Ser Phe Ile Thr Asn Gly Ser Cys Leu Ala
            100                 105                 110 tcc aga aag acc tct ttt atg atg gcc ctg tgc ctt agt agt att tat     384
Ser Arg Lys Thr Ser Phe Met Met Ala Leu Cys Leu Ser Ser Ile Tyr
        115                 120                 125 gaa gac ttg aag atg tac cag gtg gag ttc aag acc atg aat gca aag     432
Glu Asp Leu Lys Met Tyr Gln Val Glu Phe Lys Thr Met Asn Ala Lys
    130                 135                 140 ctt ctg atg gat cct aag agg cag atc ttt cta gat caa aac atg ctg     480
Leu Leu Met Asp Pro Lys Arg Gln Ile Phe Leu Asp Gln Asn Met Leu
145                 150                 155                 160 gca gtt att gat gag ctg atg cag gcc ctg aat ttc aac agt gag act     528
Ala Val Ile Asp Glu Leu Met Gln Ala Leu Asn Phe Asn Ser Glu Thr
                165                 170                 175 gtg cca caa aaa tcc tcc ctt gaa gaa ccg gat ttt tat aaa act aaa     576
Val Pro Gln Lys Ser Ser Leu Glu Glu Pro Asp Phe Tyr Lys Thr Lys
            180                 185                 190 atc aag ctc tgc ata ctt ctt cat gct ttc aga att cgg gca gtg act     624
Ile Lys Leu Cys Ile Leu Leu His Ala Phe Arg Ile Arg Ala Val Thr
        195                 200                 205 att gat aga gtg atg agc tat ctg aat gct tcc taa                     660
Ile Asp Arg Val Met Ser Tyr Leu Asn Ala Ser
    210                 215

<210> SEQ ID NO 24
<211> LENGTH: 219
<212> TYPE: PRT
<213> ORGANISM: Artificial Sequence
<220> FEATURE:
<223> OTHER INFORMATION: Synthetic Construct

<400> SEQUENCE: 24

Met Gly Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
```

```
                35                  40                  45
Ser Asn Met Leu Gln Lys Ala Arg Gln Thr Leu Glu Phe Tyr Pro Cys
 50                  55                  60
Thr Ser Glu Glu Ile Asp His Glu Asp Ile Thr Lys Asp Lys Thr Ser
 65                  70                  75                  80
Thr Val Glu Ala Cys Leu Pro Leu Glu Leu Thr Lys Asn Glu Ser Cys
                 85                  90                  95
Leu Asn Ser Arg Glu Thr Ser Phe Ile Thr Asn Gly Ser Cys Leu Ala
                100                 105                 110
Ser Arg Lys Thr Ser Phe Met Met Ala Leu Cys Leu Ser Ser Ile Tyr
            115                 120                 125
Glu Asp Leu Lys Met Tyr Gln Val Glu Phe Lys Thr Met Asn Ala Lys
            130                 135                 140
Leu Leu Met Asp Pro Lys Arg Gln Ile Phe Leu Asp Gln Asn Met Leu
145                 150                 155                 160
Ala Val Ile Asp Glu Leu Met Gln Ala Leu Asn Phe Asn Ser Glu Thr
                165                 170                 175
Val Pro Gln Lys Ser Ser Leu Glu Glu Pro Asp Phe Tyr Lys Thr Lys
                180                 185                 190
Ile Lys Leu Cys Ile Leu Leu His Ala Phe Arg Ile Arg Ala Val Thr
            195                 200                 205
Ile Asp Arg Val Met Ser Tyr Leu Asn Ala Ser
        210                 215

<210> SEQ ID NO 25
<211> LENGTH: 17
<212> TYPE: PRT
<213> ORGANISM: Drosophila melanogaster

<400> SEQUENCE: 25

Arg Arg Gly Gly Thr Thr Cys Ala Asn Thr Gly Ala Cys Ala Cys Tyr
1               5                   10                  15

Tyr

<210> SEQ ID NO 26
<211> LENGTH: 13
<212> TYPE: DNA
<213> ORGANISM: Drosophila melanogaster
<220> FEATURE:
<221> NAME/KEY: misc_feature
<222> LOCATION: (7)..(7)
<223> OTHER INFORMATION: n is a, c, g, or t

<400> SEQUENCE: 26
aggtcanagg tca                                                          13

<210> SEQ ID NO 27
<211> LENGTH: 15
<212> TYPE: DNA
<213> ORGANISM: Drosophila melanogaster

<400> SEQUENCE: 27
gggttgaatg aattt                                                        15

<210> SEQ ID NO 28
<211> LENGTH: 18
<212> TYPE: DNA
<213> ORGANISM: Artificial Sequence
<220> FEATURE:
<223> OTHER INFORMATION: Synthetic homing endonuclease (HE) enzyme
```

(I-SceI)

<400> SEQUENCE: 28 taggataac aggtaat                                                    18

<210> SEQ ID NO 29
<211> LENGTH: 37323
<212> TYPE: DNA
<213> ORGANISM: Artificial Sequence
<220> FEATURE:
<223> OTHER INFORMATION: Synthetic Ad-RTS-hIL-12 (SP1-RheoIL-12)

<400> SEQUENCE: 29

| | | |
|---|---|---|
| catcatcaat aatataccTt attttggatt gaagccaata tgataatgag ggggtggagt | 60 |
| ttgtgacgtg gcgcgggcg tgggaacggg gcggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggagatccg | 360 |
| gtaccggcgc gcgcgccgtt tggccgcctc gagtctagag atccggtgag tattaggcgc | 420 |
| gcaccaggtg ccgcaataaa atatctttat tttcattaca tctgtgtgtt ggttttttgt | 480 |
| gtgaatcgat agtactaaca tacgctctcc atcaaaacaa aacgaaacaa acaaactag | 540 |
| caaaataggc tgtccccagt gcaagtgcag gtgccagaac atttctctat cgataatgca | 600 |
| ggtcggagta ctgtcctccg agcggagtac tgtcctccga gcggagtact gtcctccgag | 660 |
| cggagtactg tcctccgagc ggagtactgt cctccgagcg gagtactgtc ctccgagcgg | 720 |
| agactcttcg aaggaagagg ggcggggtcg atcgaccccg cccctcttcc ttcgaaggaa | 780 |
| gaggggcggg gtcgaagacc tagagggtat ataatgggtg ccttagctgg tgtgtgagct | 840 |
| catcttcctg tagatcacgc gtgccaccat gggtcaccag cagttggtca tctcttggtt | 900 |
| ttccctggtt tttctggcat ctccccctcgt ggccatatgg gaactgaaga agatgtttta | 960 |
| tgtcgtagaa ttggattggt atccggatgc ccctggagaa atggtggtcc tcacctgtga | 1020 |
| caccccctgaa gaagatggta tcacctggac cttggaccag agcagtgagg tcttaggctc | 1080 |
| tggcaaaacc ctgaccatcc aagtcaaaga gtttggagat ctggccagt acacctgtca | 1140 |
| caaaggaggc gaggttctaa gccattcgct cctgctgctt cacaaaaagg aagatggaat | 1200 |
| ttggtccact gatatttaa aggaccagaa agaaacccaaa aataagacct ttctaagatg | 1260 |
| cgaggccaag aattattctg gacgtttcac ctgctggtgg ctgacgacaa tcagtactga | 1320 |
| tttgacattc agtgtcaaaa gcagcagagg ctcttctgac ccccaagggg tgacgtgcgg | 1380 |
| agctgctaca ctctctgcag agagagtcag aggggacaac aaggagtatg agtactcagt | 1440 |
| ggagtgccag gaggacagtg cctgcccagc tgctgaggag agtctgccca ttgaggtcat | 1500 |
| ggtggatgcc gttcacaagc tcaagtatga aaactacacc agcagcttct tcatcaggga | 1560 |
| catcatcaaa cctgacccac ccaagaactt gcagctgaag ccattaaaga attctcggca | 1620 |
| ggtggaggtc agctgggagt accctgacac ctggagtact ccacattcct acttctccct | 1680 |
| gacattctgc gttcaggtcc agggcaagag caagagagaa agaaagata gagtcttcac | 1740 |
| ggacaagacc tcagccacgg tcatctgccg caaaaatgcc agcattagcg tgcgggccca | 1800 |
| ggaccgctac tatagctcat cttggagcga atgggcatct gtgccctgca gttaggttgg | 1860 |
| gcgagctcga attcattgat ccccgggct gcaggaattc gatatcaagc tcgggatccg | 1920 |

```
aattccgccc cccccccccc ccccccccta acgttactgg ccgaagccgc ttggaataag    1980
gccggtgtgc gtttgtctat atgttatttt ccaccatatt gccgtctttt ggcaatgtga    2040
gggcccggaa acctggccct gtcttcttga cgagcattcc tagggtgtctt tccctctcg    2100 ccaaaggaat gcaaggtctg ttgaatgtcg tgaaggaagc agttcctctg gaagcttctt    2160
gaagacaaac aacgtctgta gcgacccttt gcaggcagcg aaccccccca cctggcgaca    2220
ggtgcctctg cggccaaaag ccacgtgtat aagatacacc tgcaaaggcg gcacaacccc    2280
agtgccacgt tgtgagttgg atagttgtgg aaagagtcaa atggctctcc tcaagcgtat    2340
tcaacaaggg gctgaaggat gcccagaagg taccccattg tatgggatct gatctggggc    2400
ctcggtgcac atgctttaca tgtgtttagt cgaggttaaa aaaacgtcta ggccccccga    2460
accacgggga cgtggttttc ctttgaaaaa cacgatgata atatggccac aaccatgggt    2520
ccagcgcgca gcctcctcct tgtggctacc ctggtcctcc tggaccacct cagtttggcc    2580
agaaacctcc ccgtggccac tccagaccca ggaatgttcc catgccttca ccactcccaa    2640
aacctgctga gggccgtcag caacatgctc cagaaggcca gacaaactct agaattttac    2700
ccttgcactt ctgaagagat tgatcatgaa gatatcacaa aagataaaac cagcacagtg    2760
gaggcctgtt taccattgga attaaccaag aatgagagtt gcctaaattc cagagagacc    2820
tctttcataa ctaatgggag ttgcctggcc tccagaaaga cctcttttat gatgccctg    2880 tgccttagta gtatttatga agacttgaag atgtaccagg tggagttcaa gaccatgaat    2940
gcaaagcttc tgatggatcc taagaggcag atctttctag atcaaaacat gctggcagtt    3000
attgatgagc tgatgcaggc cctgaatttc aacagtgaga ctgtgccaca aaaatcctcc    3060
cttgaagaac cggatttta taaaactaaa atcaagctct gcatacttct tcatgctttc    3120
agaattcggg cagtgactat tgatagagtg atgagctatc tgaatgcttc ctaacgtacg    3180
tcgacatcga gaacttgttt attgcagctt ataatggtta caaataaagc aatagcatca    3240
caaatttcac aaataaagca ttttttttcac tgcattctag ttgtggtttg tccaaactca    3300
tcaatgtatc ttatcatgtc tgggcgcgcc ggcctccgcg ccgggttttg gcgcctccg    3360 cgggcgcccc cctcctcacg gcgagcgctg ccacgtcaga cgaagggcgc agcgagcgtc    3420
ctgatccttc cgcccggacg ctcaggacag cggcccgctg ctcataagac tcggccttag    3480
aaccccagta tcagcagaag gacattttag gacgggactt gggtgactct agggcactgg    3540
ttttctttcc agagagcgga acaggcgagg aaaagtagtc ccttctcggc gattctgcgg    3600
agggatctcc gtgggcggt gaacgccgat gattatataa ggacgcgccg ggtgtggcac    3660
agctagttcc gtcgcagccg ggatttgggt cgcggttctt gtttgtggat cgctgtgatc    3720
gtcacttggt gagtagcggg ctgctgggct gggtacgtgc gctcgggtt ggcgagtgtg    3780 ttttgtgaag tttttaggc acctttgaa atgtaatcat ttgggtcaat atgtaatttt    3840
cagtgttaga ctagtaaatt gtccgctaaa ttctggccgt ttttggcttt tttgttagac    3900
gagctagcgc cgccaccatg ggccctaaaa agaagcgtaa agtcgccccc ccgaccgatg    3960
tcagcctggg ggacgagctc cacttagacg gcgaggacgt ggcgatggcg catgccgacg    4020
cgctagacga tttcgatctg gacatgttgg gggacgggga ttccccgggt ccgggattta    4080
ccccccacga ctccgccccc tacggcgctc tggatatggc cgacttcgag tttgagcaga    4140
tgtttaccga tgcccttgga attgacgagt acggtgggga attcgagatg cctgtggaca    4200
ggatcctgga ggcagagctt gctgtggaac agaagagtga ccagggcgtt gagggtcctg    4260
```

```
ggggaaccgg gggtagcggc agcagcccaa atgaccctgt gactaacatc tgtcaggcag    4320
ctgacaaaca gctattcacg cttgttgagt gggcgaagag gatcccacac ttttcctcct    4380
tgcctctgga tgatcaggtc atattgctgc gggcaggctg gaatgaactc ctcattgcct    4440
ccttttcaca ccgatccatt gatgttcgag atggcatcct ccttgccaca ggtcttcacg    4500
tgcaccgcaa ctcagcccat tcagcaggag taggagccat ctttgatcgg gtgctgacag    4560
agctagtgtc caaaatgcgt gacatgagga tggacaagac agagcttggc tgcctgaggg    4620
caatcattct gtttaatcca gaggtgaggg gtttgaaatc cgcccaggaa gttgaacttc    4680
tacgtgaaaa agtatatgcc gctttggaag aatatactag aacaacacat cccgatgaac    4740
caggaagatt tgcaaaactt ttgcttcgtc tgccttcttt acgttccata ggccttaagt    4800
gtttggagca tttgtttttc tttcgcctta ttggagatgt tccaattgat acgttcctga    4860
tggagatgct tgaatcacct tctgattcat aatctagcct agccccctc tccctccccc    4920 cccctaacg ttactggccg aagccgcttg gaataaggcc ggtgtgcgtt tgtctatatg    4980
ttattttcca ccatattgcc gtcttttggc aatgtgaggg cccggaaacc tggccctgtc    5040
ttcttgacga gcattcctag gggtcttttc cctctcgcca aaggaatgca aggtctgttg    5100
aatgtcgtga aggaagcagt tcctctggaa gcttcttgaa gacaaacaac gtctgtagcg    5160 acccttgca ggcagcggaa cccccacct ggcgacaggt gcctctgcgg ccaaaagcca    5220
cgtgtataag atacacctgc aaaggcggca caaccccagt gccacgttgt gagttggata    5280
gttgtggaaa gagtcaaatg gctctcctca agcgtattca acaaggggct gaaggatgcc    5340
cagaaggtac cccattgtat gggatctgat ctggggcctc ggtgcacatg ctttacatgt    5400
gtttagtcga ggttaaaaaa cgtctaggcc ccccgaacca cggggacgtg gttttccttt    5460
gaaaaacacg atctctaggc gccaccatga agctactgtc ttctatcgaa caagcatgcg    5520
atatttgccg acttaaaaag ctcaagtgct ccaagaaaa accgaagtgc gccaagtgtc    5580
tgaagaacaa ctgggagtgt cgctactctc ccaaaaccaa aaggtctccg ctgactaggg    5640
cacatctgac agaagtggaa tcaaggctag aaagactgga acagctattt ctactgattt    5700
ttcctcgaga agaccttgac atgatttttga aaatggattc tttacaggat ataaaagcat    5760
tgttaacagg attatttgta caagataatg tgaataaaga tgccgtcaca gatagattgg    5820
cttcagtgga gactgatatg cctctaacat tgagacagca tagaataagt gcgacatcat    5880
catcggaaga gagtagtaac aaaggtcaaa gacagttgac tgtatcgccg gaattcccgg    5940
ggatccggcc tgagtgcgta gtacccgaga ctcagtgcgc catgaagcgg aaagagaaga    6000
aagcacagaa ggagaaggac aaactgcctg tcagcacgac gacggtggac gaccacatgc    6060
cgcccattat gcagtgtgaa cctccacctc ctgaagcagc aaggattcac gaagtggtcc    6120
caaggtttct ctccgacaag ctgttggtga caaaccggca gaaaaacatc ccccagttga    6180
cagccaacca gcagttcctt atcgccaggc tcatctggta ccaggacggg tacgagcagc    6240
cttctgatga agatttgaag aggattacgc agacgtggca gcaagcggac gatgaaaacg    6300
aagagtcgga cactcccttc cgccagatca cagagatgac tatcctcacg gtccaactta    6360
tcgtggagtt cgcgaaggga ttgccagggt tcgccaagat ctcgcagcct gatcaaatta    6420
cgctgcttaa ggcttgctca agtgaggtaa tgatgctccg agtcgcgcga cgatacgatg    6480
cggcctcaga cagtattctg ttcgcgaaca ccaagcgtac cactcgcgac aactaccgca    6540
aggctggcat ggccgaggtc atcgaggatc tactgcactt ctgccggtgc atgtactcta    6600
tggcgttgga caacatccat tacgcgctgc tcacggctgt cgtcatcttt tctgaccggc    6660
```

```
cagggttgga gcagccgcaa ctggtggaag agatccagcg gtactacctg aatacgctcc   6720
gcatctatat cctgaaccag ctgagcgggt cggcgcgttc gtccgtcata tacggcaaga   6780
tcctctcaat cctctctgag ctacgcacgc tcggcatgca aaactccaac atgtgcatct   6840
ccctcaagct caagaacaga aagctgccgc ctttcctcga ggagatctgg gatgtggcgg   6900
acatgtcgca cacccaaccg ccgcctatcc tcgagtcccc cacgaatctc taggcggcct   6960
ctagagcggc cgccaccgcg gggagatcca gacatgataa gatacattga tgagtttgga   7020
caaaccacaa ctagaatgca gtgaaaaaaa tgctttattt gtgaaatttg tgatgctatt   7080
gctttatttg taaccattat aagctgcaat aaacaagtta acaacaacaa ttgcattcat   7140
tttatgtttc aggttcaggg ggaggtgtgg gaggtttttt aaagcaagta aaacctctac   7200
aaatgtggta tggctgatta tgatccggct gcctcgcgcg tttcggtgat gacggtgaaa   7260
acctctgaca catgcagctc ccggagacgg tcacagcttg tctgtaagcg gatgccggga   7320
gcagacaagc ccgtcagggc gcgtcagcgg gtgttggcgg gtgtcgggc gcagccatga    7380
ggtcgactct agtccccgcg gtggcagatc tggaaggtgc tgaggtacga tgagacccgc   7440
accaggtgca gaccctgcga gtgtggcggt aaacatatta ggaaccagcc tgtgatgctg   7500
gatgtgaccg aggagctgag gcccgatcac ttggtgctgg cctgcacccg cgctgagttt   7560
ggctctagcg atgaagatac agattgaggt actgaaatgt gtgggcgtgg cttaagggtg   7620
ggaaagaata tataaggtgg gggtcttatg tagttttgta tctgttttgc agcagccgcc   7680
gccgccatga gcaccaactc gtttgatgga agcattgtga gctcatattt gacaacgcgc   7740
atgcccccat gggccggggt gcgtcagaat gtgatgggct ccagcattga tggtcgcccc   7800
gtcctgcccg caaactctac taccttgacc tacgagaccg tgtctggaac gccgttggag   7860
actgcagcct ccgccgccgc ttcagccgct gcagccaccg cccgcgggat tgtgactgac   7920
tttgcttttc tgagcccgct tgcaagcagt gcagcttccc gttcatccgc ccgcgatgac   7980
aagttgacgg ctcttttggc acaattggat tctttgaccc gggaacttaa tgtcgtttct   8040
cagcagctgt tggatctgcg ccagcaggtt tctgccctga aggcttcctc ccctcccaat   8100
gcggtttaaa acataaataa aaaaccagac tctgtttgga tttggatcaa gcaagtgtct   8160
tgctgtcttt atttaggggt tttgcgcgcg cggtaggccc gggaccagcg gtctcggtcg   8220
ttgagggtcc tgtgtatttt ttccaggacg tggtaaaggt gactctggat gttcagatac   8280
atgggcataa gcccgtctct ggggtggagg tagcaccact gcagagcttc atgctgcggg   8340
gtggtgttgt agatgatcca gtcgtagcag gagcgctggg cgtggtgcct aaaaatgtct   8400
ttcagtagca agctgattgc caggggcagg cccttggtgt aagtgtttac aaagcggtta   8460
agctgggatg ggtgcatacg tggggatatg agatgcatct tggactgtat ttttaggttg   8520
gctatgttcc cagccatatc cctccgggga ttcatgttgt gcagaaccac cagcacagtg   8580
tatccggtgc acttgggaaa tttgtcatgt agcttagaag gaaatgcgtg gaagaacttg   8640
gagacgccct tgtgacctcc aagatttttcc atgcattcgt ccataatgat ggcaatgggc   8700
ccacgggcgg cggcctgggc gaagatattt ctgggatcac taacgtcata gttgtgttcc   8760
aggatgagat cgtcataggc catttttaca aagcgcgggc ggagggtgcc agactgcggt   8820
ataatggttc catccggccc aggggcgtag ttaccctcac agatttgcat ttcccacgct   8880
ttgagttcag atggggggat catgtctacc tgcgggcga tgaagaaaac ggtttccggg    8940
gtaggggaga tcagctggga agaaagcagg ttcctgagca gctgcgactt accgcagccg   9000
```

-continued

```
gtgggcccgt aaatcacacc tattaccggc tgcaactggt agttaagaga gctgcagctg      9060
ccgtcatccc tgagcagggg ggccacttcg ttaagcatgt ccctgactcg catgttttcc      9120
ctgaccaaat ccgccagaag gcgctcgccg cccagcgata gcagttcttg caaggaagca      9180
aagttttcca acggtttgag accgtccgcc gtaggcatgc ttttgagcgt ttgaccaagc      9240
agttccaggc ggtcccacag ctcggtcacc tgctctacgg catctcgatc cagcatatct      9300
cctcgtttcg cgggttgggg cggctttcgc tgtacggcag tagtcggtgc tcgtccagac      9360
gggccagggt catgtctttc cacgggcgca gggtcctcgt cagcgtagtc tgggtcacgg      9420
tgaaggggtg cgctccgggc tgcgcgctgg ccagggtgcg cttgaggctg gtcctgctgg      9480
tgctgaagcg ctgccggtct tcgccctgcg cgtcggccag gtagcatttg accatggtgt      9540
catagtccag cccctccgcg gcgtggccct tggcgcgcag cttgcccttg gaggaggcgc      9600
cgcacgaggg gcagtgcaga cttttgaggg cgtagagctt gggcgcgaga aataccgatt      9660
ccggggagta ggcatccgcg ccgcaggccc cgcagacggt ctcgcattcc acgagccagg      9720
tgagctctgg ccgttcgggg tcaaaaacca ggtttccccc atgcttttg atgcgtttct       9780 tacctctggt ttccatgagc cggtgtccac gctcggtgac gaaaaggctg tccgtgtccc      9840
cgtatacaga cttgagaggc ctgtcctcga gcggtgttcc gcggtcctcc tcgtatagaa      9900
actcggacca ctctgagaca aaggctcgcg tccaggccag cacgaaggag gctaagtggg      9960
aggggtagcg gtcgttgtcc actaggggt ccactcgctc cagggtgtga agacacatgt      10020
cgccctcttc ggcatcaagg aaggtgattg gtttgtaggt gtaggccacg tgaccgggtg      10080
ttcctgaagg ggggctataa aaggggtgg gggcgcgttc gtcctcactc tcttccgcat      10140
cgctgtctgc gagggccagc tgttgggtg agtactccct ctgaaaagcg ggcatgactt      10200
ctgcgctaag attgtcagtt ccaaaaacg aggaggattt gatattcacc tggcccgcgg      10260
tgatgccttt gagggtggcc gcatccatct ggtcagaaaa gacaatcttt tgttgtcaa       10320 gcttggtggc aaacgacccg tagagggcgt tggacagcaa cttggcgatg gagcgcaggg      10380
tttggttttt gtcgcgatcg gcgcgctcct tggccgcgat gtttagctgc acgtattcgc      10440
gcgcaacgca ccgccattcg ggaaagacgg tggtgcgctc gtcgggcacc aggtgcacgc      10500
gccaaccgcg gttgtgcagg gtgacaaggt caacgctggt ggctacctct ccgcgtaggc      10560
gctcgttggt ccagcagagg cggccgcct tgcgcgagca gaatggcggt aggggggtcta     10620 gctgcgtctc gtccgggggg tctgcgtcca cggtaaagac cccgggcagc aggcgcgcgt      10680
cgaagtagtc tatcttgcat ccttgcaagt ctagcgcctg ctgccatgcg cgggcggcaa      10740
gcgcgcgctc gtatgggttg agtgggggac cccatggcat ggggtgggtg agcgcggagg      10800
cgtacatgcc gcaaatgtcg taaacgtaga gggctctct gagtattcca agatatgtag       10860
ggtagcatct tccaccgcgg atgctggcgc gcacgtaatc gtatagttcg tgcgagggag      10920
cgaggaggtc gggaccgagg ttgctacggg cgggctgctc tgctcggaag actatctgcc      10980
tgaagatggc atgtgagttg gatgatatgg ttggacgctg gaagacgttg aagctggcgt      11040
ctgtgagacc taccgcgtca cgcacgaagg aggcgtagga gtcgcgcagc ttgttgacca      11100
gctcggcggt gacctgcacg tctagggcgc agtagtccag ggtttccttg atgatgtcat      11160
acttatcctg tccctttttt ttccacagct cgcggttgag gacaaactct tcgcggtctt      11220
tccagtactc ttggatcgga aaccgtcgg cctccgaacg gtaagagcct agcatgtaga       11280
actggttgac ggcctggtag gcgcagcatc ccttttctac gggtagcgcg tatgcctgcg      11340
cggccttccg gagcgaggtg tgggtgagcg caaaggtgtc cctgaccatg actttgaggt      11400
```

```
actggtattt gaagtcagtg tcgtcgcatc cgccctgctc ccagagcaaa aagtccgtgc   11460 gcttttgga  acgcggattt ggcagggcga aggtgacatc gttgaagagt atctttcccg   11520
cgcgaggcat aaagttgcgt gtgatgcgga agggtcccgg cacctcggaa cggttgttaa   11580
ttacctgggc ggcgagcacg atctcgtcaa agccgttgat gttgtggccc acaatgtaaa   11640
gttccaagaa gcgcgggatg cccttgatgg aaggcaattt tttaagttcc tcgtaggtga   11700
gctcttcagg ggagctgagc ccgtgctctg aaagggccca gtctgcaaga tgagggttgg   11760
aagcgacgaa tgagctccac aggtcacggg ccattagcat ttgcaggtgg tcgcgaaagg   11820
tcctaaactg gcgacctatg gccatttttt ctggggtgat gcagtagaag gtaagcgggt   11880
cttgttccca gcggtcccat ccaaggttcg cggctaggtc tcgcgcggca gtcactagag   11940
gctcatctcc gccgaacttc atgaccagca tgaaggcac gagctgcttc ccaaaggccc    12000
ccatccaagt ataggtctct acatcgtagg tgacaaagag acgctcggtg cgaggatgcg   12060
agccgatcgg gaagaactgg atctcccgcc accaattgga ggagtggcta ttgatgtggt   12120
gaaagtagaa gtccctgcga cgggccgaac actcgtgctg gcttttgtaa aaacgtgcgc   12180
agtactggca gcggtgcacg ggctgtacat cctgcacgag gttgacctga cgaccgcgca   12240
caaggaagca gagtgggaat tgagcccct cgcctggcgg gtttggctgg tggtcttcta    12300
cttcggctgc ttgtccttga ccgtctggct gctcgagggg agttacggtg gatcggacca   12360
ccacgccgcg cgagcccaaa gtccagatgt ccgcgcgcgg cggtcggagc ttgatgacaa   12420
catcgcgcag atgggagctg tccatggtct ggagctcccg cggcgtcagg tcaggcggga   12480
gctcctgcag gtttacctcg catagacggg tcagggcgcg ggctagatcc aggtgatacc   12540
taatttccag gggctggttg gtggcggcgt cgatggcttg caagaggccg catccccgcg   12600
gcgcgactac ggtaccgcgc ggcgggcggt gggccgcggg ggtgtccttg gatgatgcat   12660
ctaaaagcgg tgacgcgggc gagccccgg  aggtagggg  ggctccggac ccgccgggag   12720 aggggggcagg ggcacgtcgg cgccgcgcgc gggcaggagc tggtgctgcg cgcgtaggtt   12780
gctggcgaac gcgacgacgc ggcggttgat ctcctgaatc tggcgcctct gcgtgaagac   12840
gacgggcccg gtgagcttga acctgaaaga gagttcgaca gaatcaattt cggtgtcgtt   12900
gacggcggcc tggcgcaaaa tctcctgcac gtctcctgag ttgtcttgat aggcgatctc   12960
ggccatgaac tgctcgatct cttcctcctg gagatctccg cgtccggctc gctccacggt   13020
ggcggcgagg tcgttggaaa tgcgggccat gagctgcgag aaggcgttga ggcctccctc   13080
gttccagacg cggctgtaga ccacgccccc ttcggcatcg cgggcgcgca tgaccacctg   13140
cgcgagattg agctccacgt gccgggcgaa gacggcgtag tttcgcaggc gctgaaagag   13200
gtagttgagg gtggtggcgg tgtgttctgc cacgaagaag tacataaccc agcgtcgcaa   13260
cgtggattcg ttgatatccc ccaaggcctc aaggcgctcc atggcctcgt agaagtccac   13320
ggcgaagttg aaaaactggg agttgcgcgc cgacacggtt aactcctcct ccagaagacg   13380
gatgagctcg gcgacagtgt cgcgcacctc gcgctcaaag gctacagggg cctcttcttc   13440
ttcttcaatc tcctcttcca taagggcctc cccttcttct tcttctggcg gcggtggggg   13500
aggggggaca cggcggcgac gacggcgcac cgggaggcg  tcgacaaagc gctcgatcat   13560
ctccccgcgg cgacggcgca tggtctcggt gacggcgcgg ccgttctcgc gggggcgcag   13620
ttggaagacg ccgcccgtca tgtcccggtt atgggttggc gggggggctgc catgcggcag   13680 ggatacggcg ctaacgatgc atctcaacaa ttgttgtgta ggtactccgc cgccgaggga   13740
```

```
cctgagcgag tccgcatcga ccggatcgga aaacctctcg agaaaggcgt ctaaccagtc   13800
acagtcgcaa ggtaggctga gcaccgtggc gggcggcagc gggcggcggt cggggttgtt   13860
tctggcggag gtgctgctga tgatgtaatt aaagtaggcg gtcttgagac ggcggatggt   13920
cgacagaagc accatgtcct tgggtccggc ctgctgaatg cgcaggcggt cggccatgcc   13980
ccaggcttcg ttttgacatc ggcgcaggtc tttgtagtag tcttgcatga gcctttctac   14040
cggcacttct tcttctcctt cctcttgtcc tgcatctctt gcatctatcg ctgcggcggc   14100
ggcggagttt ggccgtaggt ggcgccctct tcctcccatg cgtgtgaccc cgaagcccct   14160
catcggctga agcagggcta ggtcggcgac aacgcgctcg gctaatatgg cctgctgcac   14220
ctgcgtgagg gtagactgga agtcatccat gtccacaaag cggtggtatg cgcccgtgtt   14280
gatggtgtaa gtgcagttgg ccataacgga ccagttaacg gtctggtgac ccggctgcga   14340
gagctcggtg tacctgagac gcgagtaagc cctcgagtca aatacgtagt cgttgcaagt   14400
ccgcaccagg tactggtatc ccaccaaaaa gtgcggcggc ggctggcggt agaggggcca   14460
gcgtagggtg gccggggctc cggggcgag atcttccaac ataaggcgat gatatccgta   14520
gatgtacctg gacatccagg tgatgccggc ggcggtggtg gaggcgcgcg gaaagtcgcg   14580
gacgcggttc cagatgttgc gcagcggcaa aaagtgctcc atggtcggga cgctctggcc   14640
ggtcaggcgc gcgcaatcgt tgacgctcta gcgtgcaaaa ggagagcctg taagcgggca   14700
ctcttccgtg gtctggtgga taaattcgca agggtatcat ggcggacgac cggggttcga   14760
gccccgtatc cggccgtccg ccgtgatcca tgcggttacc gcccgcgtgt cgaacccagg   14820
tgtgcgacgt cagacaacgg gggagtgctc cttttggctt ccttccaggc gcggcggctg   14880
ctgcgctagc ttttttggcc actggccgcg cgcagcgtaa gcggttaggc tggaaagcga   14940
aagcattaag tggctcgctc cctgtagccg gagggttatt ttccaagggt tgagtcgcgg   15000 gaccccggt tcgagtctcg gaccggccgg actgcggcga acgggggttt gcctccccgt   15060
catgcaagac cccgcttgca aattcctccg gaaacaggga cgagcccctt ttttgctttt   15120
cccagatgca tccggtgctg cggcagatgc gcccccctcc tcagcagcgg caagagcaag   15180
agcagcggca gacatgcagg gcaccctccc ctcctcctac cgcgtcagga ggggcgacat   15240
ccgcggttga cgcggcagca gatggtgatt acgaaccccc gcggcgccgg gcccggcact   15300
acctggactt ggaggagggc gagggcctgg cgcggctagg agcgccctct cctgagcggc   15360
acccaagggt gcagctgaag cgtgatacgc gtgaggcgta cgtgccgcgg cagaacctgt   15420
ttcgcgaccg cgagggagag gagcccgagg agatgcggga tcgaaagttc cacgcagggc   15480
gcgagctgcg gcatggcctg aatcgcgagc ggttgctgcg cgaggaggac tttgagcccg   15540
acgcgcgaac cgggattagt cccgcgcgcg cacacgtggc ggccgccgac ctggtaaccg   15600
catacgagca gacggtgaac caggagatta actttcaaaa aagctttaac aaccacgtgc   15660
gtacgcttgt ggcgcgcgag gaggtggcta taggactgat gcatctgtgg gactttgtaa   15720
gcgcgctgga gcaaaaccca aatagcaagc cgctcatggc gcagctgttc cttatagtgc   15780
agcacagcag ggacaacgag gcattcaggg atgcgctgct aaacatagta gagcccgagg   15840
gccgctggct gctcgatttg ataaacatcc tgcagagcat agtggtgcag gagcgcagct   15900
tgagcctggc tgacaaggtg gccgccatca actattccat gcttagcctg gcaagttttt   15960
acgcccgcaa gatataccat accccttacg ttcccataga caaggaggta aagatcgagg   16020
ggttctacat gcgcatggcg ctgaaggtgc ttacctgag cgacgacctg ggcgtttatc   16080
gcaacgagcg catccacaag gccgtgagcg tgagccggcg gcgcgagctc agcgaccgcg   16140
```

```
agctgatgca cagcctgcaa agggccctgg ctggcacggg cagcggcgat agagaggccg   16200
agtcctactt tgacgcgggc gctgacctgc gctgggcccc aagccgacgc gccctggagg   16260
cagctggggc cggacctggg ctggcggtgg cacccgcgcg cgctggcaac gtcggcggcg   16320
tggaggaata tgacgaggac gatgagtacg agccagagga cggcgagtac taagcggtga   16380
tgtttctgat cagatgatgc aagacgcaac ggacccggcg gtgcgggcgg cgctgcagag   16440
ccagccgtcc ggccttaact ccacggacga ctggcgccag gtcatggacc gcatcatgtc   16500
gctgactgcg cgcaatcctg acgcgttccg gcagcagccg caggccaacc ggctctccgc   16560
aattctggaa gcgtggtgcc cggcgcgcgc aaaccccacg cacgagaagg tgctggcgat   16620
cgtaaacgcg ctggccgaaa acagggccat ccggcccgac gaggccggcc tggtctacga   16680
cgcgctgctt cagcgcgtgg ctcgttacaa cagcggcaac gtgcagacca acctggaccg   16740
gctggtgggg gatgtgcgcg aggccgtggc gcagcgtgag cgcgcgcagc agcagggcaa   16800
cctgggctcc atggttgcac taaacgcctt cctgagtaca cagcccgcca acgtgccgcg   16860
gggacaggag gactacacca actttgtgag cgcactgcgg ctaatggtga ctgagacacc   16920
gcaaagtgag gtgtaccagt ctgggccaga ctatttttc cagaccagta gacaaggcct   16980
gcagaccgta aacctgagcc aggctttcaa aaacttgcag gggctgtggg gggtgcgggc   17040
tcccacaggc gaccgcgcga ccgtgtctag cttgctgacg cccaactcgc gcctgttgct   17100
gctgctaata gcgcccttca cggacagtgg cagcgtgtcc cgggacacat acctaggtca   17160
cttgctgaca ctgtaccgcg aggccatagg tcaggcgcat gtggacgagc atactttcca   17220
ggagattaca agtgtcagcc gcgcgctggg gcaggaggac acgggcagcc tggaggcaac   17280
cctaaactac ctgctgacca accggcggca gaagatcccc tcgttgcaca gtttaaacag   17340
cgaggaggag cgcattttgc gctacgtgca gcagagcgtg agccttaacc tgatgcgcga   17400
cggggtaacg cccagcgtgg cgctggacat gaccgcgcgc aacatggaac cgggcatgta   17460
tgcctcaaac cggccgttta tcaaccgcct aatggactac ttgcatcgcg cggccgccgt   17520
gaaccccgag tatttcacca atgccatctt gaacccgcac tggctaccgc cccctggttt   17580
ctacaccggg ggattcgagg tgcccgaggg taacgatgga ttcctctggg acgacataga   17640
cgacagcgtg ttttcccgc aaccgcagac cctgctagag ttgcaacagc gcgagcaggc   17700
agaggcggcg ctgcgaaagg aaagcttccg caggccaagc agcttgtccg atctaggcgc   17760
tgcggccccg cggtcagatg ctagtagccc atttccaagc ttgatagggt ctcttaccag   17820
cactcgcacc acccgcccgc gcctgctggg cgaggaggag tacctaaaca actcgctgct   17880
gcagccgcag cgcgaaaaaa acctgcctcc ggcatttccc aacaacggga tagagagcct   17940
agtggacaag atgagtagat ggaagacgta cgcgcaggag cacagggacg tgccaggccc   18000
gcgcccgccc acccgtcgtc aaaggcacga ccgtcagcgg ggtctggtgt gggaggacga   18060
tgactcggca gacgacagca gcgtcctgga tttgggaggg agtggcaacc cgtttgcgca   18120
ccttcgcccc aggctgggga gaatgtttta aaaaaaaaa aagcatgatg caaaataaaa   18180
aactcaccaa ggccatggca ccgagcgttg gttttcttgt attccccttta gtatgcggcg   18240
cgcggcgatg tatgaggaag gtcctcctcc ctcctacgag agtgtggtga gcgcggcgcc   18300
agtggcggcg gcgctgggtt ctcccttcga tgctcccctg gacccgccgt tgtgcctcc   18360
gcggtacctg cggcctaccg gggggagaaa cagcatccgt tactctgagt tggcaccct   18420
attcgacacc cccgtgtgt acctggtgga caacaagtca acggatgtgg catccctgaa   18480
```

```
ctaccagaac gaccacagca actttctgac cacggtcatt caaaacaatg actacagccc    18540
gggggaggca agcacacaga ccatcaatct tgacgaccgg tcgcactggg gcggcgacct    18600
gaaaaccatc ctgcatacca acatgccaaa tgtgaacgag ttcatgttta ccaataagtt    18660
taaggcgcgg gtgatggtgt cgcgcttgcc tactaaggac aatcaggtgg agctgaaata    18720
cgagtgggtg gagttcacgc tgcccgaggg caactactcc gagaccatga ccatagacct    18780
tatgaacaac gcgatcgtgg agcactactt gaaagtgggc agacagaacg gggttctgga    18840
aagcgacatc ggggtaaagt ttgacacccg caacttcaga ctggggtttg accccgtcac    18900
tggtcttgtc atgcctgggg tatatacaaa cgaagccttc catccagaca tcattttgct    18960
gccaggatgc ggggtggact tcacccacag ccgcctgagc aacttgttgg gcatccgcaa    19020
gcggcaaccc ttccaggagg gctttaggat cacctacgat gatctggagg gtggtaacat    19080
tcccgcactg ttggatgtgg acgcctacca ggcgagcttg aaagatgaca ccgaacaggg    19140
cggggggtggc gcaggcggca gcaacagcag tggcagcggc gcggaagaga actccaacgc    19200
ggcagccgcg gcaatgcagc cggtggagga catgaacgat catgccattc gcggcgacac    19260
cttttgccaca cgggctgagg agaagcgcgc tgaggccgaa gcagcggccg aagctgccgc    19320
ccccgctgcg caacccgagg tcgagaagcc tcagaagaaa ccggtgatca aacccctgac    19380
agaggacagc aagaaacgca gttacaacct aataagcaat gacagcacct tcacccagta    19440
ccgcagctgg taccttgcat acaactacgg cgaccctcag accggaatcc gctcatggac    19500
cctgctttgc actcctgacg taacctgcgg ctcggagcag gtctactggt cgttgccaga    19560
catgatgcaa gaccccgtga ccttccgctc cacgcgccag atcagcaact ttccggtggt    19620
gggcgccgag ctgttgcccg tgcactccaa gagcttctac aacgaccagg ccgtctactc    19680
ccaactcatc cgccagttta cctctctgac ccacgtgttc aatcgctttc ccgagaacca    19740
gattttggcg cgcccgccag cccccaccat caccaccgtc agtgaaaacg ttcctgctct    19800
cacagatcac gggacgctac cgctgcgcaa cagcatcgga ggagtccagc gagtgaccat    19860
tactgacgcc agacgccgca cctgccccta cgtttacaag gccctgggca tagtctcgcc    19920
gcgcgtccta tcgagccgca ctttttgagc aagcatgtcc atccttatat cgcccagcaa    19980
taacacaggc tggggcctgc gcttcccaag caagatgttt ggcggggcca agaagcgctc    20040
cgaccaacac ccagtgcgcg tgcgcgggca ctaccgcgcg ccctggggcg cgcacaaacg    20100
cggccgcact gggcgcacca ccgtcgatga cgccatcgac gcggtggtgg aggaggcgcg    20160
caactacacg cccacgccgc caccagtgtc cacagtggac gcggccattc agaccgtggt    20220
gcgcggagcc cggcgctatg ctaaaatgaa gagacggcgg aggcgcgtag cacgtcgcca    20280
ccgccgccga cccggcactg ccgcccaacg cgcggcggcg gccctgctta accgcgcacg    20340
tcgcaccggc cgacgggcgg ccatgcgggc cgctcgaagg ctggccgcgg gtattgtcac    20400
tgtgcccccc aggtccaggc gacgagcggc cgccgcagca gccgcggcca ttagtgctat    20460
gactcagggt cgcaggggca acgtgtattg ggtgcgcgac tcggttagcg gcctgcgcgt    20520
gcccgtgcgc acccgccccc cgcgcaacta gattgcaaga aaaaactact tagactcgta    20580
ctgttgtatg tatccagcgg cggcggcgcg caacgaagct atgtccaagc gcaaaatcaa    20640
agaagagatg ctccaggtca tcgcgccgga gatctatggc cccccgaaga aggaagagca    20700
ggattacaag ccccgaaagc taaagcgggt caaaaagaaa aagaaagatg atgatgatga    20760
acttgacgac gaggtggaac tgctgcacgc taccgcgccc aggcgacggg tacagtggaa    20820
aggtcgacgc gtaaaacgtg ttttgcgacc cggcaccacc gtagtcttta cgcccggtga    20880
```

```
gcgctccacc cgcacctaca agcgcgtgta tgatgaggtg tacggcgacg aggacctgct   20940
tgagcaggcc aacgagcgcc tcggggagtt tgcctacgga aagcggcata aggacatgct   21000
ggcgttgccg ctggacgagg gcaacccaac acctagccta agcccgtaa cactgcagca    21060 ggtgctgccc gcgcttgcac cgtccgaaga aaagcgcggc ctaaagcgcg agtctggtga   21120
cttggcaccc accgtgcagc tgatggtacc caagcgccag cgactggaag atgtcttgga   21180
aaaaatgacc gtggaacctg gctggagcc cgaggtccgc gtgcggccaa tcaagcaggt    21240
ggcgccggga ctgggcgtgc agaccgtgga cgttcagata cccactacca gtagcaccag   21300
tattgccacc gccacagagg gcatggagac acaaacgtcc ccggttgcct cagcggtggc   21360
ggatgccgcg gtgcaggcgg tcgctgcggc cgcgtccaag acctctacgg aggtgcaaac   21420
ggacccgtgg atgtttcgcg tttcagcccc ccggcgcccg cgccgttcga ggaagtacgg   21480
cgccgccagc gcgctactgc ccgaatatgc cctacatcct tccattgcgc ctaccccgg    21540 ctatcgtggc tacacctacc gccccagaag acgagcaact acccgacgcc gaaccaccac   21600
tggaacccgc cgccgccgtc gccgtcgcca gcccgtgctg gccccgattt ccgtgcgcag   21660
ggtggctcgc gaaggaggca ggaccctggt gctgccaaca gcgcgctacc accccagcat   21720
cgtttaaaag ccggtctttg tggttcttgc agatatggcc ctcacctgcc gcctccgttt   21780
cccggtgccg ggattccgag gaagaatgca ccgtaggagg gcatggccg gccacggcct    21840 gacgggcggc atgcgtcgtg cgcaccaccg gcggcggcgc gcgtcgcacc gtcgcatgcg   21900
cggcggtatc ctgcccctcc ttattccact gatcgccgcg gcgattggcg ccgtgcccgg   21960
aattgcatcc gtggccttgc aggcgcagag acactgatta aaaacaagtt gcatgtggaa   22020
aaatcaaaat aaaagtctg gactctcacg ctcgcttggt cctgtaacta ttttgtagaa    22080
tggaagacat caactttgcg tctctggccc cgcgacacgg ctcgcgcccg ttcatgggaa   22140
actggcaaga tatcggcacc agcaatatga gcggtggcgc cttcagctgg ggctcgctgt   22200
ggagcggcat taaaaatttc ggttccaccg ttaagaacta tggcagcaag gcctggaaca   22260
gcagcacagg ccagatgctg agggataagt tgaaagagca aaatttccaa caaaaggtgg   22320
tagatggcct ggcctctggc attagcgggg tggtggacct ggccaaccag gcagtgcaaa   22380
ataagattaa cagtaagctt gatccccgcc ctcccgtaga ggagcctcca ccggccgtgg   22440
agacagtgtc tccagagggg cgtggcgaaa agcgtccgcg ccccgacagg gaagaaactc   22500
tggtgacgca aatagacgag cctccctcgt acgaggaggc actaaagcaa ggcctgccca   22560
ccacccgtcc catcgcgccc atggctaccg gagtgctggg ccagcacaca cccgtaacgc   22620
tggacctgcc tcccccgcc gacacccagc agaaacctgt gctgccaggc ccgaccgccg   22680
ttgttgtaac ccgtcctagc cgcgcgtccc tgcgccgcgc cgccagcggt ccgcgatcgt    22740
tgcggcccgt agccagtggc aactggcaaa gcacactgaa cagcatcgtg gtctggggg    22800 tgcaatccct gaagcgccga cgatgcttct gatagctaac gtgtcgtatg tgtgtcatgt   22860
atgcgtccat gtcgccgcca aggagctgc tgagccgccg cgcgcccgct ttccaagatg    22920 gctaccctt cgatgatgcc gcagtggtct tacatgcaca tctcgggcca ggacgcctcg    22980
gagtacctga gccccgggct ggtgcagttt gcccgcgcca ccgagacgta cttcagcctg   23040
aataacaagt ttagaaaccc cacggtggcg cctacgcacg acgtgaccac agaccggtcc   23100
cagcgtttga cgctgcggtt catccctgtg gaccgtgagg atactgcgta ctcgtacaag   23160
gcgcggttca ccctagctgt gggtgataac cgtgtgctgg acatggcttc cacgtactt    23220
```

-continued

```
gacatccgcg gcgtgctgga caggggccct acttttaagc cctactctgg cactgcctac    23280
aacgccctgg ctcccaaggg tgccccaaat ccttgcgaat gggatgaagc tgctactgct    23340
cttgaaataa acctagaaga agaggacgat gacaacgaag acgaagtaga cgagcaagct    23400
gagcagcaaa aaactcacgt atttgggcag gcgccttatt ctggtataaa tattacaaag    23460
gagggtattc aaataggtgt cgaaggtcaa acacctaaat atgccgataa acatttcaa     23520 cctgaacctc aaataggaga atctcagtgg tacgaaacag aaattaatca tgcagctggg    23580
agagtcctaa aaaagactac cccaatgaaa ccatgttacg gttcatatgc aaaacccaca    23640
aatgaaaatg gagggcaagg cattcttgta aagcaacaaa atggaaagct agaaagtcaa    23700
gtggaaatgc aattttttctc aactactgag gcagccgcag gcaatggtga taacttgact    23760
cctaaagtgg tattgtacag tgaagatgta gatatagaaa ccccagacac tcatatttct    23820
tacatgccca ctattaagga aggtaactca cgagaactaa tgggccaaca atctatgccc    23880
aacaggccta attacattgc ttttagggac aatttttattg gtctaatgta ttacaacagc    23940
acgggtaata tgggtgttct ggcgggccaa gcatcgcagt tgaatgctgt tgtagatttg    24000
caagacagaa acacagagct ttcataccag cttttgcttg attccattgg tgatagaacc    24060
aggtactttt ctatgtggaa tcaggctgtt gacagctatg atccagatgt tagaattatt    24120
gaaaatcatg gaactgaaga tgaacttcca aattactgct ttccactggg aggtgtgatt    24180
aatacagaga ctcttaccaa ggtaaaacct aaaacaggtc aggaaaatgg atgggaaaaa    24240
gatgctacag aattttcaga taaaaatgaa ataagagttg gaaataattt tgccatggaa    24300
atcaatctaa atgccaacct gtggagaaat ttcctgtact ccaacatagc gctgtatttg    24360
cccgacaagc taaagtacag tccttccaac gtaaaaattt ctgataaccc aaacacctac    24420
gactacatga acaagcgagt ggtggctccc gggctagtgg actgctacat taaccttgga    24480
gcacgctggt cccttgacta tatggacaac gtcaacccat ttaaccacca ccgcaatgct    24540
ggcctgcgct accgctcaat gttgctgggc aatggtcgct atgtgccctt ccacatccag    24600
gtgcctcaga agttctttgc cattaaaaac ctccttctcc tgccgggctc atacacctac    24660
gagtggaact tcaggaagga tgttaacatg gttctgcaga gctccctagg aaatgaccta    24720
agggttgacg gagccagcat taagtttgat agcatttgcc tttacgccac cttcttcccc    24780
atggcccaca acaccgcctc cacgcttgag gccatgctta gaaacgacac caacgaccag    24840
tcctttaacg actatctctc cgccgccaac atgctctacc ctatacccgc caacgctacc    24900
aacgtgccca tatccatccc ctcccgcaac tgggcggctt ccgcggctg ggccttcacg     24960 cgccttaaga ctaaggaaac cccatcactg ggctcgggct acgacccttat ttacacctac    25020 tctggctcta taccctacct agatggaacc ttttacctca accacacctt taagaaggtg     25080
gccattacct ttgactcttc tgtcagctgg cctggcaatg accgcctgct taccccccaac    25140 gagtttgaaa ttaagcgctc agttgacggg gaggttaca acgttgccca gtgtaacatg     25200
accaaagact ggttcctggt acaaatgcta gctaactata acattggcta ccagggcttc    25260
tatatcccag agagctacaa ggaccgcatg tactccttct ttagaaactt ccagcccatg    25320
agccgtcagg tggtggatga tactaaatac aaggactacc aacaggtggg catcctacac    25380
caacacaaca actctggatt tgttggctac cttgccccca ccatgcgcga aggacaggcc    25440
taccctgcta acttcccta tccgcttata ggcaagaccg cagttgacag cattacccag    25500
aaaaagtttc tttgcgatcg cacccttggg cgcatcccat tctccagtaa ctttatgtcc    25560
atgggcgcac tcacagacct gggccaaaac cttctctacg ccaactccgc ccacgcgcta    25620
```

```
gacatgactt tgaggtgga tcccatggac gagcccaccc ttctttatgt tttgtttgaa   25680
gtctttgacg tggtccgtgt gcaccagccg caccgcggcg tcatcgaaac cgtgtacctg   25740
cgcacgccct tctcggccgg caacgccaca acataaagaa gcaagcaaca tcaacaacag   25800
ctgccgccat gggctccagt gagcaggaac tgaaagccat tgtcaaagat cttggttgtg   25860
ggccatattt tttgggcacc tatgacaagc gctttccagg ctttgtttct ccacacaagc   25920
tcgcctgcgc catagtcaat acggccggtc gcgagactgg gggcgtacac tggatggcct   25980
ttgcctggaa cccgcactca aaaacatgct acctctttga gccctttggc ttttctgacc   26040
agcgactcaa gcaggtttac cagtttgagt acgagtcact cctgcgccgt agcgccattg   26100
cttcttcccc cgaccgctgt ataacgctgg aaaagtccac ccaaagcgta caggggccca   26160
actcggccgc ctgtggacta ttctgctgca tgtttctcca cgcctttgcc aactggcccc   26220
aaactcccat ggatcacaac cccaccatga accttattac cggggtaccc aactccatgc   26280
tcaacagtcc ccaggtacag cccacccgtc gtcgcaacca ggaacagctc tacagcttcc   26340
tggagcgcca ctcgccctac ttccgcagcc acagtgcgca gattaggagc gccacttctt   26400
tttgtcactt gaaaaacatg taaaaataat gtactagaga cactttcaat aaaggcaaat   26460
gcttttattt gtacactctc gggtgattat ttaccccac ccttgccgtc tgcgccgttt   26520
aaaaatcaaa ggggttctgc cgcgcatcgc tatgcgccac tggcagggac acgttgcgat   26580
actggtgttt agtgctccac ttaaactcag gcacaaccat ccgcggcagc tcggtgaagt   26640
tttcactcca caggctgcgc accatcacca acgcgtttag caggtcgggc gccgatatct   26700
tgaagtcgca gttggggcct ccgccctgcg cgcgcgagtt gcgatacaca gggttgcagc   26760
actggaacac tatcagcgcc gggtggtgca cgctggccag cacgctcttg tcggagatca   26820
gatccgcgtc caggtcctcc gcgttgctca gggcgaacgg agtcaacttt ggtagctgcc   26880
ttcccaaaaa gggcgcgtgc ccaggctttg agttgcactc gcaccgtagt ggcatcaaaa   26940
ggtgaccgtg cccggtctgg gcgttaggat acagcgcctg cataaaagcc ttgatctgct   27000
taaaagccac ctgagccttt gcgccttcag agaagaacat gccgcaagac ttgccggaaa   27060
actgattggc cggacaggcc gcgtcgtgca cgcagcacct tgcgtcggtg ttggagatct   27120
gcaccacatt tcggccccac cggttcttca cgatcttggc cttgctagac tgctccttca   27180
gcgcgcgctg cccgttttcg ctcgtcacat ccatttcaat cacgtgctcc ttatttatca   27240
taatgcttcc gtgtagacac ttaagctcgc cttcgatctc agcgcagcgg tgcagccaca   27300
acgcgcagcc cgtgggctcg tgatgcttgt aggtcacctc tgcaaacgac tgcaggtacg   27360
cctgcaggaa tcgccccatc atcgtcacaa aggtcttgtt gctggtgaag gtcagctgca   27420
acccgcggtc ctcctcgttc agccaggtct tgcatacggc cgccagagct tccacttggt   27480
caggcagtag tttgaagttc gcctttagat cgttatccac gtggtacttg tccatcagcg   27540
cgcgcgcagc ctccatgccc ttctcccacg cagacacgat cggcacactc agcgggttca   27600
tcaccgtaat ttcactttcc gcttcgctgg gctcttcctc ttcctcttgc gtccgcatac   27660
cacgcgccac tgggtcgtct tcattcagcc gccgcactgt gcgcttacct cctttgccat   27720
gcttgattag caccggtggg ttgctgaaac ccaccatttg tagcgccaca tcttctcttt   27780
cttcctcgct gtccacgatt acctctggtg atggcgggcg ctcgggcttg ggagaagggc   27840
gcttcttttt cttcttgggc gcaatggcca aatccgccgc cgaggtcgat ggccgcgggc   27900
tgggtgtgcg cggcaccagc gcgtcttgtg atgagtcttc ctcgtcctcg gactcgatac   27960
```

```
gccgcctcat ccgcttttt gggggcgccc gggaggcgg cggcgacggg gacggggacg    28020
acacgtcctc catggttggg ggacgtcgcg ccgcaccgcg tccgcgctcg ggggtggttt    28080
cgcgctgctc ctcttcccga ctggccattt ccttctccta taggcagaaa aagatcatgg    28140
agtcagtcga gaagaaggac agcctaaccg cccctctga gttcgccacc accgcctcca    28200
ccgatgccgc caacgcgcct accaccttcc ccgtcgaggc accccgctt gaggaggagg    28260 aagtgattat cgagcaggac ccaggttttg taagcgaaga cgacgaggac cgctcagtac    28320
caacagagga taaaaagcaa gaccaggaca acgcagaggc aaacgaggaa caagtcgggc    28380 gggggacga aaggcatggc gactacctag atgtgggaga cgacgtgctg ttgaagcatc    28440
tgcagcgcca gtgcgccatt atctgcgacg cgttgcaaga gcgcagcgat gtgcccctcg    28500
ccatagcgga tgtcagcctt gcctacgaac gccacctatt ctcaccgcgc gtaccccca    28560 aacgccaaga aaacggcaca tgcgagccca acccgcgcct caacttctac cccgtattg    28620 ccgtgccaga ggtgcttgcc acctatcaca tctttttcca aaactgcaag ataccctat    28680 cctgccgtgc caaccgcagc cgagcggaca agcagctgg cttgcggcag ggcgctgtca    28740
tacctgatat cgcctcgctc aacgaagtgc caaaatctt tgagggtctt ggacgcgacg    28800
agaagcgcgc ggcaaacgct ctgcaacagg aaacagcga aatgaaagt cactctggag    28860 tgttggtgga actcgagggt gacaacgcgc gcctagccgt actaaaacgc agcatcgagg    28920
tcacccactt tgcctacccg gcacttaacc taccccccaa ggtcatgagc acagtcatga    28980
gtgagctgat cgtgcgccgt gcgcagcccc tggagaggga tgcaaatttg caagaacaaa    29040
cagaggaggg cctacccgca gttggcgacg agcagctagc gcgctggctt caaacgcgcg    29100
agcctgccga cttggaggag cgacgcaaac taatgatggc cgcagtgctc gttaccgtgg    29160
agcttgagtg catgcagcgg ttctttgctg acccggagat gcagcgcaag ctagaggaaa    29220
cattgcacta caccttcga cagggctacg tacgccaggc ctgcaagatc tccaacgtgg    29280
agctctgcaa cctggtctcc taccttggaa ttttgcacga aaccgcctt gggcaaaacg    29340 tgcttcattc cacgctcaag ggcgaggcgc gccgcgacta cgtccgcgac tgcgtttact    29400
tatttctatg ctacacctgg cagacggcca tgggcgtttg gcagcagtgc ttggaggagt    29460
gcaacctcaa ggagctgcag aaactgctaa agcaaaactt gaaggaccta tggacggcct    29520
tcaacgagcg ctccgtggcc gcgcacctgg cggacatcat tttccccgaa cgcctgctta    29580
aaaccctgca acagggtctg ccagacttca ccagtcaaag catgttgcag aactttagga    29640
actttatcct agagcgctca ggaatcttgc ccgccacctg ctgtgcactt cctagcgact    29700
ttgtgcccat taagtaccgc gaatgccctc cgccgctttg gggccactgc taccttctgc    29760
agctagccaa ctaccttgcc taccactctg acataatgga agacgtgagc ggtgacggtc    29820
tactggagtg tcactgtcgc tgcaacctat gcaccccgca ccgctccctg gtttgcaatt    29880
cgcagctgct taacgaaagt caaattatcg gtacctttga gctgcagggt ccctcgcctg    29940
acgaaaagtc cgcggctccg gggttgaaac tcactccggg gctgtggacg tcggcttacc    30000
ttcgcaaatt tgtacctgag gactaccacg cccacgagat taggttctac gaagaccaat    30060 cccgccgcc taatgcggag cttaccgcct gcgtcattac ccaggccac attcttggcc    30120 aattgcaagc catcaacaaa gcccgccaag agtttctgct acgaaaggga cgggggttt    30180 acttggaccc ccagtccggc gaggagctca acccaatccc ccgccgccg cagccctatc    30240 agcagcagcc gcgggccctt gcttcccagg atggcaccca aaaagaagct gcagctgccg    30300
ccgccaccca cggacgagga ggaatactgg gacagtcagg cagaggaggt tttggacgag    30360
```

```
gaggaggagg acatgatgga agactgggag agcctagacg aggaagcttc cgaggtcgaa    30420
gaggtgtcag acgaaacacc gtcaccctcg gtcgcattcc cctcgccggc gccccagaaa    30480
tcggcaaccg gttccagcat ggctacaacc tccgctcctc aggcgccgcc ggcactgccc    30540
gttcgccgac ccaaccgtag atgggacacc actggaacca gggccggtaa gtccaagcag    30600
ccgccgccgt tagcccaaga gcaacaacag cgccaaggct accgctcatg gcgcgggcac    30660
aagaacgcca tagttgcttg cttgcaagac tgtgggggca acatctcctt cgcccgccgc    30720
tttcttctct accatcacgg cgtggccttc ccccgtaaca tcctgcatta ctaccgtcat    30780
ctctacagcc catactgcac cggcggcagc ggcagcaaca gcagcggcca cacagaagca    30840
aaggcgaccg gatagcaaga ctctgacaaa gcccaagaaa tccacagcgg cggcagcagc    30900
aggaggagga gcgctgcgtc tggcgcccaa cgaacccgta tcgacccgcg agcttagaaa    30960
caggattttt cccactctgt atgctatatt tcaacagagc aggggccaag aacaagagct    31020
gaaaataaaa aacaggtctc tgcgatccct caccccgcagc tgcctgtatc acaaaagcga    31080
agatcagctt cggcgcacgc tggaagacgc ggaggctctc ttcagtaaat actgcgcgct    31140
gactcttaag gactagtttc gcgccctttc tcaaatttaa gcgcgaaaac tacgtcatct    31200
ccagcggcca cacccggcgc cagcacctgt tgtcagcgcc attatgagca aggaaattcc    31260
cacgccctac atgtggagtt accagccaca aatgggactt gcggctggag ctgcccaaga    31320
ctactcaacc cgaataaact acatgagcgc gggaccccac atgatatccc gggtcaacgg    31380
aatacgcgcc caccgaaacc gaattctcct ggaacaggcg gctattacca ccacacctcg    31440
taataacctt aatccccgta gttggcccgc tgccctggtg taccaggaaa gtcccgctcc    31500
caccactgtg gtacttccca gagacgccca ggccgaagtt cagatgacta actcaggggc    31560
gcagcttgcg ggcggctttc gtcacagggt gcggtcgccc gggcagggta taactcacct    31620
gacaatcaga gggcgaggta ttcagctcaa cgacgagtcg gtgagctcct cgcttggtct    31680
ccgtccggac gggacatttc agatcggcgg cgccggccgc tcttcattca cgcctcgtca    31740
ggcaatccta actctgcaga cctcgtcctc tgagccgcgc tctggaggca ttggaactct    31800
gcaatttatt gaggagtttg tgccatcggt ctactttaac cccttctcgg gacctccgg    31860
ccactatccg gatcaattta ttcctaactt tgacgcggta aaggactcgg cggacggcta    31920
cgactgaatg ttaagtggag aggcagagca actgcgcctg aaacacctgg tccactgtcg    31980
ccgccacaag tgctttgccc gcgactccgg tgagttttgc tactttgaat gcccgagga    32040
tcatatcgag ggcccggcgc acggcgtccg gcttaccgcc cagggagagc ttgcccgtag    32100
cctgattcgg gagtttaccc agcgccccct gctagttgag cgggacaggg gaccctgtgt    32160
tctcactgtg atttgcaact gtcctaaccc tggattacat caagatctta ttcccttaa    32220
ctaataaaaa aaataataa agcatcactt acttaaaatc agttagcaaa tttctgtcca    32280
gtttattcag cagcacctcc ttgccctcct cccagctctg gtattgcagc ttcctcctgg    32340
ctgcaaactt tctccacaat ctaaatggaa tgtcagtttc ctcctgttcc tgtccatccg    32400
cacccactat cttcatgttg ttgcagatga agcgcgcaag accgtctgaa gataccttca    32460
accccgtgta tccatatgac acggaaaccg gtcctccaac tgtgcctttt cttactcctc    32520
cctttgtatc ccccaatggg tttcaagaga gtcccctgg ggtactctct ttgcgcctat    32580
ccgaacctct agttacctcc aatgcatgc ttgcgctcaa aatgggcaac ggcctctctc    32640
tggacgaggc cggcaacctt acctcccaaa atgtaaccac tgtgagccca cctctcaaaa    32700
```

```
aaaccaagtc aaacataaac ctggaaatat ctgcacccct cacagttacc tcagaagccc    32760
taactgtggc tgccgccgca cctctaatgg tcgcgggcaa cacactcacc atgcaatcac    32820
aggccccgct aaccgtgcac gactccaaac ttagcattgc cacccaagga cccctcacag    32880
tgtcagaagg aaagctagcc ctgcaaacat caggcccccct caccaccacc gatagcagta   32940
cccttactat cactgcctca cccctctaa ctactgccac tggtagcttg ggcattgact     33000
tgaaagagcc catttataca caaaatggaa actaggact aaagtacggg gctcctttgc      33060
atgtaacaga cgacctaaac actttgaccg tagcaactgg tccaggtgtg actattaata    33120
atacttcctt gcaaactaaa gttactggag ccttgggttt tgattcacaa ggcaatatgc    33180
aacttaatgt agcaggagga ctaaggattg attctcaaaa cagacgcctt atacttgatg    33240
ttagttatcc gtttgatgct caaaaccaac taaatctaag actaggacag ggccctcttt    33300
ttataaactc agcccacaac ttggatatta actacaacaa aggcctttac ttgtttacag    33360
cttcaaacaa ttccaaaaag cttgaggtta acctaagcac tgccaagggg ttgatgtttg    33420
acgctacagc catagccatt aatgcaggag atgggcttga atttggttca cctaatgcac   33480
caaacacaaa tcccctcaaa acaaaaattg gccatggcct agaatttgat tcaaacaagg    33540
ctatggttcc taaactagga actggcctta gttttgacag cacaggtgcc attacagtag    33600
gaaacaaaaa taatgataag ctaactttgt ggaccacacc agctccatct cctaactgta    33660
gactaaatgc agagaaagat gctaaactca ctttggtctt aacaaaatgt ggcagtcaaa    33720
tacttgctac agtttcagtt ttggctgtta aaggcagttt ggctccaata tctggaacag    33780
ttcaaagtgc tcatcttatt ataagatttg acgaaaatgg agtgctacta acaattcct     33840 tcctggaccc agaatattgg aactttagaa atggagatct tactgaaggc acagcctata    33900
caaacgctgt tggatttatg cctaacctat cagcttatcc aaaatctcac ggtaaaactg    33960
ccaaaagtaa cattgtcagt caagtttact aaacggaga caaaactaaa cctgtaacac     34020
taaccattac actaaacggt acacaggaaa caggagacac aactccaagt gcatactcta   34080
tgtcattttc atgggactgg tctggccaca actacattaa tgaaatattt gccacatcct    34140
cttacctttt tcatacatt gcccaagaat aaagaatcgt tgtgttatg tttcaacgtg       34200 tttatttttc aattgcagaa aatttcaagt cattttttcat tcagtagtat agccccacca    34260
ccacatagct tatacagatc accgtacctt aatcaaactc acagaaccct agtattcaac    34320
ctgccacctc cctcccaaca cacagagtac acagtccttt ctccccggct ggccttaaaa    34380
agcatcatat catgggtaac agacatattc ttaggtgtta tattccacac ggtttcctgt    34440
cgagccaaac gctcatcagt gatattaata aactccccgg gcagctcact taagttcatg    34500
tcgctgtcca gctgctgagc cacaggctgc tgtccaactt gcggttgctt aacgggcggc    34560
gaaggagaag tccacgccta catgggggta gagtcataat cgtgcatcag datagggcgg    34620
tggtgctgca gcagcgcgcg aataaactgc tgccgccgcc gctccgtcct gcaggaatac    34680
aacatggcag tggtctcctc agcgatgatt cgcaccgccc gcagcataag gcgccttgtc    34740
ctccgggcac agcagcgcac cctgatctca cttaaatcag cacagtaact gcagcacagc    34800
accacaatat tgttcaaaat cccacagtgc aaggcgctgt atccaaagct catggcgggg    34860
accacagaac ccacgtggcc atcataccac aagcgcaggt agattaagtg gcgacccctc    34920
ataaacacgc tggacataaa cattacctct tttggcatgt tgtaattcac cacctcccgg    34980
taccatataa acctctgatt aaacatggcg ccatccacca ccatcctaaa ccagctggcc    35040
aaaacctgcc cgccggctat acactgcagg gaaccgggac tggaacaatg acagtggaga    35100
```

-continued

```
gcccaggact cgtaaccatg gatcatcatg ctcgtcatga tatcaatgtt ggcacaacac   35160
aggcacacgt gcatacactt cctcaggatt acaagctcct cccgcgttag aaccatatcc   35220
cagggaacaa cccattcctg aatcagcgta aatcccacac tgcagggaag acctcgcacg   35280
taactcacgt tgtgcattgt caaagtgtta cattcgggca gcagcggatg atcctccagt   35340
atggtagcgc gggtttctgt ctcaaaagga ggtagacgat ccctactgta cggagtgcgc   35400
cgagacaacc gagatcgtgt tggtcgtagt gtcatgccaa atggaacgcc ggacgtagtc   35460
atatttcctg aagcaaaacc aggtgcgggc gtgacaaaca gatctgcgtc tccggtctcg   35520
ccgcttagat cgctctgtgt agtagttgta gtatatccac tctctcaaag catccaggcg   35580
cccctggct tcgggttcta tgtaaactcc ttcatgcgcc gctgccctga taacatccac   35640
caccgcagaa taagccacac ccagccaacc tacacattcg ttctgcgagt cacacacggg   35700
aggagcggga agagctggaa gaaccatgtt ttttttttta ttccaaaaga ttatccaaaa   35760
cctcaaaatg aagatctatt aagtgaacgc gctcccctcc ggtggcgtgg tcaaactcta   35820
cagccaaaga acagataatg gcatttgtaa gatgttgcac aatggcttcc aaaaggcaaa   35880
cggccctcac gtccaagtgg acgtaaaggc taaacccttc agggtgaatc tcctctataa   35940
acattccagc accttcaacc atgcccaaat aattctcatc tcgccacctt ctcaatatat   36000
ctctaagcaa atcccgaata ttaagtccgg ccattgtaaa aatctgctcc agagcgccct   36060
ccaccttcag cctcaagcag cgaatcatga ttgcaaaaat tcaggttcct cacagacctg   36120
tataagattc aaaagcggaa cattaacaaa aataccgcga tcccgtaggt cccttcgcag   36180
ggccagctga acataatcgt gcaggtctgc acggaccagc gcggccactt ccccgccagg   36240
aaccatgaca aaagaaccca cactgattat gacacgcata ctcggagcta tgctaaccag   36300
cgtagccccg atgtaagctt gttgcatggg cggcgatata aaatgcaagg tgctgctcaa   36360
aaaatcaggc aaagcctcgc gcaaaaaaga aagcacatcg tagtcatgct catgcagata   36420
aaggcaggta agctccggaa ccaccacaga aaaagacacc attttctct caaacatgtc   36480
tgcgggtttc tgcataaaca caaaataaaa taacaaaaaa acatttaaac attagaagcc   36540
tgtcttacaa caggaaaaac aaccctatta agcataagac ggactacggc catgccggcg   36600
tgaccgtaaa aaaactggtc accgtgatta aaaagcacca ccgacagctc ctcggtcatg   36660
tccggagtca taatgtaaga ctcggtaaac acatcaggtt gattcacatc ggtcagtgct   36720
aaaaagcgac cgaaatagcc cggggggaata catacccgca ggcgtagaga caacattaca   36780
gcccccatag gaggtataac aaaattaata ggagagaaaa acacataaac acctgaaaaa   36840
ccctcctgcc taggcaaaat agcaccctcc cgctccagaa caacatacag cgcttccaca   36900
gcggcagcca taacagtcag ccttaccagt aaaaagaaaa acctattaaa aaaacaccac   36960
tcgacacggc accagctcaa tcagtcacag tgtaaaaaag ggccaagtgc agagcgagta   37020
tatataggac taaaaaatga cgtaacggtt aaagtccaca aaaaacaccc agaaaaccgc   37080
acgcgaacct acgcccagaa acgaaagcca aaaaacccac aacttcctca aatcgtcact   37140
tccgtttttcc cacgttacgt cacttcccat tttaagaaaa ctacaattcc caacacatac   37200
aagttactcc gccctaaaac ctacgtcacc cgccccgttc ccacgcccccg cgccacgtca   37260
caaactccac cccctcatta tcatattggc ttcaatccaa aataaggtat attattgatg   37320
atg                                                                37323
```

ENGINEERED CELLS EXPRESSING MULTIPLE IMMUNOMODULATORS AND USES THEREOF

CROSS-REFERENCE TO RELATED APPLICATIONS

This application is claims priority benefit of U.S. Provisional Application No. 61/103,810, filed Oct. 8, 2008, which is hereby incorporated by reference in its entirety.

REFERENCE TO SEQUENCE LISTING SUBMITTED ELECTRONICALLY VIA EFS-WEB

The content of the electronically submitted sequence listing (Name: sequence listing.ST25.txt; Size: 213,102 bytes; Date Of Creation: Oct. 8, 2009) filed with this application is incorporated herein by reference in its entirety.

BACKGROUND OF THE INVENTION

Field of the Invention

This invention relates to the field of gene therapy for the treatment of diseases and disorders, such as cancer. In one embodiment, the invention provides the engineering of immune cells or therapy support cells (TSC) to express one or more immunomodulators and use of the cells as therapeutics.

Background

Interleukin-12 (IL-12) is a member of the type I cytokine family involved in contributing to a number of biological processes including, but not limited to, protective immune response and suppression of tumorigenesis (Abdi et al., 2006; Adorini, 1999; Adorini, 2001; Adorini et al., 2002; Adorini et al., 1996; Akhtar et al., 2004; Akiyama et al., 2000; Al-Mohanna et al., 2002; Aliberti et al., 1996; Allavena et al., 1994; Alli and Khar, 2004; Alzona et al., 1996; Amemiya et al., 2006; Araujo et al., 2001; Arulanandam et al., 1999; Athie et al., 2000; Athie-Morales et al., 2004; Bertagnolli et al., 1992; Bhardwaj et al., 1996; Biedermann et al., 2006; Brunda and Gately, 1994; Buchanan et al., 1995; Romani et al., 1997; Rothe et al., 1996; Satoskar et al., 2000; Schopf et al., 1999; Thomas et al., 2000; Tsung et al., 1997; Wolf et al., 1994; Yuminamochi et al., 2007). A growing body of evidence suggests that IL-12 may be a promising target to control human diseases (e.g., cancer).

Despite the fact that IL-12 remains promising as a cancer therapeutic agent based on its potent supportive activity on Type-1 anti-tumor NK cells, CD4$^+$ T cells and CD8$^+$ T cells (Trinchieri, 2003), the reported toxicity of recombinant human IL-12 (rhTL-12) in patients (Atkins et al., 1997), together with limited sources of GMP-grade rhIL-12 for clinical application, have prevented successful IL-12-based therapeutic approaches. Thus it seems reasonable that gene therapy approaches may represent safer, more tenable treatment options. Indeed, phase I clinical trials implementing intra- or peri-tumoral delivery of recombinant viral- (Sangro et al., 2004; Triozzi et al., 2005) or plasmid-based IL-12 cDNA (Heinzerling et al., 2005), or IL-12 gene modified autologous fibroblasts (Kang et al., 2001) have been found safe and well-tolerated.

However, objective clinical responses in patients with melanoma or a diverse range of carcinomas receiving these gene therapies have been rare, variable, transient and largely focused at the site of treatment (Heinzerling et al., 2005; Kang et al., 2001; Sangro et al., 2004; Triozzi et al., 2005). In cases where disease resolution was partial or complete, increased frequencies of tumor-infiltrating lymphocytes (Heinzerling et al., 2005; Sangro et al., 2004) and elevated levels of circulating tumor-specific CD8$^+$ T cells (Heinzerling et al., 2005) have been noted, consistent with the improved cross-priming of antigen-specific T cells in these patients.

Since the cross-priming of specific T cells is best accomplished by dendritic cells (DC) that serve as a natural but regulated source of IL-12 (Berard et al., 2000), recent reports of the superior pre-clinical efficacy of DC-based IL-12 gene therapy have been of great interest (Satoh et al., 2002; Tatsumi et al., 2003; Yamanaka et al., 2002). For example, it was shown that intratumoral (i.t.) injection of DC engineered to produce IL-12p70 (via recombinant adenovirus infection) results in the dramatically improved cross-priming of a broadly-reactive, tumor-specific CD8$^+$ T cell repertoire in concert with tumor rejection in murine models (Tatsumi et al., 2003). Given the previous use of a recombinant adenovirus encoding mIL-12 under a CMV-based promoter (rAd.cIL12, (Tatsumi et al., 2003)), engineered DC production of IL-12 was constitutive, hence the immunologic impact of this cytokine early within the tumor lesion and later within tumor-draining lymph nodes could not be resolved with regards to therapeutic outcome. Thus, a need exists for DC engineered for conditional expression of IL-12 for the purpose of regulating both the level of transgene expression and the timing of the transgene activation. The invention provides a promising therapeutic outcome for the use of such cells.

SUMMARY OF THE INVENTION

The invention provides a recombinant vector encoding protein(s) having the function(s) of one or more immunomodulators, under the control of one or more promoters. In one embodiment, the one or more promoters are conditional. In another embodiment, the one or more promoters are constitutive. In another embodiment, the vector is an adenovirus vector encoding the protein(s) driven off a promoter that can be conditionally activated by provision of a soluble small molecule ligand such as diacylhydrazines (e.g., RG-115819, RG-115830 or RG-115932). This vector allows for the control of expression of the protein(s) from immune cells and TSC.

In one embodiment, the invention provides a vector for conditionally expressing protein(s) having the function(s) of one or more immunomodulators comprising a polynucleotide encoding a gene switch, wherein said polynucleotide encoding a gene switch comprises (1) at least one transcription factor sequence operably linked to a promoter, wherein said at least one transcription factor sequence encodes a ligand-dependent transcription factor, and (2) a polynucleotide encoding one or more proteins having the function of an immunomodulator linked to a promoter which is activated by said ligand-dependent transcription factor. In one embodiment, the immunomodulator is selected from IL-1, IL-2, IL-3, IL-4, IL-5, IL-7, IL-8, IL-9, IL-10R DN or a subunit thereof, IL-15, IL-18, IL-21, IL-23, IL-24, IL-27, GM-CSF, IFN-alpha, IFN-gamma, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, TGF-alpha, PD-L1RNAi, a PD-L1 antisense oligonucleotide, TGFbRII DN, ICOS-L and S100.

In another embodiment, the invention provides a vector for expressing protein(s) having the function(s) of one or more immunomodulators and a protein having the function of IL-12, comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more immunomodulators, and (3) a polynucleotide encoding a protein having the function of the IL-12; wherein at least one polynucleotide of (2) and (3) are linked to the promoter which is activated by the ligand-dependent transcription factor.

The invention further provides a method of producing a population of cells, e.g., immune cells or TSC, expressing protein(s) having the function of one or more immunomodulators, by modifying (e.g., transfecting, electroporating, etc.) the cells with a recombinant vector conditionally expressing protein(s) having the function(s) of the one or more immunomodulators, wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins having the function of an immunomodulator linked to a promoter which is activated by said ligand-dependent transcription factor.

In another embodiment, the invention provides a method of producing a population of cells, e.g., immune cells or TSC, expressing proteins having the function(s) of one or more immunomodulators and a protein having the function of IL-12, by modifying the cells with a recombinant vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more immunomodulators, and (3) a polynucleotide encoding a protein having the function of the IL-12; wherein at least one polynucleotide of (2) and (3) are linked to the promoter which is activated by said ligand-dependent transcription factor.

The invention further provides a population of cells, e.g., immune cells or TSC, expressing protein(s) having the function of one or more immunomodulators, which has been modified (e.g., transfected, electroporated, etc.) with a recombinant vector conditionally the expressing protein(s) having the function(s) of the one or more immunomodulators, wherein the vector comprises a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding one or more proteins having the function of an immunomodulator linked to the promoter which is activated by said ligand-dependent transcription factor.

In another embodiment, the invention provides a population of cells, e.g., immune cells or TSC, expressing proteins having the function(s) of one or more immunomodulators and a protein having the function of IL-12, which has been modified with a recombinant vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding said protein(s) having the function(s) of the one or more immunomodulators and (3) a polynucleotide encoding a protein having the function of the IL-12; wherein at least one polynucleotide of (2) and (3) are linked to a promoter which is activated by said ligand-dependent transcription factor.

In another embodiment, the invention provides a composition comprising two or more populations of cells of the present invention, e.g., immune cells or TSC, wherein each population of cells in the composition expresses one or more immunomodulators that are different from the one or more immunomodulators expressed in the other population(s) of cells in the composition. In one embodiment, the composition contains two populations of cells. In another embodiment, the composition contains more than two populations of cells. In another embodiment, the composition contains three populations of cells. In another embodiment, the composition contains four populations of cells.

In another embodiment, the invention provides an in vitro engineered cell, e.g., immune cell or TSC, comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein having the function of an immunomodulator linked to a promoter which is activated by said ligand-dependent transcription factor. In another embodiment, the invention provides an in vitro engineered cell, e.g., immune cell or TSC, comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding a protein having the function of an immunomodulator, and (3) a polynucleotide encoding a protein having the function of IL-12; wherein at least one polynucleotide of (2) and (3) are linked to a promoter which is activated by said ligand-dependent transcription factor.

In another embodiment, the invention provides a composition comprising two or more populations of in vitro engineered cells, e.g., immune cells or TSCs, of the present invention, wherein each of the populations of in vitro engineered cells in the composition comprises a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, and (2) a polynucleotide encoding a protein having the function of an immunomodulator linked to a promoter which is activated by said ligand-dependent transcription factor, and wherein each population of in vitro engineered cells in the composition expresses one or more immunomodulators that are different from the one or more immunomodulators expressed in the other population(s) of in vitro engineered cell in the composition. In one embodiment, the invention provides a composition comprising two or more populations of in vitro engineered cells, e.g., immune cell or TSC, each of said populations of cells comprising a vector comprising a polynucleotide encoding a gene switch, wherein said polynucleotide comprises (1) at least one transcription factor sequence operably linked to a promoter, wherein said at least one transcription factor sequence encodes a ligand-dependent transcription factor, (2) a polynucleotide encoding a protein having the function of an immunomodulator, and (3) a polynucleotide encoding a protein having the function of IL-12; wherein at least one polynucleotide of (2) and (3) are linked to a promoter which is activated by said ligand-dependent transcription factor. In one embodiment, the composition contains two populations of in vitro engineered cells. In another embodiment, the composition contains more than two populations of in vitro engineered cells. In another embodiment, the composition contains three populations of in vitro engineered cells. In another embodiment, the composition contains four populations of in vitro engineered cells.

The invention also provides a pharmaceutical composition comprising a population of cells, e.g., immune cells or TSC, as described herein.

In one embodiment, the polynucleotide coding for the one or more proteins having the functions of the immunomodulator is under control of the promoter of the gene switch and the polynucleotide coding for a protein having the function of IL-12 is under control of a constitutive promoter. In another embodiment, both the polynucleotide coding for protein(s) having the functions of the immunomodulator(s) and the polynucleotide coding for a protein having the function of IL-12 are both under control of a multicistronic promoter of the gene switch. In another embodiment, the polynucleotide coding for a protein(s) having the function of the immunomodulator(s) is under control of the promoter of the gene switch and the polynucleotide coding for a protein having the function of IL-12 is under control of a conditional promoter which is different than the gene switch promoter. In a further embodiment, the gene regulation system for the polynucleotide coding for the protein(s) having the function of the immunomodulator(s) and the gene regulation system for the polynucleotide having the function of IL-12 are orthogonal. In a further embodiment, the gene regulation system for each polynucleotide coding for each protein is orthogonal.

In one embodiment, the invention also provides a treatment of cancer, such as, but not limited to, melanoma tumors, glioma tumors, renal cancer, and prostate cancers, as well as the cancers listed herein in Table 1. IL-12 gene therapy has demonstrated anti-tumor efficacy in animal model studies when applied as a recombinant cDNA vector (Faure et al., 1998; Sangro et al., 2005), but even more so, when applied in the context of gene-modified DC (Satoh et al., 2002; Svane et al., 1999; Tatsumi et al., 2003; Yamanaka et al., 2002). To date, however, human phase I trials of IL-12 gene therapy implementing plasmids or viral vectors have failed to achieve durable, objective clinical responses in the cancer setting (Heinzerling et al., 2005; Kang et al., 2001; Sangro et al., 2004; Triozzi et al., 2005). gene therapy as described herein provides a promising therapeutic modality.

In one embodiment, the invention provides a method for treating a tumor in a mammal, comprising the steps of:
(a) administering intratumorally to tumor microenvironments a population of immune cells or TSC, which are in vitro engineered to conditionally express one or more proteins having the function of an immunomodulator; and
(b) administering to said mammal a therapeutically effective amount of an activating ligand;
thereby inducing expression of a protein having the function of the immunomodulator and treating said tumor.

In another embodiment, the invention provides a method for treating a tumor in a mammal, comprising the steps of:
(a) administering intratumorally to tumor microenvironments two or more populations of immune cells or TSCs, which are in vitro engineered to conditionally express one or more proteins having the function of an immunomodulator, wherein each population of immune cells or TSCs expresses a different set of one or more immunomodulators; and
(b) administering to said mammal a therapeutically effective amount of one or more activating ligands;
thereby inducing expression of proteins having the function of the immunomodulators and treating said tumor.

In another embodiment, the invention provides a method for treating a tumor in a mammal, comprising the steps of:
(a) administering intratumorally to tumor microenvironments a population of an immune cells or TSC, which are in vitro engineered to conditionally express one or more proteins having the function of an immunomodulator and a protein having the function of IL-12, wherein at least one of the proteins having the function of the immunomodulator or IL-12 is under control of a conditional promoter that is activated by a ligand; and
(b) administering to said mammal a therapeutically effective amount of the activating ligand;
thereby inducing expression of a protein having the function of the immunomodulator and/or the protein having the function of IL-12 and treating said tumor.

In another embodiment, the invention provides a method for treating a tumor in a mammal, comprising the steps of:
(a) administering intratumorally to tumor microenvironments two or more populations of an immune cells or TSCs, which are in vitro engineered to conditionally express one or more proteins having the function of an immunomodulator and a protein having the function of IL-12, wherein each population of immune cells or TSCs expresses a different set of one or more proteins having the function of an immunomodulator, wherein at least one of the proteins having the function of the immunomodulator or IL-12 is under control of a conditional promoter that is activated by a ligand; and
(b) administering to said mammal a therapeutically effective amount of one or more activating ligands;
thereby inducing expression of a protein having the function of the immunomodulators and/or the protein having the function of IL-12 and treating said tumor.

In another embodiment, the invention provides a method for treating a disease or disorder in a mammal, comprising the steps of:
(a) administering to said mammal a population of modified cells, which are modified to conditionally express one or more proteins having the function of an immunomodulator; and
(b) administering to said mammal a therapeutically effective amount of an activating ligand;
thereby inducing expression of a protein having the function of the immunomodulator and treating said disease or disorder.

In another embodiment, the invention provides a method for treating a disease or disorder in a mammal, comprising the steps of:
(a) administering to said mammal two or more populations of modified cells, which are modified to conditionally express one or more proteins having the function of an immunomodulator, wherein each population of modified cells expresses a different set of one or more immunomodulators; and
(b) administering to said mammal a therapeutically effective amount of one or more activating ligands;

thereby inducing expression of proteins having the function of the immunomodulators and treating said disease or disorder.

In another embodiment, the invention provides a method for treating a disease or disorder in a mammal, comprising the steps of:
(a) administering to said mammal a population of a modified cells, which are modified to conditionally express one or more proteins having the function of an immunomodulator and a protein having the function of IL-12, wherein at least one of the proteins having the function of the immunomodulator or IL-12 is under control of a conditional promoter that is activated by a ligand; and
(b) administering to said mammal a therapeutically effective amount of the activating ligand;
thereby inducing expression of a protein having the function of the immunomodulator and/or the protein having the function of IL-12 and treating said disease or disorder.

In another embodiment, the invention provides a method for treating a disease or disorder in a mammal, comprising the steps of:
(a) administering to said mammal two or more populations of modified cells, which are modified to conditionally express one or more proteins having the function of an immunomodulator and a protein having the function of IL-12, wherein each population of modified cells expresses a different set of one or more proteins having the function of an immunomodulator, wherein at least one of the proteins having the function of the immunomodulator or IL-12 is under control of a conditional promoter that is activated by a ligand; and
(b) administering to said mammal a therapeutically effective amount of one or more activating ligands;
thereby inducing expression of a protein having the function of the immunomodulators and/or the protein having the function of IL-12 and treating said disease or disorder.

The invention also provides a method for determining the efficacy of engineered cell-, e.g., immune cell- or TSC-, based therapy by measuring the level of expression or activity of IFN-gamma in a patient before the start of therapy, thereby generating a control level, followed by the administration of cells engineered to express one or more proteins having the functions of an immunomodulator and optionally a protein having the function of IL-12, administering an effective amount of an activating ligand, and then measuring the level of expression of IFN-gamma to generate a test level, and comparing the control level to the test level to determine if the therapeutic regime is effective.

In one embodiment, the invention provides a method for determining the efficacy of an in vitro engineered cell-, e.g., immune cell- or TSC-, based therapeutic regime in a patient comprising:
(a) measuring the level of expression or the level of activity or both of interferon-gamma (IFN-gamma) in a first biological sample obtained from said patient in need thereof before administration of the in vitro engineered cells, thereby generating a control level;
(b) administering to a patient in need thereof the in vitro engineered cells engineered to conditionally express one or more proteins having the functions of an immunomodulator and optionally a protein having the function of IL-12;
(c) administering to said patient in need thereof an effective amount of an activating ligand;
(d) measuring the level of expression or the level of activity or both of IFN-gamma in a second biological sample obtained from said patient in need thereof following administration of in vitro engineered immune cells and activating ligand, thereby generating a test level; and
(e) comparing the control level to the test level of IFN-gamma, wherein an increase in the test level of expression, activity or both of IFN-gamma relative to the control level indicates that the therapeutic regime is effective in said patient in need thereof.

DETAILED DESCRIPTION OF DRAWINGS

DETAILED DESCRIPTION OF SEQUENCES

Figure 1:
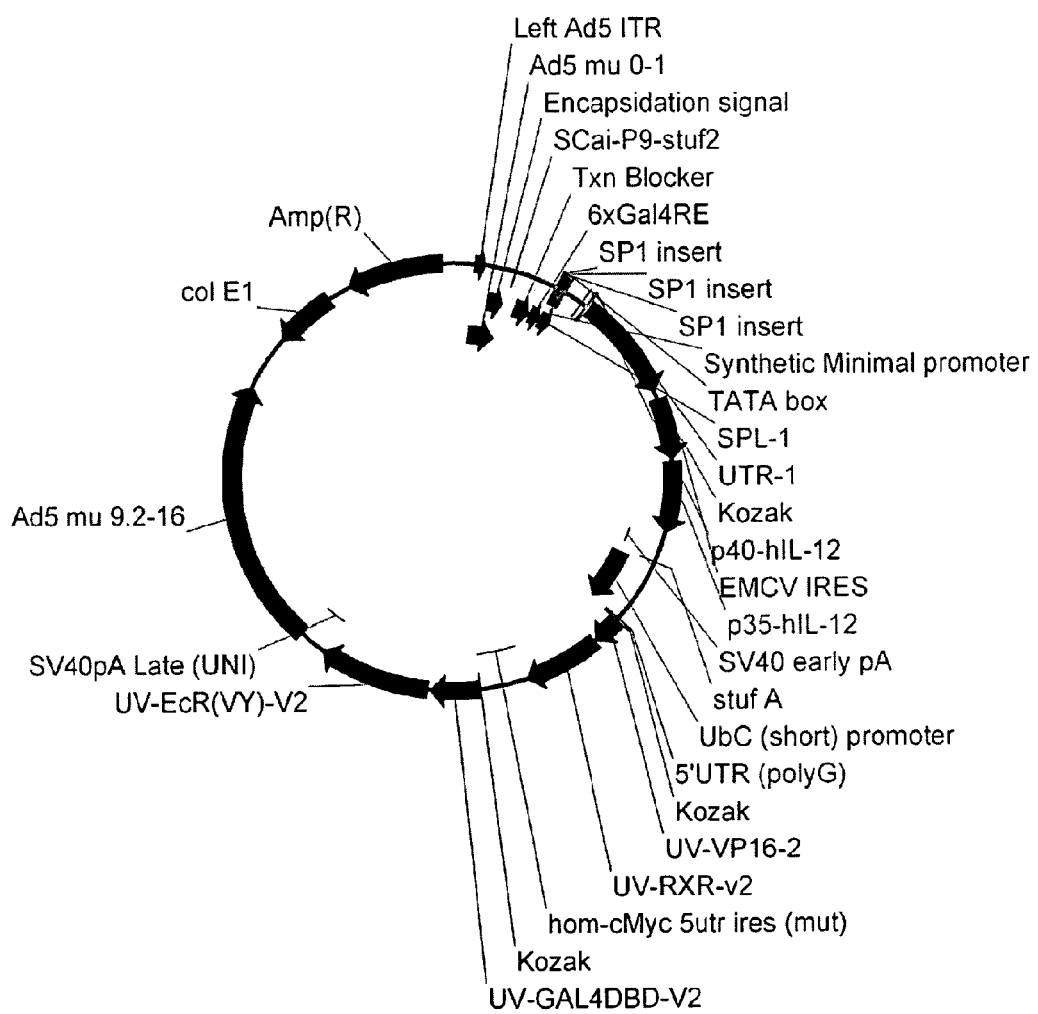
FIG. 1 shows a plasmid map for a regulated promoter expression system for a bicistronic transcript encoding hIL-12.

Immunomodulators
Cytokines
The polynucleotide sequences of interleukin 1 (IL-1), which are cytokines important for inflammatory response against infection, are available from public databases as accession numbers M28983 (human IL-1α); M15330 (human IL-1β); AF201830 (human IL-1δ); AF201831 (human IL-1ε); AF201832 (human 1L-1ζ); AF201833 (human IL-1η); NM_010554 (mouse IL-1α); NM_008361 (mouse IL-1β); NM_019451 (mouse L-1δ); NM_019450 (mouse IL-1f6); NM_027163 (mouse IL-1f8); NM_153511 (mouse IL-1f9); NM_204524 (chicken IL-1β); NM_017019 (rat IL-1α); and NM_031512 (rat IL-1β), sequences of which are incorporated by reference herein.

The amino acid sequences of interleukin 1 (IL-1) are available from public databases as accession numbers AAA59134 (human IL-1α); AAA59135 (human IL-1β); AAF25210 (human IL-1δ); AAF25211 (human IL-1ε); AAF25212 (human 1L-1ζ); AAF25213 (human IL-1η); NP_034684 (mouse IL-1α); NP_032387 (mouse IL-1β); NP_062324 (mouse L-1δ); NP_062323 (mouse IL-1f6); NP_081439 (mouse IL-1f8); NP_705731 (mouse IL-1f9);

NP_989855 (chicken IL-1β); NP_058715 (rat IL-1α); and NP_113700 (rat IL-1β), sequences of which are incorporated by reference herein. Laurent et al., *Psychiatr. Genet.* 7: 103 (1997) identified polymorphic mutations in human interleukin-1 beta gene.

The polynucleotide sequences of interleukin 2 (IL-2), which belongs to a family of cytokines, including IL-4, IL-7, IL-9, IL-15, and IL-21, are available from public databases as accession numbers U25676 (human); NM_008366 (mouse); NM_204153 (chicken); and NM_053836 (rat), sequences of which are incorporated by reference herein.

The amino acid sequences of interleukin 2 (IL-2) are available from public databases as accession numbers AAA70092 (human); NP_032392 (mouse); NP_989484 (chicken); and NP_446288 (rat), sequences of which are incorporated by reference herein.

Liu et al., *Appl. Biochem. Biotechnol.* 133: 77 (2006) generated mutant human IL-2, and Lorberboum et al., *J. Biol. Chem.* 265: 16311 (1990) describes generation of chimeric IL-2.

The polynucleotide sequences of interleukin 4 (IL-4), which is a cytokine that induces differentiation of naïve helper T cells to Th2 cells, are available from public databases as accession numbers M23442 (human); NM_021283 (mouse); NM_001007079 (chicken); and NM_201270 (rat), sequences of which are incorporated by reference herein.

The amino acid sequences of interleukin 4 (IL-4) are available from public databases as accession numbers AAA59150 (human); NP_067258 (mouse); NP_001007080 (chicken); and NP_958427 (rat), sequences of which are incorporated by reference herein.

Kawashima et al., *J. Med. Genet.* 35: 502 (1998) describes polymorphisms in IL-4 gene, that are associated with atopic dermatitis.

Interleukin 7 (IL-7) is a cytokine important for B and T cell development. The polynucleotide sequences of IL-7 are available from public databases as accession numbers J04156 (human); NM_008371 (mouse); NM_001037833 (chicken); and NM_013110 (rat), sequences of which are incorporated by reference herein.

The amino acid sequences of interleukin 7 (IL-7) are available from public databases as accession numbers AAA59156 (human); NP_032397 (mouse); NP_001032922 (chicken); and NP_037242 (rat), sequences of which are incorporated by reference herein.

Feng et al., *Genetics* 175:545 (2007) have identified point mutations in IL-7 that results in functional deficiency.

Interleukin 9 (IL-9) is a cytokine produced by T-cells and is a regulator of hematopoietic cells. The polynucleotide sequences of IL-9 are available from public databases as accession numbers NM_000590 (human); NM_008373 (mouse); NM_001037825 (chicken); and NM_001105747 (rat), sequences of which are incorporated by reference herein.

The amino acid sequences of interleukin 9 (IL-9) are available from public databases as accession numbers NP_000581 (human); NP_032399 (mouse); NP_001032914 (chicken); and NP_001099217 (rat), sequences of which are incorporated by reference herein.

IL-12 is a cytokine that can act as a growth factor for activated T and NK cells, enhance the lytic activity of NK/lymphokine-activated Killer cells, and stimulate the production of IFN-gamma by resting peripheral blood mononuclear cells (PBMC). The polynucleotide sequences of IL-12 are available from public databases as accession numbers NM_000882 (human IL12A); NM_002187 (human IL12B); NM_008351 (mouse IL12a); NM_008352 (mouse IL12b); NM_213588 (chicken IL12A); NM_213571 (chicken IL12B); NM_053390 (rat IL12a); and NM_022611 (rat IL12b), sequences of which are incorporated by reference herein.

The amino acid sequences of interleukin 12 (IL-12) are available from public databases as accession numbers NP_000873 (human IL12A); NP_002178 (human IL12B); NP_032377 (mouse IL12a); NP_032378 (mouse IL12b); NP_998753 (chicken IL12A); NP_998736 (chicken IL12B); NP_445842 (rat IL12a); and NP_072133 (rat IL12b), sequences of which are incorporated by reference herein.

Interleukin 15 (IL-15) is a cytokine that regulates T and natural killer cell activation and proliferation. The polynucleotide sequences of IL-15 are available from public databases as accession numbers U14407 (human); NM_008357 (mouse); EU334509 (chicken); and AF015719 (rat), sequences of which are incorporated by reference herein.

The amino acid sequences of interleukin 15 (IL-15) are available from public databases as accession numbers AAA21551 (human); NP_032383 (mouse); ABY55312 (chicken); and AAB94536 (rat), sequences of which are incorporated by reference herein.

Interleukin 18 (IL-18), a cytokine produced by macrophage that together with interleukin 12 induces cell-mediated immunity following infection with microbial products. The polynucleotide sequences of IL-18 are available from public databases as accession numbers U90434 (human); NM_008360 (mouse); EU747333 (chicken); and AY258448 (rat), sequences of which are incorporated by reference herein.

The amino acid sequences of interleukin 18 (IL-18) are available from public databases as accession numbers AAB50010 (human); NP_032386 (mouse); ACE79188 (chicken); and AAP14669 (rat), sequences of which are incorporated by reference herein.

The polynucleotide sequences of interleukin 21 (IL-21), which is a cytokine that has a potent regulatory effects on cells of the immune system, including natural killer cells and cytotoxic T cells by inducing cell proliferation, are available from public databases as accession numbers AF254069 (human); NM_021782 (mouse); NM_001024835 (chicken); and NM_001108943 (rat), sequences of which are incorporated by reference herein.

The amino acid sequences of interleukin 21 (IL-21) are available from public databases as accession numbers, AAG29348 (human); NP_068554 (mouse); NP_001020006 (chicken); and NP_001102413 (rat), sequences of which are incorporated by reference herein.

Interleukin 27 (IL-27) is a cytokine that plays important function in regulating the activity of B and T lymphocytes. The polynucleotide sequences of IL-27 are available from public databases as accession numbers AY099296 (human); NM_145636 (mouse); and XM_344962 (rat), sequences of which are incorporated by reference herein.

The amino acid sequences of interleukin 27 (IL-27) are available from public databases as accession numbers AAM34498 (human); NP_663611 (mouse); and XP_344963 (rat), sequences of which are incorporated by reference herein.

The polynucleotide sequences of interferon beta 1 (IFNB1), which is a member of group of interferon proteins that bind to specific cell surface receptors (IFNAR), and stimulates both macrophages and natural killer (NK) cells to elicit an anti-viral response, are available from public databases as accession numbers NM_002176 (human);

NM_010510 (mouse); NM_001024836 (chicken); and NM_019127 (rat), sequences of which are incorporated by reference herein.

The amino acid sequences of interferon beta 1 (IFNB1) are available from public databases as accession numbers NP_002167 (human); NP_034640 (mouse); NP_001020007 (chicken); and NP_062000 (rat), sequences of which are incorporated by reference herein.

Interferon gamma (IFN-gamma) is a soluble cytokine that is the only Type II interferon and has antiviral, immunoregulatory, and anti-tumor activity. The polynucleotide sequences of IFN-gamma are available from public databases as accession numbers NM_000619 (human); NM_008337 (mouse); and NM_138880 (rat), sequences of which are incorporated by reference herein.

The amino acid sequences of interferon gamma (IFN-gamma) are available from public databases as accession numbers NP_000610 (human); NP_032363 (mouse); and NP_620235 (rat) sequences of which are incorporated by reference herein.

The polynucleotide sequences of tumor necrosis factor (TNF-alpha), which is a multifunctional proinflammatory cytokine secreted predominantly by monocytes/macrophages that has effects on lipid metabolism, coagulation, insulin resistance, and endothelial function, are available from public databases as accession numbers X02910 (human); NM_013693 (mouse); and BC107671 (rat), sequences of which are incorporated by reference herein.

The amino acid sequences of TNF-alpha are available from public databases as accession numbers CAA26669 (human); NP_038721 (mouse); and AAI07672 (rat), sequences of which are incorporated by reference herein.

Chemokines

Chemokine (C motif) ligand 1 (XCL1, also known as Lymphotactin) is chemotactic for CD4+ and CD8+ T cells but not for monocytes, and induces a rise in intracellular calcium in peripheral blood lymphocytes. The polynucleotide sequences of XCL1 are available from public databases as accession numbers NM_002995 (human); NM_008510 (mouse); and NM_134361 (rat), sequences of which are incorporated by reference herein.

The amino acid sequences of XCL1 are available from public databases as accession numbers NP_002986 (human); NP_032536 (mouse); and NP_599188 (rat), sequences of which are incorporated by reference herein. U.S. Pat. No. 6,022,534 discloses lymphotactin and use to either attract cytotoxic T cells and/or NK cells, and/or to induce proliferation or resident cells. Methods for isolation and usage of an anti-lymphotactin antibody, and XCL1 fusion protein are also disclosed.

The polynucleotide sequences of CC chemokine ligand 3 (CCL3), also known as macrophage inflammatory protein-1 (MIP-1), which is a so-called monokine (a type of cytokine produced primarily by monocytes and macrophages) that is involved in the acute inflammatory state in the recruitment and activation of polymorphonuclear leukocytes, are available from public databases as accession numbers NM_002983 (human); NM_011337 (mouse); and NM_013025 (rat), sequences of which are incorporated by reference herein.

The amino acid sequences of CCL3 are available from public databases as accession numbers NP_002974 (human); NP_035467 (mouse); and NP_037157 (rat), sequences of which are incorporated by reference herein.

The polynucleotide sequences of CCL5 (RANTES), which is a proinflammatory cytokine involved in inflammation and asthma, are available from public databases as accession numbers AF043341 (human); NM_013653 (mouse); and NM_031116 (rat), sequences of which are incorporated by reference herein.

The amino acid sequences of CCL5 are available from public databases as accession numbers AAC03541 (human); NP_038681 (mouse); and NP_112378 (rat), sequences of which are incorporated by reference herein.

The polynucleotide sequences of CC chemokine ligand 7 (CCL7), which is a chemokine involved in macrophage recruitment during inflammation and cancer invasion, are available from public databases as accession numbers NM_006273 (human); NM_013654 (mouse); and NM_001007612 (rat), sequences of which are incorporated by reference herein.

The amino acid sequences of CCL7 are available from public databases as accession numbers NP_006264 (human); NP_038682 (mouse); and NP_001007613 (rat), sequences of which are incorporated by reference herein.

Chemokine (CXC motif) ligand 9 (CXCL9, also known as MIG) is a T-cell chemoattractant inducible by gamma interferon. The polynucleotide sequences of CXCL9 are available from public databases as accession numbers NM_002416 (human); NM_0108599 (mouse); and NM_145672 (rat), sequences of which are incorporated by reference herein.

The amino acid sequences of CXCL9 are available from public databases as accession numbers NP_002407 (human); NP_032625 (mouse); and NP_663705 (rat), sequences of which are incorporated by reference herein.

Chemokine (C-X-C motif) ligand 10 (CXCL10) is a small cytokine with roles in chemoattraction for cells in the immune system, adhesion of T cells to endothelial cells, anti-tumor activity and angiogenesis. The polynucleotide sequences of CXCL10 are available from public databases as accession numbers X02530 (human); NM_021274 (mouse); and BC058444 (rat), sequences of which are incorporated by reference herein.

The amino acid sequences of chemokine (C-X-C motif) ligand 10 (CXCL10) are available from public databases as accession numbers CAA26370 (human); NP_067249 (mouse); and AAH58444 (rat), sequences of which are incorporated by reference herein.

Chemokine (C-X-C motif) ligand 12 (CXCL12), also known as stromal cell-derived factor 1 (SDF-1), is a small cytokine that belong to the intercrine family, members of which activate leukocytes and are often induced by proinflammatory stimuli such as LPS, TNF or IL1. The polynucleotide sequences of CXCL12 are available from public databases as accession numbers NM_000609 (human); NM_001012477 (mouse); NM_204510 (chicken); and NM_001033883 (rat), sequences of which are incorporated by reference herein.

The amino acid sequences of CXCL12 are available from public databases as accession numbers NP_000600 (human); NP_001012495 (mouse); NP_989841 (chicken); and NP_001029055 (rat), sequences of which are incorporated by reference herein.

Harmon et al., *Microbes and Infection* 8:841 (2006) discusses that interaction between chemokine (C-C motif) receptor 7 (CCR7) and chemokine (C-C motif) ligand 19 (CCL19, also known as MIP-3β) is crucial for the generation of primary immune responses. The polynucleotide sequences of CCR7 are available from public databases as accession numbers NM_001838 (human); and NM_007719 (mouse), sequences of which are incorporated by reference herein.

The amino acid sequences of CCR7 are available from public databases as accession numbers NP_001829 (human); and NP_031745 (mouse), sequences of which are incorporated by reference herein.

The polynucleotide sequences of CCL19 are available from public databases as accession numbers NM_006274 (human); and NM_011888 (mouse), sequences of which are incorporated by reference herein.

The amino acid sequences of CCL19 are available from public databases as accession numbers NP_006265 (human); and NP_036018 (mouse), sequences of which are incorporated by reference herein.

The polynucleotide sequences of CC chemokine ligand 21 (CCL21), a well established ligand for CCR7 which is necessary for CD4+ but not CD8+ T cells to reach their steady state 'set point', and perturbations in the expression of CCL21 may alter susceptibility to autoimmunity, are available from public databases as accession numbers AB002409 (human); NM_011335 (mouse CCL21a); NM_011124 (mouse CCL21b); and NM_023052 (mouse CCL21c); sequences of which are incorporated by reference herein.

The amino acid sequences of CCL21 are available from public databases as accession numbers BAA21817 (human); NP_035465 (mouse CCL21a); NP_035254 (mouse CCL21b); and NP_075539 (mouse CCL21c), sequences of which are incorporated by reference herein.

Interleukin-8 (IL-8), is a chemokine, also called neutrophil-activating peptide-1 or SCYB8, is a tissue-derived peptide secreted by several types of cells in response to inflammatory stimuli. U.S. Pat. Nos. 6,133,426 and 6,177,980 disclose amino acid and polynucleotide sequences of humanized anti-IL-8 antibodies. The polynucleotide sequence of human IL-8 is available from public database as accession number NM_000584, sequence of which is incorporated by reference herein.

The amino acid sequence of human IL-8 is available from public database as accession number NP_000575, sequence of which is incorporated by reference herein.

Growth Factors

Granulocyte/macrophage colony-stimulating factor (GM-CSF) is a cytokine that functions as a white blood cell growth factor, stimulates stems cells to produce granulocytes (neutrophils, eosinophils, and basophils) and monocytes. The polynucleotide sequences of GM-CSF are available from public databases as accession numbers M11734 (human); NM_009969 (mouse); EU520303 (chicken); NM_001037660 (rat Csf2ra); and NM_133555 (rat Csf2rb), sequences of which are incorporated by reference herein.

The amino acid sequences of granulocyte/macrophage colony-stimulating factor (GM-CSF) are available from public databases as accession numbers AAA52122 (human); NP_034099 (mouse); ACB11534 (chicken); NP_001032749 (rat Csf2ra); and NP_598239 (Csf2rb), sequences of which are incorporated by reference herein.

The polynucleotide sequences of FMS-related tyrosine kinase ligand (FLT3/FLK2 ligand, Flt3L), which may function as a growth factor receptor on hematopoietic stem cells or progenitor cells or both, are available from public databases as accession numbers U04806 (human); and NM_013520 (mouse), sequences of which are incorporated by reference herein.

The amino acid sequences of FLT3/FLK2 ligand (Flt3L) are available from public databases as accession numbers AAA17999 (human); and NP_038548 (mouse), sequences of which are incorporated by reference herein.

The polynucleotide sequence of transforming growth factor, alpha (TGF-alpha), which is upregulated in some human cancers can reversibly confer the transformed phenotype on cultured cells, is available from public databases as accession numbers NM_001099691 (human); NM_031199 (mouse); NM_001001614 (chicken); and NM_012671 (rat), sequences of which are incorporated by reference herein.

The amino acid sequences of TGF-alpha is available from public databases as accession numbers NP_001093161 (human); NP_112476 (mouse); NP_001001614 (chicken); and NP_036803 (rat), sequences of which are incorporated by reference herein.

Adjuvants

Beta-defensins are antimicrobial peptides implicated in innate immune response against many Gram-negative and Gram-positive bacteria, fungi and viruses. The polynucleotide sequences of beta-defensins are available from public databases as accession numbers X92744 (human hBD-1); AJ000152 (human hBD-2); AF217245 (human beta defensin-3); AJ314835 (human beta defensin-4); AB089180 (human hBD-5); AY122466 (human defensin beta 106, DEFB106); AF540979 (human beta defensin 107, DEFB107); AF529416 (human beta defensin, DEFB108); DQ012014 (human beta defensin 110, DEFB110); DQ012015 (human beta defensin 111, DEFB111); DQ012016 (human beta defensin 112, DEFB112); DQ012017 (human beta defensin 113, DEFB113); DQ012018 (human beta defensin 114, DEFB114); DQ012019 (human beta defensin 115, DEFB115); DQ012020 (human beta defensin 116, DEFB116); DQ012021 (human beta defensin 117, DEFB117); NM_007843 (mouse defensin beta 1); NM_010030 (mouse defensin beta 2, Defb2); NM_013756 (mouse defensin beta 3, Defb3); NM_019728 (mouse defensin beta 4, Defb4); NM_030734 (mouse defensin beta 5, Defb5); NM_054074 (mouse defensin beta 6, Defb6); NM_139220 (mouse defensin beta 7); NM_153108 (mouse defensin beta 8, Defb8); NM_139219 (mouse defensin beta 9, Defb9); and NM_139225 (mouse defensin beta 10, Defb10); sequences of which are incorporated by reference herein.

The amino acid sequences of beta-defensins are available from public databases as accession numbers CAA63405 (human hBD-1); CAB65126 (human hBD-2); AAF73853 (human beta defensin-3); CAC85520 (human beta defensin-4); BAC10630 (human hBD-5); AAM93908 (human defensin beta 106, DEFB106); AAN33115 (human beta defensin 107, DEFB107); AAQ09525 (human beta defensin, DEFB108); AAY59750 (human beta defensin 110, DEFB110); AAY59751 (human beta defensin 111, DEFB111); AAY59752 (human beta defensin 112, DEFB112); AAY59753 (human beta defensin 113, DEFB113); AAY59754 (human beta defensin 114, DEFB114); AAY59755 (human beta defensin 115, DEFB115); AAY59756 (human beta defensin 116, DEFB116); AAY59757 (human beta defensin 117, DEFB117); NP_031869 (mouse defenin beta 1); NP_034160 (mouse defensin beta 2, Defb2); NP_038784 (mouse defensin beta 3, Defb3); NP_062702 (mouse defensin beta 4, Defb4); NP_109659 (mouse defensin beta 5, Defb5); NP_473415 (mouse defensin beta 6, Defb6); NP_631966 (mouse defensin beta 7, Defb7); NP_694748 (mouse defensin beta 8, Defb8); NP_631965 (mouse defensin beta 9, Defb9); and NP_631971 (mouse defensin beta 10, Defb10), sequences of which are incorporated by reference herein. See also U.S. Pat. No. 5,242,902 for additional human and rat defensin peptide sequences.

High-mobility group box-1 (HMGB1) proteins are non-histone chromosomal proteins that function as cytokines, mediating local and systemic responses to necrotic cell death and cancer, invasion by pathogens, trauma, and sepsis. The polynucleotide sequences of HMGB1 proteins are available from public databases as accession numbers NM_002128 (human); NM_010439 (mouse); NM_204902 (chicken); and NM_012963 (rat), sequences of which are incorporated by reference herein.

The amino acid sequences of high-mobility group box-1 (HMGB1) are available from public databases as accession numbers NP_002119 (human); NP_034569 (mouse); NP_990233 (chicken); and NP_037095 (rat), sequences of which are incorporated by reference herein.

Phagocytic S100 proteins mediate inflammatory responses and recruit inflammatory cells to sites of tissue damage, and are members of Damage-associated molecular pattern (DAMP) molecules that are important for innate immunity. See Foell et al., *J Leukocyte Biol.* 81:1 (2006). The polynucleotide sequences of S100 proteins are available from public databases as accession numbers BC014392 (human S100 A1); BC002829 (human S100 A2); BC012893 (human S100 A3); BC016300 (human S100 A4); Z18954 (human S100D); BC001431 (human S100 A6); BC034687 (human S100 A7); BC005928 (human S100 A8); BC047681 (human S100 A9); BC015973 (human S100 A10); D38583 (human clagizzarin); NM_011309 (mouse S100a1); NM_009115 (mouse S100b); NM_013650 (mouse S100a8); NM_009114 (mouse S100a9); NM_011310 (mouse S100a3); NM_011311 (mouse S100a4); and NM_011312 (mouse S100a5), sequences of which are incorporated by reference herein.

The amino acid sequences of S100 proteins are available from public databases as accession numbers AAH14392 (human S100 A1); AAH02829 (human S100 A2); AAH12893 (human S100 A3); AAH16300 (human S100 A4); CAA79479 (human S100D); AAH01431 (human S100 A6); AAH34687 (human S100 A7); AAH05928 (human S100 A8); AAH47681 (human S100 A9); AAH15973 (human S100 A10); BAA07597 (human clagizzarin); NP_035439 (mouse S100a1); NP_033141 (mouse S100b); NP_038678 (mouse S100a8); NP_033140 (mouse S100a9); NP_035440 (mouse S100a3); NP_035441 (mouse S100a4); and NP_035442 (mouse S100a5), sequences of which are incorporated by reference herein.

Mannan, a plant polysaccharide, that is a polymer of the sugar mannose, is useful for generation of an immune response. U.S. Pat. No. 5,807,559, discloses immunogenic conjugates of Mannan that may be useful for generating T cell immunity against tumor-associated carbohydrate structures or against carbohydrate structures expressed on infectious agents and/or infected host cells. U.S. Pat. No. 5,773,425 discloses use of mannan to relieve symptoms and/or cure viral diseases and to enhance immune response.

Bacille Calmette-Guerin (BCG), live attenuated *Mycobacterium* species, are used as vaccine against to prevent severe and fatal tuberculosis. U.S. Pat. No. 7,393,541 discloses generation of an adjuvant vaccine for producing an in vivo T-cell mediated immune response to a mycobacterium in a mammalian subject. See also Hubbard and Collins, *Infect. Immun.* 59(2): 570. U.S. Pat. No. 5,292,513 discloses a method for priming macrophages in vivo in patients in need of enhanced bactericidal and anti-viral activity with heat killed BCG. The complete genome sequence of BCG is available from public databases as accession number NC_008769 (*M. bovis* BCG str. Pasteur 1173P2, complete genome).

Bacterial lipopolysaccharides (LPS) are endotoxins that induces a strong immune response upon infection with Gram-negative bacteria. U.S. Pat. No. 4,148,877 discloses fractionation of LPS from bacterial culture and use the fraction as a drug to induce resistance to bacterial infection. U.S. Pat. No. 5,292,513 discloses a method for priming macrophages in vivo in patients in need of enhanced bactericidal and anti-viral activity with LPS.

Co-Stimulatory Molecules (Positive)

OX40 ligand (OX40L) belongs to tumor necrosis factor (ligand) superfamily member 4 (Tnfsf4), is expressed on dendritic cells and promotes Th2 cell differentiation. The polynucleotide sequences of OX40 ligand are available from public databases as accession numbers X79929 (human); U12763 (mouse); and AF037067 (rat), sequences of which are incorporated by reference herein.

The amino acid sequences of OX40 ligand (OX40L) are available from public databases as accession numbers CAA56284 (human); AAA21871 (mouse); and AAC67236 (rat), sequences of which are incorporated by reference herein.

The 4-1BB ligand (4-1BBL) belongs to tumor necrosis factor (ligand) superfamily member 9 (Tnfsf9), which is a type 2 transmembrane glycoprotein and is expressed on activated T lymphocytes. The polynucleotide sequences of 4-1BBL are available from public databases as accession numbers NM_003811 (human); NM_009404 (mouse); and AY332409 (rat), sequences of which are incorporated by reference herein.

The amino acid sequences of 4-1BB ligand (4-1BBL) are available from public databases as accession numbers NP_003802 (human); NP_033430 (mouse); and AAQ01228 (rat), sequences of which are incorporated by reference herein.

The CD40 protein belongs to the tumor necrosis factor receptor superfamily member 5, is essential in mediating a broad variety of immune and inflammatory responses including T cell-dependent immunoglobulin class switching, memory B cell development, and germinal center formation. The polynucleotide sequences of CD40 proteins are available from public databases as accession numbers X60592 (human); NM_170701 (mouse); NM_204665 (chicken); and NM_134360 (rat), sequences of which are incorporated by reference herein.

The amino acid sequences of CD40 proteins are available from public databases as accession numbers CAA43045 (human); NP_733802 (mouse); NP_989996 (chicken); and NP_599187 (rat), sequences of which are incorporated by reference herein.

The glucocorticoid-induced tumor necrosis factor receptor family-related protein (GITR) can evoke effective tumor immunity via T cell stimulation. Administration of anti-GITR monoclonal antibody (mAb) can provoke potent tumor-specific immunity and eradicated established tumors without eliciting overt autoimmune disease. See Ko et al., *J. Exp. Med.* 7: 885 (2005). U.S. Pat. No. 6,503,184 B1 discloses an Anti-GITR antibody.

The polynucleotide sequences of GITR ligand (GITRL) are available from public databases as accession numbers AY358868 (human); and AY359852 (mouse), sequences of which are incorporated by reference herein.

The amino acid sequences of GITR ligand (GITRL) are available from public databases as accession numbers AAQ89227 (human); and AAQ55265 (mouse), sequences of which are incorporated by reference herein.

Herpes virus entry mediator (HVEM) binding ligand (HSVgD), also referred to as p30, or LIGHT is a TNF family member involved in co-stimulation of T cells. LIGHT has two receptors, herpes virus entry mediator (HVEM) and lymphotoxin-β receptor (LT-βR). Being a ligand for HVEM, HSVgD activates T cells by acting as a costimulatory factor to T cells that results in T cell proliferation and cytokine secretion. See U.S. Pat. No. 7,118,742 for polynucleotide and amino acid sequences of LIGHT. U.S. Pat. No. 5,654,174 describes a variant gD protein with deletion of carboxy terminal residues.

CD70 is a cytokine that binds to CD27. It plays a role in T-cell activation. Induces the proliferation of costimulated T-cells and enhances the generation of cytolytic T-cells. The polynucleotide sequences of CD70 are available from public databases as accession numbers NM_001252 (human); NM_011617 (mouse); and NM_001106878 (rat), sequences of which are incorporated by reference herein.

The amino acid sequences of CD70 are available from public databases as accession numbers NP_001243 (human); NP_035747 (mouse); and NP_001100348 (rat), sequences of which are incorporated by reference herein.

ICOS-L is a ligand for the T-cell-specific cell surface receptor ICOS and acts as a costimulatory signal for T-cell proliferation and cytokine secretion. ICOS-L also induces B-cell proliferation and differentiation into plasma cells. ICOS-L could play an important role in mediating local tissue responses to inflammatory conditions, as well as in modulating the secondary immune response by co-stimulating memory T-cell function. The polynucleotide sequences of ICOS-L are available from public databases as accession numbers NM_015259 (human); and NM_015790 (mouse), sequences of which are incorporated by reference herein.

The amino acid sequences of ICOS-L are available from public databases as accession numbers NP_056074 (human); and NP_056605 (mouse), sequences of which are incorporated by reference herein.

PD-L1 (also known as CD274) protein is expressed in activated monocytes, T and B cells. PD-L1 is upregulated in monocytes upon treatment with IFN-gamma, and in dendritic cells and keratinocytes upon treatment with IFN-gamma, together with other activators. The polynucleotide sequences of PD-L1 proteins are available from public databases as accession numbers NM_014143 (human); and NM_021893 (mouse), sequences of which are incorporated by reference herein.

The amino acid sequences of PD-L1 proteins are available from public databases as accession numbers NP_054862 (human); and NP_068693 (mouse), sequences of which are incorporated by reference herein.

Co-Stimulatory Molecule (Negative)

Cytotoxic T lymphocyte-associated 4 (CTLA4) is a member of the immunoglobulin superfamily and is a costimulatory molecule expressed in activated T cells. U.S. Pat. Nos. 7,034,121 and 6,984,720 disclose methods of preparation and usage of antibodies against CTLA4. U.S. Pat. No. 6,984,720 also discloses amino acid sequences of heavy and light chain of anti-CTLA4 antibody.

PD-1 molecules are members of the immunoglobulin gene superfamily, which binds to PD-1 ligand (PD-L1). Binding of a PD-1 receptor on a T-cell by PD-L1 transmits a costimulatory signal to the cell, which prevents the cells from progressing through the cell cycle, and increases T cell proliferation. Inhibition of an interaction between PD-L1 and receptor on the T cell with an anti-PD-L1 antibody results in the down regulation of the immune response termed as immune cell energy. U.S. Pat. No. 7,029,674 discloses methods of preparation and sequence of anti-PD-L1 antibody.

PD-L2 is primarily known as a ligand for PD-1 (or the human homologue PDCD1). However, PD-12 has been reported to be involved in the costimulatory signal, essential for T lymphocyte proliferation and IFN-gamma production in a PDCD1-independent manner. Interaction with PDCD1 inhibit T-cell proliferation by blocking cell cycle progression, and cytokine production. Yamazaki et al., *J. of Immunol.* 169: 5538 (2002) and Ansari et al., *J. Exp. Med.* 198: 63 (2003) describe preparation of anti-PD-L2 monoclonal antibodies.

Counter Immune Suppressants (Tolerance Inhibitors)

Transforming growth factor-beta (TGF-β) is a multifunctional protein that regulates cell proliferation and differentiation, by interacting with one of the two transmembrane serine/threonine kinase receptors, type I and type II. See Chen et al., *Science* 28: 1335 (1993). TGF receptor type II (TGFR2) phosphorylate and activate type I receptors which autophosphorylate, then bind and activate SMAD transcriptional regulators. Lynch M A et al., *Cancer Res.* 58: 4227 (1998) describes mutations in the transforming growth factor β receptor type II gene (TGFBR2) that are associated with human ovarian carcinomas. Brand et al., *J. Biol. Chem.* 268:11500-11503 (1993) describes that deletion of predicted serine/theronine kinase cytoplasmic domain (nucleotides 1172-2036 of TGFβR2 cDNA H2-3FF, available from public databases as accession number M85079 and amino acid sequence available as accession number AAA61164) impairs the all three TGF-β (1, 2 and 3) dependent gene expressions. TGF-β is produced in most human tumors and inhibits tumor antigen-specific cellular immunity. Foster et al., *J. Immunother.* 31:500 (2008) describes that expression of dominant negative TGFβR2 in cytotoxic T lymphocytes can lead to resistance to the inhibitory effects of TGF-β.

TGFβ acts synergistically with TGFα in inducing transformation. It also acts as a negative autocrine growth factor. Dysregulation of TGFβ activation and signaling may result in apoptosis. Ziyadeh et al., *Proc. Natl. Acad. Sci.* 97: 8015 (2000) describes that administration of anti-TGFβ antibody can prevent renal insufficiency and glomerulosclerosis in the db/db mouse, a model of type II diabetes that develops overt nephropathy. Methods of generation and use of TGFβ monoclonal antibodies are described in U.S. Pat. No. 6,419,928. Barcellos-Hoff et al., *Am J. Pathol.* 147:5 (1995) also describes a method for generation of TGFβ antibody. Amino acid and nucleotide sequences for TGFβ fusion protein constructs are described in U.S. Pat. No. 6,756,215.

IL-10 is a cytokine produced by activated Th2 cells, B cells, keratinocytes, monocytes, and macrophages. IL-10 inhibits the synthesis of a number of cytokines, including IFN-gamma, IL-2, IL-3, TNF and GM-CSF produced by activated macrophages and by helper T-cells. IL-10 is useful in promoting growth and differentiation of activated human B cells, inhibiting Th1 responses to prevent transplant rejection and T cell-mediated autoimmune diseases. O'Farrell et al., *EMBO J.* 17:1006 (1998); Kanbayashi et al., *Cell Immunol.* 171:153 (1996); Fukushima et al., *Br. J. Ophthalmol.* 90:1535 (2006); and van Lent et al., *Ann. Rheum. Dis.* 66:334 (2007) describe the preparation of anti-IL10 antibodies. U.S. Pat. No. 7,326,567 discloses polynucleotide sequence of IL-10 antibody. U.S. Pat. No. 5,837,232 discloses a method to treat a B-cell mediated autoimmune disorder with anti-IL-10 antibodies.

Suppressor of cytokine signaling (SOCS) family proteins form part of a classical negative feedback system that regulates cytokine signal transduction. Alexander et al. *Cell* 98: 597 (1999) describes that suppressor of cytokine signaling 1 (SOCS1) is a critical inhibitor of interferon-gamma signaling and prevents the potentially fatal neonatal actions of this cytokine. Hilton et al., *Proc. Natl. Acad. Sci. USA* 95:114 (1999) discusses that SOCS1 is involved in negative regulation of cytokines that signal through the JAK/STAT3 pathway. Ohya et al. *J. Biol. Chem.* 272: 27178 (1997) describes that SOCS proteins appear to be a major regulator of signaling by interleukin 6 (IL-6) and leukemia inhibitory factor (LIF). U.S. Pat. No. 6,534,277 discloses a method for the preparation and use of anti-SOCS1 antibody, where a nucleic acid sequence encoding SOCS1 antibody is introduced into cells such that the antibody is expressed by the cells or their progeny, and the recombinant cells are then administered in vivo for therapeutic effect. U.S. Pat. Nos. 6,323,317 and 7,049,418 also disclose anti-SOCS1 antibodies.

TGF-α is a mitogenic polypeptide that is able to bind to the EGF receptor and to act synergistically with TGF-β to promote anchorage-independent cell proliferation in soft agar. Ellis et al., *N. Engl. J. Med.* 317:158 (1987) describes that TGF-α plays a role in certain paraneoplastic manifestations of melanoma. U.S. Pat. No. 4,742,003 and Xian et al., *The J. of Histochem. & Cytochem.* 47:949 (1999) describe methods of preparation of Anti-TGF-α antibodies.

Both tumor necrosis factor receptor (TNFR1) and Fas contain cytoplasmic Fas-associated protein with death domain (FADD), which is essential for Fas and TNF-induced signaling for programmed cell death (apoptosis) and receptor oligomerization. A mammalian protein designated FADD having the ability to bind the cytoplasmic region or domain of the Fas receptor and inhibits FAS mediated apoptosis has been identified. The polynucleotide sequence of FADD is available from public database as accession number U24231, and the amino acid sequence as accession number AAA86517, which are incorporated by reference herein. A FADD fragment or nucleic acid encoding it which is a dominant negative inhibitor of functionally intact native FADD is described in U.S. Pat. No. 6,562,797 B1.

DESCRIPTION OF SEQUENCE LISTING

SEQ ID NO: 1 is a polynucleotide sequence of a construct coding for mIL-12 and m-IL21.
SEQ ID NO: 2 is a polynucleotide sequence of a construct coding for hIL-12 and hIL-21.
SEQ ID NO: 3 is a polynucleotide sequence of a construct coding for mIL-21 and mIL-15.
SEQ ID NO: 4 is a polynucleotide sequence of a construct coding for mIL-12.
SEQ ID NO: 5 is a polynucleotide sequence of a construct coding for hIL-21 and hIL-15.
SEQ ID NO: 6 is a polynucleotide sequence of a construct coding for hIL-21.
SEQ ID NO: 7 is a polynucleotide sequence of a construct coding for mIL-21.
SEQ ID NO: 8 is a polynucleotide sequence of a construct coding for hIL-21.
SEQ ID NO: 9 is a polynucleotide sequence coding for mIL-21.
SEQ ID NO: 10 is an amino acid sequence of mIL-21.
SEQ ID NO: 11 is a polynucleotide sequence coding for mIL-15.
SEQ ID NO: 12 is an amino acid sequence of mIL-15.
SEQ ID NO: 13 is a polynucleotide sequence coding for mp40 of mIL-12.
SEQ ID NO: 14 is the amino acid sequence of mp40 of mIL-12.
SEQ ID NO: 15 is a polynucleotide sequence coding for mp35 of mIL-12.
SEQ ID NO: 16 is the amino acid sequence of mp35 of mIL-12.
SEQ ID NO: 17 is a polynucleotide sequence coding for hIL-21.
SEQ ID NO: 18 is the amino acid sequence of hIL-21.
SEQ ID NO: 19 is a polynucleotide sequence coding for hIL-15.
SEQ ID NO: 20 is the amino acid sequence of hIL-15.
SEQ ID NO: 21 is a polynucleotide sequence coding for p40 of hIL-12.
SEQ ID NO: 22 is the amino acid sequence of p40 of hIL-12.
SEQ ID NO: 23 is a polynucleotide sequence coding for p35 of hIL-12.
SEQ ID NO: 24 is the amino acid sequence of p35 of hIL-12.
SEQ ID NO: 25 is a nucleic acid sequence of an ecdysone response element found in *Drosophila*.
SEQ ID NO: 26 is a nucleic acid sequence of an ecdysone response element found in *Drosophila melanogaster*.
SEQ ID NO: 27 is a nucleic acid sequence of an ecdysone response element found in *Drosophila melanogaster*.
SEQ ID NO: 28 is a restriction site of a homing endonuclease (HE) enzyme (I-SceI)
SEQ ID NO: 29 is a DNA sequence of adenovirus vector comprising human IL-12 coding sequence: Ad-RTS-hIL-12 (SP1-RheoIL-12).

DETAILED DESCRIPTION OF INVENTION

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference and understanding, and the inclusion of such definitions herein should not necessarily be construed to mean a substantial difference over what is generally understood in the art. Commonly understood definitions of molecular biology terms and/or methods and/or protocols can be found in Rieger et al., Glossary of Genetics: Classical and Molecular, 5th edition, Springer-Verlag: New York, 1991; Lewin, Genes V, Oxford University Press: New York, 1994; Sambrook et al., Molecular Cloning, A Laboratory Manual (3d ed. 2001) and Ausubel et al., Current Protocols in Molecular Biology (1994). As appropriate, procedures involving the use of commercially available kits and/or reagents are generally carried out in accordance with manufacturer's guidance and/or protocols and/or parameters unless otherwise noted.

The term "isolated" for the purposes of the invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," "nucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. For example, the interleukin-12 (IL-12) gene encodes the IL-12 protein. IL-12 is a heterodimer of a 35-kD subunit (p35) and a 40-kD subunit (p40) linked through a disulfide linkage to make fully functional IL-12p70. The IL-12 gene encodes both the p35 and p40 subunits.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. A preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in an eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←3').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the invention is the UltraVector™ Production System (Intrexon Corp., Blacksburg, Va.) as described in WO 2007/038276.

For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad. Sci. USA* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

In any of the vectors of the present invention, the vector optionally comprises a promoter disclosed herein. In one embodiment, the promoter is a promoter listed in Table 1 herein.

In any of the vectors of the present invention, the vector optionally comprises a tissue-specific promoter. In one embodiment, the tissue-specific promoter is a tissue specific promoter disclosed herein. In another embodiment, the tissue-specific promoter is a tissue specific promoter listed in Table 2 herein.

The promoter sequence is typically bounded at its 3' terminus by the transcription initiation site and extends upstream (5' direction) to include the minimum number of bases or elements necessary to initiate transcription at levels detectable above background. Within the promoter sequence is found a transcription initiation site (conveniently defined for example, by mapping with nuclease S1), as well as protein binding domains (consensus sequences) responsible for the binding of RNA polymerase.

"Therapeutic switch promoter" ("TSP") refers to a promoter that controls expression of a gene switch component. Gene switches and their various components are described in detail elsewhere herein. In certain embodiments a TSP is constitutive, i.e., continuously active. A constitutive TSP may be either constitutive-ubiquitous (i.e., generally functions, without the need for additional factors or regulators, in any tissue or cell) or constitutive-tissue or cell specific (i.e., generally functions, without the need for additional factors or regulators, in a specific tissue type or cell type). In certain embodiments a TSP of the invention is activated under conditions associated with a disease, disorder, or condition. In certain embodiments of the invention where two or more TSPs are involved the promoters may be a combination of constitutive and activatable promoters. As used herein, a "promoter activated under conditions associated with a disease, disorder, or condition" includes, without limitation, disease-specific promoters, promoters responsive to particular physiological, developmental, differentiation, or pathological conditions, promoters responsive to specific biological molecules, and promoters specific for a particular tissue or cell type associated with the disease, disorder, or condition, e.g. tumor tissue or malignant cells. TSPs can comprise the sequence of naturally occurring promoters, modified sequences derived from naturally occurring promoters, or synthetic sequences (e.g., insertion of a response element into a minimal promoter sequence to alter the responsiveness of the promoter).

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element is incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 25) (see Cherbas et. al., *Genes Dev.* 5:120 (1991)); AGGTCAN$_{(n)}$AGGTCA, where N$_{(n)}$ can be one or more spacer nucleotides (SEQ ID NO: 26) (see D'Avino et al., *Mol. Cell. Endocrinol.* 113:1 (1995)); and GGGTTGAATGAATTT (SEQ ID NO: 27) (see Antoniewski et al., *Mol. Cell Biol.* 14:4465 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated. The term "a polynucleotide encoding a gene switch" refers to the combination of a response element associated with a promoter, and a polynucleotide encoding a ligand-dependent transcription factor-based system which, in the presence of one or more ligands, modulates the expression of a gene into which the response element and promoter are incorporated.

The therapeutic switch promoters of the invention may be any promoter that is useful for treating, ameliorating, or preventing a specific disease, disorder, or condition. Examples include, without limitation, promoters of genes that exhibit increased expression only during a specific disease, disorder, or condition and promoters of genes that exhibit increased expression under specific cell conditions (e.g., proliferation, apoptosis, change in pH, oxidation state, oxygen level). In some embodiments where the gene switch comprises more than one transcription factor sequence, the specificity of the therapeutic methods can be increased by combining a disease- or condition-specific promoter with a tissue- or cell type-specific promoter to limit the tissues in which the therapeutic product is expressed. Thus, tissue- or cell type-specific promoters are encompassed within the definition of therapeutic switch promoter.

As an example of disease-specific promoters, useful promoters for treating cancer include the promoters of oncogenes. Examples of classes of oncogenes include, but are not limited to, growth factors, growth factor receptors, protein kinases, programmed cell death regulators and transcription factors. Specific examples of oncogenes include, but are not limited to, sis, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as therapeutic switch promoters in the present invention are disclosed in the references listed in Tables 1 and 2, along with the disease/disorder (Table 1) or tissue specificity (Table 2) associated with each promoter. The promoter sequences disclosed in these references are herein incorporated by reference in their entirety.

TABLE 1

| Promoter Sequence | Disease/Disorder | Patent/Published Application No. |
|---|---|---|
| Her-2/neu (ERBB2/c-erbB-2) | cancer | 5,518,885 |
| osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| insulin | pancreatic cancer | 6,716,824 |
| PEG-3 | cancer | 6,737,523 |
| telomerase reverse transcriptase | cancer | 6,777,203 |
| melanoma differentiation associated gene-7 | cancer | 6,841,362 |
| prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| PCA3$_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid transporter-2 | nervous system ischemia | 2004/0171108 |

TABLE 1-continued

| Promoter Sequence | Disease/Disorder | Patent/Published Application No. |
|---|---|---|
| MDTS9 | renal failure | 2006/0014931 |
| LIM, pyrroline 5-carboxylate reductase, SIM2 | prostate disorders | 2006/0134688 |
| Bax | apoptosis | 5,744,310 |
| fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/Published Application No. |
|---|---|---|
| troponin T | skeletal muscle | 5,266,488 |
| myoD | muscle | 5,352,595 |
| actin | muscle | 5,374,544 |
| smooth muscle 22α | arterial smooth muscle | 5,837,534 |
| utrophin | muscle | 5,972,609 |
| myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| CRF$_{2\alpha}$ receptor | brain | 7,071,323 |
| nerve growth factor | neurons | 2003/159159 |
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| megsin | renal cells | 6,790,617 |
| prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |

Other genes that exhibit changes in expression levels during specific diseases or disorders and therefore may provide promoters that are useful in the present invention include, without limitation, the genes (along with the associated disease/disorder) listed in Table 3.

TABLE 3

| Gene | Disease/Disorder | Patent/Published Application No. |
|---|---|---|
| MLH1, MSH2, MSH6, PMS1, APC | Colorectal cancer | 7,148,016 |
| LEF-1 | Colon cancer | 2002/0169300 |
| F$_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM-1 | Prostate cancer | 2002/0042062 |
| PCADM-1 | Prostate cancer | 2003/0100033 |
| PCA3$_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the patent 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/0115094 |
| SEQ ID NO: 1 of the patent U.S. application publication 2005/0037372, incorporated by reference herein | Hepatocellular carcinoma | 2005/0037372 |
| ATB$_0$ | Hepatocellular carcinoma | 2006/0280725 |

TABLE 3-continued

| Gene | Disease/Disorder | Patent/Published Application No. |
|---|---|---|
| SEQ ID NOS: 1, 3 of the U.S. patent application publication 2007/0042420 | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application publication 2002/0198362, incorporated by reference herein | Hematological cancers | 2002/0198362 |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, incorporated by reference herein | Ovarian cancer | 2007/0054268 |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/hTAF$_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S. patent application publication 2003/0044813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |
| Cables | Cancer | 2003/0109443 |
| Pp 32r1 | Cancer | 2003/0129631 |

TABLE 3-continued

| Gene | Disease/Disorder | Patent/Published Application No. |
|---|---|---|
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1, 3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| JAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HLJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2002/0064786 |
| GCA-associated genes | Giant cell arteritis | 6,743,903 |
| PRV-1 | Polycythemia vera | 6,686,153 |
| SEQ ID NOS: 2, 4 of the U.S. Pat. No. 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEGI | Pathological angiogenesis | 2002/0111325 |
| PRO256 | Cardiovascular disorders | 2002/0123091 |
| AOP2 | Atherosclerosis | 2002/0142417 |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |

TABLE 3-continued

| Gene | Disease/Disorder | Patent/Published Application No. |
|---|---|---|
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. Pat. No. 5,763,591, incorporated by reference herein | Insulin-dependent diabetes mellitus | 5,763,591 |
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, incorporated by reference herein | Diabetes, hyperlipidemia | 2004/0053397 |
| Neuronatin | Metabolic disorders | 2004/0259777 |
| Ncb5or | Diabetes | 2005/0031605 |
| 7B2 | Endocrine disorders | 2005/0086709 |
| PTHrP, PEX | Metabolic bone diseases | 2005/0113303 |
| KChIPl | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Bodyweight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |

TABLE 3-continued

| Gene | Disease/Disorder | Patent/Published Application No. |
|---|---|---|
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders, wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Corneodesmosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi syndrome | 2002/0115144 |
| SEQ ID NOS: 1-16 of the U.S. patent application publication 2002/0127555, incorporated by reference herein | Endometriosis | 2002/0127555 |
| FGF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |
| CXCL10 | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease, disorder, or condition is identified, the promoter of the gene may be used in the gene switch of the invention. The sequence of many genes, including the promoter region, is known in the art and available in public databases, e.g., GenBank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it is a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J. Physiol. Lung Cell. Mol. Physiol.* 287: L52 (2004), which is incorporated by reference) by progressively deleting the 5'-flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene.

Another example of a protocol for acquiring and validating gene promoters includes the following steps: (1) acquire diseased and non-diseased cell/tissue samples of similar/ same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

Gene Switch Systems

The gene switch may be any gene switch that regulates gene expression by addition or removal of a specific ligand. In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.). In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

Ecdysone receptor (878aa) from *Drosophila melanogaster* (Fruit fly) (SEQ ID NO:5)

```
  1 mkrrwsnngg fmrlpeesss evtsssnglv lpsgvnmsps sldshdycdq dlwlcgnesg 61 sfggsnghgl sqqqqsvitl amhgcsstlp aqttiiping nangnggstn gqyvpgatnl 121 galangmlng gfngmqqqiq nghglinstt pstpttplhl qqnlggaggg giggmgilhh 181 angtpnglig vvgggggvgl gvggggvggl gmqhtprsds vnsissgrdd lspssslngy 241 sanescdakk skkgpaprvq eelclvcgdr asgyhynalt cegckgffrr svtksavycc 301 kfgracemdm ymrrkcqecr lkkclavgmr pecvvpenqc amkrrekkaq kekdkmttsp 361 ssqhggngsl asgggqdfvk keildlmtce ppqhatipll pdeilakcqa rnipsltynq 421 laviykliwy qdgyeqpsee dlrrimsqpd enesqtdvsf rhiteitilt vqlivefakg 481 lpaftkipqe dqitllkacs sevmmlrmar rydhssdsif fannrsytrd sykmagmadn 541 iedllhfcrq mfsmkvdnve yalltaivif sdrpglekaq lveaiqsyyi dtlriyilnr 601 hcgdsmslvf yakllsilte lrtlgnqnae mcfslklknr klpkfleeiw dvhaippsvq 661 shlqitqeen erleraermr asvggaitag idcdsastsa aaaaaqhqpq pqpqpqpssl 721 tqndsqhqtq pqlqpqlppq lqgqlqpqlq pqlqtqlqpq iqpqpqllpv sapvpasvta 781 pgslsaysts seymggsaai gpitpattss itaavtasst tsavpmgngv gvgvgvggnv 841 smyanaqtam almgvalhsh qeqliggvav ksehstta
```

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises a AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

Figure 2:
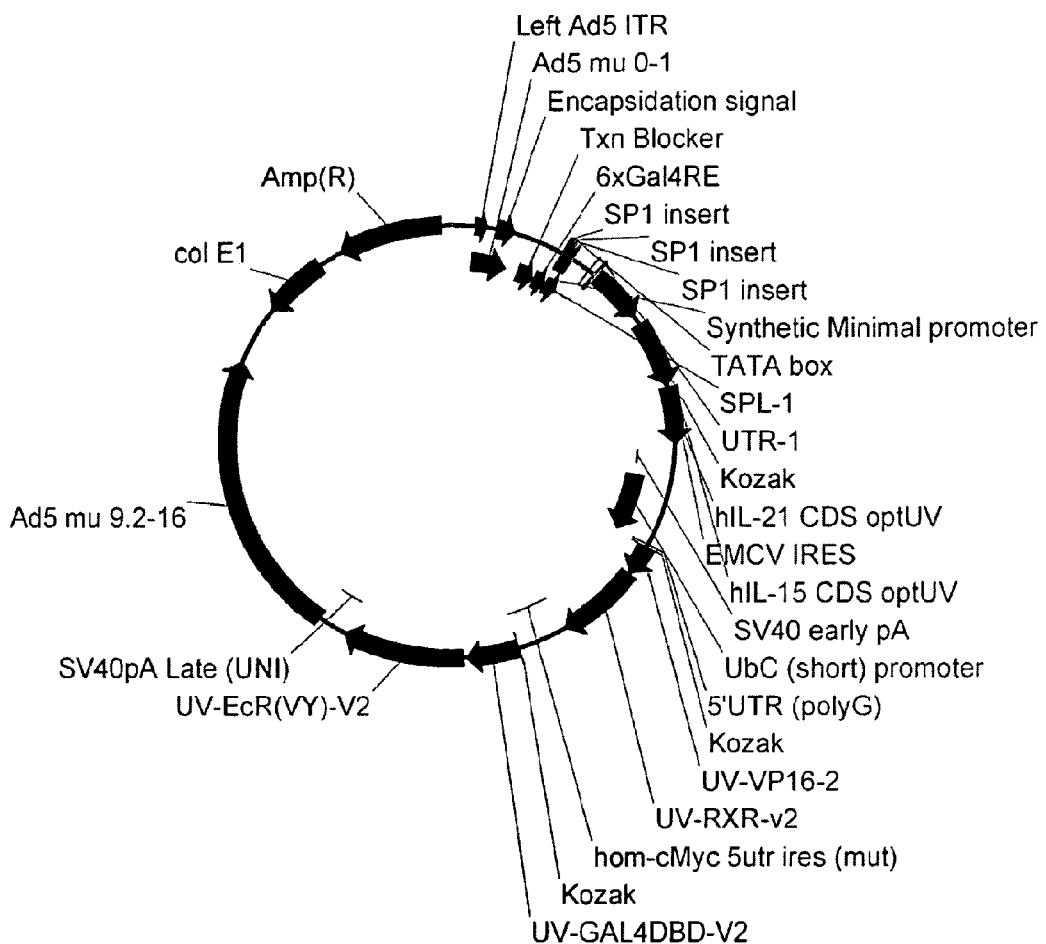
FIG. 2 shows a plasmid map for a regulated promoter expression system for a bicistronic transcript encoding hIL-21 and hIL-15.

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2). FIG. 2 also demonstrates the ability to modify the therapeutic gene switch to treat any disease, disorder, or condition simply by inserting the appropriate TSPs.

In a further embodiment, both the first and the second transcription factor sequence, e.g., a CAP or a LTF, are under the control of a single therapeutic switch promoter (e.g. TSP-1 in FIG. 1). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex are synthesized upon activation of TSP-1. TSP-1 can be a constitutive promoter or only activated under conditions associated with the disease, disorder, or condition.

Figure 4:
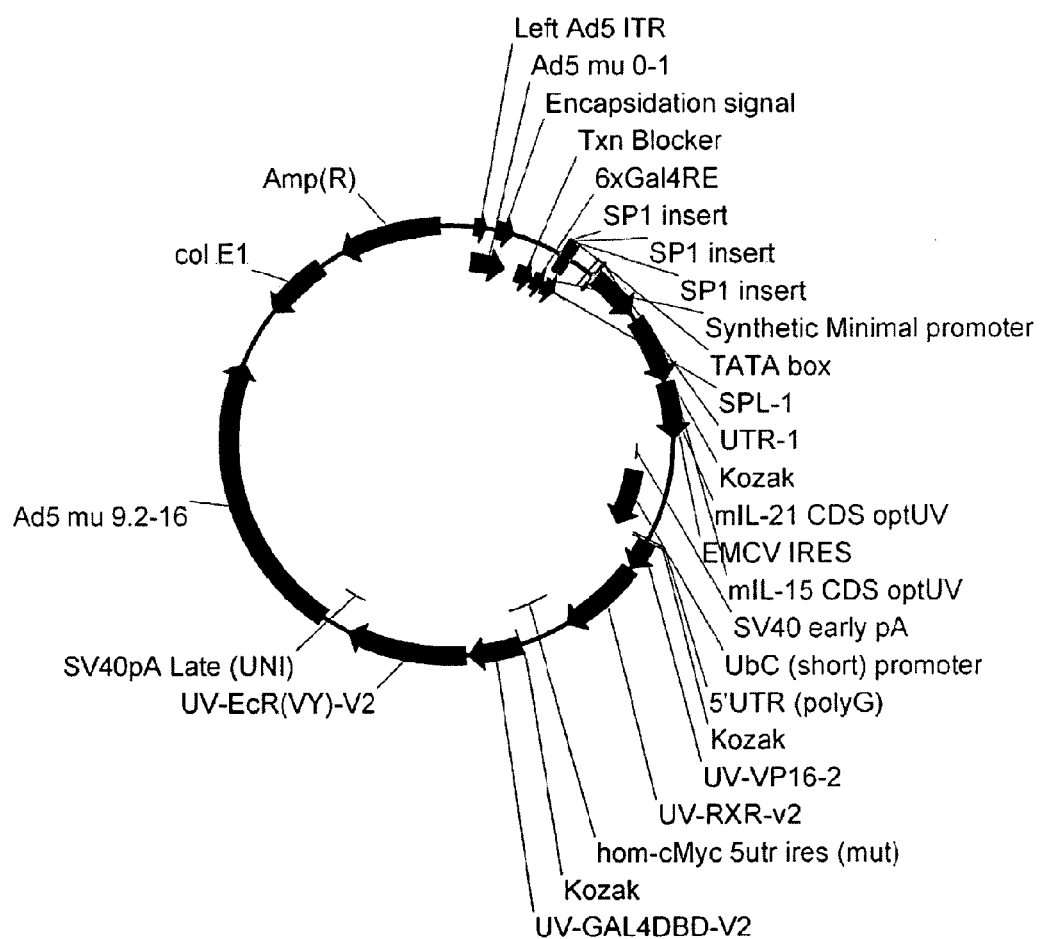
FIG. 4 shows a plasmid map for a regulated promoter expression system for a bicistronic transcript encoding mIL-21 and mIL-15.
Figure 5:
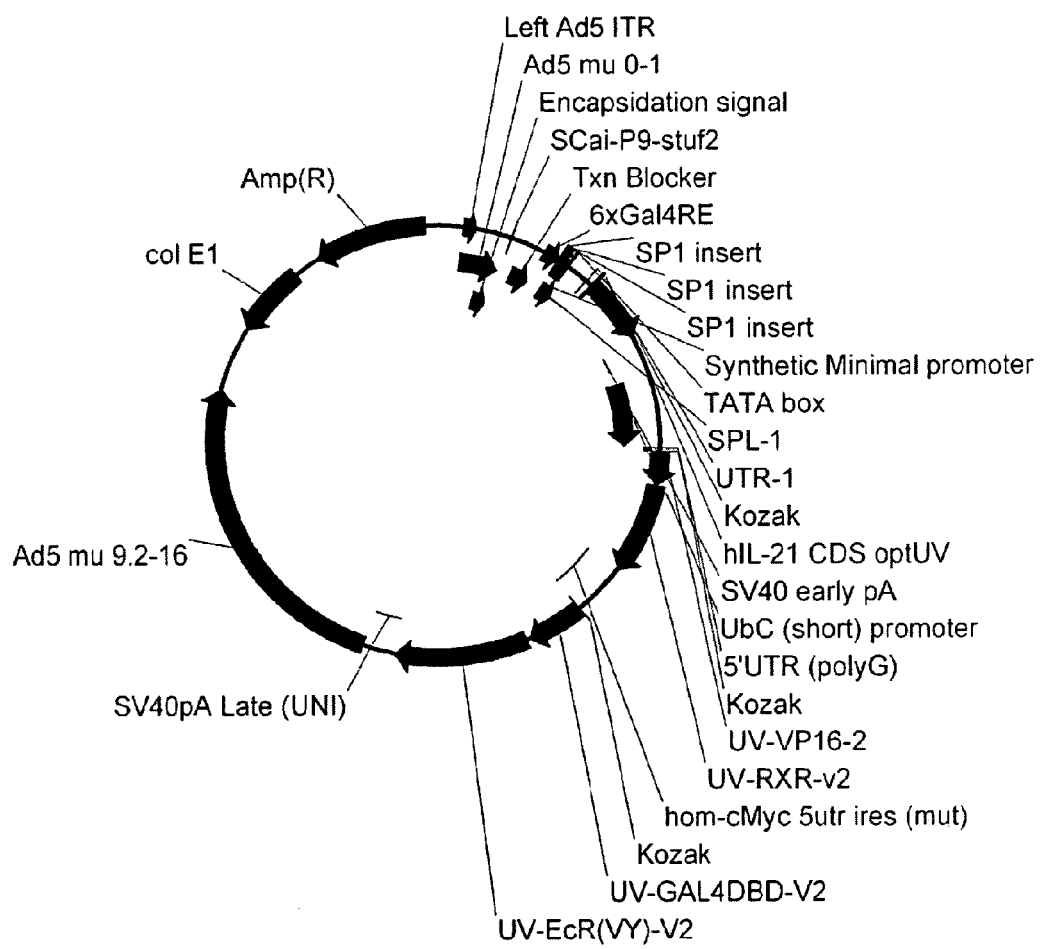
FIG. 5 shows a plasmid map for a regulated promoter expression system for hIL-21.
Figure 6:
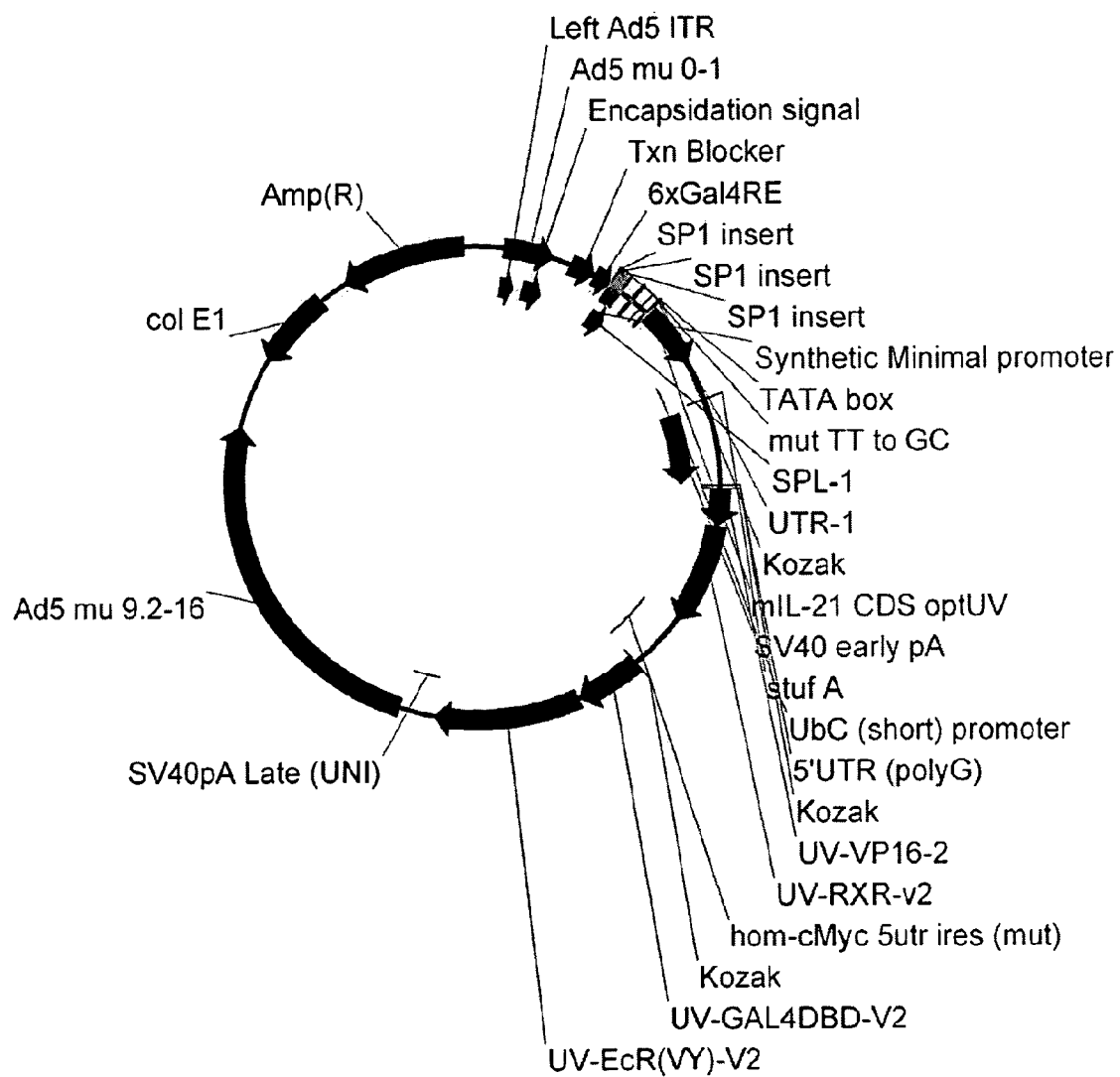
FIG. 6 shows a plasmid map for a regulated promoter expression system for mIL-21.

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4) and the other transcription factor sequence, e.g., CAP, is under the control of a constitutive therapeutic switch promoter (e.g., TSP-1 in FIG. 4). In this embodiment, one portion of the ligand-dependent transcription factor complex is constitutively present while the second portion will only be synthesized under conditions associated with the disease, disorder, or condition.

Figure 3:
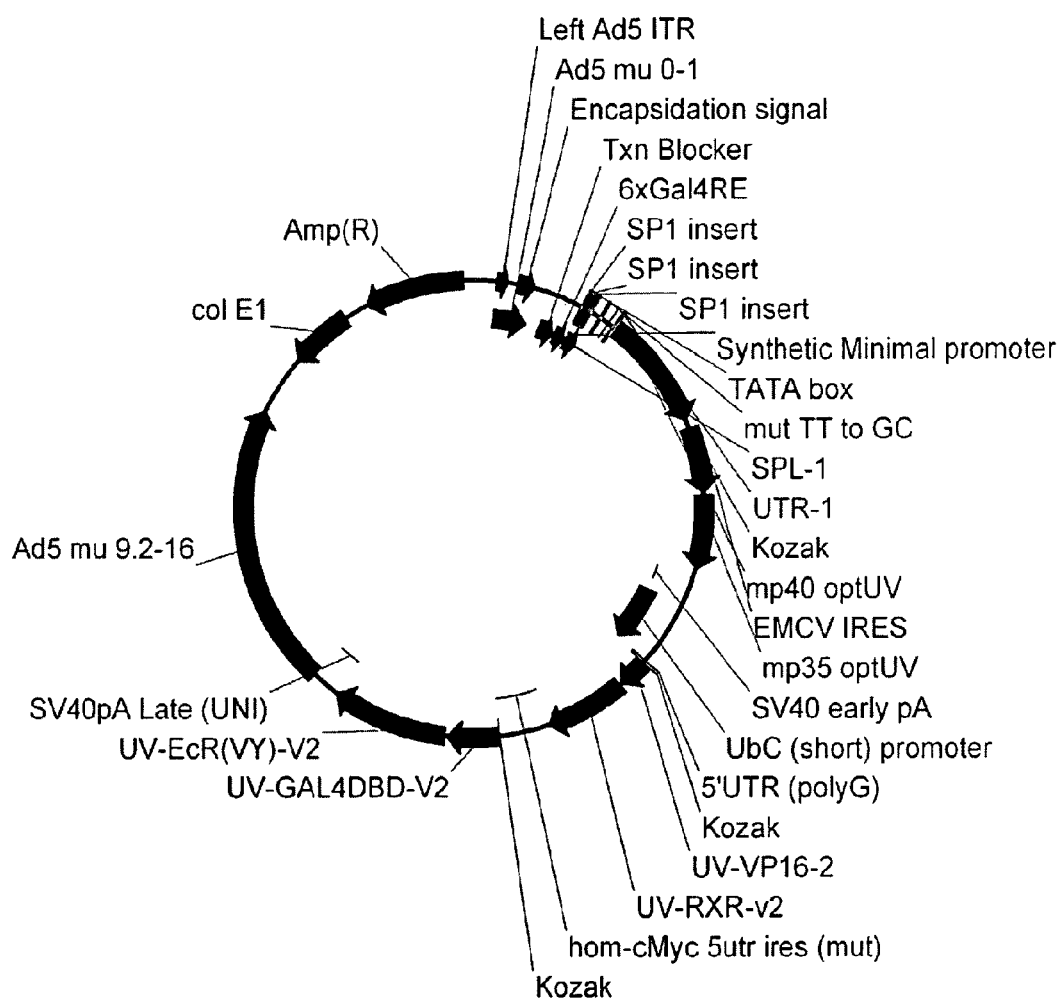
FIG. 3 shows a plasmid map for a regulated promoter expression system for a bicistronic transcript encoding mIL-12.

In another embodiment, one transcription factor sequence, e.g., CAP, is under the control of a first TSP (e.g., TSP-1 in FIG. 3) and two or more different second transcription factor sequences, e.g., LTF-1 and LTF-2 are under the control of different TSPs (e.g., TSP-2 and TSP-3 in FIG. 3). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising a AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from a vertebrate retinoid X receptor (RXR), an invertebrate RXR, an ultraspiracle protein (USP), or a chimeric nuclear receptor comprising at least two different nuclear receptor ligand binding domain polypeptide fragments selected from a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In a preferred embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, or a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa* domestica, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, or a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA*, 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises
  (a) a first polynucleotide encoding a first chimeric protein which binds to rapamycin or an analog thereof and which comprises at least one FK506-binding protein (FKBP) domain and at least one protein domain heterologous thereto, wherein the FKBP domain comprises a peptide sequence selected from:
    (1) a naturally occurring FKBP
    (2) a variant of a naturally occurring FKBP in which up to 10 amino acid residues have been deleted, inserted, or replaced with substitute amino acids, and
    (3) an FKBP encoded by a DNA sequence which selectively hybridizes to a DNA sequence encoding an FKBP of (1) or (2);
  (b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:
    (4) a naturally occurring FRB domain,
    (5) a variant of a naturally occurring FRB domain in which up to 10 amino acid residues have been deleted, inserted, or replaced with substitute amino acids, and
    (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Procaryotic Repressor/Operator Based Gene Switch System

In one embodiment, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a therapeutic protein or therapeutic polypeptide, wherein said second polynucleotide is operably linked to a minimal promoter and at least one tet operator sequence. The first polynucleotide coding for a transactivator fusion protein may comprise therapeutic switch promoter as described elsewhere herein. The expression of the lethal protein is up-regulated in the absence of tetracycline. (see, e.g., Gossen et al. (1992) *Proc. Natl. Acad. Sci.* 89: 5547-5551; Gossen et al. (1993) *TIBS* 18: 471-475; Furth et al. (1994) *Proc. Natl. Acad. Sci.* 91: 9302-9306; and Shockett et al. (1995) *Proc. Natl. Acad. Sci.* 92: 6522-6526). The TetO expression system is disclosed in U.S. Pat. No. 5,464,758 B1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a therapeutic protein or therapeutic polypeptide, wherein said second polynucleotide is operably linked to a therapeutic switch promoter. In the Lac system, a lac operon is inactivated in the absence of lactose, or synthetic analogs such as isopropyl-b-D-thiogalactoside.

Additional gene switch systems include those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more therapeutic polypeptides or therapeutic polynucleotides, upon binding to one or more ligands. Within the scope of the present invention are any numbers of and/or combinations of gene switch systems.

In one embodiment, the present invention provides a nucleic acid composition comprising:
a. a first gene switch system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide, and
b. a second gene expression system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide.

The multiple inducible gene expression systems provide for expression of a given therapeutic polynucleotide or therapeutic polypeptide under conditions associated with different diseases, disorders or conditions, or expression of multiple therapeutic polypeptides or therapeutic polynucleotides either under the same conditions associated with the same disease disorder or condition, or under different conditions associated with different diseases, disorders, or conditions.

In certain embodiments, the combination of two or more gene switch systems may be (1) a dual-switch ecdysone receptor based gene expression system and (2) a single-switch ecdysone receptor based gene switch. In other embodiments, the combination may be (1) an single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention.

Ligands

As used herein, the term "ligand," as applied to LDTFC-based gene switches e.g., EcD complex based gene switches, describes small and soluble molecules having the capability of activating a gene switch to stimulate expression of a polypeptide encoded therein. The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3- sulfate (ECHS), 7-ketocholesterol-3-sulfate, farnesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethyl-benzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057 B1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I

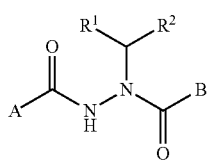

Formula I wherein
A is alkoxy, arylalkyloxy or aryloxy;
B is optionally substituted aryl or optionally substituted heteroaryl; and
R¹ and R² are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;
or pharmaceutically acceptable salts, hydrates, crystalline forms or amorphous forms thereof.

In another embodiment, the ligand may be enantiomerically enriched compounds of Formula II

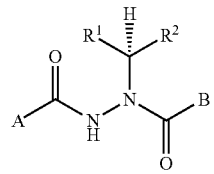

Formula II wherein
A is alkoxy, arylalkyloxy, aryloxy, arylalkyl, optionally substituted aryl or optionally substituted heteroaryl;
B is optionally substituted aryl or optionally substituted heteroaryl; and
R¹ and R² are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;
with the proviso that R¹ does not equal R²;
wherein the absolute configuration at the asymmetric carbon atom bearing R¹ and R² is predominantly S;
or pharmaceutically acceptable salts, hydrates, crystalline forms or amorphous forms thereof.

In certain embodiments, the ligand may be enantiomerically enriched compounds of Formula III

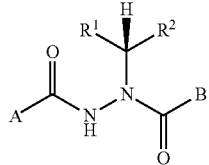

Formula III wherein
A is alkoxy, arylalkyloxy, aryloxy, arylalkyl, optionally substituted aryl or optionally substituted heteroaryl;
B is optionally substituted aryl or optionally substituted heteroaryl; and
R¹ and R² are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;
with the proviso that R¹ does not equal R²;
wherein the absolute configuration at the asymmetric carbon atom bearing R¹ and R² is predominantly R;
or pharmaceutically acceptable salts, hydrates, crystalline forms or amorphous forms thereof.

In one embodiment, a ligand may be (R)-3,5-dimethyl-benzoic acid N-(1-tert-butyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. application Ser. No. 12/155,111, filed May 29, 2008, which is fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmacetical compoistion are in the form of solutions, suspensions, tablets, capsules, ointments, elixirs, or injectable compositions.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain. Examples of ecdysone-responsive systems are described in U.S. Pat. Nos. 7,091,038 and 6,258,603. In one embodiment, the system is the RheoSwitch® Therapeutic System (RTS), which contains two fusion proteins, the DEF domains of a mutagenized ecdysone receptor (EcR) fused with a Gal4 DNA binding domain and the EF domains of a chimeric RXR fused with a VP16 transcription activation domain, expressed under a constitutive promoter as illustrated in FIG. 1.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., *DNA* 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art.

For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667 (1987)). Such proteins (and their encoding genes) have sequence homology, as reflected by their high degree of sequence similarity. However, in common usage and in the application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., Cell 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., J. Mol. Biol. 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS.* 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentiality of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." Useful orthogonal ligands and orthogonal receptor-based gene expression systems are described in US 2002/0110861 A1.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The term "therapeutic product" refers to a therapeutic polypeptide or therapeutic polynucleotide which imparts a beneficial function to the host cell in which such product is expressed. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. The therapeutic product may comprise a naturally occurring sequence, a synthetic sequence or a combination of natural and synthetic sequences.

The term "ligand-dependent transcription factor complex" or "LDTFC" refers to a transcription factor comprising one or more protein subunits, which complex can regulate gene expression driven by a "factor-regulated promoter" as defined herein. A model LDTFC is an "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor ("RXR") protein or a chimera of USP and RXR. The terms "LDTFC" and "EcR complex" also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the LDTFC, e.g., EcR complex, may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). The functional EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. The EcR complex can also be a heterodimer of EcR protein and the vertebrate homolog of ultraspiracle protein, retinoic acid-X-receptor ("RXR") protein or a chimera of USP and RXR. The term EcR complex also encompasses homodimer complexes of the EcR protein or USP.

An EcR complex can be activated by an active ecdysteroid or non-steroidal ligand bound to one of the proteins of the complex, inclusive of EcR, but not excluding other proteins of the complex. As used herein, the term "ligand," as applied to EcR-based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See U.S. application Ser. No. 12/155,111, filed May 29, 2008, and PCT/US2008/006757 filed May 29, 2008, for additional diacylhydrazines that are useful in the practice of the invention.

The EcR complex includes proteins which are members of the nuclear receptor superfamily wherein all members are characterized by the presence of an amino-terminal transactivation domain ("TA"), a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the EcR complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

EcR ligands, when used with the EcR complex which in turn is bound to the response element linked to an exogenous gene (e.g., IL-12), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the EcR complex to a specific control, or regulatory, DNA element. The EcR protein, like other members of the nuclear receptor family, possesses at least three domains, a transactivation domain, a DNA binding domain, and a ligand binding domain. This receptor, like a subset of the nuclear receptor family, also possesses less well-defined regions responsible for heterodimerization properties. Binding of the ligand to the ligand binding domain of EcR protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g., EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., Nature 335:563 (1988) or LexA protein from E. coli (see Brent et al., Cell 43:729 (1985)) to accommodate chimeric EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

In certain embodiments, the therapeutic switch promoter described in the methods is consititutive. In certain embodiments, the therapeutic switch promoter is activated under conditions associated with a disease, disorder, or condition, e.g., the promoter is activated in response to a disease, in response to a particular physiological, developmental, differentiation, or pathological condition, and/or in response to one or more specific biological molecules; and/or the promoter is activated in particular tissue or cell types. In certain embodiments, the disease, disorder, or condition is responsive to the therapeutic polypeptide or polynucleotide. For example in certain non-limiting embodiments the therapeutic polynucleotide or polypeptide is useful to treat, prevent, ameliorate, reduce symptoms, prevent progression, or cure the disease, disorder or condition, but need not accomplish any one or all of these things. In certain embodiments, the first and second polynucleotides are introduced so as to permit expression of the ligand-dependent transcription factor complex under consitions associated with a disease, disorder or condition. In one embodiment, the therapeutic methods are carried out such that the therapeutic polypeptide or therapeutic polynucleotide is expressed and disseminated through the subject at a level sufficient to treat, ameliorate, or prevent said disease, disorder, or condition. As used herein, "disseminated" means that the polypeptide is expressed and released from the modified cell sufficiently to have an effect or activity in the subject. Dissemination may be systemic, local or anything in between. For example, the therapeutic polypeptide or therapeutic polynucleotide might be systemically disseminated through the bloodstream or lymph system. Alternatively, the therapeutic polypeptide or therapeutic polynucleotide might be disseminated locally in a tissue or organ to be treated.

Numerous genomic and cDNA nucleic acid sequences coding for a variety of polypeptides, such as transcription factors and reporter proteins, are well known in the art. Those skilled in the art have access to nucleic acid sequence information for virtually all known genes and can either obtain the nucleic acid molecule directly from a public depository, the institution that published the sequence, or employ routine methods to prepare the molecule. See for example the description of the sequence accession numbers, infra.

The gene switch may be any gene switch system that regulates gene expression by addition or removal of a specific ligand. In one embodiment, the gene switch is one in which the level of gene expression is dependent on the level of ligand that is present. Examples of ligand-dependent transcription factors that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617. An example of a non-steroidal ecdysone agonist-regulated system is the RheoSwitch® Mammalian Inducible Expression System (New England Biolabs, Ipswich, Mass.).

In one embodiment, a polynucleotide encoding the gene switch comprises a single transcription factor sequence encoding a ligand-dependent transcription factor under the control of a promoter. The transcription factor sequence may encode a ligand-dependent transcription factor that is a naturally occurring or an artificial transcription factor. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain (LBD). In one embodiment, the Group H nuclear receptor LBD is from an EcR, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor LBD is from an ecdysone receptor.

The EcR and the other Group H nuclear receptors are members of the nuclear receptor superfamily wherein all members are generally characterized by the presence of an amino-terminal transactivation domain (TD), a DNA binding domain (DBD), and a LBD separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and TD may be interchanged.

In another embodiment, the transcription factor comprises a TD, a DBD that recognizes a response element associated with the exogenous gene whose expression is to be modulated; and a Group H nuclear receptor LBD. In certain embodiments, the Group H nuclear receptor LBD comprises a substitution mutation.

In another embodiment, a polynucleotide encoding the gene switch comprises a first transcription factor sequence under the control of a first promoter and a second transcription factor sequence under the control of a second promoter, wherein the proteins encoded by said first transcription factor sequence and said second transcription factor sequence interact to form a protein complex which functions as a ligand-dependent transcription factor, i.e., a "dual switch"- or "two-hybrid"-based gene switch. The first and second promoters may be the same or different.

In certain embodiments, the polynucleotide encoding a gene switch comprises a first transcription factor sequence and a second transcription factor sequence under the control of a promoter, wherein the proteins encoded by said first transcription factor sequence and said second transcription factor sequence interact to form a protein complex which functions as a ligand-dependent transcription factor, i.e., a "single gene switch". The first transcription factor sequence and a second transcription factor sequence may be connected by an internal ribosomal entry site (IRES). The IRES may be an EMCV IRES.

In one embodiment, the first transcription factor sequence encodes a polypeptide comprising a TD, a DBD that recognizes a response element associated with the exogenous gene whose expression is to be modulated; and a Group H nuclear receptor LBD, and the second transcription factor sequence encodes a transcription factor comprising a nuclear receptor LBD selected from a vertebrate RXR LBD, an invertebrate RXR LBD, an ultraspiracle protein LBD, and a chimeric LBD comprising two polypeptide fragments, wherein the first polypeptide fragment is from a vertebrate RXR LBD, an invertebrate RXR LBD, or an ultraspiracle protein LBD, and the second polypeptide fragment is from a different vertebrate RXR LBD, invertebrate RXR LBD, or ultraspiracle protein LBD.

In another embodiment, the gene switch comprises a first transcription factor sequence encoding a first polypeptide comprising a nuclear receptor LBD and a DBD that recognizes a response element associated with the exogenous gene whose expression is to be modulated, and a second transcription factor sequence encoding a second polypeptide comprising a TD and a nuclear receptor LBD, wherein one of the nuclear receptor LBDs is a Group H nuclear receptor LBD. In a preferred embodiment, the first polypeptide is substantially free of a TD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimer partner and a TD and the second transcription factor sequence encodes a protein comprising a DBD and a LBD.

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from a vertebrate RXR, an invertebrate RXR, and a USP (see WO 01/70816 A2, International Patent Application No. PCT/US02/05235 and US 2004/0096942 A1). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa* domestica, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element linked to the exogenous gene, provides external temporal regulation of expression of the exogenous gene. The binding mechanism or the order in which the various components of this invention bind to each other, that is, for example, ligand to LBD, DBD to response element, TD to promoter, etc., is not critical.

In a specific example, binding of the ligand to the LBD of a Group H nuclear receptor and its nuclear receptor LBD partner enables expression of the exogenous gene. This mechanism does not exclude the potential for ligand binding to the Group H nuclear receptor (GHNR) or its partner, and the resulting formation of active homodimer complexes (e.g., GHNR+GHNR or partner+partner). Preferably, one or more of the receptor domains is varied producing a hybrid gene switch. Typically, one or more of the three domains, DBD, LBD, and TD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA*, 94:3616 (1997)) to accommodate hybrid receptors.

The functional EcR complex may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

The exogenous gene is operably linked to a promoter comprising at least one response element that is recognized by the DBD of the ligand-dependent transcription factor encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

To introduce the polynucleotides into the cells, a vector can be used. The vector may be, for example, a plasmid vector or a single- or double-stranded RNA or DNA viral vector. Such vectors may be introduced into cells by well-known techniques for introducing DNA and RNA into cells. Viral vectors may be replication competent or replication defective. In the latter case, viral propagation generally will occur only in complementing host cells. As used herein, the term "host cell" or "host" is used to mean a cell of the invention that is harboring one or more polynucleotides of the invention.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the invention, the vectors that are introduced into the cells further comprise a "selectable marker gene" which, when expressed, indicates that the gene switch construct of the invention has been integrated into the genome of the host cell. In this manner, the selector gene can be a positive marker for the genome integration. While not critical to the methods of the invention, the presence of a selectable marker gene allows the practitioner to select for a population of live cells where the vector construct has been integrated into the genome of the cells. Thus, certain embodiments of the invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.*, 103:9958 (2006). Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Particular vectors for use with the invention are expression vectors that code for proteins or polynucleotides. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express proteins or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the invention. Generally, any vector suitable to maintain, propagate or express polynucleotides or proteins in a host may be used for expression in this regard.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* 290:304 (1981)); and the vaccinia virus promoter. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCM-VDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231. An example of such vectors is the UltraVector™ Production System (Intrexon Corp., Blacksburg, Va.), as described in WO 2007/038276. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MIV, Ase I, Flp I, Pme I, Sda I, Sgf I, Srf I, Nru I, Acl I, Cla I, Csp45 I, Age I, Bst1107 I, BstB I, Hpa I, Aat II, EcoR V, Nhe I, Spe I, Avi II, Avr II, Mfe I, Afe I, Fsp I, Kpn I, Sca I, BspE I, Nde I, Bfr I, Xho I, Pml I, ApaL I, Kas I, Xma I, BsrB I, Nsi I, Sac II, Sac I, Blp I, PspOM I, Pci I, Stu I, Sph I, BamH I, Bsu36 I, Xba I, BbvC I, Bgl II, Nco I, Hind III, EcoR I, BsrG I and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-SceI has an 18 bp restriction site (5'TAGGGATAACA-GGGTAAT3' (SEQ ID NO: 28)), predicted to occur only once in every $7 \times 10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites are included in appropriate locations in a cloning vector plasmid.

Selection of appropriate vectors and promoters for expression in a host cell is a well-known procedure, and the requisite techniques for vector construction and introduction into the host, as well as its expression in the host are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y. These stable transfection methods result in random insertion of the vector into the genome of the cell. Further, the copy number and orientation of the vectors are also, generally speaking, random.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements, or even all elements present on the vector.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001). Other examples of recombinases and their respective sites that may be used for recombinase-site specific gene insertion include, but are not limited to, serine recombinases such as R4 and TP901-1 and recombinases described in WO 2006/083253.

In a further embodiment, the vector may comprise a chemo-resistance gene, e.g., the multidrug resistance gene mdr1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease or disorder. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the exogenous gene into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polypeptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g., intraperitoneally, intrathecally, intraventricularly, direct injection into the tissue or organ where the cells are reintroduced). The optimal timing of ligand administration can be determined for each type of cell and disease or disorder using only routine techniques.

The in vivo therapeutic methods of the invention involve direct in vivo introduction of the polynucleotides into the cells of the subject. The polynucleotides may be introduced into the subject systemically or locally (e.g., at the site of the disease or disorder). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathecally, intraventricularly, direct injection into the tissue or organ where the disease or disorder is occurring). The optimal timing of ligand administration can be determined for each type of cell and disease or disorder using only routine techniques.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intratumoral, intradermal, intrathecal and epidural) and by naso-gastric tube. It will be understood by those skilled in the art that the preferred route of administration will depend upon the condition being treated and may vary with factors such as the condition of the recipient.

As used herein, the term "rAD.RheoIL12" refers to an adenoviral polynucleotide vector harboring the IL-12 gene under the control of a gene switch of the RheoSwitch® Therapeutic System (RTS), which is capable of producing IL-12 protein in the presence of activating ligand. As used herein, the term "rAd.cIL12" refers to an adenoviral polynucleotide control vector containing the IL-12 gene under the control of a constitutive promoter.

As used herein, the term "IL-12p70" refers to IL-12 protein, which naturally has two subunits commonly referred to as p40 and p35. The term IL-12p70 encompasses fusion proteins comprising the two subunits of IL-12 (p40 and p35), wherein the fusion protein may include linker amino acids between subunits.

As used herein, the term "a protein having the function of an immunomodulator" refers to a protein that has at least 20% (e.g., at least 30%, 40%, 50%, 60%, 70%, 80% or 90%) of any bioactivity of an immunomodulator selected from IL-1, IL-2, IL-3, IL-4, IL-5, IL-7, IL-8, IL-9, IL-10R or a subunit thereof DN, IL-15, IL-18, IL-21, IL-23, IL-24, IL-27, GM-CSF, IFN-alpha, IFN-gamma, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, BCG, TGF-alpha, PD-L1, TGFbRII DN, ICOS-L and S100. Likewise, the term "a protein having the function of IL-12" refers to a protein that has at least 20% (e.g., at least 30%, 40%, 50%, 60%, 70%, 80% or 90%) of any bioactivity of human IL-12. The bioactivities of such immunomodulators are well known. See the following Table.

TABLE 4

Immunomodulators and their functions

| Immunomodulator | Function |
| --- | --- |
| Cytokines | |
| Interleukin-1 (IL-1) | IL-1 is a cytokine produced by activated macrophages. IL-1 stimulates thymocyte proliferation by inducing IL-2 release, B-cell maturation and proliferation, and fibroblast growth factor activity. IL-1 proteins are involved in the inflammatory response. |
| Interleukin-2 (IL-2) | IL-2 is a family of cytokines, that is produced by T-cells in response to antigenic or mitogenic stimulation, this protein is required for T-cell proliferation and other activities crucial to regulation of the immune response. IL-2 can stimulate B-cells, monocytes, lymphokine-activated killer cells, natural killer cells, and glioma cells. |
| Interleukin-3 (IL-3) | IL-3 stimulates the proliferation of hematopoietic pluripotent progenitor cells. It is secreted by activated T cells to support growth and differentiation of T cells from the bone marrow in an immune response. The combined intratumoral Ad-mIL-3 gene therapy in combination with radiation therapy was shown to significantly suppress tumor growth (Oh 2004). |
| Interleukin-4 (IL-4) | IL-4 is a cytokine that participates in at least several B-cell activation processes as well as of other cell types. It is a costimulator of DNA-synthesis. It induces the expression of class II MHC molecules on resting B-cells. It enhances both secretion and cell surface expression of IgE and IgG1. It also regulates the expression of the low affinity Fc receptor for IgE (CD23) on both lymphocytes and monocytes. |
| Interleukin-5 (IL-5) | IL-5 stimulates B cell growth and increase immunoglobulin secretion and induce tumor suppression (Nakashima 1993, Wu 1992). |
| Interleukin-7 (IL-7) | IL-7 is a cytokine that is a hematopoietic growth factor capable of stimulating the proliferation of lymphoid progenitors. It is important for proliferation during certain stages of B-cell maturation. |
| Interleukin-9 (IL-9) | IL-9 supports IL-2 independent and IL-4 independent growth of helper T-cells. |
| Interleukin-15 (IL-15) | IL-15 is a cytokine that stimulates the proliferation of T-lymphocytes. Stimulation by IL-15 requires interaction of IL-15 with components of IL-2R, including IL-2R beta and probably IL-2R gamma but not IL-2R alpha. |
| Interleukin-18 (IL-18) | IL-18 augments natural killer cell activity in spleen cells and stimulates interferon gamma production in T-helper type I cells. |
| Interleukin-21 (IL-21) | IL-21 is a cytokine with immunoregulatory activity. IL-21 may promote the transition between innate and adaptive immunity. |
| Interleukin-23 (IL-23) | IL-23 acts directly on DC to promote immunogenic presentation of tumor peptide and can I resulted in robust intratumoral CD8(+) and CD4(+) T-cell infiltration and induced a specific TH1-type response to the tumor in regional lymph nodes and spleen. (Hu 2006). |

TABLE 4-continued

Immunomodulators and their functions

| Immunomodulator | Function |
| --- | --- |
| Interleukin-27 (IL-27) | IL-27 is a cytokine with pro- and anti-inflammatory properties, that can regulate T helper cell development, suppress T-cell proliferation, stimulate cytotoxic T cell activity, induce isotype switching in B-cells, and that has diverse effects on innate immune cells. |
| Intereukin-24 (IL-23) | IL-24 has been shown to suppress tumor growth (Susan 2004, Fisher 2003). |
| INF-alpha (IFNα) | IFN-alpha has anti-tumor function (Taqliaferri 2005). |
| Interferon beta 1 (IFNB1) | IFNB1 is a member of group of interferon proteins that bind to specific cell surface receptors (IFNAR), and stimulates both macrophages and natural killer (NK) cells to elicit an antiviral, antibacterial and anticancer activities. |
| Interferon gamma (IFN-gamma) | IFN-gamma is produced by lymphocytes activated by specific antigens or mitogens. IFN-gamma, in addition to having antiviral activity, has important immunoregulatory functions. It is a potent activator of macrophages, it has antiproliferative effects on transformed cells and it can potentiate the antiviral and antitumor effects of the type I interferons. |
| Tumor necrosis factor (TNF-alpha) | TNF-α is mainly secreted by macrophages and can induce cell death of certain tumor cell lines. It is a potent pyrogen, causing fever by direct action or by stimulation of interleukin-1 secretion. |

Chemokines

| | |
| --- | --- |
| Chemokine (C motif) ligand 1 (XCL1) | Chemokine (C motif) ligand 1 (XCL1, also known as Lymphotactin) is chemotactic for CD4+ and CD8+ T cells but not for monocytes, and induces a rise in intracellular calcium in peripheral blood lymphocytes. The combination of XCL1 with IL-2 and IL-12 can enhance immunotherapy and augment the antitumor response (Emtage 1999, Wang 2002). |
| CC chemokine ligand 3 (CCL3) | CC chemokine ligand 3 (CCL3), also known as macrophage inflammatory protein-1 (MIP-1), which is a so-called monokine (a type of cytokine produced primarily by monocytes and macrophages) that is involved in the acute inflammatory state in the recruitment and activation of polymorphonuclear leukocytes. |
| CCL5 (RANTES) | CCL5 (RANTES), is a chemoattractant for blood monocytes, memory T-helper cells and eosinophils. Causes the release of histamine from basophils and activates eosinophils. Binds to CCR1, CCR3, CCR4 and CCR5. One of the major HIV-suppressive factors produced by CD8+ T-cells. |
| CC chemokine ligand 7 (CCL7) | CCL7 is a chemotactic factor that attracts monocytes and eosinophils, but not neutrophils. CCL7 also augments monocyte anti-tumor activity. Also induces the release of gelatinase B. |
| Chemokine (CXC motif) ligand 9 (CXCL9) | CXCL9 is a cytokine that affects the growth, movement, or activation state of cells that participate in immune and inflammatory response. Chemotactic for activated T-cells. |
| Chemokine (C—X—C motif) ligand 10 (CXCL10) | Chemokine (C—X—C motif) ligand 10 (CXCL10) is a small cytokine with roles in chemoattraction for cells in the immune system, adhesion of T cells to endothelial cells, anti-tumor activity and angiogenesis. |
| Chemokine (C—X—C motif) ligand 12 (CXCL12) | Chemokine (C—X—C motif) ligand 12 (CXCL12), also known as stormal cell-derived factor 1 (SDF-1), is a small cytokine that belong to the intercrine family, members of which activate leukocytes and are often induced by proinflammatory stimuli such as LPS, TNF or IL1. |
| Chemokine (C-C motif) receptor 7 (CCR7) | CCR7 is the receptor for the MIP-3-beta chemokine. Probable mediator of EBV effects on B-Lymphocytes or of normal lymphocyte functions. |
| Chemokine (C-C motif) ligand 19 (CCL19, also known as MIP-3β) | CCL19 plays a role not only in inflammatory and immunological responses but also in normal lymphocyte recirculation and homing. CCL19 has an important role in trafficking of T-cells in thymus, and T-cell and B-cell migration to secondary lymphoid organs. It specifically binds to chemokine receptor CCR7. |
| CC chemokine ligand 21 (CCL21) | CCL21 inhibits hemopoiesis and stimulates chemotaxis. CCL21 is chemotactic in vitro for thymocytes and activated T-cells, but not for B-cells, macrophages, or neutrophils. |
| Interleukin-8 (IL-8) | IL-8 is a chemotactic factor that attracts neutrophils, basophils, and T-cells, but not monocytes. It is also involved in neutrophil activation. It is released from several cell types in response to an inflammatory stimulus. |

Growth Factors

| | |
| --- | --- |
| Granulocyte/macrophage colony-stimulating factor (GM-CSF) | GM-CSF is a cytokine that stimulates the growth and differentiation of hematopoietic precursor cells from various lineages, including granulocytes, macrophages, eosinophils and erythrocytes. |

TABLE 4-continued

Immunomodulators and their functions

| Immunomodulator | Function |
| --- | --- |
| FMS-related tyrosine kinase ligand (FLT3/FLK2 ligand, Flt3L) | FMS-related tyrosine kinase ligand (FLT3/FLK2 ligand, Flt3L), which may function as a growth factor receptor on hematopoietic stem cells or progenitor cells or both. |
| TGFA | TGF alpha is a mitogenic polypeptide that is able to bind to the EGF receptor and to act synergistically with TGF beta to promote anchorage-independent cell proliferation in soft agar. |
| Adjuvants | |
| Beta-defensin | Beta-defensins are antimicrobial peptides implicated in innate immune response against many Gram-negative and Gram-positive bacteria, fungi and viruses. |
| High-mobility group box-1 (HMGB1) | High-mobility group box-1 (HMGB1) proteins are nonhistone chromosomal proteins that function as cytokines, mediating local and systemic responses to necrotic cell death and cancer, invasion by pathogens, trauma, and sepsis. |
| S100 | Phagocytic S100 proteins mediate inflammatory responses and recruit inflammatory cells to sites of tissue damage, and are members of Damage-associated molecular pattern (DAMP) molecules that are important for innate immunity. |
| Mannan | Mannan, a plant polysaccharide, that is a polymer of the sugar mannose, is useful for generation of a immune response. |
| Bacille Calmette-Guerin (BCG) | Bacille Calmette-Guerin (BCG), live attenuated *Mycobacterium* species, are used as vaccine against to prevent severe and fatal tuberculosis. |
| Bacterial lipopolysaccharides (LPS) | Bacterial lipopolysaccharides (LPS) are endotoxins that induces a strong immune response upon infection with Gram-negative bacteria. |
| Co-stimulatory Molecule (Positive) | |
| OX40 ligand | OX40 ligand (OX40L) belongs to tumor necrosis factor (ligand) superfamily member 4 (Tnfsf4), is expressed on dendritic cells and promotes Th2 cell differentiation. |
| 4-1BB ligand (4-1BBL) | 4-1BB ligand (4-1BBL) belongs to tumor necrosis factor (ligand) superfamily member 9 (Tnfsf9), which is a type 2 transmembrane glycoprotein and is expressed on activated T lymphocytes. 4-1BBL induces the proliferation of activated peripheral blood T-cells, and has a role in activation-induced cell death (AICD). |
| CD40 | The CD40 protein belongs to the tumor necrosis factor receptor superfamily member 5, is essential in mediating a broad variety of immune and inflammatory responses including T cell-dependent immunoglobulin class switching, memory B cell development, and germinal center formation. |
| Glucocorticoid-induced tumor necrosis factor receptor family-related protein (GITR) | GITR can evoke effective tumor immunity via T cell stimulation. Administration of anti-GITR monoclonal antibody (mAb) can provoke potent tumor-specific immunity and eradicated established tumors without eliciting overt autoimmune disease. |
| GITR Ligand (GITRL) | GITRL is the ligand for GITR. |
| CD70 | CD70 is a cytokine that binds to CD27. It plays a role in T-cell activation. Induces the proliferation of costimulated T-cells and enhances the generation of cytolytic T-cells. |
| LIGHT (HSVgD) | Herpes virus entry mediator (HVEM) binding ligand (HSVgD), also referred to as p30, or LIGHT is a TNF family member involved in co-stimulation of T cells. |
| PD-L1 (also known as CD274) | PD-L1 (also known as CD274) protein is expressed in activated monocytes, T and B cells. PD-L1 is upregulated in monocytes upon treatment with IFN-gamma, and in dendritic cells and keratinocytes upon treatment with IFN-gamma, together with other activators. |
| ICOS-L | ICOS-L is a ligand for the T-cell-specific cell surface receptor ICOS and acts as a costimulatory signal for T-cell proliferation and cytokine secretion; induces also B-cell proliferation and differentiation into plasma cells. |
| Co-stimulatory Molecule (Negative) | |
| Anti-CTLA4 | Cytotoxic T lymphocyte-associated 4 (CTLA4) is a member of the immunoglobulin superfamily and is a costimulatory molecule expressed in activated T cells. |
| Anti-PD-L1 | Binding of a PD-1 receptor on a T-cell by PD-L1 transmits a negative costimulatory signal to the cell, which prevents the cells to progress through the cell cycle, and increases T cell proliferation. Inhibition of an interaction between PD-L1 and receptor on the T cell with an anti-PD-L1 antibody results in the downregulation of the immune response termed as immune cell anergy. |

TABLE 4-continued

Immunomodulators and their functions

| Immunomodulator | Function |
| --- | --- |
| Anti-PD-L2 | PD-L2 is involved in the costimulatory signal, essential for T lymphocyte proliferation and IFN-gamma production in a PDCD1-independent manner, but the ligand is known to primarily act through PD-1 resulting in anergic responses. |
| Counter Immune Suppressant (Tolerance Inhibitors) | |
| TGFR2DN | On ligand binding, TGFR2 forms a receptor complex consisting of two type II and two type I transmembrane serine/threonine kinases. Type II receptors phosphorylate and activate type I receptors which autophosphorylate, then bind and activate SMAD transcriptional regulators. Receptor for TGF-beta. Deletion of predicted serine/threonine kinase cytoplasmic domain (nucleotides 1172-2036 of TGFβR2 cDNA H2-3FF, available from public databases as accession number M85079 and amino acid sequence available as accession number AAA61164) impairs the all three TGF-β (1, 2 and 3) dependent gene expressions. |
| Anti-TGFβ | TGFβ is a multifunctional peptide that controls proliferation, differentiation, and other functions in many cell types. TGFβ acts synergistically with TGFα in inducing transformation. It also acts as a negative autocrine growth factor. Dysregulation of TGFβ activation and signaling may result in apoptosis. administration of anti-TGFβ antibody can prevent renal insufficiency and glomerulosclerosis in the db/db mouse, a model of type II diabetes that develops overt nephropathy. |
| Anti-IL10 | IL-10 is a cytokine produced by activated Th2 cells, B cells, keratinocytes, monocytes, and macrophages. IL-10 is useful in promoting growth and differentiation of activated human B cells, inhibiting Th1 responses to prevent transplant rejection and T cell-mediated autoimmune diseases. |
| Anti-Suppressor of cytokine signaling1 (SOCS1) | Suppressor of cytokine signaling1 (SOCS1) is a critical inhibitor of interferon-gamma signaling and prevents the potentially fatal neonatal actions of this cytokine. |
| Anti-TGF-α | TGF-α is a mitogenic polypeptide that is able to bind to the EGF receptor and to act synergistically with TGF-β to promote anchorage-independent cell proliferation in soft agar. |
| Fas contain cytoplasmic Fas-associated protein with death domain (FADD) | FADD is essential for Fas and TNF-induced signaling for programmed cell death (apoptosis) and receptor oligomerization. |

The bioactivities of IL-12 are also well known and include, without limitation, differentiation of naive T cells into Th1 cells, stimulation of the growth and function of T cells, production of interferon-gamma (IFN-gamma) and tumor necrosis factor-alpha (TNF-α) from T and natural killer (NK) cells, reduction of IL-4 mediated suppression of IFN-gamma, enhancement of the cytotoxic activity of NK cells and CD8$^+$ cytotoxic T lymphocytes, stimulation of the expression of IL-12R-β1 and IL-12R-β2, facilitation of the presentation of tumor antigens through the upregulation of MHC I and II molecules, and anti-angiogenic activity. The term "a protein having the function of IL-12" encompasses mutants of a wild type IL-12 sequence, wherein the wild type sequence has been altering by one or more of addition, deletion, or substitution of amino acids, as well as non-IL-12 proteins that mimic one or more of the bioactivities of IL-12.

As used herein, the terms "activating" or "activate" refer to any measurable increase in cellular activity of a gene switch, resulting in expression of a gene of interest (e.g., selected from IL-1, IL-2, IL-3, IL-4, IL-5, IL-7, IL-8, IL-9, IL-10R or a subunit thereof DN, IL-15, IL-18, IL-21, IL-23, IL-24, IL-27, GM-CSF, IFN-alpha, IFN-gamma, CCL3 (MIP-1a), CCL5 (RANTES), CCL7 (MCP3), XCL1 (lymphotactin), CXCL1 (MGSA-alpha), CCR7, CCL19 (MIP-3b), CXCL9 (MIG), CXCL10 (IP-10), CXCL12 (SDF-1), CCL21 (6Ckine), OX40L, 4-1BBL, CD40, CD70, GITRL, LIGHT, b-Defensin, HMGB1, Flt3L, IFN-beta, TNF-alpha, dnFADD, TGF-alpha, PD-L1 RNAi, a PD-L1 antisense oligonucleotide, TGFbRII DN, ICOS-L and S100.

As used herein, the terms "treating" or "treatment" of a disease refer to executing a protocol, which may include administering one or more drugs or in vitro engineered cells to a mammal (human or non-human), in an effort to alleviate signs or symptoms of the disease. Thus, "treating" or "treatment" should not necessarily be construed to require complete alleviation of signs or symptoms, does not require a cure, and specifically includes protocols that have only marginal effect on the subject.

As used herein, "immune cells" include dendritic cells, macrophages, neurophils, mast cells, eosinophils, basophils, natural killer cells and lymphocytes (e.g., B and T cells).

As used herein, the terms "dendritic cells" and "DC" are interchangeably used.

As used herein, the term "therapy support cells" (TSC) are cells that can be modified (e.g., transfected, electroporated, etc.) with the vector of the invention to deliver the one or more proteins having the function of an immunomodulator and, optionally, a protein having the function of IL-12, to tumor microenvironments. Such TSC include, but are not limited to, stem cells, fibroblasts, endothelial cells and keratinocytes.

As used herein, the terms "in vitro engineered immune cells" or "in vitro engineered population of immune cells" or "a population of engineered immune cells" or "immune cells expressing an immunomodulator" or "immune cells expressing IL-12" refer to immune cells, e.g., dendritic cells, conditionally expressing an immunomodulator and/or IL-12 as the case may be under the control of a gene switch, which can be activated by an activating ligand.

As used herein, the terms "in vitro engineered TSC" or "in vitro engineered population of TSC" or "a population of engineered TSC" or "TSC expressing an immunomodulator" or "TSC expressing IL-12" refer to therapy support cells, e.g., stem cells, fibroblasts, endothelial cells and keratinocytes, conditionally expressing an immunomodulator and/or IL-12 as the case may be under the control of a gene switch, which can be activated by activating ligand.

As used herein, the term "modified cell" refers to cells which have been altered by a process including, but not limited to, transfection, electroporation, microinjection, transduction, cell fusion, DEAE dextran, calcium phosphate precipitation and lipofection (lysosome fusion).

As used herein, the terms "MOI" or "Multiplicity of Infection" refer to the average number of adenovirus particles that infect a single cell in a specific experiment (e.g., recombinant adenovirus or control adenovirus)

As used herein, the term "tumor" refers to all benign or malignant cell growth and proliferation either in vivo or in vitro, whether precancerous or cancerous cells and/or tissues.

Examples of cancers that can be treated according to the invention include breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, mesothelioma, osteogenic sarcoma, primary macroglobulinemia, and retinoblastoma, and the like.

The invention provides engineering of cells, e.g., immune cells and TSC, to conditionally express a protein having the function of an immunomodulator and, optionally, IL-12 and therapeutic uses and/or applications for the treatment of cancer or tumors or both. In vitro engineered immune cells and TSC that conditionally express a protein having the function of an immunomodulator and optionally IL-12 are a safe improvement over constitutive production of the protein(s). Additionally, the ability to control the timing and level of immunomodulator and optionally IL-12 expression provides improved control of the efficacy of the treatment. Therefore, in vitro engineered immune cells and TSC may be formulated into pharmaceutical compositions as therapeutics for the treatment of a cancer or a tumor in a human or a non-human organism. Alternatively, in vitro engineered populations of immune cells, TSC or subsets thereof may be used as vehicles to conditionally deliver an immunomodulator and optionally IL-12 protein production to a specific area (normal tissue, cancer, or tumor) in the body of a human or non-human organism. The immune cells may be autologous or non-autologous dendritic cells. The dendritic cells may be isolated from bone marrow or from peripheral blood circulation. In human patients, dendritic cell populations may be isolated via a leukophoresis procedure, where a white blood cell fraction is isolated and removed and other blood components are re-infused to the patient.

In another embodiment, the dendritic cells may be prepared by transfecting human hematopoietic stem cells with a vector of the invention expressing a protein having the function of an immunomodulator and optionally a protein having the function of IL-12, and differentiating the transfected stem cell to give a dendritic cell. See U.S. Pat. No. 6,734,014.

In one embodiment, a nucleic acid adenoviral vector is provided containing a gene switch, wherein the coding sequences for VP16-RXR and Gal4-EcR are separated by the EMCV internal ribosome entry site (IRES) sequence are inserted into the adenoviral shuttle vector under the control of the human ubiquitin C promoter. The coding sequences for the p40 and p35 subunits of IL12 separated by an IRES sequence, and placed under the control of a synthetic inducible promoter, are inserted upstream of the ubiquitin C promoter.

In another embodiment, the invention provides a shuttle vector carrying transcription units (VP16-RXR and Gal4-EcR) for the two fusion proteins and inducible IL-12 subunits recombined with the adenoviral backbone (AdEasy1) in *E. coli* BJ5183 cells. After verifying the recombinant clone, the plasmid carrying the rAd.RheoIL12 genome is grown in and purified from XL10-Gold cells, digested off the plasmid backbone and packaged by transfection into HEK 293 cells.

In a particular embodiment, the resulting primary viral stock is amplified by re-infection of HEK 293 cells and is purified by CsCl density-gradient centrifugation.

In one embodiment the immunomodulator and/or IL-12 gene is a wild-type gene sequence. In another embodiment, the immunomodulator and/or IL-12 gene is a modified gene sequence, e.g., a chimeric sequence or a sequence that has been modified to use preferred codons.

In one embodiment, the immunomodulator and/or IL-12 gene is the human wild type sequence. In another embodiment, the sequence is at least 85% identical to wild type human sequence, e.g., at least 90%, 95%, or 99% identical to wild type human sequence. In a further embodiment, the gene sequence encodes the human polypeptide. In another embodiment, the gene encodes a polypeptide that is at least 85% identical to wild type human polypeptide e.g., at least 90%, 95%, or 99% identical to wild type human polypeptide.

In one embodiment, the IL-12 gene is the wild type mouse IL-12 sequence. In another embodiment, the sequence is at least 85% identical to wild type mouse IL-12, e.g., at least 90%, 95%, or 99% identical to wild type mouse IL-12. In a further embodiment, the IL-12 gene sequence encodes the mouse IL-12 polypeptide. In another embodiment, the gene encodes a polypeptide that is at least 85% identical to wild type mouse IL-12, e.g., at least 90%, 95%, or 99% identical to wild type mouse IL-12.

DC may be isolated from bone marrow from humans, mice, or other mammals. The dendritic cells may be isolated from the blood of humans, mice or other mammals. In human patients, dendritic cell populations may be isolated via a leukophoresis procedure as is known in the art, where a white blood cell fraction is isolated and removed and other blood components are re-infused to the patient. In one embodiment, DC are derived from murine bone marrow as previously described (Tatsumi et al., 2003). Briefly, wild-type or EGFP Tg mouse bone marrow (BM) is cultured in conditioned medium (CM) supplemented with 1000 units/ml recombinant murine granulocyte/macrophage colony-stimulating factor and recombinant mIL-4 (Peprotech, Rocky Hill, N.J.) at 37° C. in a humidified, 5% $CO_2$ incubator for 7 days. $CD11c^+$ DC are then isolated, e.g., using specific MACSTM beads, per the manufacturer's instructions (Miltenyi Biotec, Auburn, Calif.). $CD11c^+$ DC produced in this manner are >95% pure based on morphology and co-expression of the CD11b, CD40, CD80, and class I and class II MHC antigens.

One embodiment of the invention provides engineered immune cells and TSC conditionally expressing a protein having the function of an immunomodulator and optionally IL-12 suitable for therapeutic applications for the treatment of cancer, or tumors or both as gene therapy in human or non-human organism. In an embodiment, the invention provides engineered immune cells and TSC containing the gene switch.

In another embodiment, the invention provides engineered immune cells and TSC containing at least a portion of an ecdysone receptor. In another embodiment, the invention provides engineered immune cells and TSC containing an ecdysone receptor-based gene switch. In another embodiment, the invention provides engineered immune cells and TSC containing RheoSwitch. In another embodiment, the invention provides a kit comprising engineered immune cells and TSC containing a gene switch and a ligand that modulates the gene switch. In another embodiment, the kits further comprise a diacylhydrazine ligand. In another embodiment, the kit further comprises RG-115830 or RG-115932.

In one embodiment, the invention provides an engineered population of immune cells and TSC. In one embodiment, day 7 cultured DC are treated with recombinant adenovirus encoding an immunomodulator and/or IL-12 driven off a constitutive or inducible promoter, or are infected with mock, control adenovirus vector (rAdψ5), over a range of multiplicity of infection (MOIs). After 48 h, infected DC are harvested and analyzed for phenotype and for production of an immunomodulator and/or IL-12 using a specific ELISA kit (BD-PharMingen, San Diego, Calif.), with a lower level of detection of 62.5 pg/ml.

In another embodiment, the invention provides in vitro engineered population of immune cells and TSC comprising a vector, e.g., a DNA vector, having a gene switch capable of conditionally expressing a protein having the function of an immunomodulator and/or IL-12, and further comprising activating ligand.

In a further embodiment, the invention provides a method of treating cancer, e.g., melanoma or glioma, by administering engineered DC to a patient and then administering an activating ligand, such as RG-115819, RG-115830 or RG-115932, to said patient. The patient may be a human or an animal with cancer. The treatment methods and products, engineered cells, kits, and ligands have application in human therapy and in veterinary animal therapy. Therefore, the products and methods are contemplated to be used for human and veterinary animal purposes.

In one aspect, the invention provides a pharmaceutical composition suitable for administration to a human or a non-human comprising a population of in vitro engineered immune cells or TSC expressing a protein having the function of an immunomodulator and/or IL-12, wherein the formulation is suitable for administration by intratumoral administration. The invention further provides a pharmaceutical composition comprising an activating ligand, such as RG-115819, RG-115830 or RG-115932, wherein the composition is suitable for administration by intraperitoneal, oral, or subcutaneous administration.

In the particular embodiment described herein, the invention provides a method for treating a tumor, comprising the steps in order of:
  a. administering intratumorally in a mammal a population of an in vitro engineered immune cells or TSC; and
  b. administering to said mammal a therapeutically effective amount of an activating ligand.

In one embodiment, the activating ligand is administered at substantially the same time as the in vitro engineered immune cells or TSC, e.g., within one hour before or after administration of the cells. In another embodiment, the activating ligand is administered at or less than about 24 hours after administration of the in vitro engineered immune cells or TSC. In still another embodiment, the activating ligand is administered at or less than about 48 hours after the in vitro engineered immune cells or TSC. In another embodiment, the ligand is RG-115932. In another embodiment, the ligand is administered at a dose of about 1 to 50 mg/kg/day. In another embodiment, the ligand is administered at a dose of about 30 mg/kg/day. In another embodiment, the ligand is administered daily for a period of 7 to 28 days. In another embodiment, the ligand is administered daily for a period of 14 days. In another embodiment, about $1 \times 10^6$ to $1 \times 10^8$ cells are administered. In another embodiment, about $1 \times 10^7$ cells are administered.

In one embodiment, dendritic cells are engineered to conditionally express IL-2 and IL-12. IL-2 exerts potent immunoregulatory effects on effector and regulatory T, NK and NK-T cells. It is expected that expressing IL-2 and IL-12 in cells will result in reciprocal upregulation of each others receptor and induce different by complementary biological effects by virtue of separate signaling pathways. It is also expected that the combination of IL-2 and IL-12 will lengthen the duration of immune stimulation and reduce the effective dose of cells that may be more tolerated by the animal. See Dietrich 2002, Wigginton 2002, 2001, 1996 and Koyama, 1997, McDermott and Atkins 2008; Berntsen et al 2008; Tarhini et al 2008; Heemskerk et al 2008; Horton et al 2008. The polynucleotide sequences of IL-2 are available under accession numbers U25676 (human); NM_008366 (mouse); NM_204153 (chicken); and NM_053836 (rat). The polynucleotide sequences of IL-12 are available under accession numbers NM_000882 (human IL12A); NM_002187 (human IL12B); NM_008351 (mouse IL12a); NM_008352 (mouse IL12b); NM_213588 (chicken IL12A); NM_213571 (chicken IL12B); NM_053390 (rat IL12a); and NM_022611 (rat IL12b). SEQ ID NOS: 13, 15, 21 and 23 code for human and mouse IL-12 and subunits thereof.

In another embodiment, dendritic cells are engineered to conditionally express IL-18 and IL-12. IL-18 induces IFN-gamma production and promotes T helper cell development and NK activation. In addition, IL-18 can augment GM-CSF production and decrease IL-10 production. It is expected that expressing IL-18 and IL-12 will overcome the limitations observed when either cytokine is administered alone. It is expected that expression of IL-12 and IL-18 in dendritic cells will stimulate more vigorous tumor antigen-specific Th1 responses than when dendritic cells are transduced with either cytokine alone.

The intratumoral injection of DCs engineered to secrete both IL-12 and IL-18 mediated the highest levels of INF-γ production and complete tumor rejection (Tatsumi 2003).

See, Vujanovic, 2006. See also Coughlin, 1998, Subleski, 206, Tatsumi, 2003, and Sabel, 2007; Shiratori et al 2007; Lian et al 2007; Iinuma et al 2006. See above for IL-12 polynucleotide sequences. The polynucleotide sequences of IL-18 are available under accession numbers U90434 (human); NM_008360 (mouse); EU747333 (chicken); and AY258448 (rat).

In another embodiment, dendritic cells are engineered to conditionally express IL-15 and IL-12. IL-15 shares some biologic activities with IL-2 that also makes it potentially useful for therapies against cancer. IL-15 stimulates the proliferation of NK cells and activated T cells, and supports the expansion of effector T cells. It has been reported that IL-15 presentation synergized with IL-12 for enhanced IFN-gamma production by NK cells. Koka, 2004; Basak 2008; Lasek et al 2004. Intratumoral delivery of IL-15 and IL-12 induced significant tumor regression in a melanoma model (Lasek 1999). See above for the IL-12 polynucleotide sequences. SEQ ID NOS: 11 and 19 code for the human and mouse IL-15. FIGS. 2 and 4 are plasmid maps for expression systems which may be used for the human and mouse IL-12 and IL-15.

Figure 7:
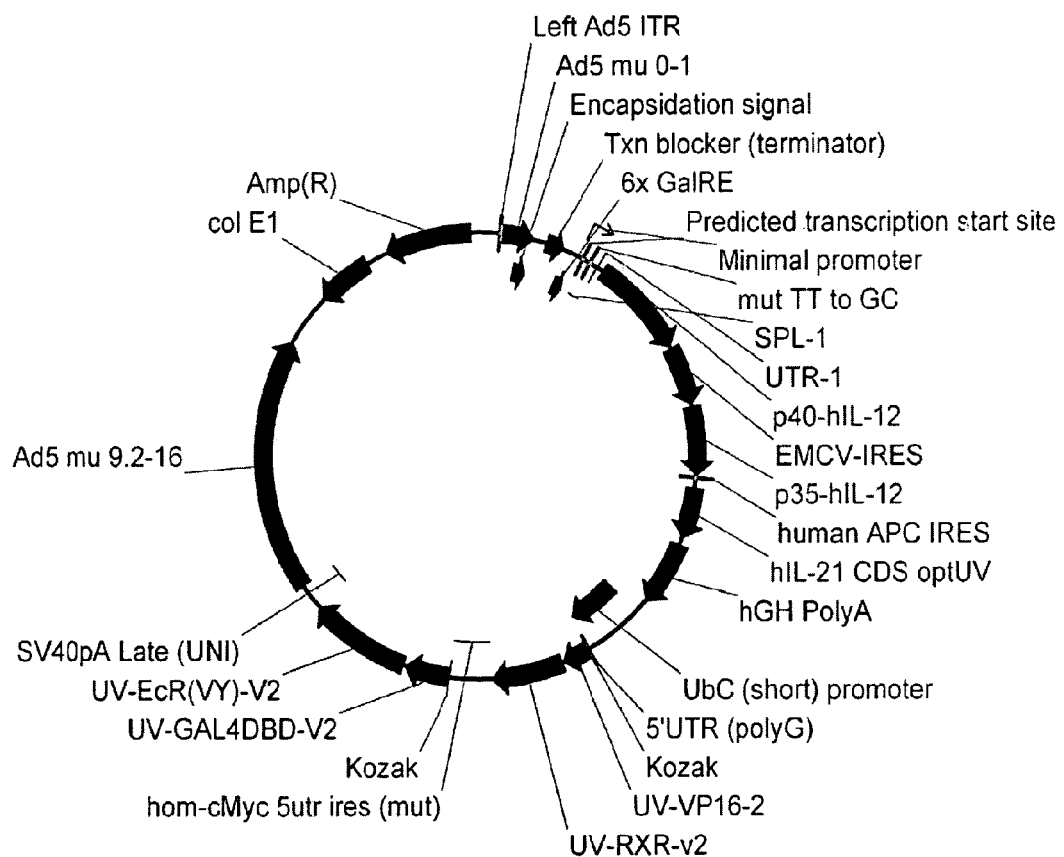
FIG. 7 shows a plasmid map for a regulated promoter expression system for a tricistronic transcript encoding hIL-12 and hIL-21.
Figure 8:
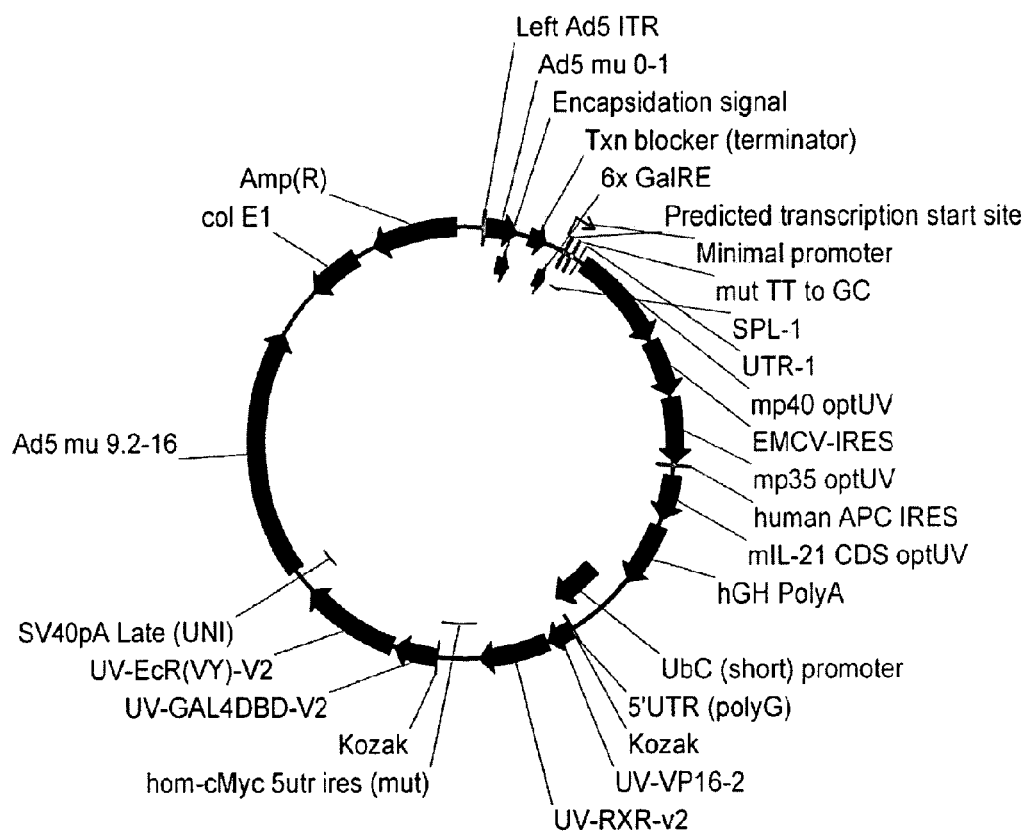
FIG. 8 shows a plasmid map for a regulated promoter expression system for a tricistronic transcript encoding mIL-12 and mIL-21.
Figure 9:
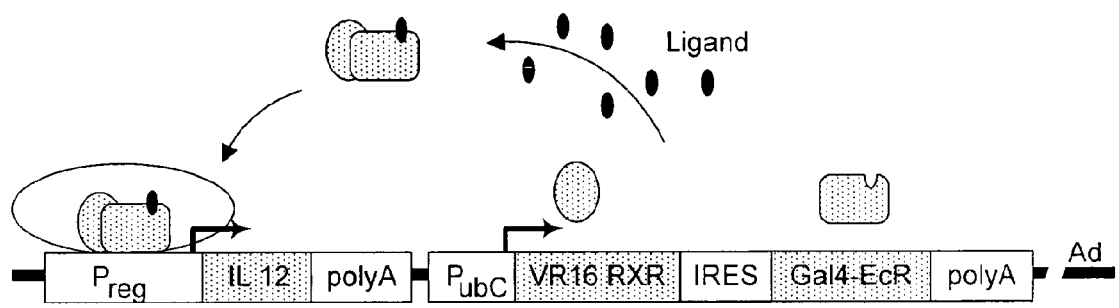
FIG. 9 shows the structure of the vector rAd.RheoIL12 in which the E1 and E3 regions have been deleted and the RheoSwitch® Therapeutic System (RTS)-IL-12 components replace the E1 region. The box labeled "IL12" represents the IL-12p40 and IL-12p35 coding sequences separated by IRES.

In another embodiment, dendritic cells are engineered to conditionally express IL-21 and IL-12. IL-21 and its receptor shares sequence homology with IL-2 and IL-15. IL-21 promotes the expansion and maturation of NK cells. The biologic effects of IL-21 potentially synergize with IL-12 as treatment of NK cells with IL-21 results in a significant upregulation of IL-12 receptor. In addition, IL-21 can enhance IL-12 signal transduction and cooperated for increased IFN-gamma production. See above for IL-12 polynucleotide sequences. The polynucleotide sequences of IL-21 are available under accession numbers AF254069 (human); NM_021782 (mouse); NM_001024835 (chicken); and NM_001108943 (rat). SEQ ID NOS: 6, 7, 8, 9, and 17 code for human and mouse IL-21. SEQ ID NOS: 1 and 2 are polynucleotide constructs that code for mouse and human IL-12 and IL-21. FIGS. 7 and 8 are plasmid maps for expression systems which may be used to express human and mouse IL-12 and IL-21, respectively.

In another embodiment, dendritic cells are engineered to conditionally express TNF-alpha and IL-12. TNF-alpha is a potent activator of immune cells and mediates antitumor properties. In addition, TNF-alpha can synergize with IL-12 for enhanced expression of IFN-gamma and IL-12 receptor on T cells. In an animal study, application of both IL-12 and TNF-alpha resulted in tumor infiltration by DN8+ T cells, significant IFN-gamma production, and subsequent tumor regression. See Sabel, 2003, 2004, 2007, Taniguchi, 1998, Lasek, 2000; and Xia et al 2008. See above for IL-12 polynucleotide sequences. The polynucleotide sequences coding for TNF-alpha are available from under accession numbers X02910 (human); NM_013693 (mouse); and BC107671 (rat).

In another embodiment, dendritic cells are engineered to conditionally express IL-7 and IL-12. IL-7 is a member of the IL-2 family and is important for T cell and B cell lymphopoiesis. IL-7 regulates the homeostasis of survival and proliferation of naïve and memory CD8+ T cells. IL-7 has been proved to enhance CTL generation against tumors. In addition, IL-12 acts directed on CD8+ T cells to enhance IL-7 mediated proliferation. Further, it has been reported that IL-7 and IL-12 synergistically enhance CD8+ T cell cytotoxicity. Mehrotra, 1995; Sharma et al 2003; Tirapu et al 2002. Thus, it is expected that IL-7 and IL-12 coexpression will provide more optimal antitumor responses. See above for polynucleotide sequences coding for IL-12. The polynucleotide sequences coding for IL-7 are available under accession numbers J04156 (human); NM_008371 (mouse); NM_001037833 (chicken); and NM_013110 (rat).

In another embodiment, dendritic cells are engineered to conditionally express GM-CSF and IL-12. GM-CSF regulates hematopoietic progenitor cell differentiation and proliferation, and plays a particularly important role in the maturation of professional antigen presenting cells (APC) such as dendritic cells. GM-CSF also enhances the capacity of dendritic cells to process and present antigens. GM-CSF functions differently than IL-12 and both elicit significant antitumor responses in animal studies. The combination of IL-12 (T cell activation) and GM-CSF (dendritic cell activation) is expected to result in more potent antitumor immunity. In animal studies, GM-CSF in combination with IL-12 treatment significantly suppressed tumor growth in multiple cancer models. Wang, 2001; Chang, 2007; Jean, 2004; Nair, 2006; Hill 2002; Small et al 2007. In human trials, GM-CSF+IL-12 were used successfully for treating myeloma patients, where the combined actions of both cytokines led to a reduction in circulating B cells. Rasmussen, 2003; Hansson, 2007; Abdalla, 2007. It is expected that coexpression of GM-CSF and IL-12 in a single cell will avoid unwanted systemic effects such as reductions in circulating B cells. See above for polynucleotide sequences coding for IL-12. The polynucleotide sequences of GM-CSF are available under accession numbers M11734 (human); NM_009969 (mouse); EU520303 (chicken); NM_001037660 (rat Csf2ra); and NM_133555 (rat Csf2rb).

In another embodiment, dendritic cells are engineered to conditionally express a chemokine (e.g., CCL3 (MIP-1a), CCL5 (RANTES), CCL7 (MCP3), XCL1 (lymphotactin), CCL19 (MIP-3b), CXCL9 (MIG), CXCL10 (IP-10), CXCL12 (SDF-1), or CCL21 (6Ckine)) and IL-12. Chemokines are chemoattractant cytokines that regulate the trafficking and activation of leukocytes and other cell types under a variety of inflammatory and noninflammatory conditions. Inflammatory cytokines control the recruitment of leukocytes in inflammation and tissue injury. Homeostatic chemokines fulfill housekeeping functions such as navigating leukocytes (e.g., dendritic cells) to and within secondary lymphoid organs as well as in bone marrow and the thymus during hematopoiesis. In animal studies, intratumoral co-injection of two separate adenoviruses expressing IL-12 and CXCL10 led to 100% regression of tumor nodules derived from the CT26 murine colorectal adenocarcinoma cell line. Narvaiza et al., 2000. Emtage et al., 1999, describe two double recombinant adenovirus vectors expressing either IL2 and XCL1 (lymphotactin) or IL-12 and XCL1. Intratumoral injection of the vectors breast adenocarcinoma tumors in mice elicited potent antitumor responses and gave rise to protective immunity. In other animal studies, co transduction of adenoviral vectors expressing IL-12 and CCL27 resulted in tumor regression and long term specific immunity. Gao et al., 2007. Thus, it is expected that the coexpression of a chemokine and IL-12 according to the invention will result in synergistic antitumor activity.

In another embodiment, dendritic cells are engineered to conditionally express an antiangiogenic cytokine (e.g., IP-10 and Mig) and IL-12. IP-10 and Mig are chemoattractants for T cells and NK cells and their ability to inhibit angiogenesis is dependent on NK cells. Animal studies have shown that combination therapy with two adenoviruses, one expressing IP10 and another expressing IL-12, resulted in marked antitumoral synergy. Narvaiza et al., 2000. In other studies, adenovirus vectors expressing IP10 or MIG and/or IL-12 were administered intratumorally in a murine model of mammary adenocarcinoma and fibrosarcoma. It was found that administration of IP-10 or MIG in combination with IL-12 resulted in considerable tumor regression and increased survival time of tumor-bearing animals as compared to IP10, MIG, IL-12 alone or control treated animals, with the IP-10, IL12 combination being most effective. Palmer, 2001. See also Mazzolini, 2003; and Huang 2004. Thus, it is expected that the coexpression of an antiangiogenic cytokine and IL-12 will result in synergistic antitumor activity.

To demonstrate an effective IL-12-mediated gene therapy, a conditional cDNA expression system is used that allows one to turn on an immunomodulator and/or IL-12 production by immune cells or TSC at various time points post-intratumoral injection. Based on the results in the aggressive B16 melanoma model in C57BL/6 mice, the following conclusions are made: 1) elevated levels of IL-12 are secreted from DC.RheoIL12 in the presence of the activating ligand RG-115830 but not in the absence of the ligand; 2) intratumoral DC.RheoIL12-based therapy is as effective as intratumoral DC.cIL12-based therapy as long as RG-115830 is administered to treated animals within 24 h of DC injection (and at later time points of ligand provision, RG-115830 therapy fails); 3) IL-12 expression in DC appears to prolong the survival of these cells in the tumor microenvironment and is associated with higher numbers of intratumorally-injected DC that migrate to tumor-draining lymph nodes; and 4) the strongest immune correlate to therapy outcome is the level of tumor-specific CD8$^+$ T cells cross-primed by the therapy and not the number of injected DC sustained in the tumor microenvironment. Overall, these data suggest that DC.IL12-based therapies likely succeed based on their positive influence on the afferent (cross-priming) of Type-1 CD8$^+$ T cell effectors and not on later efferent events, such as injected DC-mediated recruitment of anti-tumor T cells into the tumor microenvironment, etc.

Prior to intratumoral injection, the cells (immune cells or TSC) may be treated with a factor to stimulate the activity of the cells. For example, the cells may be treated with a co-stimulatory molecule such as positive co-stimulatory molecule including OX40L, 4-1BBL, CD40, CD40L, GITRL, CD70, LIGHT or ICOS-L or a negative co-stimulatory molecule such as anti-CTLA4, anti-PD-L1 or anti-PD-L2 antibodies. For example, the cells (e.g., immune cells or TSC) may be incubated with a cell expressing one or more co-stimulatory molecule, e.g., J588 lymphoma cells expressing CD40 ligand molecule. In another embodiment, the cells (immune cells or TSC) may be treated with a counter immune suppressant molecule (tolerance inhibitor) such as anti-TGF-beta antibodies (for inhibiting TGF signaling within the microenvironment), anti-IL10 antibodies, TGF-bRII DN (to inhibit TGF signaling within gene modified cells), IL-10R DN, dnFADD (to inhibit cell death pathways within the cells), anti-SOCS1 antibodies, siRNA or decoy (to inhibit suppressive cytokine signaling within the cells), or anti-TGFa antibodies.

The recombinant adenoviruses carrying the polynucleotide sequences shown in FIGS. 1-8 are produced. For example, hIL-21 is produced by cotransfection of the hIL-21 expression vector, linearized by restriction digestion at a site upstream of the left ITR, and the appropriate (example E3 deleted) adenoviral backbone in a permissive cell line such as HEK293 cells. The adenoviral vector carrying the murine immunomodulatory genes is used for transduction of murine dendritic cells or TSC for use in murine therapeutic models. For human therapeutic application, a polynucleotide encoding the human homologue of the immunomodulatory gene is inserted in the appropriate vector. The adenoviral vector for human therapeutic application is produced under GMP conditions. Example of a treatment outline (clinical trial) for stage III/IV melanoma patients is as follows: The treatment in this case involves an intratumoral injection of the adenoviral transduced dendritic cells and 14 daily oral administration of the activator drug (ligand). Subjects are screened 30 days to one week prior to the clinical trial. Each subject is asked to sign an informed consent before any procedures are initiated. The investigator will inform all subjects of the nature, aims, duration, potential hazards, and procedures to be performed during the trial and the possibility that their medical records may be reviewed by FDA. Subjects (a total of 16 to 20) are randomly grouped into 4 cohorts. All cohorts will receive an intratumoral injection of up to $5\times10^7$ transduced dendritic cells approximately 3 hours after the first dose of oral administration of the ligand. The 4 cohorts differ in the daily oral dose of ligand received: example cohort 1=0.01 mg/kg; cohort 2=0.3 mg/kg; cohort 3=1 mg/kg; cohort 4=3 mg/kg. During the course of the treatment, blood is drawn at specified time intervals for evaluation of single dose and steady state pharmacokinetics of the Activator Drug and its major metabolites. Also, blood is drawn at specified time points for the evaluation of humoral and cellular immune responses against the viral vector, RTS components and the tumor. Urine is collected and blood drawn at specific time points for serum chemistry, urinalysis, and hematology (safety profile). Tumor and/or draining lymph node biopsies are taken at specified time points to assess the transgene expression and the immune response to the tumor as a result of the therapy. Criteria for early termination are established for patients in case of adverse events, and the adverse events are recorded. The patients are followed up at 1, 2, 3 and 4 months for adverse events and therapeutic outcome.

In another embodiment, a subject in need of treatment of a tumor is (a) administered dendritic cells engineered to express an immunomodulator, for example, an immunomodulator disclosed herein, either consitutively or conditionally, and (b) a vector expressing an immunomodulator, for example, an immunomodulator disclosed herein, either constitutively or conditionally, is injected intratumorally to the subject. In a preferred embodiment, the dentritic cells are engineered to express an Ad-immunomodulator vector, and particularly the Ad-RTS-immunomodulator vector. In another preferred embodiment, the vector that is injected intratumorally to the subject is an Ad-immunomodulator vector, and particularly the Ad-RTS-immunomodulator vector.

In another embodiment, a subject in need of treatment of a tumor is (a) administered dendritic cells engineered to express IL-12, either consitutively or conditionally, and (b) a vector expressing IL-12, either constitutively or conditionally, is injected intratumorally to the subject. In a preferred embodiment, the dentritic cells are engineered to express an Ad-IL-12 vector, and particularly the Ad-RTS-IL-12 vector. In another preferred embodiment, the vector that is injected intratumorally to the subject is an Ad-IL-12 vector, and particularly the Ad-RTS-IL-12 vector.

In another embodiment, a subject in need of treatment of a tumor is (a) administered dendritic cells engineered to express IL-12, either consitutively or conditionally, and (b) the subject is administered one or more anticancer chemotherapeutic agents. In a preferred embodiment, the engineered dentritic cells are engineered to express an Ad-IL-12 vector, and particularly the Ad-RTS-IL-12 vector. The one or more anticancer chemotherapeutic agents can be administered prior to the engineered dendritic cells are administered, after the engineered dendritic cells are administered, or concurrently with the administration of the engineered dendritic cells. In a preferred embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express IL-12, either consitutively or conditionally, (b) a vector expressing IL-12, either constitutively or conditionally, is injected intratumorally to the subject, and (c) the subject is administered one or more anticancer chemotherapeutic agents. In a preferred embodiment, the dentritic cells are engineered to express an Ad-IL-12 vector, and particularly the Ad-RTS-IL-12 vector. In another preferred embodiment, the vector that is injected intratumorally to the subject is an Ad-IL-12 vector, and particularly the Ad-RTS-IL-12 vector. The one or more anticancer chemotherapeutic agents can be administered prior to the engineered dendritic cells and the vector expressing IL-12 are administered, after the engineered dendritic cells and vector expressing IL-12 are administered, or concurrently with the administration of the engineered dendritic cells and the vector expressing IL-12. In a preferred embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express an immunomodulator, for example, an immunomodulator disclosed herein, either consitutively or conditionally, and (b) a vector expressing an immunomodulator, for example, an immunomodulator disclosed herein, either constitutively or conditionally, is injected intratumorally to the subject. In a preferred embodiment, the dentritic cells are engineered to express an Ad-immunomodulator vector, and particularly the Ad-RTS-immunomodulator vector. In another preferred embodiment, the vector that is injected intratumorally to the subject is an Ad-IL-immunomodulator vector, and particularly the Ad-RTS-immunomodulator vector.

In another embodiment, a subject in need of treatment of a tumor is (a) administered dendritic cells engineered to express an immunomodulator, for example, an immunomodulator disclosed herein, either consitutively or conditionally, and (b) the subject is administered one or more anticancer chemotherapeutic agents. In a preferred embodiment, the engineered dentritic cells are engineered to express an Ad-immunomodulator vector, and particularly the Ad-RTS-immunomodulator vector. The one or more anticancer chemotherapeutic agents can be administered prior to the engineered dendritic cells are administered, after the engineered dendritic cells are administered, or concurrently with the administration of the engineered dendritic cells. In a preferred embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In another embodiment, a subject in need of treatment of a tumor is (a) administered dendritic cells engineered to express an immunomodulator, for example, an immunomodulator disclosed herein, either consitutively or conditionally, (b) a vector expressing an immunomodulator, for example, an immunomodulator disclosed herein, either constitutively or conditionally, is injected intratumorally to the subject, and (c) the subject is administered one or more anticancer chemotherapeutic agents. In a preferred embodiment, the dentritic cells are engineered to express an Ad-immunomodulator vector, and particularly the Ad-RTS-immunomodulator vector. In another preferred embodiment, the vector that is injected intratumorally to the subject is an Ad-immunomodulator vector, and particularly the Ad-RTS-immunomodulator vector. The one or more anticancer chemotherapeutic agents can be administered prior to the engineered dendritic cells and the vector expressing the immunomodulator are administered, after the engineered dendritic cells and vector expressing the immunomodulator are administered, or concurrently with the administration of the engineered dendritic cells and the vector expressing the immunomodulator. In a preferred embodiment, the anticancer chemotherapeutic is paclitaxel, a paclitaxel derivative or analog, temozolomide, a temozolomide derivative or analog, sunitinib, a sunitinib derivative or analog, gemcitabine, or a gemcitabine derivative or analog.

In any of the methods of the present invention, the disease or disorder may be a disease or disorder disclosed in the present application. In one embodiment, the disease or disorder is a disease or disorder listed in Table 1 herein. In another embodiment, the disease or disorder is a disease or disorder listed in Table 3 herein.

In any of the methods of the present invention, the cancer or tumor may be a disease or disorder disclosed in the present application. In one embodiment, the cancer or tumor is a cancer or tumor listed in Table 1 herein. In another embodiment, the cancer or tumor is a cancer or tumor listed in Table 3 herein.

It is possible to measure the effect of an immunomodulator and/or IL-12 expression on a population of cells by measuring the level of expression or activity of the Th1/Tc1 type cytokine, IFN-gamma in a biological sample from a patient.

For the purposes of the invention, the invention provides a method for determining the efficacy of an in vitro engineered immune- or TSC-based therapeutic regimen in a cancer patient, comprising:

a. measuring the level of expression or the level of activity or both of interferon-gamma (IFN-gamma) in a first biological sample obtained from a human patient before administration of in vitro engineered cells, e.g., immune cells or TSC, thereby generating a control level;

b. administering intratumorally to said patient the in vitro engineered cells;

c. administering to said patient an effective amount of activating ligand;

d. measuring the level of expression or the level of activity or both of IFN-gamma in a second biological sample obtained from said patient at a time following administration of said activating ligand, thereby generating data for a test level; and e. comparing the control level to the test level of IFN-gamma, wherein data showing an increase in the level of expression, activity, or both of IFN-gamma in the test level relative to the control level indicates that the therapeutic treatment regimen is effective in said patient. The invention may also optionally comprise the additional steps of f. taking biopsy and counting tumor infiltrating lymphocytes (TIL) and/or g. observing tumor regression in response to the treatment.

The term "subject" means an intact insect, plant or animal. It is also anticipated that the ligands will work equally well when the subject is a fungus or yeast. Animals for use with the invention include, but are not limited to, vertebrates, e.g., mammals such as humans, rodents, monkeys, and other animals, with humans or mice being more preferred. Other animals include veterinary animals such as dogs, cats, horses, cattle, sheep, goats, pigs and the like.

Without wishing to be bound by theory, it is expected that the invention will support the use of intratumorally administered in vitro engineered immune- and TSC based gene therapy in the clinical setting, focusing on the objective clinical response as a primary study endpoint, and cross-primed anti-tumor CD8+ T cells (producing IFN-gamma) as a secondary study endpoint. The ability to turn the immunomodulator and/or IL-12 expression on and off in vivo adds an element of safety and therapeutic control to the treatment in that both the timing and level of protein expression may be controlled by the administration of ligand, and further that the timing of immunomodulator and/or IL-12 expression is expected to be critical to the therapeutic effectiveness of the method.

The invention further supports the therapeutic applications of in vitro engineered cells with conditionally expressed genes of interest as innovative approaches for the effective and efficient treatment of human diseases.

In the event of conflict between any teaching or suggestion of any reference cited herein and the specification, the latter shall prevail, for purposes of the invention.

All patents, patent applications and publications cited herein are fully incorporated by reference in their entireties.

It is to be understood that the foregoing described embodiments and exemplifications are not intended to be limiting in any respect to the scope of the invention, and that the claims presented herein are intended to encompass all embodiments and exemplifications whether or not explicitly presented herein.

U.S. application Ser. No. 12/247,738, entitled "Engineered Dendritic Cells And Uses For Treatment Of Cancer," filed Oct. 8, 2008, is hereby incorporated by reference in its entirety. U.S. application Ser. No. 12/241,018, entitled "Therapeutic Gene-Switch Constructs And Bioreactors For The Expression Of Biotherapeutic Molecules, And Uses Thereof," filed Sep. 29, 2008, is also hereby incorporated by reference in its entirety.

Example 1

A study is undertaken to determine the dose of dendritic cells and the most effective cytokine that is able to induce tumor-specific immune responses and antitumor activty in a Renca renal cell cancer tumor model Two tumor cell lines are used in this study: Renca and Renca-HA. The latter cell line is made by transfection of Renca cells with influenza virus hemagglutinin (HA). The advantage of Renca-HA model is the ability to trace antigen-specific T cells, since both CD8 and CD4 specific HA-derived epitopes are known and have been used.

Specific Aim—determine the induction of HA-specific immune responses after intratumoral administration of dendritic cells.

The Renca-HA tumor is established subcutaneously in BALB/c mice. When the tumor becomes palpable, dendritic cells are injected intratumorally. Dendritic cell administration is be repeated twice at 7-day intervals, for a total of 3 administrations.

The following groups of mice are used (each group includes 3 mice):
1. Untreated mice;
2. Mice treated with $5 \times 10^5$ dendritic cells transduced with control plasmid;
3. Mice treated with $10^6$ dendritic cells transuced with control plasmid;
4. Mice treated with $5 \times 10^6$ dendritic cells transduced with control plasmid;
5. The same as groups 2-4 using dendritic cells transduced with IL-12;
6. The same as groups 2-4 using dendritic cells transduced with IL-15; and
7. The same as groups 2-4 using dendritic cells transduced with IL-21.

To test the effect of combination of different cytokines, mice are treated simultaneously with:
8. $5 \times 10^5$ dendritic cells transduced with IL-12, and $5 \times 10^5$ dendritic cells transduced with IL-15,
9. $5 \times 10^5$ dendritic cells transduced with IL-12 and $5 \times 10^5$ dendritic cells transduced with IL-21, and
10. $5 \times 10^5$ dendritic cells transduced with IL-15 and $5 \times 10^5$ dendritic cells transduced with IL-21.

Four days after the last administration, lymph nodes of tumor-bearing mice are collected, and cells are stimulated with either MHC class I matched peptide (to detect CD8+ T cell responses) or MHC class II matched peptide (to detect CD4+ T cell responses).

The following assays are used:
1. ELISPOT IFN-γ and IL-2;
2. T-cell proliferation;
3. Detection of TNFα, IL-10, IL-4, and GM-CSF release by lymph node cells.

In addition, NK activity of lymph node cells is evaluated using YAC cells as targets.

In parallel, cells are stimulated with anti-CD3/CD28 antibodies to evaluate non-specific response of T cells.

The most effective dose of dendritic cells capable of inducing antigen-specific immune responses are determined.

Specific Aim 2—evaluate antitumor activity of dendritic cells transduced with cytokine genes.

Only those cytokine transduced dendritic cells that demonstrated statistically significant induction of immune responses are used in further experiments.

Treatment of Renca-HA tumor-bearing mice is performed as described in specific aim 1. One dose of DCs transduced with cytokines that shows specific activity in previous experiments is used. As a control, dendritic cells transduced with control adenovirus are used. To achieve statistical significance, each group includes 10 mice.

Tumor growth is evaluated. Renca-HA tumor contains an immunogeneic epitope that is useful for immunological monitoring and intitial testing of antitumor effect. However, to verify potential antitumor activity of the treatment non-transfected tumor cells needs to be used. Therefore, the experiments described above are repeated using the Renca tumor model.

Example 2

The safety, tolerance, transgene function, and immunological effects of intratumoral injection(s) of adenoviral transduced autologous dendritic cells engineered to express hIL-12 and one or more other immunodulators under control of the RTS, in subjects with stage III and IV melanoma will be evaluated through procedures such as those described below.

A study involving study subjects with stage III and IV melanoma will be conducted in 4 cohorts (groups) of subjects each subject receiving a single intratumoral injection (into a melanoma tumor) of adenoviral transduced autologous (reinserted into the same subject that they came from) dendritic cells (DCs) engineered to express human interleukin-12 (hIL-12), and one or more other immunodulators, at a dose of $5 \times 10^7$ in combination with daily oral doses of activator drug (activating ligand). The study will use injections of dendritic cells transduced ex vivo (after the cells are removed from the subjects) with adenoviral vector for inducible expression of human IL-12 and one or more other immunodulators. The production off IL-12 and the one or more or other immunomodulators is "turned on" (induced) from the injected DCs through the activation of the RTS by the oral administration of the activator drug (RG-115932). Safety and tolerance will be assessed through physical examinations (including ECOG performance status), vital signs measurements, serum chemistry, urinalysis, hematology, adverse events "side-effects", and antibodies and cellular immune response to the adenovirus, components of RTS, and the Activator Drug. To evaluate progress, single dose and steady-state pharmacokinetics/ADME of oral Activator Drug and its major metabolites, analysis of hIL-12 levels, other immunomodulator levels, and cellular immune response (T cells) in biopsies of the target tumors, draining lymph nodes, and peripheral circulation, as well as a serum cytokine profile will be measured.

For instance, 16 subjects with stage III and IV melanoma are divided into four cohorts with cohorts 1 and 2 containing three subjects and cohorts 3 and 4 containing 5 subjects. All subjects will receive a single intratumoral injection of $5 \times 10^7$ autologous DC transduced with adenoviral vector encoding human IL-12 and one or more other immunodulators under the RTS control. For example, the subjects are administered an intratumoral injection of autologous DC transduced with adenoviral vector encoding human IL-12 under the RTS control and an immunomodulator such as IL-15 or IL-21.

The subjects will receive a single daily oral dose of activator drug (cohort 1: 0.01 mg/kg, cohort 2: 0.1 mg/kg, cohort 3: 1.0 mg/kg or cohort 4: 3 mg/kg) the first dose starting approximately 3 hours prior to the DC injection on day 1 and continuing for 13 more consecutive days. Additional injection(s) of adenovirally transduced autologous dendritic cells in combination with 14 single (once) daily oral doses of activator drug may be administered to eligible subjects who meet the criteria for retreatment. Safety, tolerance, and dendritic cell function are assessed for all subjects in each group of cohort 1 for up to one month after injection of the in vitro engineered dendritic cells before enrolling subjects to receive the next highest dose of the activator drug. The safety assessment will continue in all subjects for 3 months after the initial injection of the engineered dendritic cells with the possibility of extending the follow-up period to a total of six months to monitor subject safety if toxicity is observed or the subject receives additional injection(s) of the dendritic cells.

Such a study demonstrates the safety and tolerance of a single or multiple intratumoral injection(s) of adenoviral transduced autologous dendritic cells in combination with an oral activator drug in subjects with melanoma. The study provides steady-state pharmacokinetics/ADME of the oral activator drug. The study demonstrates functionality of the RTS in subjects by measuring hIL-12 expression and the expression of the one or more other immunomodulators of adenovirus transduced autologous dendritic cells in target tumor and/or draining lymph nodes in response to the activation of the RTS by the oral administration of the activator drug. Furthermore, the study demonstrates the immunological effects of the adenoviral transduced autologous dendritic cells in terms of the cellular immune response in the target tumor, draining lymph nodes, and peripheral circulation following oral administration of the activator drug.

Melanoma is selected as an exemplary cancer. Melanoma in particular among solid tumors has been shown to respond to immunotherapy approaches, and melanoma tumors are readily accessible for intratumoral injection and biopsy. The subjects included in the study have unresectable stage III or IV melanoma, which has at least 0.5 cm in diameter, any tumor thickness, any number of lymph node involvement, in-transit metastases, or distant metastases.

Preparation of Adenovirus Harboring the RheoSwitch Therapeutic System, hIL-12 and One or More Other Immunomodulatiors The recombinant DNA is transferred to dendritic cells (DC) by ex vivo adenoviral vector transduction. The recombinant DNA is used to express human IL-12(p70) and one or more other immunomodulators from intratumorally injected immature dendritic cells which confers survival and stimulates maturation of DC in the tumor environment resulting in their subsequent migration to the draining lymph nodes. This leads to a bias toward the differentiation of T helper cells to Th1 type and also activation of tumor-specific cytotoxic T cells by cross priming with the tumor antigens.

The recombinant DNA used as the recombinant adenoviral vector allows the expression of human IL-12 and one or more other immunodulators under the control of the RheoSwitch® Therapeutic System (RTS). The RTS comprises a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect Choristoneura fumiferana. In another embodiment, the RTS consists of a bicistronic message expressed from the human Ubiquitin C promoter and codes for two fusion proteins: Gal4-EcR and VP16-RXR. Gal4-EcR is a fusion between the DNA binding domain (amino acids 1-147) of yeast Gal4 and the DEF domains of the ecdysone receptor from the insect Choristoneura fumiferana. VP16-RXR is a fusion between the transcription activation domain of HSV-VP16 and the EF domains of a chimeric RXR derived from human and locust sequences. These Gal4-EcR and VP16-RXR sequences are separated by an internal ribosome entry site (IRES) from EMCV. These two fusion proteins dimerize when Gal4-EcR binds to a small molecule drug (RG-115932) and activate transcription of hIL-12 and one or more other immunodulators from a Gal4-responsive promoter that contains six Gal4-binding sites and a synthetic minimal promoter. The RTS transcription unit described above is placed downstream of the hIL-12 and one or more other immunodulators transcription units. This whole RTS-hIL12-immunomodualtor cassette is incorporated into the adenovirus 5 genome at the site where the E1 region has been deleted. The adenoviral backbone also lacks the E3 gene. A map for the adenoviral vector Ad-RTS-hIL-12 is shown in FIG. 8 of US 2009/0123441 A1.

The recombinant adenoviral vector used in this study contains the following exemplary regulatory elements in addition to the viral vector sequences: Human Ubiquitin C promoter, Internal ribosome entry site derived from EMCV, an inducible promoter containing 6 copies of Gal4-binding site, 3 copies of SP-1 binding sites, and a synthetic minimal promoter sequence, SV40 polyadenylation sites, and a transcription termination sequence derived from human alpha-globin gene. It should be understood that other regulatory elements could be utilized as alternatives.

An exemplary recombinant adenoviral vector Ad-RTS-hIL-12-immunomodulator(s) is produced in the following manner. The coding sequences for the receptor fusion proteins, VP16-RXR and Gal4-EcR separated by the EMCV-IRES (internal ribosome entry site), are inserted into the adenoviral shuttle vector under the control of the human ubiquitin C promoter (constitutive promoter). Subsequently, the coding sequences for the p40 and p35 subunits of hIL-12 separated by IRES, and one or more other immunomodulators, is placed under the control of a synthetic inducible promoter containing 6 copies of Gal4-binding site are inserted upstream of the ubiquitin C promoter and the receptor sequences. The shuttle vector contains the adenovirus serotype 5 sequences from the left end to map unit 16 (mu16), from which the E1 sequences are deleted and replaced by the RTS, IL-12 and one or more other immunomodulator sequences (RTS-hIL-12). The shuttle vector carrying the RTS-hIL-12-immunodulator(s) is tested by transient transfection in HT-1080 cells for Activator Drug-dependent IL-12 and other immunomodulator(s) expression. The shuttle vector is then recombined with the adenoviral backbone by cotransfection into HEK 293 cells to obtain recombinant adenovirus Ad-RTS-hIL-12-immunomodulator(s). The adenoviral backbone contains sequence deletions of mu 0 to 9.2 at the left end of the genome and the E3 gene. The shuttle vector and the adenoviral backbone contain the overlapping sequence from mu 9.2 to mu 16 that allows the recombination between them and production of the recombinant adenoviral vector. Since the recombinant adenoviral vector is deficient in the E1 and E3 regions, the virus is replication-deficient in normal mammalian cells. However, the virus can replicate in HEK 293 cells that harbor the adenovirus-5 E1 region and hence provide the E1 function in trans.

An exemplary recombinant adenoviral vector is produced in the following manner: The linearized shuttle vector carrying the DNA elements for inducible expression of human IL12 and one or more other immunomodulators, and the adenoviral backbone are co-transfected into HEK293 cells. Recombination between the overlapping sequences on the shuttle vector and the viral backbone results in the production of recombinant adenovirus and is packaged into viral particles in the HEK293 cells. The HEK293 cells are grown in DMEM containing fetal bovine serum.

The virus used for the proposed study was purified by CsCl density gradient centrifugation. The recombinant adenovirus undergoes two rounds of plaque purification and the resulting seed stock is used to produce a master viral bank (MVB) by amplification in HEK293 cells from a fully characterized master cell bank. The MVB undergoes extensive cGMP/GLP release tests including replication competent adenovirus (RCA), sterility, mycoplasma, adventitious viruses, retrovirus, human viruses HIV1/2, HTLV1/2, HAV, HBV, HCV, EBV, B19, CMV, HHV-6, 7 and 8, bovine and porcine virus, complete vector sequencing and functional testing by AD-induced expression of IL-12 and one or more other immunomodulators in human cell lines.

The virus from MVB may be used for production of the purified virus in a cGMP facility and may again undergo release tests including identity, RCA, sterility, mycoplasma, adventitious viruses, viral particle-to-infectious units ratio, contamination of host cell DNA, endotoxin and proteins and functional testing by AD-induced expression of IL-12 and one or more other immunomodulators in human cell lines.

Transduction of Autologous Dendritic Cells by Adenovirus Containing hIL-12 Transgene And One or More Other Immunodulators and RheoSwitch® Therapeutic System (RTS)

Dendritic cells derived from the human subjects are transduced ex vivo and injected into the tumor. The DC will be characterized before viral transduction for viability, purity (typically >80% cells showing DC phenotype), sterility, mycoplasma and endotoxin. After viral transduction, the cells are washed repeatedly to remove any unabsorbed virus. Supernatant from the last wash will be tested for the content of residual virus by PCR. Since the DCs are transduced ex vivo by adenoviral vector (non-integrating virus) and the life span of DCs after intratumoral injection and the subsequent migration to draining lymph nodes is short, it is not expected that the viral DNA will be incorporated into any non-target cells. The protocol used for adenoviral transduction of DCs is expected to yield 80-90% transduction and is considered very efficient.

Harvesting of PBMC by leukapheresis: Subjects undergo a standard 90 to 120 minutes leukapheresis at the Apheresis Unit of the UPCI Outpatient. The leukapheresis procedure involves the removal of blood from a vein in one arm; the passage of blood through a centrifuge (cell separator), where its components are separated and one or more components are removed; and the return of the remaining components to the subject's vein in the same or other arm. No more than 15% of the subject's total blood volume is withdrawn at any one time as blood is processed through the cell separator device. In the cell separator, blood is separated into plasma, platelets, white cells and red blood cells. White blood cells (WBC) are removed and all the other components are returned into the subject's circulation. Every attempt is made to use two peripheral IV lines for this procedure. If that is not possible, a central line may be necessary. The subject has to be cleared by physician to undergo leukapheresis, and is routinely screened for vital signs (including blood pressure) prior to the procedure.

Processing: After collection, the leukapack is delivered by hand to the CPL, and is immediately processed by centrifugal elutriation in ELUTRA™. This is a closed system validated for clinical use. The monocyte fraction is recovered, and after the recovery and viability of cells are established, they are transferred to an Aastrom cartridge for 6-day culture in the presence of IL-4 and GM-CSF. All processing and washing procedures are performed under sterile conditions.

Initial plating: Monocytes recovered from a single leukapack are counted in the presence of a trypan blue dye to determine the number of viable cells. Monocytes are evaluated for purity by flow cytometry. Monocytes are resuspended at 5 to $10 \times 10^6$ cells/mL in serum-free and antibiotic-free CellGenix medium, containing 1,000 IU/mL of IL-4 and 1,000 IU/mL of GM-CSF per SOP-CPL-0166, and placed in an Aastrom cartridge. A minimum loading volume of 50 ml and a minimum cell number are required for cassette inoculation.

Culture: The Aastrom cartridge is placed in the incubator in the Replicell System, a fully closed, cGMP-compatible automated culture device for immature DC generation.

Immature DC harvest: On day 6, the Aastrom cartridge is removed from the incubator and immature DCs are harvested. The cells are recovered by centrifugation at 1,500 rpm, washed in CellGenix medium, counted in the presence of a trypan blue dye and checked for morphologic and phenotypic characteristics.

Viability: This is determined by performing hemocytometer cell counts in the presence of trypan blue. Generally, >95% of harvested cells are viable, i.e., exclude a trypan blue dye. If viability is less than 70% the immature DCs will be discarded.

Phenotyping: The cells generated in culture are counted by microscopic observation on a hemocytometer, and a preliminary differential count (DC vs. lymphocytes) is obtained using a trypan blue dye. Confirmation of the differential count is made by flow cytometry, gating on DC vs. lymphocytes and using high forward and side scatter properties of immature DC as the criterion for their identification. Immature DCs routinely contain >80% of cells with dendritic cell morphology and have DC phenotype.

IL-12p70 potency assay: It has been established that mature DCs (mDCs) have the ability to produce IL-12p70 spontaneously or upon activation with CD40L with or without addition of innate immunity signals (e.g., LPS). A standardized IL-12p70 production assay was recently established and is applicable to small samples or large lots of DC vaccines generated under a variety of conditions. The current potency assay consists of two distinct steps, the first involving co-incubation of responder DCs with J588 lymphoma cells stably transfected with the human CD40 ligand gene as stimulators. The second step involves testing of supernatants from these co-cultures for levels of IL-12p70 secreted by DCs stimulated with J558/CD40L+/−LPS in the Luminex system. This potency assay has an inter-assay CV of 18.5% (n=30) and a broad dynamic range, which facilitates evaluation of various DC products characterized by vastly different levels of IL-12p70 production. The normal range for the assay established using DC products generated from monocytes of 13 normal donors was 8-999 pg/mL, with a mean of 270 pg/mL Production and Release Criteria for Dendritic Cells Each lot of the in vitro generated dendritic cells is tested for the presence of microbial contaminants (aerobic and anaerobic bacteria, fungi and mycoplasma), as well as endotoxin and are phenotypically and functionally characterized. All dendritic cells to be injected into subjects will be fresh and will not undergo croypreservation.

Quality assurance testing of DC: DC generated as described above are evaluated for sterility, viability, purity, potency and stability. Criteria for release of the cellular product are established and rigorously followed.

Viability: The cells generated in culture are counted by microscopic observation on a hemacytometer, and a differential count (DC vs. lymphocytes) is obtained using a trypan blue dye. This count provides the percentage of viable cells in the tested culture. More than 70% cell viability by trypan blue exclusion and minimum 70% cells expressing HLA-DR and CD86 as the monocyte-derived DC markers are required for passing the release criteria. Additional markers may be included for exploratory analysis such as CD83 and CCR7 for assessing the DC maturation status, and CD3 and CD19 to assess the lymphocytes contamination.

Purity: Two-color flow cytometry analysis of cells stained with FITC- and PE-conjugated mAbs is used to determine that the DC population identified morphologicallly expresses the surface antigens defined for DC and lack the monocyte and T and B cell lineage antigens. For vaccine preparation, the DC generated must express HLA-DR and CD86 and must not express CD3, CD19, or CD14. To be considered as mDC, the cells must express CD83+ and CCR7+.

Potency: To define a measure of potency for the DC, we determine their ability to produce IL-12p70 as described above.

Sterility: DC are tested by bacterial (Aerobic and anaerobic) and fungal cultures using the BD Bactec system (Becton Dickinson Co., Sparks, Md.) at the University of Pittsburgh Medical Center Microbiology Laboratory. Final results of the microbial cultures are available in 14 days. Prior to release of the DC for vaccine use, a gram stain is performed and must be negative for the presence of microorganisms.

The IMCPL tests for mycoplasma by the use of the Gen-Probe Mycoplasma Tissue Culture Rapid Detection System (Gen-Probe, Inc. San Diego, Calif.), which is based on nucleic acid hybridization technology. Endotoxin testing is performed using the Limulus Amoebocyte Lysate Pyrogen Plus assay (Bio Whittaker, Inc., Walkerville, Md.). Endotoxin testing is performed on the cell culture at the time of harvest and prior to release of the final product. The acceptable endotoxin level is <5EU/kg body weight. Untransduced and transduced dendritic cells will be cryopreserved for future analysis.

It is expected that all the transduced cells will express the transgene. More than 80% of the DCs are expected to be transduced. The product will be biologically active since the native coding sequence is maintained in the transgene. The viral-transduced DCs injected into the tumor are of immature DC phenotype and do not express IL-12 and one or more other immunomodulators until they undergo maturation, and hence at this stage, the expression of IL-12 and one or more other immunomodulators is mostly from the transgene. Since the expression of the IL-12 and one or more other immunomodulators transgene is induced by the small molecule activator drug RG-115932 in a dose dependent way, one can control the level of transgene expression in the transduced DCs to the desired levels. A small portion of the transduced DCs prepared for administration to the human subjects may be tested in vitro for the activator drug-dependent induction of expression of IL12 and one or more other immunomodulators. Expression of IL-12 and one or more other immunomodulators may be assayed by ELISA with a sensitivity of 4 ng/ml.

It is expected that in vitro induction of IL-12 and one or more other immunomodulators from cells transduced by the vector used in the proposed study yields about 500 ng IL-12 and one or more other immunomodulators per $10^6$ cells in 24 hours, determined by ELISA. In preclinical studies using mouse model of melanoma, intratumoral injection of $10^6$ or more transduced DCs show efficacy. However, it is expected that the required intratumoral injection may show efficacy at levels below this amount and therefore injections of $5 \times 10^7$ transduced DCs may be utilized as a starting point to determine if less or greater amounts are required.

For instance, in vitro, human and mouse cell lines and primary dendritic cells transduced with recombinant adenoviral vector carrying the genes for IL12 and one or more other immunomodulators show induction of IL12 expression in response to the activator drug in a dose dependent way.

6.3. Formulation of Activator Drug

The activator drug used herein is formulated in any one of the following formulations:
(1) 100% Labrasol;
(2) Listerine flavored Labrasol (Latitude Pharmaceuticals Inc., USA) comprising (a) menthol, (b) thymol, (c) eucalyptol, (d) aspartame, (e) sodium saccharine, (f) citric acid, (g) peppermint flavor, (h) cream flavor, (i) labrasol;
(3) Miglyol 812 and phospholipon 90G (Latitude Pharmaceuticals Inc., USA); or
(4) Miglyol 812, phospholipon 90G and Vitamin E tocopheryl polyethylene glycol succinate (Latitude Pharmaceuticals Inc., USA).

Delivery

While a variety of concentrations and specific protocols may be imagined, one example for treating patients would include patients receiving intratumoral injection(s) of transduced autologous dendritic cells (AdDCs) at a concentration of $5 \times 10^7$ suspended in sterile saline engineered to express hIL-12 (human interleukin 12) and one or more other immunodulators under control of the RTS, in combination with the oral activator drug (RG-115932).

Initial Treatment

Day 1 Inpatient Visit: On day 1, a baseline physical examination (including vital signs, weight, and ECOG status) is performed. Urine is collected and blood drawn for baseline serum chemistry, urinanalysis, and hematology (safety profile). Approximately 3 hours before the intratumoral injection of the in vitro engineered dendritic cells, each subject is dosed with an activator drug (cohort 1-0.01 mg/kg, 0.3 mg/kg, 1.0 mg/kg, and 3 mg/kg) immediately after a meal. Blood is drawn at specified time intervals (predose, 0.5, 1, 1.5, 2, 4, 6, 8, 12, 16, and 24 hours after the AD dose) on day 1 for evaluation of single dose pharmacokinetics of the activator drug and its major metabolites. Each subject receives a single intratumoral injection of adenoviral transduced autologous dendritic cells at a concentration of $5 \times 10^7$ cells, engineered to express hIL-12 and one or more other immunomodulators under the control of the RTS. The subjects are carefully monitored for local injection site reactions and/or hypersensitivity reactions. Day 2 through 14 Inpatient Visit: On days 2 through 14, each subject is dosed with the activator drug immediately after a meal. Vital signs and adverse events are collected daily on days 2 through 14. On day 4±24 hours, biopsies of the tumor and/or draining lymph nodes are removed from approximately 50% of the subjects for measurement of hIL-12 and cellular immune response. On day 8, weight is measured. On day 8±24 hours, biopsies of the tumor and/or draining lymph nodes are removed from subjects who did not have a biopsy performed on day 4 for measurement of hIL-12 and one or more other immunomodulators and cellular immune response. Blood is drawn on day 4±24 hours and day 8±24 hours for assay of potential antibodies and cellular immune response against the adenovirus and/or the RTS components. A serum cytokine profile is also obtained to determine if the expression of other cytokines is affected by treatment with the hIL-12 and one or more other immunomodulators transgene. On day 8, urine is collected and blood is drawn for baseline serum chemistry, urine analysis, and hematology (safety profile). On Day 8, blood is drawn at specified time intervals (predose, 0.5, 1, 2, 4, 6, 8, 12, 16, and 24 hours after the AD dose) for evaluation of steady-state pharmacokinetics/ADME of the activator drug and its major metabolites.

Day 14 Inpatient Visit: On day 14, each subject is dosed with the Activator Drug immediately after a meal. Each subject receives a physical examination (including vital signs, height, weight and ECOG status). Urine is collected and blood is drawn for serum chemistry, urinalysis, and hematology (safety profile). Blood is drawn on day 14±24 hours for assay of potential antibodies and cellular immune response against the adenovirus and/or the RTS components. A serum cytokine profile is also obtained to determine if the expression of other cytokines is affected.

Blood is collected from the subjects at specified inpatient and outpatient visits to measure potential antibodies and cellular immune response to the adenovirus and components of the RTS. Blood is obtained for a baseline serum cytokine profile. The AdVeGFP infectivity blocking type assay is used to detect an antibody response to the adenoviral vector (Gambotto, Robins et al. 2004). Antibody response to the RTS components will be assessed by western blot and/or ELISA using serum from the patient and the RTS proteins produced from an expression vector. In addition, multiplex cytokine testing will be done in the serum by Luminex for IL-12, IFN-gamma, IP-10, and other Th1/Th2 cytokines such as IL-2, TNF-alpha, IL-4, IL-5, and IL-10. These antibody and cytokine assays will need about 10 ml of blood.

Potential Antibody and Cellular Immune Response to Adenovirus and/or Components of the RTS: Blood will be collected from the subjects at specified inpatient and outpatient visits to evaluate the potential antibody and cellular immune response to the adenovirus and components of the RTS and tumor antigens. The AdVeGFP infectivity blocking type assay will be used to detect an antibody response to the adenoviral vector (Nwanegbo, et al. 2004). Antibody response to the RTS components will be assessed by western blot and/or ELISA using serum from the subjects and the RTS proteins produced from an expression vector. In addition, multiplex cytokine testing will be done in the serum by Luminex for IL-12, IFN-gamma, IP-10, and other Th1/Th2 cytokines such as IL-2, TNFa, IL-4, IL-5 and IL-10. These antibody and cytokine assays will need about 10 ml of blood.

The cellular immune response assays use about 50-60 ml blood and CD4 and CD8 T cell subsets will be separated from it. The separated T cells will be mixed with autologous DCs transduced with empty AdV vector, AdV-RTS, or AdV-RTS-hIL12-immunomodulator(s) vectors in an ELISPOT assay for IFN-gamma production by the T cells activated by the AdV- and RTS-derived antigens, if any. Similar assays will be performed using the tumor cells as such and/or DCs expressing shared melanoma antigens to assess the early immune response to the tumor. Additional assays may also be performed as necessary.

PREGNANCY TESTING: Females of childbearing potential is administered a urine pregnancy test at the screening visit and before the first inpatient visit of the retreatment phase. The testing is performed at least 72, 48, 24, or 12 hours prior to the administration of Activator Drug during both the initial treatment and all retreatment periods. If the urine pregnancy test is positive, then confirmation will be obtained with a serum pregnancy test. If pregnancy is confirmed, the subject will not be allowed to enter the trial or continue into the retreatment phase. The pregnancy testing may be reperformed as many times as necessary.

CONCOMITANT MEDICATION INQUIRY: At screening, and before the first inpatient visit of the retreatment phase, each subject will be asked to provide a list of concurrent medications to determine any possible relationship to adverse events that occur during the trial and follow-up phase.

RETREATMENT CRITERIA: If a subject has tolerated prior AdDC inoculation without adverse reactions that are limiting, and has shown no progression of disease or symptomatic decline at the time of potential retreatment, they will be considered for retreatment. If, in the opinion of the principal investigator, and treating physician there is a potential clinical benefit for additional intratumoral injection(s) of AdDCs in combination with Activator Drug (maximum tolerated dose from cohort 1) for 14 consecutive days, retreatment will be offered to the subject, provided the following criteria are met:
1. There have been no limiting toxicities,
2. The subject's disease is stable or showing clinical or subjective signs of improvement, and
3. There is no evidence of antibody or cellular immune response to adenovirus components of RheoSwitch® Therapeutic System.

Assessment of Transgene Function and Immunological Effects: Punch or Excisional Biopsies of the Tumor and Associated Draining Lymph nodes will be collected during screening (day −12 to day −7), day 4, day 8 and day 14 of the trial and at month 1 of the follow-up (see Tables 3-5) for in vivo assessment of transgene expression of hIL-12 and one or more other immunomodulators, and cellular immune response. Fine needle aspiration biopsies of the tumor and associated draining lymph nodes will be collected on day −12 to −7 and day 14 of the retreatment period for in vivo assessment of transgene expression of hIL-12 and one or more other immunomodulators, and cellular immune response. Biopsies will be evaluated by standard light microscopy and immunohistochemistry to assess cellular infiltration of T cells into the tumor and draining lymph nodes. Biopsy sections will be read by a pathologist unaware of study subject background. To distinguish between endogenous and induced IL-12 expression by DCs in the tumor and draining lymph nodes, RT-PCR on RNA will be used with appropriately designed primers. Blood will be drawn for a serum cytokine profile at screening, day 4, day 8 and day 14 of the trial, at month 1 of the follow-up and on day −12 to −7, day 8 and day 14 of the retreatment period (see Tables 3-5). A serum cytokine profile will be obtained to determine if the expression of other cytokines is affected by treatment with the hIL-12 transgene. Multiplex cytokine testing will be done in the serum by Luminex for IL-12, IFN-gamma, IP-10, and other Th1/Th2 cytokines such as IL-2, TNFa, IL-4, IL-5 and IL-10. These antibody and cytokine assays will need about 10 ml of blood.

Single Dose and Steady-State Pharmacokinetics of Activator Drug: Blood Will be Drawn at Specified Time Intervals (Predose, 0.5, 1, 1.5, 2, 4, 6, 8, 12, 16, and 24 hours after the morning dose) on day 1 of the trial for evaluation of single dose pharmacokinetics and on day 8 of the trial for measurement of steady state pharmacokinetics/ADME of the Activator Drug and its major metabolites. Plasma will be evaluated by HPLC to obtain the following steady-state pharmacokinetic endpoints of the Activator Drug and major metabolites: Cmax (maximum observed plasma concentration), Tmax (time to maximum observed plasma concentration), Ctrough (minimum observed plasma concentration computed as the average of the concentrations at 0 and 24 hours), C24h (plasma concentration at 24 hours), AUC24h (area under plasma concentration-time curve from time 0 to 24 hours), Ke (apparent elimination rate), and T1⁄2 (apparent half-life).

It is to be understood that the foregoing described embodiments and exemplifications are not intended to be limiting in any respect to the scope of the invention, and that the claims presented herein are intended to encompass all embodiments and exemplifications whether or not explicitly presented herein.

LITERATURE

Abdalla, 2007.

Abdi K, Singh N, Matzinger P (2006). T-cell control of IL-12p75 production. *Scand J Immunol* 64: 83-92.

Adorini L (1999). Interleukin-12, a key cytokine in Th1-mediated autoimmune diseases. *Cell Mol Life Sci* 55: 1610-25.

Adorini L (2001). Interleukin 12 and autoimmune diabetes. *Nat Genet* 27: 131-2.

Adorini L, Gregori S, Harrison L C (2002). Understanding autoimmune diabetes: insights from mouse models. *Trends Mol Med* 8: 31-8.

Adorini L, Gregori S, Magram J, Trembleau S (1996). The role of IL-12 in the pathogenesis of Th1 cell-mediated autoimmune diseases. *Ann N Y Acad Sci* 795: 208-15.

Akhtar N, Padilla M L, Dickerson E B, Steinberg H, Breen M, Auerbach R et al (2004). Interleukin-12 inhibits tumor growth in a novel angiogenesis canine hemangiosarcoma xenograft model. *Neoplasia* 6: 106-16.

Akiyama Y, Watanabe M, Maruyama K, Ruscetti F W, Wiltrout R H, Yamaguchi K (2000). Enhancement of antitumor immunity against B16 melanoma tumor using genetically modified dendritic cells to produce cytokines. *Gene Ther* 7: 2113-21.

Al-Mohanna F, Saleh S, Parhar R S, Collison K (2002). IL-12-dependent nuclear factor-kappaB activation leads to de novo synthesis and release of IL-8 and TNF-alpha in human neutrophils. *J Leukoc Biol* 72: 995-1002.

Aliberti J C, Cardoso M A, Martins G A, Gazzinelli R T, Vieira L Q, Silva J S (1996). Interleukin-12 mediates resistance to *Trypanosoma cruzi* in mice and is produced by murine macrophages in response to live trypomastigotes. *Infect Immun* 64: 1961-7.

Allavena P, Paganin C, Zhou D, Bianchi G, Sozzani S, Mantovani A (1994). Interleukin-12 is chemotactic for natural killer cells and stimulates their interaction with vascular endothelium. *Blood* 84: 2261-8.

Alli R S, Khar A (2004). Interleukin-12 secreted by mature dendritic cells mediates activation of NK cell function. *FEBS Lett* 559: 71-6.

Alzona M, Jack H M, Simms P E, Ellis T M (1996). Interleukin-12 activates interferon-gamma production by targeted activation of CD30+ T cells. *Ann N Y Acad Sci* 795: 127-36.

Amemiya K, Meyers J L, Trevino S R, Chanh T C, Norris S L, Waag D M (2006). Interleukin-12 induces a Th1-like response to *Burkholderia mallei* and limited protection in BALB/c mice. *Vaccine* 24: 1413-20.

Araujo M I, Bliss S K, Suzuki Y, Alcaraz A, Denkers E Y, Pearce E J (2001). Interleukin-12 promotes pathologic liver changes and death in mice coinfected with *Schistosoma mansoni* and *Toxoplasma gondii*. *Infect Immun* 69: 1454-62.

Arulanandam B P, Van Cleave V H, Metzger D W (1999). IL-12 is a potent neonatal vaccine adjuvant. *Eur J Immunol* 29: 256-64.

Athie M V, Flotow H, Hilyard K L, Cantrell D A (2000). IL-12 selectively regulates STAT4 via phosphatidylinositol 3-kinase and Ras-independent signal transduction pathways. *Eur Immunol* 30: 1425-34.

Athie-Morales V, Smits H H, Cantrell D A, Hilkens C M (2004). Sustained IL-12 signaling is required for Th1 development. *J Immunol* 172: 61-9.

Atkins M B, Robertson M J, Gordon M, Lotze M T, DeCoste M, DuBois J S et al (1997). Phase I evaluation of intravenous recombinant human interleukin 12 in patients with advanced malignancies. *Clin Cancer Res* 3: 409-17.

Berard F, Blanco P, Davoust J, Neidhart-Berard E M, Nouri-Shirazi M, Taquet N et al (2000). Cross-priming of naive CD8 T cells against melanoma antigens using dendritic cells loaded with killed allogeneic melanoma cells. *J Exp Med* 192: 1535-44.

Bertagnolli M M, Lin B Y, Young D, Herrmann S H (1992). IL-12 augments antigen-dependent proliferation of activated T lymphocytes. *J Immunol* 149: 3778-83.

Bhardwaj N, Seder R A, Reddy A, Feldman M V (1996). IL-12 in conjunction with dendritic cells enhances antiviral CD8+ CTL responses in vitro. *J Clin Invest* 98: 715-22.

Biedermann T, Lametschwandtner G, Tangemann K, Kund J, Hinteregger S, Carballido-Perrig N et al (2006). IL-12 instructs skin homing of human Th2 cells. *J Immunol* 177: 3763-70.

Brunda M J, Gately M K (1994). Antitumor activity of interleukin-12. *Clin Immunol Immunopathol* 71: 253-5.

Buchanan J M, Vogel L A, Van Cleave V H, Metzger D W (1995). Interleukin 12 alters the isotype-restricted antibody response of mice to hen eggwhite lysozyme. *Int Immunol* 7: 1519-28.

Chang, 2007.

Coughlin, 1998.

Dietrich 2002.

Emtage et al., "Adenoviral Vectors Expressing Lymphotactin and Interleukin 2 or Lymphotactin and Interleukin 12 Synergize to Facilitate Tumor Regression in Murine Breast Cancer Models," *Hum. Gene Ther.* 10:697 (1999).

Faure F, Even J, Kourilsky P (1998). Tumor-specific immune response: current in vitro analyses may not reflect the in vivo immune status. *Crit Rev Immunol* 18: 77-86.

Gao et al., "Cotransduction of CCL27 gene can improve the efficacy and safety of IL-12 gene therapy for cancer," *Gene Ther.* 14:491-502 (2007)

Hansson, 2007.

Heinzerling L, Burg G, Dummer R, Maier T, Oberholzer P A, Schultz J et al (2005). Intratumoral injection of DNA encoding human interleukin 12 into patients with metastatic melanoma: clinical efficacy. *Hum Gene Ther* 16: 35-48.

Hill 2002.

Itoh T, Storkus W J, Gorelik E, Lotze M T (1994). Partial purification of murine tumor-associated peptide epitopes common to histologically distinct tumors, melanoma and sarcoma, that are presented by H-2 Kb molecules and recognized by CD8+ tumor-infiltrating lymphocytes. *J Immunol* 153: 1202-15.

Jean, 2004.

Kang W K, Park C, Yoon H L, Kim W S, Yoon S S, Lee M H et al (2001). Interleukin 12 gene therapy of cancer by peritumoral injection of transduced autologous fibroblasts: outcome of a phase I study. *Hum Gene Ther* 12: 671-84.

Koka, 2004.

Koyama, 1997

Lasek, 2000.

Mehrotra, 1995.

Narvaiza et al., "Intratumoral coinjection of two adenoviruses, one encoding the chemokine IFN-gamma-inducible protein-10 and another encoding IL-12, results in marked antitumoral synergy," *J. Immunol.* 164:3112 (2000).

Nair, 2006.

Narvaiza et al., Intratumoral Coinjection of Two Adenoviruses, One Encoding the Chemokine IFN-γ-Inducible Protein-10 and Another Encoding IL-12, Results in Marked Antitumoral Synergy," *J. Immunol.* 164:3112-3122 (2000).

Palmer et al., "Combined CXC chemokine and interleukin-12 gene transfer enhances antitumor activity," *Gene Ther.* 8:282-290 (2001).

Rasmussen, 2003.

Romani L, Puccetti P, Bistoni F (1997). Interleukin-12 in infectious diseases. *Clin Microbiol Rev* 10: 611-36.

Rothe H, Burkart V, Faust A, Kolb H (1996). Interleukin-12 gene expression mediates the accelerating effect of cyclophosphamide in autoimmune disease. *Ann N Y Acad Sci* 795: 397-9.

Sabel, 2003, 2004, 2007.

Sangro B, Mazzolini G, Ruiz J, Herraiz M, Quiroga J, Herrero I et al (2004). Phase I trial of intratumoral injection of an adenovirus encoding interleukin-12 for advanced digestive tumors. *J Clin Oncol* 22: 1389-97.

Sangro B, Melero I, Qian C, Prieto J (2005). Gene therapy of cancer based on interleukin 12. *Curr Gene Ther* 5: 573-81.

Satoh Y, Esche C, Gambotto A, Shurin G V, Yurkovetsky Z R, Robbins P D et al (2002). Local administration of IL-12-transfected dendritic cells induces antitumor immune responses to colon adenocarcinoma in the liver in mice. *J Exp Ther Oncol* 2: 337-49.

Satoskar A R, Rodig S, Telford S R, 3rd, Satoskar A A, Ghosh S K, von Lichtenberg F et al (2000). IL-12 gene-deficient C57BL/6 mice are susceptible to *Leishmania donovani* but have diminished hepatic immunopathology. *Eur J Immunol* 30: 834-9.

Schopf L R, Bliss J L, Lavigne L M, Chung C L, Wolf S F, Sypek J P (1999). Interleukin-12 is capable of generating an antigen-specific Th1-type response in the presence of an ongoing infection-driven Th2-type response. *Infect Immun* 67: 2166-71.

Subleski, 2006.

Svane I M, Boesen M, Engel A M (1999). The role of cytotoxic T-lymphocytes in the prevention and immune surveillance of tumors—lessons from normal and immunodeficient mice. *Med Oncol* 16: 223-38.

Taniguchi, 1998.

Tatsumi T, Huang J, Gooding W E, Gambotto A, Robbins P D, Vujanovic N L et al (2003). Intratumoral delivery of dendritic cells engineered to secrete both interleukin (IL)-12 and IL-18 effectively treats local and distant disease in association with broadly reactive Tc1-type immunity. *Cancer Res* 63: 6378-86.

Thomas G R, Chen Z, Enamorado I, Bancroft C, Van Waes C (2000). IL-12- and IL-2-induced tumor regression in a new murine model of oral squamous-cell carcinoma is promoted by expression of the CD80 co-stimulatory molecule and interferon-gamma. *Int J Cancer* 86: 368-74.

Trinchieri G (2003). Interleukin-12 and the regulation of innate resistance and adaptive immunity. *Nat Rev Immunol* 3: 133-46.

Triozzi P L, Allen K O, Carlisle R R, Craig M, LoBuglio A F, Conry R M (2005). Phase I study of the intratumoral administration of recombinant canarypox viruses expressing B7.1 and interleukin 12 in patients with metastatic melanoma. *Clin Cancer Res* 11: 4168-75.

Tsung K, Meko J B, Peplinski G R, Tsung Y L, Norton J A (1997). IL-12 induces T helper 1-directed antitumor response. *J Immunol* 158: 3359-65.

Vujanovic, 2006.

Wang, 2001.

Wigginton 2002, 2001, 1996

Wolf S F, Sieburth D, Sypek J (1994). Interleukin 12: a key modulator of immune function. *Stem Cells* 12: 154-68.

Yamanaka R, Zullo S A, Ramsey J, Yajima N, Tsuchiya N, Tanaka R et al (2002). Marked enhancement of antitumor immune responses in mouse brain tumor models by genetically modified dendritic cells producing Semliki Forest virus-mediated interleukin-12. *J Neurosurg* 97: 611-8.

Yuminamochi E, Koike T, Takeda K, Horiuchi I, Okumura K (2007). Interleukin-12- and interferon-gamma-mediated natural killer cell activation by *Agaricus blazei* Murill. *Immunology*.

McDermott, D. F. and Atkins, M. B. (2008) Immunotherapy of metastatic renal cell carcinoma. Cancer J. 14, 320-324.

Berntsen, A., Trepiakas, R., Wenandy, L., Geertsen, P. F., thor Straten, P., Andersen, M. H., Pedersen, A. E., Claesson, M. H., Lorentzen, T., Johansen, J. S, and Svane, I. M. (2008) Therapeutic dendritic cell vaccination of patients with metastatic renal cell carcinoma: a clinical phase ½ trial. J. Immunother. 31, 771-780.

Tarhini, A. A., Kirkwood, J. M., Gooding, W. E., Moschos, S, and Agarwala, S. S. (2008) A phase 2 trial of sequential temozolomide chemotherapy followed by high-dose interleukin 2 immunotherapy for metastatic melanoma. Cancer. 113, 1632-1640.

Heemskerk, B., Liu, K., Dudley, M. E., Johnson, L. A., Kaiser, A., Downey, S., Zheng, Z., Shelton, T. E., Matsuda, K., Robbins, P. F., Morgan, R. A., Rosenberg, S. A. (2008) Adoptive cell therapy for patients with melanoma, using tumor-infiltrating lymphocytes genetically engineered to secrete interleukin-2. Hum Gene Ther. 19, 496-510.

Horton, H. M., Lalor, P. A. and Rolland, A. P. (2008) IL-2 plasmid electroporation: from preclinical studies to phase I clinical trial. Methods Mol Biol. 423, 361-372.

Shiratori, I., Suzuki, Y., Oshiumi, H., Begum, N. A., Ebihara, T., Matsumoto, M., Hazeki, K., Kodama, K., Kashiwazaki, Y. and Seya, T. (2007) Recombinant interleukin-12 and interleukin-18 antitumor therapy in a guinea-pig hepatoma cell implant model. Cancer Sci. 98, 1936-1942.

Lian H, Jin N, Li X, Mi Z, Zhang J, Sun L, Li X, Zheng H, Li P. (2007) Induction of an effective anti-tumor immune response and tumor regression by combined administration of IL-18 and Apoptin. Cancer Immunol Immunother. 56, 181-192.

Iinuma, H., Okinaga, K., Fukushima, R., Inaba, T., Iwasaki, K., Okinaga, A., Takahashi, I. and Kaneko, M. (2006) Superior protective and therapeutic effects of IL-12 and IL-18 gene-transduced dendritic neuroblastoma fusion cells on liver metastasis of murine neuroblastoma. J. Immunol. 176, 3461-3469.

Basak, G. W., Zapala, L., Wysocki, P. J., Mackiewicz, A., Jakóbisiak, M. and Lasek, W. (2008) Interleukin 15 augments antitumor activity of cytokine gene-modified melanoma cell vaccines in a murine model. Oncol Rep. 19, 1173-1179.

Lasek, W., Basak, G., Switaj, T., Jakubowska, A. B., Wysocki, P. J., Mackiewicz, A., Drela, N., Jalili, A., Kamiński, R., Kozar, K. and Jakóbisiak, M. (2004) Complete tumour regressions induced by vaccination with IL-12 gene-transduced tumour cells in combination with IL-15 in a melanoma model in mice. Cancer Immunol Immunother. 53, 363-372.

Xia, Y., Dai, J., Lu, P., Huang, Y., Zhu, Y. and Zhang, X. (2008) Distinct effect of CD40 and TNF-signaling on the chemokine/chemokine receptor expression and function of the human monocyte-derived dendritic cells. Cell Mol Immunol. 5, 121-131.

Sharma, S., Batra, R. K., Yang, S. C., Hillinger, S., Zhu, L., Atianzar, K., Strieter, R. M., Riedl, K., Huang, M. and Dubinett, S. M. (2003) Interleukin-7 gene-modified dendritic cells reduce pulmonary tumor burden in spontaneous murine bronchoalveolar cell carcinoma. Hum Gene Ther. 14, 1511-1524.

Tirapu, I., Rodriguez-Calvillo, M., Qian, C., Duarte, M., Smerdou, C., Palencia, B., Mazzolini, G., Prieto, J. and Melero, I. (2002) Cytokine gene transfer into dendritic cells for cancer treatment. Curr. Gene Ther. 2, 79-89.

Small, E. J., Sacks, N., Nemunaitis, J., Urba, W. J., Dula, E., Centeno, A. S., Nelson, W. G., Ando, D., Howard, C., Borellini, F., Nguyen, M., Hege, K. and Simons, J. W. (2007) Granulocyte macrophage colony-stimulating factor-secreting allogeneic cellular immunotherapy for hormone-refractory prostate cancer. Clin Cancer Res. 13, 3883-3891.

Huang, H. and Xiang, J. (2004) Synergistic effect of lymphotactin and interferon gamma-inducible protein-10 transgene expression in T-cell localization and adoptive T-cell therapy of tumors. Int. J. Cancer. 109, 817-825.

What is claimed is:

1. An in vitro engineered immune cell comprising an adenoviral vector for conditionally expressing proteins, the vector comprising a polynucleotide encoding an ecdysone gene switch, wherein said polynucleotide comprises
   (1) a polynucleotide sequence comprising a first transcription factor sequence and a second transcription factor sequence under the control of a promoter, wherein the proteins encoded by the first transcription factor sequence and second transcription factor sequence interact to form a ligand-dependent transcription factor complex,
      wherein the first transcription factor sequence comprises a nucleic acid encoding a VP-16 transactivation domain and a retinoic acid-X-receptor (RXR) polypeptide,
      wherein the RXR polypeptide is a genetically engineered chimera comprising vertebrate RXR and invertebrate RXR domains,
      wherein said vertebrate RXR ligand binding domain is a human RXR ligand binding domain,
      wherein the second transcription factor sequence comprises a nucleic acid encoding a GAL-4 DNA binding domain and an ecdysone receptor protein,
      wherein said ecdysone receptor ligand binding domain is derived from a *Choristoneura fumiferna* ecdysone receptor ligand binding domain, and
      wherein said *Choristoneura fumiferna* ecdysone receptor ligand binding domain further comprises a genetically engineered substitution mutation compared to the naturally occurring *Choristoneura fumiferna* ecdysone receptor ligand binding domain from which it was derived;
   (2) a polynucleotide encoding a polypeptide at least 90% identical to IL-12; and
   (3) a polynucleotide encoding a polypeptide at least 90% identical to IL-21;
   wherein at least one polynucleotide of (2) or (3) are linked to a promoter capable of being activated by said ligand dependent transcription factor complex.

2. An in vitro population of immune cells comprising the in vitro engineered immune cell of claim 1.

3. A pharmaceutical composition comprising the population of in vitro engineered immune cells according to claim 2.

4. A kit comprising the immune cells of claim 1.

5. The in vitro engineered immune cell or a TSC of claim 1, wherein the polypeptide at least 90% identical to IL-12 is at least 95% identical to IL-12, and wherein the polypeptide at least 90% identical to IL-21 is at least 95% identical to IL-21.

6. The in vitro engineered immune cell or a TSC of claim 1, wherein the polypeptide at least 90% identical to IL-12 is at least 99% identical to IL-12, and wherein the polypeptide at least 90% identical to IL-21 is at least 99% identical to IL-21.

7. The in vitro engineered immune cell of claim 1, wherein the polynucleotide sequence comprising a first transcription factor sequence and a second transcription factor sequence is under the control of a Ubiquitin C promoter.

8. The in vitro engineered immune cell of claim 1, wherein the RXR polypeptide comprises human RXR and locust RXR domains.

9. The in vitro engineered immune cell of claim 1, wherein the nucleic acid encoding a GAL-4 DNA binding domain and an ecdysone receptor protein encodes amino acids 1-147 of yeast Gal4 and the DEF domains of the ecdysone receptor from *Choristoneura fumiferna*.

10. The in vitro engineered immune cell of claim 1, wherein the first transcription factor sequence and the second transcription factor sequence are separated by an internal ribosome entry site.

11. The in vitro engineered immune cell of claim 10, wherein the internal ribosome entry site is from EMCV.

* * * * *